(12) United States Patent
Nakano et al.

(10) Patent No.: US 8,304,443 B2
(45) Date of Patent: Nov. 6, 2012

(54) INDAZOLE DERIVATIVES

(75) Inventors: Seiji Nakano, Tokyo (JP); Akifumi Morimoto, Tokyo (JP); Yasuhiro Wada, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 370 days.

(21) Appl. No.: 12/569,324

(22) Filed: Sep. 29, 2009

(65) Prior Publication Data
US 2010/0152265 A1 Jun. 17, 2010

Related U.S. Application Data

(60) Provisional application No. 61/104,024, filed on Oct. 9, 2008.

(51) Int. Cl.
*A61K 31/415* (2006.01)
*C07D 231/56* (2006.01)
(52) U.S. Cl. ................... 514/406; 548/361.5
(58) Field of Classification Search ............... 548/361.5; 514/406
See application file for complete search history.

(56) References Cited

U.S. PATENT DOCUMENTS

| 2,787,515 | A | 4/1957 | Frederic et al. |
| 4,378,361 | A | 3/1983 | Schromm et al. |
| 5,767,133 | A | 6/1998 | Dow et al. |
| 5,859,044 | A | 1/1999 | Dow et al. |

(Continued)

FOREIGN PATENT DOCUMENTS

| CA | 2728098 | 1/2010 |
| CA | 2740772 | 4/2010 |
| DE | 24 29 253 | 6/1974 |
| DE | 26 51 572 | 6/1977 |
| EP | 0 008 653 | 3/1980 |
| EP | 0 023 385 | 2/1981 |

(Continued)

OTHER PUBLICATIONS

Australia Office action that issued with respect tom patent family member Australian Patent Application No. 2009301797, mail date is Oct. 21, 2011.
U.S. Appl. No. 12/569,295 to Seiji Nakano et al., which was filed on Sep. 29, 2009.
U.S. Appl. No. 12/608,483 to Seiji Nakano et al., which was filed on Oct. 29, 2009.
Zhong et al., "$\alpha_1$-Adrenoceptor subtypes," Eur. J. Phamacol., vol. 375, pp. 261-276, 1999.
Arch et al., "Atypical β-adrenoceptor on brown adipocytes as target for anti-obesity drugs," Nature, vol. 309, pp. 163-165, May 1984.
Arch et al., "Prospects for $\beta_3$-adrenoceptor agonists in the treatment of obesity and diabetes", International Journal of Obesity, vol. 20, pp. 191-199, 1996.
Largis et al., "Antidiabetic and Antiobesity Effects of a Highly Selective $\beta_3$-Adrenoceptor Agonist (CL 316,243)", Drug Development Research, vol. 32, pp. 69-76, 1994.
Fisher et al., "A Selective Human $\beta_3$-Adrenergic Receptor Agonist Increases Metabolic Rate in Rhesus Monkeys", J. Clin. Invest., vol. 101, pp. 2387-2393, 1998.
Berkowitz et al., "Distribution of $\beta_3$-Adrenoceptor mRNA in human tissues," Eur. J. Phamacol., vol. 289, pp. 223-228, 1995.

(Continued)

*Primary Examiner* — Shengjun Wang
(74) *Attorney, Agent, or Firm* — Greenblum and Bernstein, P.L.C.

(57) ABSTRACT

Compounds represented by the Formula (A-1) and the Formula (1) or salt thereof are provided. The compounds represented by the Formula (A-1) and the Formula (1) or salt thereof have a β3 adrenergic receptor agonist activity, and therefore are useful as an agent for the prevention and treatment of diabetes, obesity, hyperlipidemia, depression, biliary stone, a disorder derived from hyperactivity of biliary tract, a disorder derived from hyperactivity of digestive tract, interstitial cystitis, overactive bladder, urinary incontinence or a disorder derived from decreased tear secretion, etc.

Formula

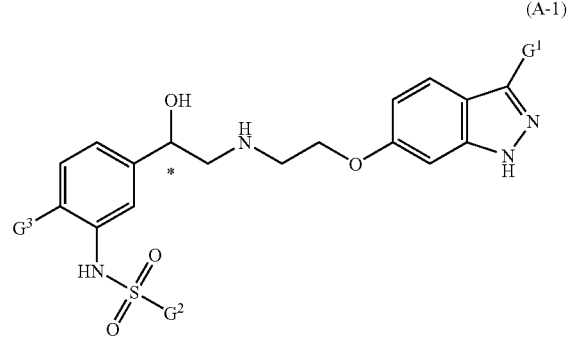

(A-1)

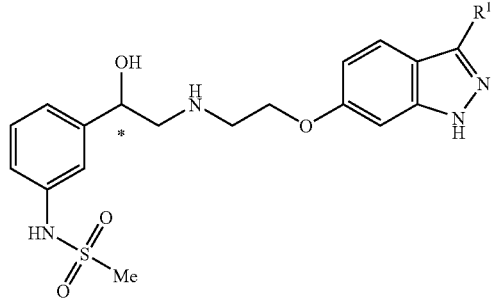

(1)

16 Claims, No Drawings

U.S. PATENT DOCUMENTS

| | | |
|---|---|---|
| 6,037,362 A | 3/2000 | Miyoshi et al. |
| 6,172,099 B1 | 1/2001 | Miyoshi et al. |
| 6,187,809 B1 | 2/2001 | Miyoshi et al. |
| 6,353,025 B1 | 3/2002 | Tamai et al. |
| 6,495,701 B1 | 12/2002 | Matsubara et al. |
| 6,545,053 B1 | 4/2003 | Miyoshi et al. |
| 6,861,444 B2 | 3/2005 | Ikuta et al. |
| 7,049,445 B2 | 5/2006 | Ikuta et al. |
| 7,199,147 B2 | 4/2007 | Imazaki et al. |
| 7,217,724 B2 | 5/2007 | Ueno et al. |
| 7,271,190 B2 | 9/2007 | Miyoshi et al. |
| 7,511,069 B2 | 3/2009 | Miyoshi et al. |
| 7,598,284 B2 | 10/2009 | Miyoshi et al. |
| 7,994,202 B2 | 8/2011 | Atobe et al. |
| 2002/0120148 A1 | 8/2002 | Taniguchi et al. |
| 2003/0040538 A1 | 2/2003 | Miyoshi et al. |
| 2003/0139475 A1 | 7/2003 | Miyoshi et al. |
| 2003/0191174 A1 | 10/2003 | Ikuta et al. |
| 2004/0053967 A1 | 3/2004 | Hara et al. |
| 2004/0102437 A1 | 5/2004 | Takami et al. |
| 2004/0127546 A1 | 7/2004 | Ikuta et al. |
| 2004/0138286 A1 | 7/2004 | Imazaki et al. |
| 2005/0020602 A1 | 1/2005 | Miyoshi et al. |
| 2006/0063762 A1 | 3/2006 | Ueno et al. |
| 2008/0015242 A1 | 1/2008 | Miyoshi et al. |
| 2008/0076815 A1 | 3/2008 | Miyoshi et al. |
| 2008/0306160 A1 | 12/2008 | Kobayashi et al. |
| 2009/0170826 A1 | 7/2009 | Hagihara et al. |
| 2010/0029733 A1 | 2/2010 | Atobe et al. |
| 2010/0160256 A1 | 6/2010 | Nakano et al. |

FOREIGN PATENT DOCUMENTS

| | | |
|---|---|---|
| EP | 0 171 702 | 2/1986 |
| EP | 0 238 973 | 3/1987 |
| EP | 0 455 006 | 4/1991 |
| EP | 659 737 | 6/1995 |
| EP | 1 174 425 | 3/2000 |
| EP | 1 043 308 | 10/2000 |
| EP | 1 142 883 | 10/2001 |
| EP | 1447400 | 8/2004 |
| EP | 2298767 | 3/2011 |
| EP | 2345644 | 7/2011 |
| GB | 1 565 080 | 11/1976 |
| JP | 55-53262 | 4/1980 |
| JP | 58-41860 | 3/1983 |
| JP | 8-165276 | 6/1996 |
| JP | 2010-111624 | 5/2010 |
| WO | 94/29290 | 12/1994 |
| WO | 95/29159 | 11/1995 |
| WO | 96/35670 | 11/1996 |
| WO | 97/25311 | 7/1997 |
| WO | 99/01431 | 1/1999 |
| WO | 99/31045 | 6/1999 |
| WO | 99/51564 | 10/1999 |
| WO | 00/35890 | 6/2000 |
| WO | 00/59287 | 10/2000 |
| WO | 00/59885 | 10/2000 |
| WO | 01/56988 | 8/2001 |
| WO | 01/83451 | 11/2001 |
| WO | 01/83452 | 11/2001 |
| WO | 01/83453 | 11/2001 |
| WO | 02/060873 | 8/2002 |
| WO | 02/074306 | 9/2002 |
| WO | 02/100833 | 12/2002 |
| WO | 03/035620 | 5/2003 |
| WO | 03/106418 | 12/2003 |
| WO | 2007/026630 | 3/2007 |
| WO | 2007/063821 | 6/2007 |

OTHER PUBLICATIONS

Howe, "$\beta_3$-Adrenergic Agonists," Drugs of the Future, vol. 18, No. 6, pp. 529-549, 1993.

De Ponti et al., "Functional evidence for the presence of $\beta_3$-adrenoceptors in the guinea pig common bile duct and colon," Pharmacology, vol. 51, pp. 288-297, 1995.

Rodriguez et al., "Evidence for the presence of $\beta_3$-adrenergic receptor mRNA in the human brain," Brain Res. Mol. Brain Res., vol. 29, No. 2, pp. 369-375, 1995.

Fujimura et al., "Expression and Possible Functional Role of the $\beta_3$-Adrenoceptor in Human and Rat Detrusor Muscle", The Journal of Urology, vol. 161, pp. 680-685, 1999.

Takeda et al., "Evidence for $\beta_3$-Adrenoceptor Subtypes in Relaxation of the Human Urinary Bladder Detrusor: Analysis by Molecular Biological and Pharmacological Methods," The Journal of Pharmacology and Experimental Therapeutics, vol. 288, pp. 1367-1373, 1999.

Bishop, "Recent advances in the discovery of $\alpha_1$-adrenoceptor agonists," Current Topics in Medicinal Chemistry, vol. 7, pp. 135-145, 2007.

Michel et al., "$\alpha_1$-, $\alpha_2$- and $\beta$-adrenoceptors in the urinary bladder, urethra and prostate," Br. J. Pharmacol., vol. 147, pp. S88-S119, 2006.

Patani et al., "Bioisosterism: A Rational Approach in Drug Design," Chem Rev, vol. 96 (8), pp. 3147-3176, 1996.

Hoey et al., "Characteristics of cyanopindolol analogues active at the $\beta_3$-adrenoceptor in rate ileum" Br. J. Pharm, vol. 119, pp. 564-568, 1996.

Cantello et al., "BRL 35135," Drugs of the Future, vol. 16(9), pp. 797-800, 1991.

Humber et al., "Disodium (R,R)-5-[2-[[2-(3-Chlorophenyl-2-hydroxyethyl)-amino]propyl]1,3-benzodioxole-2,2-dicarboxylate (CL 316,243). A Potent $\beta$-Adreneric Agonist Virtually Specific for $\beta_3$ Receptors. A Promising Antidiabetic and Antiobesity Agent", J. Med. Chem., 1992, vol. 35, pp. 3081-3084.

Search report from E.P.O. that issued with respect to patent family member European Patent Application No. 09819103.4, mail date is Feb. 29, 2012.

Canadian Office Action issued with respect to counterpart Canadian Application No. 2,737,349, dated Jun. 12, 2012.

INDAZOLE DERIVATIVES

CROSS REFERENCE TO RELATED APPLICATIONS

This application claims the benefit of U.S. Provisional Application No. 61/104,024, filed Oct. 9, 2008.

TECHNICAL FIELD

The present invention relates to novel indazole derivatives having a β3 adrenergic receptor agonist activity, a pharmaceutical composition comprising the same, and use thereof.

BACKGROUND ART

It has been known that noradrenaline and adrenaline have various activities on nerves or smooth muscles and the like as neurotransmitters and hormones present in a living body. Thus, adrenergic receptors which are responsive to such neurotransmitters/hormones via binding are considered to be target molecules for various drug compounds that are therapeutically important.

Adrenergic receptor belongs to a G-protein coupled receptor family and is classified into three subfamilies, i.e., α1, α2 and β adrenergic receptor. It is known that all the subfamilies of adrenergic receptor are activated by binding with noradrenaline and adrenaline, but different cellular signal transduction mechanisms are employed thereafter. It is demonstrated that increase in calcium ion is caused by α1 adrenergic receptor, inhibition of an adenylyl cyclase is caused by α2 adrenergic receptor, and stimulation of an adenylyl cyclase is mostly caused by β adrenergic receptor (for example, see Non-Patent Document 1).

Thus, the physiological mechanism of activation is different for each subfamily described above. For example, β adrenergic receptor subfamilies are further classified into three classes, i.e., β1, β2 and β3. With respect to these, it is recognized that stimulation of β1 adrenergic receptor causes an increase in heart rate and stimulation of β2 adrenergic receptor causes a relaxation of the smooth muscle tissue, especially resulting in lower the blood pressure when vascular smooth muscle tissue is relaxed.

It is also reported that β3 adrenergic receptor is present in adipocyte, brain, gallbladder, prostate, gut and the like. Thus, it is believed that β3 adrenergic receptor agonist activity is useful as an agent for prevention and treatment of diabetes, obesity, hyperlipidemia, depression, biliary stone, a disorder derived from hyperactivity of biliary tract, or a disorder derived from hyperactivity of digestive tract, or a disorder derived from decreased tear secretion, etc. (for example, see Non-Patent Documents No. 2 to 9 and Patent Documents No. 1 and 2).

It was also shown that β3 adrenergic receptor is expressed in urinary bladder smooth muscle and, with the stimulation of β3 adrenergic receptor, relaxation of the urinary bladder smooth muscle is caused (for example, see Non-Patent Documents No. 10 and 11). Thus, it is expected that an agonist of β3 adrenergic receptor is useful as an agent for prevention or treatment of frequent urination or urinary incontinence, which occurs in overactive bladder.

Meanwhile, with regard to α1 adrenergic receptor, which is other subfamily of the adrenergic receptor, it is reported that the receptor is expressed in vas deferens, submaxillary gland, kidney, spleen, liver, aorta, prostate, urinary tract and the like in rats. Further, a certain type of selective antagonists of the receptor has been used for the treatment of benign prostatic hyperplasia (for example, see Non-Patent Documents No. 1 and 13).

In this regard, agonists of α1 adrenergic receptor, for example, phenylephrine, methoxamine, metaraminol, midodrine, etc., are known to have an activity of increasing blood pressure by contracting blood vessels, and therefore used as hypertensors (see, for example, Non-Patent Document 12). Further, in Non-Patent Document 12, relationship between selective activation of α1 adrenergic receptor subtype and urinary incontinence is discussed. Specifically, the α1 adrenergic receptor is classified into subtypes of α1A, α1B, α1D, etc., and among these, the α1A subtype is expected to be useful for prevention or treatment of stress incontinence based on its activity of contracting a urinary bladder neck or urethral smooth muscles.

As it is evident from the above descriptions, when agonists or antagonists which bind to an adrenergic receptor are used for treatment of a certain disorder under specific purpose, generally it is preferable to consider their selectivity for receptor subfamily, in particular their selectivity for subtype. In particular, when an agonist of β3 adrenergic receptor is used under the purpose of treating diabetes, obesity, hyperlipidemia, depression, biliary stone, a disorder derived from hyperactivity of biliary tract, a disorder derived from hyperactivity of digestive tract, frequent urination or urine incontinence derived from overactive bladder, or a disorder derived from decreased tear secretion, etc., an agonist which has high selectivity for the subtype of β3 adrenergic receptor is generally selected and used. As described above, there can be also a case in which stimulation of β1 and β2 adrenergic receptor subtypes may cause increased heart rate or low blood pressure, that can be undesirable for certain patients.

Similarly, it is preferable that stimulation of α1 adrenergic receptor as other subfamily is also considered as a factor which may also cause a secondary physiological reaction in blood vessels of peripheral tissues, etc. of certain patients, although it is not originally intended.

In the Patent Documents No. 3 to 5, a specific kind of compound having β3 adrenergic receptor agonist activity is disclosed [i.e., the compounds of the Formula (4) to (6) shown below]. However, the compounds of the present invention are not disclosed in any of prior art documents.

Formula (4) that is described in Patent Document 3:

[Chemical Formula 1]

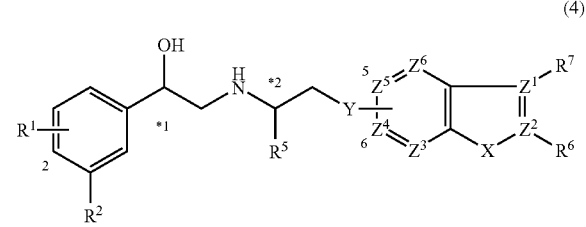

(4)

Formula (5) that is described in Patent Document 4:

[Chemical Formula 2]

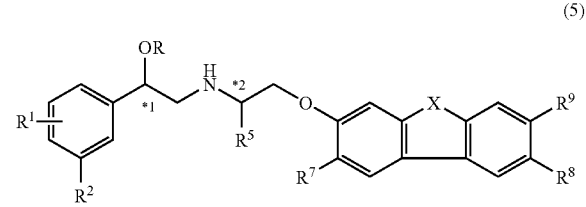

(5)

Formula (6) that is described in Patent Document 5:

[Chemical Formula 3]

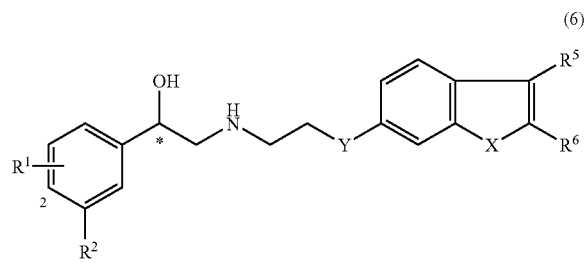

(6)

Furthermore, Patent Documents No. 3 to 5 include no descriptions regarding selective stimulation of β3 adrenergic receptor compared to stimulation of α1 adrenergic receptor.

PRIOR ART DOCUMENTS

Non-Patent Documents

[Non-Patent Document 1] Eur. J. Phamacol., Vol. 375, pp. 261-276, 1999
[Non-Patent Document 2] Nature, Vol. 309, pp. 163-165, 1984
[Non-Patent Document 3] Int. J. Obes. Relat. Metab. Disord., Vol. 20, pp. 191-199, 1996
[Non-Patent Document 4] Drug Development Research, Vol. 32, pp. 69-76, 1994
[Non-Patent Document 5] J. Clin. Invest., Vol. 101, pp. 2387-2393, 1998
[Non-Patent Document 6] Eur. J. Phamacol., Vol. 289, pp. 223-228, 1995
[Non-Patent Document 7] Drugs of the Future, Vol. 18, No. 6, pp. 529-549, 1993
[Non-Patent Document 8] Pharmacology, Vol. 51, pp. 288-297, 1995
[Non-Patent Document 9] Brain Res. Mol. Brain Res., Vol. 29, No. 2, pp. 369-375, 1995
[Non-Patent Document 10] J. Urinol., Vol. 161, pp. 680-685, 1999
[Non-Patent Document 11] J. Pharmacol. Exp. Ther., Vol. 288, pp. 1367-1373, 1999
[Non-Patent Document 12] Current Topics in Medicinal Chemistry, Vol. 7, pp. 135-145, 2007
[Non-Patent Document 13] Br. J. Pharmacol., Vol. 147, pp. S88-S119, 2006

Patent Documents

[Patent Document 1] International Publication No. WO99/31045 pamphlet
[Patent Document 2] International Publication No. WO2007/026630 pamphlet
[Patent Document 3] International Publication No. WO97/25311 pamphlet
[Patent Document 4] International Publication No. WO01/83451 pamphlet
[Patent Document 5] International Publication No. WO03/035620 pamphlet

SUMMARY OF THE INVENTION

Problems to be Solved by the Invention

Object of the present invention is to provide a medicine which can selectively stimulate β3 adrenergic receptor, in particular a medicine which can primarily stimulate β3 adrenergic receptor over α1 adrenergic receptor (in the present specification, it is also referred to as "selective (β3/α1 adrenergic receptor agonist"). This medicine can be used for prevention and treatment of diabetes, obesity, hyperlipidemia, depression, biliary stone, a disorder derived from hyperactivity of biliary tract, a disorder derived from hyperactivity of digestive tract, interstitial cystitis, overactive bladder, urinary incontinence or a disorder derived from decreased tear secretion, etc., while exhibition of undesirable physiological responses caused by stimulation of α1 adrenergic receptor is decreased to the minimum level.

Means for Solving the Problems

It was found that compounds having a certain structure can primarily stimulate β3 adrenergic receptor over α1 adrenergic receptor. Thus, those compounds can be used as a selective β3/α1 adrenergic receptor agonist of the present invention.

Specifically, the present invention is related to the followings.

[1] A compound having the following Formula (A-1)

[Chemical Formula 4]

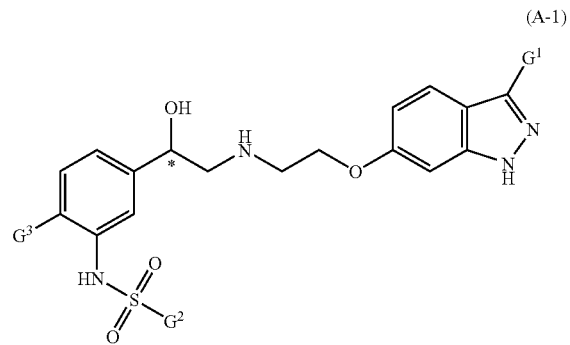

(A-1)

[in the Formula (A-1), $G^1$ represents —CH($G^4$)OMe, —OCHF$_2$, —OCF$_3$, a halogen atom, or a group that is represented by the following Formula (A-2) to (A-3),

[Chemical Formula 5]

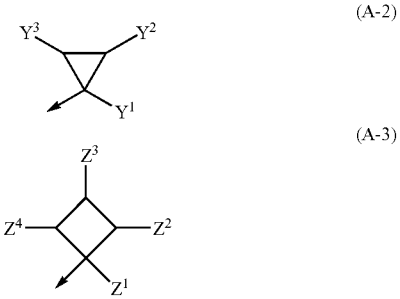

(A-2)

(A-3)

$G^2$ represents a methyl group, an ethyl group, an n-propyl group, an isopropyl group, an isobutyl group, a sec-butyl group, a benzyl group, or a phenyl group, $G^3$ represents a hydrogen atom, or a halogen atom, $G^4$ represents a methyl group, an ethyl group, an n-propyl group, or an isopropyl group, $Y^1$, $Y^2$, $Y^3$, $Z^1$, $Z^2$, $Z^3$ and $Z^4$ can be the same or different to each other and each independently represent a hydrogen atom or a methyl group; with the proviso that, a compound in which $G^2$ represents a methyl group and $G^3$ represents a hydrogen atom or a halogen atom when $G^1$ represents a halogen atom and a compound in which $G^2$ represents a methyl group and $G^3$ represents a hydrogen atom when $G^1$ represents —OCHF$_2$ are excluded; asterisk * represents an asymmetric carbon.], or salt thereof.

[2] A compound having the following Formula (1)

[Chemical Formula 6]

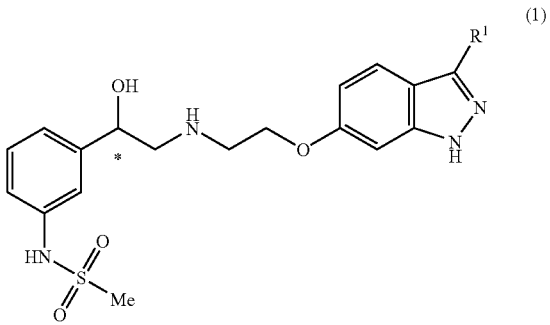

(1)

[in the Formula (1), $R^1$ represents —CH($R^2$)OMe or a group that is represented by the following Formula (2-1) to (2-2),

[Chemical Formula 7]

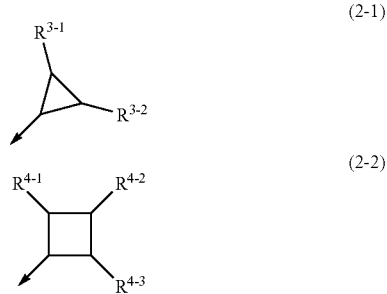

$R^2$ represents a methyl group, an ethyl group, an n-propyl group, or an isopropyl group, $R^{3-1}$, $R^{3-2}$, $R^{4-1}$, $R^{4-2}$ and $R^{4-3}$ can be the same or different to each other and each independently represent a hydrogen atom or a methyl group. Asterisk * represents an asymmetric carbon.], or salt thereof.

[3] The compound described in the above [1] or salt thereof in which $G^1$ represents —OCHF$_2$, a halogen atom, a cyclopropyl group, a cyclobutyl group, $G^2$ represents a methyl group, an ethyl group, an n-propyl group, an isopropyl group, an isobutyl group, a sec-butyl group, a benzyl group, or a phenyl group, and $G^3$ represents a hydrogen atom, a fluorine atom, or a chlorine atom.

[4] The compound described in the above [1] or salt thereof in which $G^1$ represents —CH(Me)OMe, a cyclopropyl group, or a cyclobutyl group.

[5] The compound described in the above [2] or salt thereof in which $R^1$ represents —CH(Me)OMe, a cyclopropyl group, or a cyclobutyl group.

[6] The compound described in any one of the above [1] to [5] or salt thereof in which stereo configuration of an asymmetric carbon that is marked with asterisk * is (R) configuration.

[7] A compound that is selected from a group consisting of
(R)—N-(3-(2-(2-(3-(1-methoxyethyl)indazol-6-yloxy)ethylamino)-1-hydroxyethyl)phenyl)methanesulfonamide;
(R)—N-(3-(2-(2-(3-cyclopropylindazol-6-yloxy)ethylamino)-1-hydroxyethyl)phenyl)methanesulfonamide;
(R)—N-(3-(2-(2-(3-cyclobutylindazol-6-yloxy)ethylamino)-1-hydroxyethyl)phenyl)methanesulfonamide;
(R)—N-(5-(2-(2-(3-cyclopropylindazol-6-yloxy)ethylamino)-1-hydroxyethyl)-2-fluorophenyl)methanesulfonamide;
(R)—N-(2-chloro-5-(2-(2-(3-cyclopropylindazol-6-yloxy)ethylamino)-1-hydroxyethyl)phenyl)methanesulfonamide;
(R)—N-(2-chloro-5-(2-(2-(3-cyclobutylindazol-6-yloxy)ethylamino)-1-hydroxyethyl)phenyl)methanesulfonamide; and
(R)—N-(2-chloro-5-(2-(2-(3-(difluoromethoxy)-indazol-6-yloxy)ethylamino)-1-hydroxyethyl)phenyl)methanesulfonamide;
or a salt thereof.

[7-1]
(R)—N-(3-(2-(2-(3-(1-methoxyethyl)indazol-6-yloxy)ethylamino)-1-hydroxyethyl)phenyl)methanesulfonamide or salt thereof.

[7-2]
(R)—N-(3-(2-(2-(3-cyclopropylindazol-6-yloxy)ethylamino)-1-hydroxyethyl)phenyl)methanesulfonamide or salt thereof.

[7-3]
(R)—N-(3-(2-(2-(3-cyclobutylindazol-6-yloxy)ethylamino)-1-hydroxyethyl)phenyl)methanesulfonamide or salt thereof.

[7-4]
(R)—N-(5-(2-(2-(3-cyclopropylindazol-6-yloxy)ethylamino)-1-hydroxyethyl)-2-fluorophenyl)methanesulfonamide or salt thereof.

[7-5]
(R)—N-(2-chloro-5-(2-(2-(3-cyclopropylindazol-6-yloxy)ethylamino)-1-hydroxyethyl)phenyl)methanesulfonamide or salt thereof.

[7-6]
(R)—N-(2-chloro-5-(2-(2-(3-cyclobutylindazol-6-yloxy)ethylamino)-1-hydroxyethyl)phenyl)methanesulfonamide or salt thereof.

[7-7]
(R)—N-(2-chloro-5-(2-(2-(3-(difluoromethoxy)-indazol-6-yloxy)ethylamino)-1-hydroxyethyl)phenyl)methanesulfonamide or salt thereof.

[8] A compound that is selected from a group consisting of
(R)—N-(3-(2-(2-(3-(1-methoxyethyl)indazol-6-yloxy)ethylamino)-1-hydroxyethyl)phenyl)methanesulfonamide;
(R)—N-(3-(2-(2-(3-cyclopropylindazol-6-yloxy)ethylamino)-1-hydroxyethyl)phenyl)methanesulfonamide; and
(R)—N-(3-(2-(2-(3-cyclobutylindazol-6-yloxy)ethylamino)-1-hydroxyethyl)phenyl)methanesulfonamide;
or a salt thereof.

[9] A β3 adrenergic receptor agonist which comprises the compound described in any one of the above [1] to [8] or salt thereof as an active ingredient.

[10] A medicine which comprises the compound described in any one of the above [1] to [8] or salt thereof as an active ingredient.

[11] The medicine described in the above [10], which is a preventative and/or therapeutic agent for overactive bladder and urinary incontinence.

[12] A method of activating β3 adrenergic receptor in a living body of a patient, characterized in that the compound described in any one of the above [1] to [8] or salt thereof are administered to a patient who is in need of prevention and/or treatment of overactive bladder and urinary incontinence.

[12-1] The method described in the above [12], in which the administration does not substantially activate α1 adrenergic receptor in the living body of the patient.

[12-2] The method described in the above [12], in which the patient is a patient who needs to avoid substantial activation of α1 adrenergic receptor by drug administration.

[13] A method of prevention and/or treatment of overactive bladder and urinary incontinence, characterized in that an effective amount of the compound described in any one of the above [1] to [8] or salt thereof is administered to a patient.

[13-1] The method described in the above [13], in which the patient is a patient who needs to avoid substantial activation of α1 adrenergic receptor by drug administration.

[14] A method of prevention and/or treatment of urinary incontinence, characterized in that an effective amount of the compound described in any one of the above [1] to [8] or salt thereof is administered to a patient.

[14-1] The method described in the above [14], in which the patient is a patient who needs to avoid substantial activation of α1 adrenergic receptor by drug administration.

[15] A compound having the following Formula (A-4)

[Chemical Formula 8]

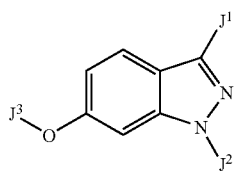

(A-4)

[in the Formula (A-1), $J^1$ represents —CH($J^4$)OMe, —OCHF$_2$, —OCF$_3$, a halogen atom, or a group that is represented by the following Formula (A-5) to (A-6),

[Chemical Formula 9]

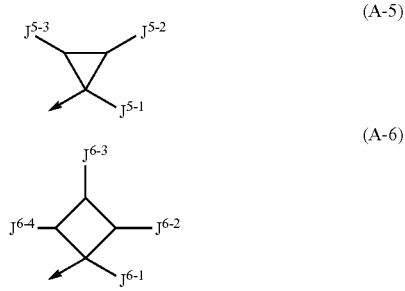

(A-5)

(A-6)

$J^2$ represents a hydrogen atom, a tert-butoxycarbonyl group, a benzyl group, or a tetrahydropyranyl group, $J^3$ represents a hydrogen atom, a benzyl group, or a tert-butyldiphenylsilyl group, $J^4$ represents a methyl group, an ethyl group, an n-propyl group, or an isopropyl group, $J^{5-1}$, $J^{5-2}$, $J^{5-3}$, $J^{6-1}$, $J^{6-2}$, $J^{6-3}$ and $J^{6-4}$ can be the same or different to each other and each independently represent a hydrogen atom or a methyl group.], or salt thereof.

[16] A compound having the following Formula (3)

[Chemical Formula 10]

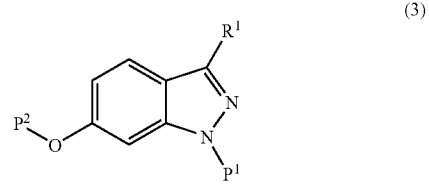

(3)

[in the Formula (3), $R^1$ represents —CH($R^2$)OMe, or a group that is represented by the Formula (2-1) to (2-2),

[Chemical Formula 11]

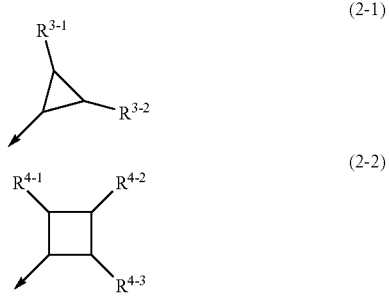

(2-1)

(2-2)

$R^2$ represents a methyl group, an ethyl group, an n-propyl group, or an isopropyl group, $R^{3-1}$, $R^{3-2}$, $R^{4-1}$, $R^{4-2}$ and $R^{4-3}$ can be the same or different to each other and each independently represent a hydrogen atom or a methyl group, $P^1$ represents a hydrogen atom, a tert-butoxycarbonyl group, a benzyl group, or a tetrahydropyranyl group, $P^2$ represents a hydrogen atom, a benzyl group, or a tert-butyldiphenylsilyl group.], or salt thereof.

[17] The compound described in the above [15] or salt thereof in which $J^1$ represents —CH(Me)OMe, —OCHF$_2$, a chlorine atom, a cyclopropyl group, or a cyclobutyl group, $J^2$ represents a hydrogen atom, a tert-butoxycarbonyl group, a benzyl group, or a tetrahydropyranyl group, $J^3$ represents a hydrogen atom, a benzyl group, or a tert-butyldiphenylsilyl group.

[18] The compound described in the above [16] or salt thereof in which $R^1$ represents —CH(Me)OMe, a cyclopropyl group, or a cyclobutyl group, $P^1$ represents a hydrogen atom, a tert-butoxycarbonyl group, a benzyl group, or a tetrahydropyranyl group, and $P^2$ represents a hydrogen atom, a benzyl group, or a tert-butyldiphenylsilyl group.

[19] A compound that is selected from a group consisting of 1-benzyl-3-cyclopropylindazol-6-ol;
3-cyclopropylindazol-6-ol;
6-(tert-butyldiphenylsilyloxy)-3-cyclopropylindazole;
tert-butyl 6-(tert-butyldiphenylsilyloxy)-3-cyclopropylindazole-1-carboxylate;
tert-butyl 6-hydroxy-3-cyclopropylindazole-1-carboxylate;
1-benzyl-3-cyclobutylindazol-6-ol;
3-cyclobutylindazol-6-ol;
6-(tert-butyldiphenylsilyloxy)-3-cyclobutylindazole;
tert-butyl 6-(tert-butyldiphenylsilyloxy)-3-cyclobutylindazole-1-carboxylate;

tert-butyl 6-hydroxy-3-cyclobutylindazole-1-carboxylate;
6-(benzyloxy)-3-(1-methoxyethyl)-1-(tetrahydro-2H-pyran-2-yl)-indazole;
3-(1-methoxyethyl)-1-(tetrahydro-2H-pyran-2-yl)-indazol-6-ol;
tert-butyl 6-(benzyloxy)-3-(difluoromethoxy)-indazole-1-carboxylate;
tert-butyl 3-(difluoromethoxy)-6-hydroxyindazole-1-carboxylate;
6-(tert-butyldiphenylsilyloxy)-3-chloroindazole;
tert-butyl 6-(tert-butyldiphenylsilyloxy)-3-chloroindazole-1-carboxylate; and
tert-butyl 3-chloro-6-hydroxyindazole-1-carboxylate;
or a salt thereof.

[20] A compound that is selected from a group consisting of
1-benzyl-3-cyclopropylindazol-6-ol;
3-cyclopropylindazol-6-ol;
6-(tert-butyldiphenylsilyloxy)-3-cyclopropylindazole;
tert-butyl 6-(tert-butyldiphenylsilyloxy)-3-cyclopropylindazole-1-carboxylate;
tert-butyl 6-hydroxy-3-cyclopropylindazole-1-carboxylate;
1-benzyl-3-cyclobutylindazol-6-ol;
3-cyclobutylindazol-6-ol;
6-(tert-butyldiphenylsilyloxy)-3-cyclobutylindazole;
tert-butyl 6-(tert-butyldiphenylsilyloxy)-3-cyclobutylindazole-1-carboxylate;
tert-butyl 6-hydroxy-3-cyclobutylindazole-1-carboxylate;
6-(benzyloxy)-3-(1-methoxyethyl)-1-(tetrahydro-2H-pyran-2-yl)-indazole; and
3-(1-methoxyethyl)-1-(tetrahydro-2H-pyran-2-yl)-indazol-6-ol;
or a salt thereof.

Effect of the Invention

"A compound having the following Formula (A-1) or salt thereof", or "A compound having the following Formula (1) or salt thereof" (herein below, it can be also simply referred to as the "compounds of the present invention") described in the above have a potent β3 adrenergic receptor agonist activity when it is administered to a human or an animal, and therefore are effective for relaxing smooth muscle of a urinary bladder. In addition, they have an excellent property of high β3/α1 adrenergic receptor selectivity, and therefore can provide a favorable pharmaceutical composition for treating overactive bladder and urinary incontinence.

MODE FOR CARRYING OUT THE INVENTION

Herein below, compounds of the present invention will be explained in greater detail.

As it will be evident to a skilled person in the pertinent art, symbols that are described in the present specification are defined as described below, unless specifically described otherwise.

[Chemical Formula 12]

indicates a bond which is directed in back of the paper plane (i.e., α-configuration),

[Chemical Formula 13]

indicates a bond which is directed in front of the paper plane (i.e., β-configuration),

[Chemical Formula 14]

indicates a bond which is any one of α-configuration and β-configuration, or a mixture thereof.

In the present specification, the halogen atom indicates a fluorine atom, a chlorine atom, a bromine atom or an iodine atom.

Compounds of the present invention are as defined below.
Formula (A-1) as follows

[Chemical Formula 15]

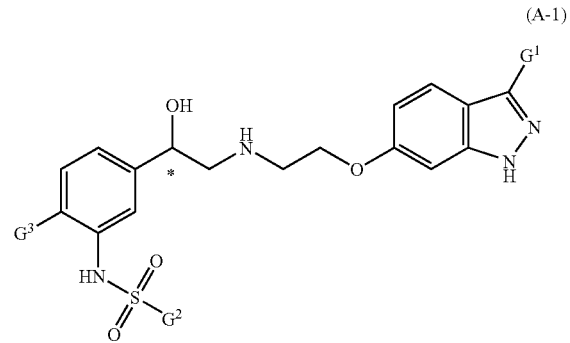

(A-1)

In the Formula (A-1), $G^1$ represents —CH($G^4$)OMe, —OCHF$_2$, —OCF$_3$, a halogen atom, or a group that is represented by the following Formula (A-2) to (A-3),

[Chemical Formula 16]

(A-2)

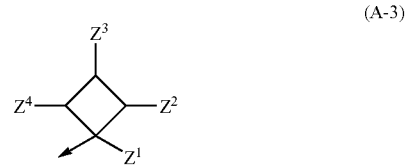

(A-3)

$G^2$ represents a methyl group, an ethyl group, an n-propyl group, an isopropyl group, an isobutyl group, a sec-butyl group, a benzyl group, or a phenyl group, $G^3$ represents a hydrogen atom, or a halogen atom, $G^4$ represents a methyl group, an ethyl group, an n-propyl group, or an isopropyl group, $Y^1$, $Y^2$, $Y^3$, $Z^1$, $Z^2$, $Z^3$ and $Z^4$ can be the same or different to each other and each independently represent a hydrogen atom or a methyl group; with the proviso that, a compound in which $G^2$ represents a methyl group and $G^3$ represents a hydrogen atom or a halogen atom when $G^1$ represents a halogen atom and a compound in which $G^2$ represents a methyl group and $G^3$ represents a hydrogen atom when $G^1$ represents —$OCHF_2$ are excluded; asterisk * represents an asymmetric carbon.

As for the $G^1$, —$CH(G^4)OMe$, —$OCHF_2$, —$OCF_3$, a halogen atom, a cyclopropyl group, or a cyclobutyl group is preferable, —$CH(Me)OMe$, —$OCHF_2$, a chlorine atom, a cyclopropyl group, or a cyclobutyl group is more preferable, —$CH(Me)OMe$, a cyclopropyl group, or a cyclobutyl group is still more preferable, and —$OCHF_2$ or a cyclopropyl group is particularly preferable. In addition, there is other embodiment in which —$CH(Me)OMe$, a chlorine atom, or a cyclobutyl group is preferable.

As for the $G^2$, a methyl group, an ethyl group, an n-propyl group, an isopropyl group, an isobutyl group, a sec-butyl group, a benzyl group, or a phenyl group is preferable, a methyl group, an ethyl group, an n-propyl group, an isopropyl group, or a phenyl group is more preferable, and a methyl group is particularly preferable. In addition, there is other embodiment in which an ethyl group, an n-propyl group, an isopropyl group, or a phenyl group is preferable.

As for the $G^3$, a hydrogen atom or a halogen atom is preferable, a hydrogen atom, a fluorine atom, or a chlorine atom is more preferable, and a hydrogen atom is particularly preferable. In addition, there is other embodiment in which a fluorine atom or a chlorine atom is preferable.

As for the $G^4$, a methyl group, an ethyl group, an n-propyl group, or an isopropyl group is preferable and a methyl group is more preferable.

As for the $Y^1$, $Y^2$, $Y^3$, $Z^1$, $Z^2$, $Z^3$ and $Z^4$, they can be the same or different to each other and preferably each independently represent a hydrogen atom or a methyl group, and more preferably each independently represent a hydrogen atom.

However, a combination in which $G^2$ represents a methyl group, an ethyl group, or an n-propyl group and $G^3$ represents a hydrogen atom or a halogen atom when $G^1$ represents —$OCHF_2$ or a halogen atom is excluded.

Asterisk * represents an asymmetric carbon.

The Formula (1):

[Chemical Formula 17]

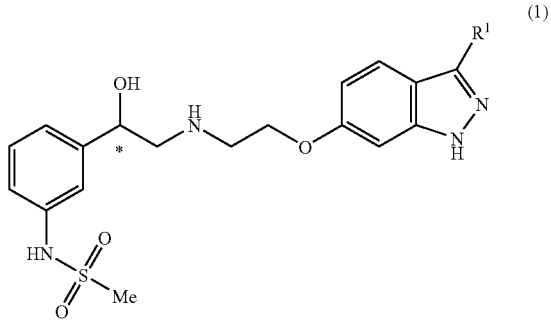

(1)

In the Formula (1), $R^1$ represents —$CH(R^2)OMe$ or a group that is represented by the following Formula (2-1) to (2-2);

[Chemical Formula 18]

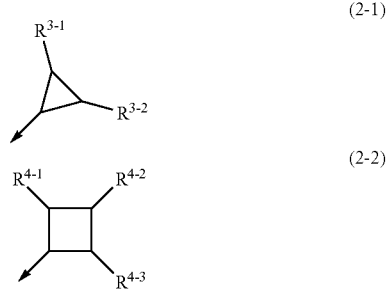

(2-1)

(2-2)

$R^2$ represents a methyl group, an ethyl group, an n-propyl group, or an isopropyl group, $R^{3-1}$, $R^{3-2}$, $R^{4-1}$, $R^{4-2}$ and $R^{4-3}$ can be the same or different to each other and each independently represent a hydrogen atom or a methyl group.

Asterisk * represents an asymmetric carbon.

As for the $R^1$, —$CH(R^2)OMe$, a cyclopropyl group, or a cyclobutyl group is preferable, —$CH(Me)OMe$, a cyclopropyl group, or a cyclobutyl group is more preferable, and a cyclopropyl group is particularly preferable. In addition, there is other embodiment in which —$CH(Me)OMe$ or a cyclobutyl group is preferable.

As for the $R^2$, a methyl group, an ethyl group, an n-propyl group, or an isopropyl group is preferable and a methyl group is more preferable.

As for the $R^{3-1}$, $R^{3-2}$, $R^{4-1}$, $R^{4-2}$ and $R^{4-3}$, it is preferable that each independently represents a hydrogen atom.

In the structural formula of the compounds of the present invention, carbon atom marked with asterisk * indicates an asymmetric carbon. Regarding stereo configuration of the asymmetric carbon atom, S configuration or R configuration is exemplified. R configuration is preferable. The compounds of the present invention include optically pure optical isomers that are based on an asymmetric carbon, a mixture of each optical isomer, and a racemate. In addition, the compounds of the present invention may have one or more asymmetric carbon atoms depending on the type of a substituent group they have. Unless specifically indicates otherwise, these are all included in the isomers. For example, an isomer based on an asymmetric carbon (R- or S-isomer, an isomer based on α- or β-configuration, an enantiomer, or a diastereomer and the like), an optically active compound having optical activity (D- or L-form, or d- or l-form), an isomer based on a difference in polarity under chiral chromatographic separation (highly polar form, or weakly polar form), an equilibrium compound, a rotationary isomer, a tautomer, or a mixture comprising them in any ratio, or a racemic mixture are all within the compounds of the present invention. For example, the compound in which $R^1$ is —$CH(Me)OMe$ and the stereo configuration of an asymmetric carbon atom marked with asterisk * is (R) configuration is a mixture of diastereomers, and each optically active compound is also included in the compounds of the present invention.

The "compounds represented by the Formula (A-1)" or the "compounds represented by the Formula (1)" are generally understood as free form of the compound represented by the Formula (A-1) or the Formula (1). In addition, regarding the salt thereof, the salts as follows can be mentioned.

If it is an acid addition salt, salt type of the compounds of the present invention is not specifically limited and intramolecular counter ion form is also acceptable. In particular, when the compounds are used as an active ingredient of a medicine, a pharmaceutically acceptable salt is particularly preferred as such salt. In the present specification, when described in connection with use as a medicine, salts of the compounds of the present invention are generally understood as a pharmaceutically acceptable salt. Type of acid which can form a pharmaceutically acceptable salt is well known to a skilled person in the art, and examples thereof include those described in J. Pharm. Sci., 1-19 (1977) by Berge, et al., for example. Examples of an acid addition salt include inorganic acid salts such as hydrochlorides, hydrobromides, hydroiodides, nitrates, sulfates, hydrogen sulfates, phosphates or hydrogen phosphates; and organic acid salts such as acetates, trifluoroacetates, gluconates, lactates, salicylates, citrates, tartrates, ascorbates, succinates, maleates, fumarates, formates, benzoates, methanesulfonates, ethanesulfonates or p-toluenesulfonates and the like.

For example, when a salt of inorganic acid is prepared, it is preferable that the compound of the Formula (A-1) or the Formula (1) is dissolved in an aqueous solution which comprises at least one equivalent inorganic acid. For such reaction, an inert organic solvent which is miscible with water, for example, methanol, ethanol, acetone, dioxane and the like, can be also mixed. For example, by using hydrochloric acid, a solution of hydrochloride can be prepared.

The compounds of the present invention can have anhydrous form. Further, hydrates are also preferable for the compounds of the present invention.

Further, although solvates are preferable as the compounds of the present invention, solvate-free forms are also mentioned as a preferred example.

Further, the compounds of the present invention can have crystalline or non-crystalline form. The crystalline form can be a single crystal, a mixture of several crystalline forms, or any mixture of a crystalline form and a non-crystalline form.

More specifically, anhydrous and solvent-free form, or a hydrate and/or a solvate of the "compounds represented by the Formula (A-1)" or the "compounds represented by the Formula (1)", or crystalline form thereof can be mentioned as a preferred example.

In addition, it can be also anhydrous and solvent-free form, or a hydrate and/or a solvate of the "salt of the compounds represented by the Formula (A-1)" or the "salt of the compounds represented by the Formula (1)", or anhydrous and solvent-free form of the salt or a hydrate and/or a solvate of the salt.

The following combinations can be mentioned as a preferred combination of the substituent groups for the compounds represented by the Formula (1).

(1) Compounds of the present invention in which stereo configuration of an asymmetric carbon that is marked with asterisk * is (R) configuration;

(2) Compounds of the present invention in which $R^1$ is —CH(Me)OMe, a cyclopropyl group, or a cyclobutyl group;

(3) Compounds of the present invention in which $R^2$ is a methyl group;

(4) Compounds of the present invention in which $R^{3-1}$, $R^{3-2}$, $R^{4-1}$, $R^{4-2}$ and $R^{4-3}$ are a hydrogen atom;

(5) Compounds of the present invention in which $R^1$ is —CH(Me)OMe, a cyclopropyl group, or a cyclobutyl group, and stereo configuration of an asymmetric carbon that is marked with asterisk * is (R) configuration;

(6) Compounds of the present invention in which $R^1$ is —CH(Me)OMe, and stereo configuration of an asymmetric carbon that is marked with asterisk * is (R) configuration;

(7) Compounds of the present invention in which $R^1$ is a cyclopropyl group, and stereo configuration of an asymmetric carbon that is marked with asterisk * is (R) configuration;

(8) Compounds of the present invention in which $R^1$ is a cyclobutyl group, and stereo configuration of an asymmetric carbon that is marked with asterisk * is (R) configuration;

The following combinations can be mentioned as a preferred combination of the substituent groups for the compounds represented by the Formula (A-1).

(9) Compounds of the present invention in which $G^1$ is —CH($G^4$)OMe, $G^2$ is a methyl group, an ethyl group, an n-propyl group, an isopropyl group, an isobutyl group, a sec-butyl group, a benzyl group, or a phenyl group, $G^3$ represents a hydrogen atom or a halogen atom, and $G^4$ is a methyl group, an ethyl group, an n-propyl group, or an isopropyl group;

(10) Compounds of the present invention in which $G^1$ is —CH(Me)OMe, $G^2$ is a methyl group, an ethyl group, an n-propyl group, an isopropyl group, an isobutyl group, a sec-butyl group, a benzyl group, or a phenyl group and $G^3$ is a hydrogen atom or a halogen atom;

(11) Compounds of the present invention in which $G^1$ is —CH(Me)OMe, $G^2$ is a methyl group and $G^3$ is a hydrogen atom, and stereo configuration of an asymmetric carbon that is marked with asterisk * is (R) configuration;

(12) Compounds of the present invention in which $G^1$ is —CH(Me)OMe, $G^2$ is a methyl group and $G^3$ is a hydrogen atom;

(13) Compounds of the present invention in which $G^1$ is —OCHF$_2$, $G^2$ is an isopropyl group, an isobutyl group, a sec-butyl group, a benzyl group, or a phenyl group, and $G^3$ is a hydrogen atom or a halogen atom;

(14) Compounds of the present invention in which $G^1$ is —OCHF$_2$, $G^2$ is an isopropyl group or a phenyl group, and $G^3$ is a hydrogen atom;

(15) Compounds of the present invention in which $G^1$ is —OCHF$_2$, $G^2$ is an isopropyl group or a phenyl group, $G^3$ is a hydrogen atom, and stereo configuration of an asymmetric carbon that is marked with asterisk * is (R) configuration;

(16) Compounds of the present invention in which $G^1$ is a halogen atom, $G^2$ is a methyl group, an ethyl group, an n-propyl group, an isopropyl group, an isobutyl group, a sec-butyl group, a benzyl group, or a phenyl group, and $G^3$ is a hydrogen atom or a halogen atom;

(17) Compounds of the present invention in which $G^1$ is a chlorine atom, $G^2$ is an isopropyl group, an isobutyl group, a sec-butyl group, a benzyl group, or a phenyl group, and $G^3$ is a hydrogen atom or a halogen atom;

(18) Compounds of the present invention in which $G^1$ is a chlorine atom, $G^2$ is an isopropyl group or a phenyl group, and $G^3$ is a hydrogen atom;

(19) Compounds of the present invention in which $G^1$ is a chlorine atom, $G^2$ is an isopropyl group or a phenyl group, $G^3$ is a hydrogen atom, and stereo configuration of an asymmetric carbon that is marked with asterisk * is (R) configuration;

(20) Compounds of the present invention in which $G^1$ is a cyclopropyl group, $G^2$ is a methyl group, an ethyl group, an n-propyl group, an isopropyl group, an isobutyl group, a sec-butyl group, a benzyl group, or a phenyl group, and $G^3$ is a hydrogen atom or a halogen atom;

(21) Compounds of the present invention in which $G^1$ is a cyclopropyl group, $G^2$ is a methyl group, an ethyl group, an n-propyl group, an isopropyl group, an isobutyl group, a sec-butyl group, a benzyl group, or a phenyl group, and $G^3$ is a hydrogen atom;

(21) Compounds of the present invention in which $G^1$ is a cyclopropyl group, $G^2$ is a methyl group, and $G^3$ is a hydrogen atom, a fluorine atom, or a chlorine atom;

(22) Compounds of the present invention in which $G^1$ is a cyclopropyl group, $G^2$ is a methyl group, $G^3$ is a hydrogen atom, a fluorine atom, a chlorine atom, and stereo configuration of an asymmetric carbon that is marked with asterisk * is (R) configuration;

(23) Compounds of the present invention in which $G^1$ is a cyclobutyl group, $G^2$ is a methyl group, an ethyl group, an n-propyl group, an isopropyl group, an isobutyl group, a sec-butyl group, a benzyl group, or a phenyl group, and $G^3$ is a hydrogen atom or a halogen atom;

(24) Compounds of the present invention in which $G^1$ is a cyclobutyl group, $G^2$ is a methyl group, an ethyl group, an n-propyl group, an isopropyl group, an isobutyl group, a sec-butyl group, a benzyl group, or a phenyl group, and $G^3$ is a hydrogen atom;

(25) Compounds of the present invention in which $G^1$ is a cyclobutyl group, $G^2$ is a methyl group, and $G^3$ is a hydrogen atom, a fluorine atom, a chlorine atom;

(26) Compounds of the present invention in which $G^1$ is a cyclobutyl group, $G^2$ is a methyl group, and $G^3$ is a hydrogen atom, a chlorine atom;

(27) Compounds of the present invention in which $G^1$ is a cyclobutyl group, $G^2$ is a methyl group, $G^3$ is a hydrogen atom, a chlorine atom, and stereo configuration of an asymmetric carbon that is marked with asterisk * is (R) configuration;

(28) Compounds of the present invention in which $G^2$ is a methyl group, an ethyl group, or an n-propyl group, $G^1$ is —CH(Me)OMe, a cyclopropyl group, or a cyclobutyl group, and $G^3$ represents a hydrogen atom or a halogen atom;

(29) Compounds of the present invention in which $G^2$ is a methyl group, $G^1$ is —CH(Me)OMe, a cyclopropyl group, or a cyclobutyl group, and $G^3$ is a hydrogen atom or a halogen atom;

(30) Compounds of the present invention in which $G^2$ is a methyl group, $G^1$ is —CH(Me)OMe, a cyclopropyl group, or a cyclobutyl group, and $G^3$ is a hydrogen atom, a fluorine atom, or a chlorine atom;

(31) Compounds of the present invention in which $G^2$ is a methyl group, $G^1$ is —CH(Me)OMe, a cyclopropyl group, or a cyclobutyl group, $G^3$ is a hydrogen atom, a fluorine atom, or a chlorine atom, and stereo configuration of an asymmetric carbon that is marked with asterisk * is (R) configuration;

(32) Compounds of the present invention in which $G^2$ is an isopropyl group, a phenyl group, $G^1$ is —CH($G^4$)OMe, —OCHF$_2$, —OCF$_3$, a halogen atom, or a group that is represented by the following Formula (A-2) to (A-3),

[Chemical Formula 19]

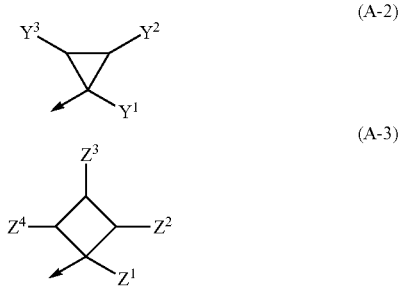

(A-2)

(A-3)

$G^3$ is a hydrogen atom or a halogen atom, $G^4$ is a methyl group, an ethyl group, an n-propyl group, or an isopropyl group, and $Y^1$, $Y^2$, $Y^3$, $Z^1$, $Z^2$, $Z^3$ and $Z^4$ can be the same or different to each other and each independently represent a hydrogen atom or a methyl group;

(33) Compounds of the present invention in which $G^2$ is an isopropyl group, a phenyl group, $G^1$ is —CH(Me)OMe, —OCHF$_2$, a chlorine atom, a cyclopropyl group, a cyclobutyl group, and $G^3$ is a hydrogen atom or a halogen atom;

(34) Compounds of the present invention in which $G^2$ is an isopropyl group, a phenyl group, $G^1$ is —CH(Me)OMe, —OCHF$_2$, a chlorine atom, a cyclopropyl group, a cyclobutyl group, and $G^3$ is a hydrogen atom, a fluorine atom, or a chlorine atom;

(35) Compounds of the present invention in which $G^2$ is an isopropyl group, a phenyl group, $G^1$ is —CH(Me)OMe, —OCHF$_2$, a chlorine atom, a cyclopropyl group, a cyclobutyl group, $G^3$ is a hydrogen atom, a fluorine atom, or a chlorine atom, and stereo configuration of an asymmetric carbon that is marked with asterisk * is (R) configuration;

(36) An embodiment in which the compounds of the present invention that are described in any one of the above (1) to (35) are present in free form can be also mentioned as a preferred embodiment. Further, their salts can be also mentioned as a preferred embodiment, and hydrochloride can be mentioned as a particularly preferred embodiment.

The compounds of the present invention can be produced according to the reaction pathways of Scheme 1 to 15 that are described below, for example. However, their production method is not specifically limited. For example, the compounds of the present invention can be produced by modifying or changing a substituent group of the precursor compounds based on a reaction described in general chemistry literatures, etc. or combination of the reactions. In addition, for the sake of convenience, the following methods are described wherein the compound is used in free form, unless specifically described otherwise. However, depending on specific case, the production method can be carried out by using a salt of such compounds present in free form.

For each reaction, reaction time is not specifically limited. However, since the progress of the reaction can be easily followed according to an analytical means that will be described below, the reaction can be terminated when yield for a desired product reaches maximum value. Regarding Scheme 1 to 15 described below, "STEP" means a reaction process and "STEP 1-1" indicates Process 1-1, for example.

With regard to the protecting group that is used for the present invention, examples include a protecting group of indazole (—NH—), a protecting group of a hydroxyl group (—OH), a protecting group of a methanesulfonamide group (—NHSO$_2$Me) a protecting group of an amino group (—NH— or —NH$_2$) and the like.

As for the protecting group of indazole (—NH—), examples thereof include a trityl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, an acetyl group, a trifluoroacetyl group, a pivaloyl group, a benzoyl group, a methoxycarbonyl group, an ethoxycarbonyl group, an aryloxycarbonyl (Alloc) group, a 2,2,2-trichloroethoxycarbonyl group, a benzyloxycarbonyl (Cbz) group, a tert-butoxycarbonyl (Boc) group, a 1-methyl-1-(4-biphenyl)ethoxycarbonyl (Bpoc) group, a 9-fluorenylmethoxycarbonyl group, an N,N-dimethylsulfonyl group, a methanesulfonyl group, a benzenesulfonyl group, a p-toluene sulfonyl group, a mesitylenesulfonyl group, a p-methoxyphenylsulfonyl group, a tetrahydropyranyl (THP) group, a tetrahydrofuryl group, an allyl group, a methoxymethyl (MOM) group, a methoxyethoxymethyl (MEM) group, a benzyloxymethyl (BOM) group, or a 2-(trimethylsilyl)ethoxymethyl (SEM) group and the like.

As for the protecting group of a hydroxyl group (—OH), examples thereof include an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, a silyl group substituted with three identical or different alkyl groups having 1 to 4 carbon atoms or a phenyl group, a tetrahydropyranyl group, a tetrahydrofuryl group, a propargyl group, a trimethylsilylethyl group and the like. Specifically, a methyl group, an ethyl group, a tert-butyl group, an allyl group, a methoxymethyl (MOM) group, a methoxyethoxymethyl (MEM) group, a trichloroethyl group, a phenyl group, a methylphenyl group, a chlorophenyl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, a trityl group, a 1-ethoxyethyl (EE) group, a tetrahydropyranyl (THP) group, a tetrahydrofuryl group, a propargyl group, a trimethylsilyl (TMS) group, a triethylsilyl (TES) group, a tert-butyldimethylsilyl (TBDMS) group, a tert-butyldiphenylsilyl (TBDPS) group, an acetyl (Ac) group, a pivaloyl group, a benzoyl group, an aryloxycarbonyl (Alloc) group, or a 2,2,2-trichloroethoxycarbonyl (Troc) group and the like can be mentioned.

As for the protecting group of a methanesulfonamide group (—NHSO$_2$Me), examples thereof include a methoxycarbonyl group, an ethoxycarbonyl group, a tert-butoxycarbonyl (Boc) group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a tert-butyl group, a diphenylmethyl group, or a methoxyphenyl group and the like.

As for the protecting group of an amino group (—NH— or —NH$_2$), examples thereof include a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, an acetyl group, a trifluoroacetyl group, a pivaloyl group, a benzoyl group, an aryloxycarbonyl group, a 2,2,2-trichloroethoxycarbonyl group, a benzyloxycarbonyl group, a tert-butoxycarbonyl (Boc) group, a 1-methyl-1-(4-biphenyl)ethoxycarbonyl (Bpoc) group, a 9-fluorenylmethoxycarbonyl group, a 2-nitrobenzenesulfonyl group, a 4-nitrobenzenesulfonyl group, a 2,4-dinitrobenzenesulfonyl group, a benzyloxymethyl (BOM) group, or a 2-(trimethylsilyl)ethoxymethyl (SEM) group and the like.

Protecting groups can be deprotected during the production process or at the final stage of the process, simultaneously or sequentially with the production so as to convert into desired compounds. Protection and deprotection reaction can be carried out according to any known method, for example, according to a method described in Protective Groups in Organic Synthesis, published by John Wiley and Sons (2007 edition). For example, it can be carried out according to the method (1) to (3) described as follows.

(1) Deprotection reaction under acidic condition can be carried out, for example in an inert solvent, in the presence of an organic acid, a Lewis acid, or an inorganic acid, or a mixture thereof at the temperature of −10 to 100° C. Use amount of acid is preferably 1 mole to a large excess amount. Further, ethanethiol or 1,2-ethanedithiol and the like can be added as an additive.

As for the inert solvent, dichloromethane, chloroform, 1,4-dioxane, ethyl acetate, methyl-tert-butyl ether, tetrahydrofuran, or anisole and the like can be mentioned for the organic acid, acetic acid, trifluoroacetic acid, methanesulfonic acid, or p-toluene sulfonic acid and the like can be mentioned. As for the Lewis acid, boron tribromide, boron trifluoride, aluminum bromide or aluminum chloride and the like can be mentioned. As for the inorganic acid, hydrochloric acid, hydrogen chloride-1,4-dioxane, hydrogen chloride-ethyl acetate, hydrobromic acid, or sulfuric acid and the like can be mentioned. As for the organic acid, a Lewis acid, an inorganic acid, or a mixture thereof, hydrogen bromic acid/acetic acid and the like can be mentioned.

(2) Deprotection reaction based on hydrogenolysis can be carried out, for example in an inert solvent, in the presence of hydrogen gas at atmospheric or increased pressure or a hydrogen source such as ammonium formate or hydrazine hydrate at the temperature of −10 to 70° C. with addition of a catalyst in an amount of 0.1 to 300% by weight. Further, 0.05 mole to a large excess amount of an inorganic acid can be further added to the reaction solution above to carry out the reaction.

With respect to the inert solvent, ethers such as tetrahydrofuran, dioxane, dimethoxy ethane, diethyl ether and the like, alcohols such as methanol, ethanol and the like, benzenes such as benzene, toluene and the like, ketones such as acetone, methylethyl ketone and the like, nitriles such as acetonitrile and the like, amides such as dimethyl formamide and the like, esters such as ethyl acetate and the like, water, acetic acid and the like can be used alone, or a mixed solvent thereof can be also used. As for the catalyst, examples thereof include palladium on carbon powder, platinum oxide (PtO$_2$) activated nickel and the like. As for the inorganic acid, hydrochloric acid, sulfuric acid and the like can be mentioned.

(3) Deprotection reaction of a silyl group can be carried out, for example in an organic solvent which is miscible with water, by using a fluoride ion and the like at the temperature of −10 to 60° C.

As for the organic solvent, tetrahydrofuran, acetic acid, or acetonitrile and the like can be mentioned. The fluoride ion can be generated by using, for example, tetra-n-butylammonium fluoride, hydrofluoric acid, hydrogen fluoride-pyridine complex, or hydrogen fluoride-triethylamine complex and the like.

In view of the following Scheme 1 to Scheme 9, one embodiment of the method for the production of the compounds represented by the Formula (1) of the present invention will be explained in greater detail.

Scheme 1
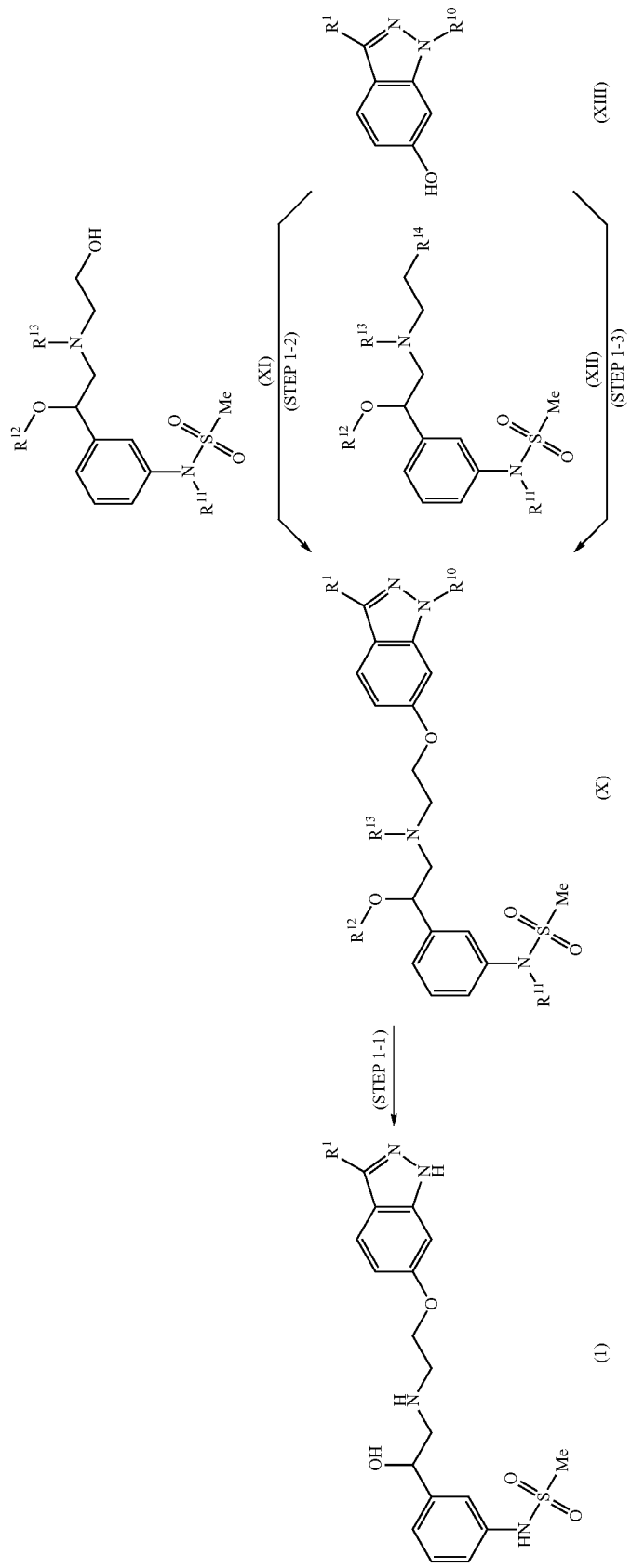

In each formula described in Scheme 1, $R^1$ has the same meaning as defined in the above. $R^{10}$ represents a hydrogen atom or the protecting group of indazole as described in the above, and preferably is a benzyl group, a tert-butoxycarbonyl group, or a tetrahydropyranyl group. $R^{11}$ represents a hydrogen atom or the protecting group of methanesulfonamide as described in the above, and preferably is a benzyl group or a tert-butoxycarbonyl group. $R^{12}$ represents a hydrogen atom or the protecting group of a hydroxyl group as described in the above, and preferably is a triethylsilyl group or a tert-butyldimethylsilyl group. $R^{13}$ represents a hydrogen atom or the protecting group of an amino group as described in the above, and preferably is a benzyl group or a tert-butoxycarbonyl group. $R^{14}$ represents a leaving group, and examples thereof include a chlorine atom, a bromine atom, an iodine atom, a p-toluene sulfonyloxy group, or a methanesulfonyloxy group and the like. Bromine atom is preferable. As a preferred combination of $R^{10}$, $R^{11}$, $R^{12}$ and $R^{13}$, $R^{10}$ (a benzyl group), $R^{11}$ (a benzyl group), $R^{12}$ (a triethylsilyl group), $R^{13}$ (a benzyl group); $R^{10}$ (a tert-butoxycarbonyl group), $R^{11}$ (a tert-butoxycarbonyl group), $R^{12}$ (a triethylsilyl group), $R^{13}$ (a tert-butoxycarbonyl group); or $R^{10}$ (a tetrahydropyranyl group), $R^{11}$ (a tert-butoxycarbonyl group), $R^{12}$ (a triethylsilyl group), $R^{13}$ (a tert-butoxycarbonyl group) can be mentioned.

Process 1-1 (Step 1-1)

By carrying out a deprotection reaction of the compounds represented by the Formula (X) based on a method, for example, according to the method described in Protective Groups in Organic Synthesis, published by John Wiley and Sons (2007 edition), the compounds represented by the Formula (1) can be produced. As an appropriate example, deprotection is carried out under the acidic condition described above, or preferably deprotection reaction based on the hydrogenolysis described above is used alone or in combination with it. That is, a deprotection reaction which is suitable for each type of protecting groups that are present in the compounds of the Formula (X) can be selected.

Process 1-2 (Step 1-2)

By reacting the compounds represented by the Formula (XI) and the compounds represented by the Formula (XIII) in an inert solvent in the presence of a phosphine and an azo compound, the compounds represented by the Formula (X) can be obtained.

With respect to the inert solvent, ethers such as diethyl ether, tetrahydrofuran, or dimethoxyethane and the like, halogenated solvents such as methylene chloride and the like, benzenes such as benzene, toluene, xylene and the like can be used alone, or a mixed solvent thereof can be also used. Toluene is preferable. With respect to the phosphine, triphenylphosphine or tributylphosphine and the like can be mentioned and triphenylphosphine is preferable. With respect to the azo compound, diethyl azodicarboxylate, diisopropyl azodicarboxylate, N,N,N',N'-tetramethylazodicarboxamide, 1,1'-(azodicarbonyl)dipiperidine, or N,N,N',N'-tetraisopropylcarboxamide and the like can be mentioned, and N,N,N',N'-tetramethylazodicarboxamide is preferable.

With respect to the use amount of the phosphine, it can be 1 to 10 moles compared to the compounds represented by the Formula (XI) or the compounds represented by the Formula (XIII), and preferably it is 1.5 to 5 moles. With respect to the use amount of the azo compound, it can be 1 to 10 moles compared to the compounds represented by the Formula (XI) or the compounds represented by the Formula (XIII), and preferably it is 1.5 to 5 moles. With respect to the molar ratio between the compounds represented by the Formula (XI) and the compounds represented by the Formula (XIII), it may satisfy the condition of the compounds represented by the Formula (XI)/the compounds represented by the Formula (XIII)=0.25 to 4. With respect to the reaction temperature, it can be −20° C. to heating under reflux, and preferably 0 to 40° C. With respect to the reaction time, it can be 0.1 to 48 hours, and preferably 0.1 to 12 hours.

Process 1-3 (Step 1-3)

By reacting the compounds represented by the Formula (XII) and the compounds represented by the Formula (XIII) in an inert solvent with addition of a base, the compounds represented by the Formula (X) can be obtained.

With respect to the inert solvent, water, alcohols such as methanol or ethanol and the like, or N,N-dimethyl formamide, tetrahydrofuran, 1,4-dioxane, acetone, 2-butanone, dimethyl sulfoxide, or acetonitrile and the like can be used alone, or a mixed solvent thereof can be used. Water, N,N-dimethyl formamide, or acetone is preferable. With respect to the base, an alkali metal compound such as potassium carbonate, sodium carbonate, cesium carbonate, sodium hydrogen carbonate, potassium hydroxide, sodium hydroxide, sodium methoxide, or potassium t-butoxide and the like, or tertiary organic amines such as pyridine, 4-dimethylaminopyridine, 1,8-diazabicyclo[5,4,0]-undecene, trimethylamine, diisopropylethylamine, or triethylamine and the like can be mentioned. Preferably, sodium hydroxide is exemplified.

With respect to the use amount of the base, it can be 1 to 10 moles compared to the compounds represented by the Formula (XII), and preferably it is 1.5 to 5 moles. With respect to the molar ratio between the compounds represented by the Formula (XII) and the compounds represented by the Formula (XIII), it may satisfy the condition of the compounds represented by the Formula (XII)/the compounds represented by the Formula (XIII)=0.2 to 5 moles. With respect to the reaction temperature, it can be −10° C. to heating under reflux, and preferably 0 to 80° C. With respect to the reaction time, it can be 0.1 to 48 hours, and preferably 0.1 to 12 hours. When the reaction progresses slowly, a catalyst such as potassium iodide or sodium iodide and the like can be added in an amount of 0.1 to 1.5 moles compared to the compounds represented by the Formula (XII), if necessary.

Scheme 2
[Chemical Formula 21]
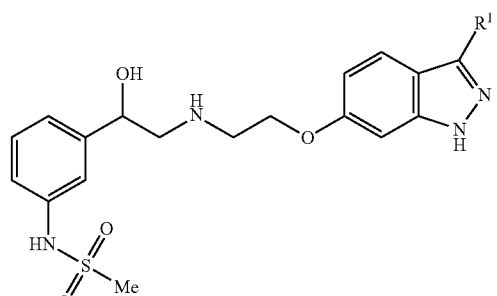
(1)
(STEP 2-2) ↗
(STEP 2-1) ↙
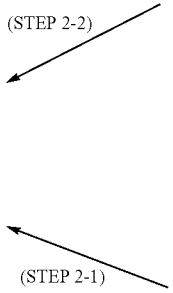
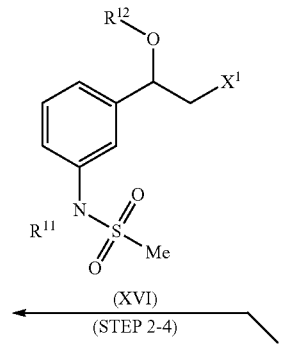
(XIV)
(XVI)
(STEP 2-4) ←
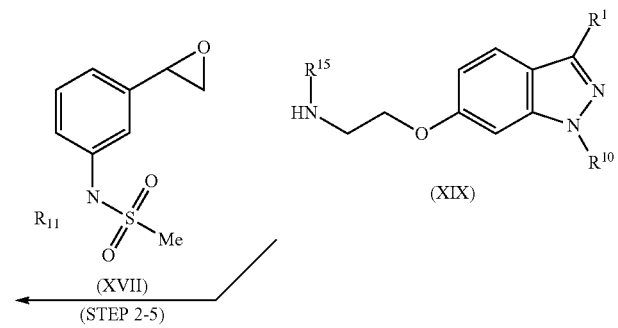
(XIX)
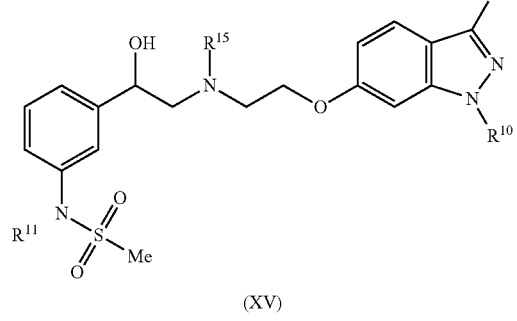
(XV)
(XVII)
(STEP 2-5) ←

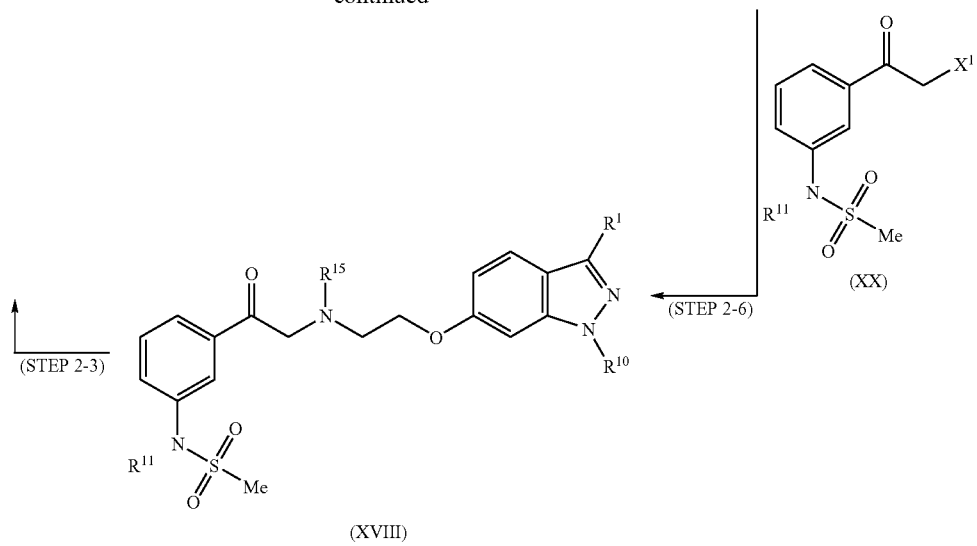

In each formula described in Scheme 2, $R^1$ has the same meaning as defined in the above. $R^{10}$ has the same meaning as defined in the above, preferably is a benzyl group, a tert-butoxycarbonyl group, or a tetrahydropyranyl group, and more preferably a benzyl group. $R^{11}$ has the same meaning as defined in the above, and preferably is a benzyl group. $R^{12}$ has the same meaning as defined in the above, and preferably is a triethylsilyl group or a tert-butyldimethylsilyl group. $R^{15}$ represents a hydrogen atom or the protecting group of the amino group as described above, and preferably is a benzyl group. $X^1$ represents a leaving group, and examples thereof include a chlorine atom, a bromine atom, an iodine atom, a p-toluene sulfonyloxy group, or a methanesulfonyloxy group and the like. A chlorine atom, a bromine atom, an iodine atom are preferable. As a preferred combination of $R^{10}$, $R^{11}$, $R^{12}$ and $R^{15}$ in the compounds represented by the Formula (XIV), $R^{10}$ (a benzyl group), $R^{11}$ (a benzyl group), $R^{12}$ (a triethylsilyl group), $R^{15}$ (a benzyl group); $R^{10}$ (a tert-butoxycarbonyl group), $R^{11}$ (a benzyl group), $R^{12}$ (a triethylsilyl group), $R^{15}$ (a benzyl group); or $R^{10}$ (a tetrahydropyranyl group), $R^{11}$ (a benzyl group), $R^{12}$ (a triethylsilyl group), $R^{15}$ (a benzyl group) can be mentioned. Combination of $R^{10}$ (a benzyl group), $R^{11}$ (a benzyl group), $R^{12}$ (a triethylsilyl group), $R^{15}$ (a benzyl group) is more preferred. As a preferred combination of $R^{10}$, $R^{11}$ and $R^{15}$ in the compounds represented by the Formula (XV), $R^{10}$ (a benzyl group), $R^{11}$ (a benzyl group), $R^{15}$ (a benzyl group); $R^{10}$ (a tert-butoxycarbonyl group), $R^{11}$ (a benzyl group), $R^{15}$ (a benzyl group); or $R^{10}$ (a tetrahydropyranyl group), $R^{11}$ (a benzyl group), $R^{15}$ (a benzyl group) can be mentioned. Combination of $R^{10}$ (a benzyl group), $R^{11}$ (a benzyl group) and $R^{15}$ (a benzyl group) is more preferred. As a preferred combination of $R^{10}$ and $R^{15}$ in the compounds represented by the Formula (XIX), $R^{10}$ (a benzyl group), $R^{15}$ (a benzyl group); $R^{10}$ (a tert-butoxycarbonyl group), $R^{15}$ (a benzyl group); or $R^{10}$ (a tetrahydropyranyl group), $R^{15}$ (a benzyl group) can be mentioned. Combination of $R^{10}$ (a benzyl group) and $R^{15}$ (a benzyl group) is more preferred.

Process 2-1 (Step 2-1)

By carrying out a deprotection reaction of the compounds represented by the Formula (XV) based on a well known method, for example, according to the method described in Protective Groups in Organic Synthesis, published by John Wiley and Sons (2007 edition), the compounds represented by the Formula (1) can be produced. As an appropriate example, deprotection is carried out under the acidic condition described above, or preferably deprotection reaction based on the hydrogenolysis described above is used alone or in combination with it. That is, a deprotection reaction which is suitable for each type of protecting groups that are present in the compounds of the Formula (XV) can be selected. For example, regarding the Formula (XV), when it is a compound having $R^{10}$ (a benzyl group), $R^{11}$ (a benzyl group) and $R^{15}$ (a benzyl group), a deprotection reaction based on hydrogenolysis is preferable. Regarding a deprotection reaction based on hydrogenolysis, a method in which a reaction is carried out in the presence of hydrogen gas in an inert solvent with addition of a catalyst and hydrochloric acid can be mentioned. A method in which, the compounds represented by the Formula (XV) are subjected to the reaction in an inert solvent in the presence of hydrogen gas with addition of a catalyst, $R^{11}$ (a benzyl group) and $R^{15}$ (a benzyl group) are deprotected, hydrochloric acid is further added to the reaction solution to perform the reaction in the presence of hydrogen gas, and $R^{10}$ (a benzyl group) is deprotected to obtain the compounds represented by the Formula (1), can be also mentioned as a particularly preferred method.

As for the inert solvent, alcohols such as methanol or ethanol and the like can be used alone, or a mixed solvent thereof can be also used. Ethanol is preferable. As for the catalyst, palladium on carbon powder is preferable.

With respect to the use amount of the catalyst, it can be 2 to 40% by weight compared to the compounds represented by the Formula (XV). With respect to the use amount of the hydrochloric acid, it can be 0.15 to 3 moles compared to the compounds represented by the Formula (XV). Pressure of the hydrogen gas used is preferably atmospheric pressure or increase pressure. With respect to the reaction temperature, it can be 20° C. to heating under reflux, and preferably 30 to 60° C. With respect to the reaction time, it can be 0.5 to 24 hours, and preferably 0.5 to 10 hours.

Process 2-2 (Step 2-2)

By carrying out a deprotection reaction of the compounds represented by the Formula (XIV) based on a well known method, for example, according to the method described in Protective Groups in Organic Synthesis, published by John Wiley and Sons (2007 edition), the compounds represented by the Formula (1) can be produced. As an appropriate example, deprotection is carried out under the acidic condition described above, or preferably deprotection reaction based on the hydrogenolysis described above is used alone or in combination with it. That is, a deprotection reaction which is suitable for each type of protecting groups that are present in the compounds of the Formula (XIV) can be selected. For example, as for the deprotection reaction based on the hydrogenolysis, the method described above in Process 2-1 and the like can be mentioned.

Process 2-3 (Step 2-3)

It can be carried out in view of the method described in International Publication No. WO03/035620 (incorporated herein as a reference). Specifically, by reacting the compounds represented by the Formula (XVIII) with a reducing agent in an inert solvent, the compounds represented by the Formula (XV) can be obtained.

As for the inert solvent, alcohols such as methanol, ethanol, or 2-propanol and the like, or tetrahydrofuran, dimethyl formamide, or dimethyl sulfoxide and the like can be mentioned. As for the reducing agent, sodium borohydride, sodium cyanoborohydride, or borane and the like can be mentioned.

Unless asymmetric reduction is carried out separately, the compounds represented by the Formula (XV) are obtained as a racemic mixture from this reduction reaction.

As for a method of obtaining an optically active isomer, a method in which a racemic mixture is converted into an acid addition salt using optically active acid such as camphor sulfonic acid, mandellic acid and the like and the acid addition salt is resolved into an optically active isomer by fractional crystallization can be mentioned. Further, a method in which a commercially available column for optical resolution is used for separation can be also mentioned. Further, asymmetric reduction can be also used. Regarding asymmetric reduction, for example, a method described in WO00/58287 (incorporated herein as a reference), i.e., asymmetric reduction is carried out using a hydrogen source compound in the presence of a catalyst for asymmetric reduction, and the like can be mentioned.

Process 2-4 (Step 2-4)

By reacting the compounds represented by the Formula (XVI) with the compounds represented by the Formula (XIX) in an inert solvent, if necessary with addition of a base, the compounds represented by the Formula (XIV) can be obtained.

As for the inert solvent, N,N-dimethyl formamide, N,N-dimethylacetamide, dimethyl sulfoxide, or acetonitrile and the like can be used alone, or a mixed solvent thereof can be also used. N,N-dimethyl formamide is preferable. As for the base, a tertiary amine such as triethylamine, diisopropylethylamine, or 1,8-diazabicyclo[5,4,0]-undecene and the like, or an alkali metal compound such as potassium carbonate, sodium carbonate, cesium carbonate, or sodium hydrogen carbonate and the like can be mentioned, and triethylamine or diisopropylethylamine is preferable.

With respect to the use amount of the base, it can be 0 to 10 moles compared to the compounds represented by the Formula (XVI), and preferably it is 0 to 5 moles. With respect to the molar ratio between the compounds represented by the Formula (XVI) and the compounds represented by the Formula (XIX), it may preferably satisfy the condition of the compounds represented by the Formula (XVI)/the compounds represented by the Formula (XIX)=0.2 to 5 moles, and more preferably 0.5 to 2 moles. With respect to the reaction temperature, it can be $-10°$ C. to heating under reflux, and preferably 0 to 80° C. With respect to the reaction time, it can be 0.1 to 48 hours, and preferably 2 to 20 hours.

When the reaction progresses slowly, a catalyst such as potassium iodide or sodium iodide and the like can be added in an amount of 0.1 to 1.5 moles compared to the compounds represented by the Formula (XVI), if necessary.

Process 2-5 (Step 2-5)

By reacting the compounds represented by the Formula (XVII) with the compounds represented by the Formula (XIX) in an inert solvent, the compounds represented by the Formula (XV) can be obtained.

As for the inert solvent, alcohols such as methanol, ethanol, 1-butanol, 2-butanol or 2-propanol and the like, or N,N-dimethyl formamide, N,N-dimethylacetamide, dimethyl sulfoxide, or acetonitrile and the like can be used alone, or a mixed solvent thereof can be also used. 2-Propanol is preferable.

With respect to the molar ratio between the compounds represented by the Formula (XVII) and the compounds represented by the Formula (XIX), it may preferably satisfy the condition of the compounds represented by the Formula (XVII)/the compounds represented by the Formula (XIX) =0.2 to 5 moles, and more preferably 0.75 to 1.5 moles. With respect to the reaction temperature, it can be $-10°$ C. to heating under reflux, and preferably 60° C. to heating under reflux. With respect to the reaction time, it can be 0.5 to 48 hours, and preferably 12 to 48 hours.

A Lewis acid can be added, if necessary.

Process 2-6 (Step 2-6)

By reacting the compounds represented by the Formula (XIX) with the compounds represented by the Formula (XX) in an inert solvent, if necessary with addition of a base, the compounds represented by the Formula (XVIII) can be obtained. As for the inert solvent, N,N-dimethyl formamide, N,N-dimethylacetamide, dimethyl sulfoxide, or acetonitrile and the like can be used alone, or a mixed solvent thereof can be also used. Preferably, N-dimethyl formamide can be exemplified. As for the base, a tertiary organic amine such as triethylamine, diisopropylethylamine, or 1,8-diazabicyclo[5,4,0]-undecene and the like, or an alkali metal compound such as potassium carbonate, sodium carbonate, cesium carbonate, or sodium hydrogen carbonate and the like can be mentioned, and triethylamine or diisopropylethylamine is preferable.

With respect to the use amount of the base, it can be 0 to 10 moles compared to the compounds represented by the Formula (XX), and preferably it is 0 to 5 moles. With respect to the molar ratio between the compounds represented by the Formula (XIX) and the compounds represented by the Formula (XX), it may preferably satisfy the condition of the compounds represented by the Formula (XIX)/the compounds represented by the Formula (XX)=0.2 to 5 moles, and more preferably 0.5 to 2 moles. With respect to the reaction temperature, it can be $-10°$ C. to heating under reflux, and preferably 0 to 80° C. With respect to the reaction time, it can be 0.5 to 48 hours, and preferably 2 to 20 hours.

When the reaction progresses slowly, a catalyst such as potassium iodide or sodium iodide and the like can be added in an amount of 0.1 to 1.5 moles compared to the compounds represented by the Formula (XX), if necessary.

The compounds of the present invention, each reacting compound and the intermediate that are obtained by the methods described above can be separated and purified according to a general method including extraction, distillation, chromatography, crystallization and the like.

Among the compounds that are used in Scheme 1 or 2, the compounds represented by the Formula (XI), (XII), (XIII), (XVI), (XVII), (XIX) or (XX) can be obtained according to the methods explained in Scheme 3 to Scheme 9. In the following Scheme 3 to Scheme 9, "STEP" is as defined in the above.

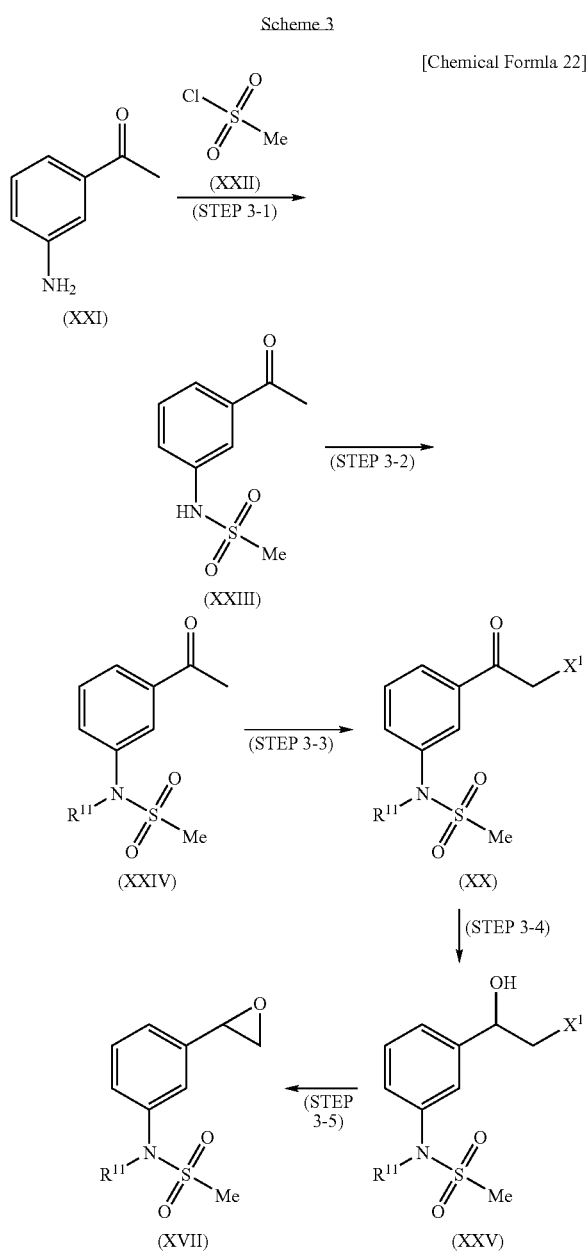

Scheme 3

With respect to Scheme 3, $R^{11}$ in each formula has the same meaning as defined in the above, and a benzyl group is preferable. $X^1$ has the same meaning as defined in the above, and a chlorine atom is preferable.

Process 3-1 (Step 3-1)

For example, by reacting 3-aminoacetophenone (XXI), which is commercially available from Wako Pure Chemical Industries, Ltd., with methanesulfonyl chloride (XXII) in an inert solvent with addition of a base, Compound (XXIII) can be obtained.

As for the inert solvent, a hydrocarbon solvent such as toluene and the like, a halogenated hydrocarbon solvent such as dichloromethane, chloroform, or 1,2-dichloroethane and the like, or acetonitrile and the like can be mentioned. As for the base, an organic base such as triethylamine, N,N-diisopropylethylamine, or pyridine and the like and an inorganic base such as potassium carbonate, or sodium hydrogen carbonate and the like can be mentioned.

With respect to the use amount of the base, it can be 1 to 6 moles compared to 3-aminoacetophenone (XXI), and preferably it is 1 to 3 moles. With respect to the use amount of methanesulfonyl chloride (XXII), it can be 1 to 6 moles compared to 3-aminoacetophenone (XXI), and preferably it is 1 to 3 moles. With respect to the reaction temperature, it can be −10 to 60° C., and preferably −10 to 30° C. With respect to the reaction time, it can be 0.1 to 48 hours, and preferably 0.2 to 24 hours.

Process 3-2 (Step 3-2)

By carrying out a protection reaction of the sulfonamide group of the compounds represented by the Formula (XXIII) based on a well known method, for example, according to the method described in Protective Groups in Organic Synthesis, published by John Wiley and Sons (2007 edition), the compounds represented by the Formula (XXIV) can be produced. As an appropriate example, for a case in which $R^{11}$ is a benzyl group, a method in which Compound (XXIII) and a benzylating agent are reacted in an inert solvent with addition of a base and a catalyst to obtain the compounds represented the Formula (XXIV) can be mentioned.

As for the inert solvent, a ketone solvent such as acetone and the like, or an aprotic polar solvent such as N,N-dimethyl formamide and the like can be used alone, or a mixed solvent thereof can be also used. As for the benzylating agent, benzyl iodide, benzyl bromide, or benzyl chloride and the like can be mentioned, and benzyl chloride is preferable. As for the base, an organic base such as triethylamine, N,N-diisopropylethylamine, or pyridine and the like, an inorganic base such as a potassium carbonate, or sodium hydrogen carbonate and the like can be mentioned, and potassium carbonate is preferable. As for the catalyst, potassium iodide, or sodium iodide and the like can be mentioned, and sodium iodide is preferable.

With respect to the use amount of the base, it is preferably 1 to 5 moles compared to Compound (XXIII). With respect to the use amount of the catalyst, it is preferably 0.005 to 0.05 moles compared to Compound (XXIII). With respect to the reaction temperature, it can be 0° C. to heating under reflux, and preferably 50 to 100° C. With respect to the reaction time, it is preferably 1 to 24 hours.

Process 3-3 (Step 3-3)

By adding a halogenating agent to the compounds represented by the Formula (XXIV) in an inert solvent, and if necessary, by further adding methanol, the compounds represented by the Formula (XX) are obtained.

As for the inert solvent, halogenated hydrocarbons such as dichloromethane, 1,2-dichloroethane, or chloroform and the like can be mentioned and dichloromethane is preferable. As a halogenating agent, chlorine gas, bromine gas or sulfuryl chloride and the like can be mentioned and sulfuryl chloride is preferable.

With respect to the use amount of the halogenating agent, it can be 1 to 2 moles compared to the compounds represented by the Formula (XXIV). With respect to the use amount of methanol, it can be 0 to 5 moles compared to the compounds represented by the Formula (XXIV), and preferably 0.1 to 2 moles. With respect to the reaction temperature, it is preferably −10 to 50° C. With respect to the reaction time, it is preferably 1 to 10 hours including time required for dropwise addition of the halogenating agent and methanol.

Process 3-4 (Step 3-4)

By reacting the compounds represented by the Formula (XX) with a reducing agent in an organic solvent, the compounds represented by the Formula (XXV) are obtained.

As for the organic solvent, an alcohol solvent such as methanol or ethanol and the like, or an ether solvent such as tetrahydrofuran and the like are exemplified. As for the reducing agent, sodium borohydride and the like is exemplified.

Unless asymmetric reduction is carried out separately, the compounds represented by the Formula (XXV) are obtained as a racemic mixture from this reduction reaction.

Regarding a method of obtaining an optically active compound, an asymmetric reduction can be mentioned. Asymmetric reduction can be carried out according to a method described in general chemistry literatures, for example, New Experimental Chemistry Series, 4$^{th}$ ed. (Vol. 26, pages 23 to 68, published by Maruzen Company, Limited) or in view of the methods that are described in the references cited therein. As an appropriate example, a method in which the compounds represented by the Formula (XX) are reacted in an organic solvent in the presence of a hydrogen source with addition of a catalyst to obtain the compounds represented by the Formula (XXV) can be mentioned.

As for the organic solvent, an alcohol solvent such as methanol, ethanol, or 2-propanol and the like, an ether solvent such as tetrahydrofuran and the like, a halogenated hydrocarbon solvent such as dichloromethane, 1,2-dichloroethane, or chloroform and the like, an ester solvent such as ethyl acetate and the like, or acetonitrile and the like can be used alone, or a mixed solvent thereof can be also used. As for the hydrogen source, hydrogen gas or formic acid-triethylamine complex and the like can be mentioned, and formic acid-triethylamine complex is preferable. As for the catalyst, arene-chiral diamine-ruthenium (II) complex and the like can be mentioned, [(s,s)-N-(p-toluene sulfonyl)-1,2-diphenylethylenediamine]-p-cymene-ruthenium complex, or [(s,s)-N-(p-toluene sulfonyl)-1,2-diphenylethylenediamine]-mesitylene-ruthenium complex is preferable.

With respect to the use amount of the formic acid-triethylamine complex, on the basis of mole number of formic acid, it is preferably 1 to 10 moles compared to the compounds represented by the Formula (XX). With respect to the ratio of formic acid-triethylamine complex, formic acid is preferably 1 to 10 moles compared to triethylamine. With respect to the use amount of the catalyst, it may satisfy the condition of the compounds represented by the Formula (XXV)/the catalyst amount=S/C=10 to 10000 moles. S/C=100 to 1000 moles is preferable. With respect to the reaction temperature, it can be 0° C. to heating under reflux, and preferably 20° C. to heating under reflux. With respect to the reaction time, it can be 0.1 to 24 hours including time required for dropwise addition of the formic acid-triethylamine complex. 0.5 to 12 hours is preferable.

Process 3-5 (Step 3-5)

By reacting the compounds represented by the Formula (XXV) in an inert solvent with addition of a base, the compounds represented by the Formula (XVII) are obtained.

As for the inert solvent, an alcohol solvent such as water, methanol or ethanol and the like, or N,N-dimethyl formamide, tetrahydrofuran, 1,4-dioxane, acetone, 2-butanone, dimethyl sulfoxide, or acetonitrile and the like can be used alone, or a mixed solvent thereof can be also used. Methanol is preferable. As for the base, an alkali metal compound such as potassium carbonate, sodium carbonate, cesium carbonate, sodium hydrogen carbonate, potassium hydroxide, sodium hydroxide, sodium methoxide, 28% sodium methoxide-methanol solution, or potassium t-butoxide and the like, or a tertiary organic amine such as pyridine, 4-dimethylaminopyridine, 1,8-diazabicyclo[5,4,0]-undecene, trimethylamine, or triethylamine and the like can be mentioned. 28% Sodium methoxide-methanol solution is preferable.

With respect to the use amount of the base, it is preferably 1 to 10 moles compared to the compounds represented by the Formula (XXV). With respect to the reaction temperature, it can be −40° C. to heating under reflux, and preferably −10 to 50° C. With respect to the reaction time, it can be 0.1 to 48 hours. 2 to 20 hours is preferable.

Scheme 4

[Chemical Formula 23]

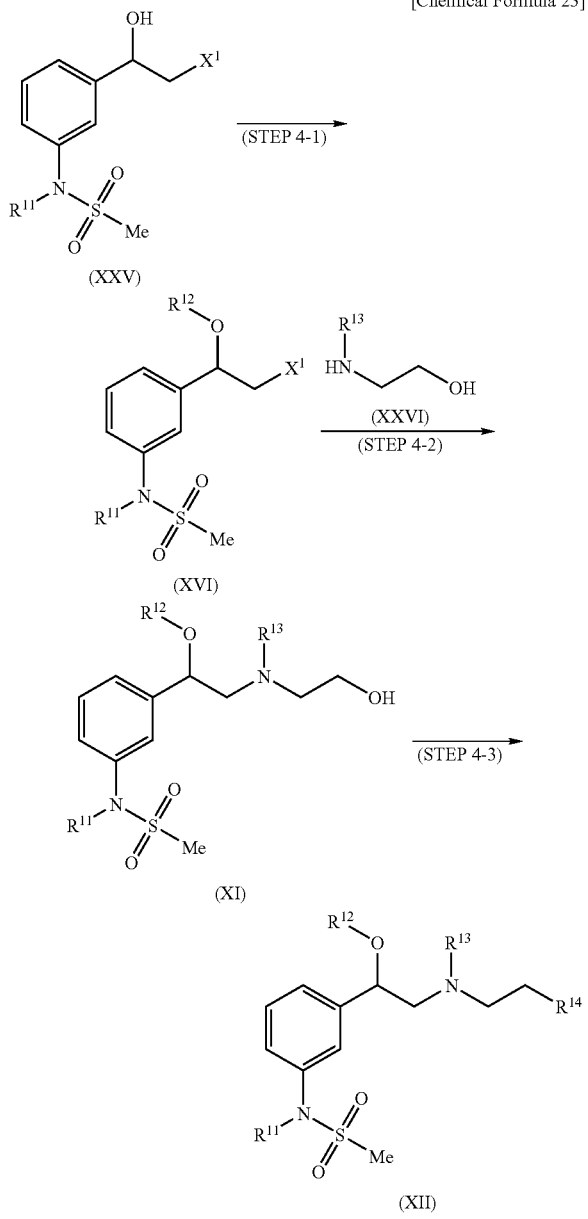

In each formula of Scheme 4, R$^{11}$ has the same meaning as defined in the above, and a benzyl group or a tert-butoxycarbonyl group is preferable. R$^{12}$ has the same meaning as defined in the above, and a triethylsilyl group or a tert-butyldimethylsilyl group is preferable. R$^{13}$ has the same meaning as defined in the above, and a hydrogen atom, a benzyl group, or a tert-butoxycarbonyl group is preferable. R$^{14}$ has the same meaning as defined in the above, and p-toluene sulfonyloxy group, a methanesulfonyloxy group, or a bromine atom is preferable. X$^{1}$ has the same meaning as defined in the above, and a chlorine atom, a bromine atom, or an iodine atom can be mentioned. Iodine atom is preferable.

With respect to the combination of $R^{11}$, $R^{12}$ and $R^{13}$ included in the Formula (XI), $R^{11}$ (a benzyl group), $R^{12}$ (a triethylsilyl group), $R^{13}$ (a benzyl group); or $R^{11}$ (a tert-butoxycarbonyl group), $R^{12}$ (a triethylsilyl group), and $R^{13}$ (a tert-butoxycarbonyl group) is preferable.

Process 4-1 (Step 4-1)

By carrying out a protection reaction of the hydroxyl group that is included in the compounds represented by the Formula (XXV), which is obtainable according to the production method described in Scheme 3, etc., based on a well known method, for example, according to the method described in Protective Groups in Organic Synthesis, published by John Wiley and Sons (2007 edition), the compounds represented by the Formula (XVI) can be produced. As an appropriate example, a method in which the compounds represented by the Formula (XXV) are reacted with a silylating agent in an inert solvent with addition of a base to obtain the compounds represented by the Formula (XVI) can be mentioned. As for the inert solvent, N,N-dimethyl formamide and the like can be mentioned. As for the base, imidazole and the like can be mentioned. As for the silylating agent, triethylchlorosilane or tert-butyldimethylchlorosilane and the like can be mentioned.

Process 4-2 (Step 4-2)

It can be carried out in view of the method described in International Publication No. WO03/035620. Specifically, by reacting the compounds represented by the Formula (XVI) with the compounds represented by the Formula (XXVI) in the absence of a solvent or in the presence of an inert solvent, if necessary, with addition of a base, the compounds represented by the Formula (XI) can be obtained.

As for the inert solvent, N,N-dimethyl formamide, N,N-dimethylacetamide, dimethyl sulfoxide, or acetonitrile and the like can be used alone, or a mixed solvent thereof can be also used. N,N-dimethyl formamide is preferable. As for the base, a tertiary organic amine such as triethylamine, diisopropylethylamine, or 1,8-diazabicyclo[5,4,0]-undecene and the like, or an alkali metal compound such as potassium carbonate, sodium carbonate, cesium carbonate, or sodium hydrogen carbonate and the like can be mentioned. Triethylamine or diisopropylethylamine is preferable.

With respect to the use amount of the base, it can be 0 to 10 moles compared to the compounds represented by the Formula (XVI), and preferably 1 to 5 moles. With respect to the use amount of the compounds represented by the Formula (XXVI), it can be 1 to 10 moles compared to the compounds represented by the Formula (XVI), and preferably 1 to 5 moles. With respect to the reaction temperature, it can be −10° C. to heating under reflux, and preferably 50° C. to heating under reflux. With respect to the reaction time, it can be 0.5 to 48 hours. 1 to 24 hours is preferable.

When the reaction progresses slowly, a catalyst such as potassium iodide or sodium iodide and the like can be added in an amount of 0.1 to 1.5 moles compared to the compounds represented by the Formula (XVI), if necessary.

Further, as exemplified in Reference example 28 and Reference example 29, it can be modified with a suitable protecting group.

Process 4-3 (Step 4-3)

By treating the compounds represented by the Formula (XI) according to a method described in general chemistry literatures, for example, New Experimental Chemistry Series, 4th ed. a (Vol. 19, pages 438 to 446, published by Maruzen Company, Limited) or in view of the methods that are described in the references cited therein, the compounds represented by the Formula (XII) can be obtained. As an appropriate example, a method in which the compounds represented by the Formula (XI) are reacted in an inert solvent with addition of a halogenating agent and a phosphine to obtain the compounds represented by the Formula (XII) can be mentioned.

As for the inert solvent, halogenated hydrocarbons such as dichloromethane or chloroform and the like, ethers such as tetrahydrofuran and the like, or a hydrocarbon solvent such as benzene or toluene and the like can be used alone, or a mixed solvent thereof can be also used. Dichloromethane is preferable. As for the halogenating agent, carbon tetrachloride, N-chlorosuccinimide, N-bromosuccinimide, carbon tetrachloride, or N-iodosuccinimide and the like can be mentioned. N-bromosuccinimide is preferable. As for the phosphine, triphenylphosphine or n-butylphosphine and the like can be mentioned. Triphenylphosphine is preferable.

With respect to the use amount of the halogenating agent, it is preferably 1 to 10 moles compared to the compounds represented by the Formula (XI). With respect to the use amount of the phosphine, it is preferably 1 to 10 moles compared to the compounds represented by the Formula (XI). With respect to the reaction temperature, it can be −10° C. to heating under reflux, and preferably −10 to 40° C. With respect to the reaction time, it can be 0.1 to 24 hours. 0.5 to 12 hours is preferable.

Further, by reacting the compounds represented by the Formula (XI) with a halogenating agent in an inert solvent, if necessary, with addition of a base, the compounds represented by the Formula (XII) can be obtained.

As for the inert solvent, halogenated hydrocarbons such as dichloromethane or chloroform and the like, ethers such as tetrahydrofuran and the like, or a hydrocarbon solvent such as benzene or toluene and the like can be used alone, or a mixed solvent thereof can be also used. As for the halogenating agent, for example, thionyl chloride or thionyl bromide and the like can be mentioned. As for the base, a tertiary organic amine such as triethylamine, diisopropylethylamine, or 1,8-diazabicyclo[5,4,0]-undecene and the like can be mentioned.

With respect to the use amount of the halogenating agent, it is preferably 1 to 10 moles compared to the compounds represented by the Formula (XI). With respect to the use amount of the base, it can be 0 to 10 moles compared to the compounds represented by the Formula (XI), and preferably 1 to 10 moles. With respect to the reaction temperature, it can be −10° C. to heating under reflux, and preferably −10 to 40° C. With respect to the reaction time, it can be 0.1 to 24 hours. 0.5 to 12 hours is preferable.

Scheme 5

[Chemical Formula 24]

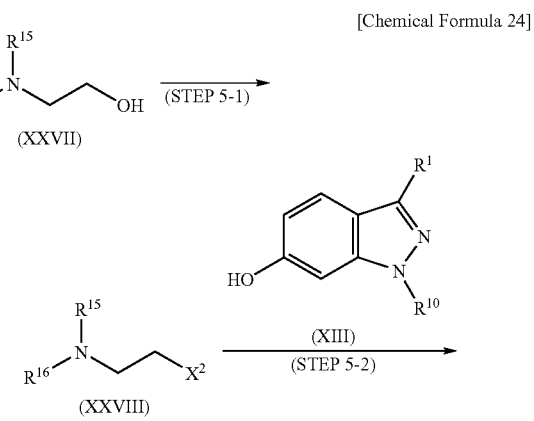

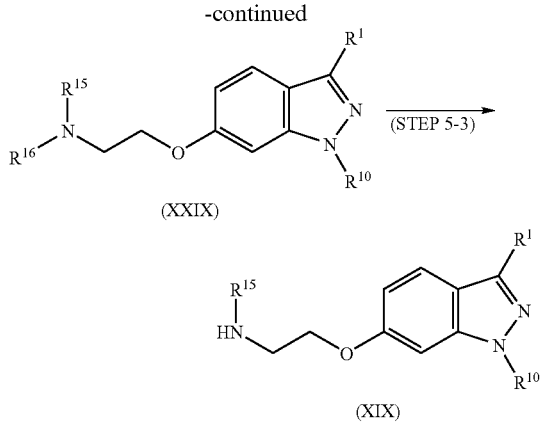

(XXIX)

(XIX)

In each formula described in Scheme 5, $R^1$ has the same meaning as defined in the above. $R^{10}$ has the same meaning as defined in the above, preferably is a benzyl group, a tert-butoxycarbonyl group, or a tetrahydropyranyl group, and more preferably a benzyl group. $R^{15}$ has the same meaning as defined in the above, and a benzyl group is preferable. $R^{16}$ represents a hydrogen atom or a protecting group of an amino group, and when it is a protecting group of an amino group, it is preferably the same group as $R^{15}$ or a group which can be selectively deprotected over $R^{15}$. There is other embodiment having a combination wherein $R^{15}$ is a group that can be selectively deprotected over $R^{16}$ is preferable. $X^2$ represents a leaving group, and a chlorine atom, a bromine atom, an iodine atom, p-toluene sulfonyloxy group, or a methanesulfonyloxy group and the like can be mentioned. As a preferred combination of $R^{15}$ and $R^{16}$ in the compounds represented by the Formula (XXVII), $R^{15}$ (a benzyl group) and $R^{16}$ (a benzyl group) is preferable. As a preferred combination of $R^{10}$, $R^{15}$ and $R^{16}$ in the compounds represented by the Formula (XXIX), $R^{10}$ (a benzyl group), $R^{15}$ (a benzyl group), $R^{16}$ (a benzyl group); $R^{10}$ (a tert-butoxycarbonyl group), $R^{15}$ (a benzyl group), $R^{16}$ (a benzyl group); or $R^{10}$ (a tetrahydropyranyl group), $R^{15}$ (a benzyl group), $R^{16}$ (a benzyl group) can be mentioned. A combination of $R^{10}$ (a benzyl group), $R^{15}$ (a benzyl group) and $R^{16}$ (a benzyl group) is more preferable. As a preferred combination of $R^{10}$ and $R^{15}$ in the compounds represented by the Formula (XIX), a combination of $R^{10}$ (a benzyl group) and $R^{15}$ (a benzyl group) is preferable.

For example, with respect to the Formula (XXVII), a compound having $R^{15}$ (a benzyl group) and $R^{16}$ (a benzyl group); a compound having $R^{15}$ (a benzyl group), $R^{16}$ (a hydrogen atom) and; a compound having $R^{15}$ (a hydrogen atom) and $R^{16}$ (a hydrogen atom) can be obtained from Tokyo Chemical Industry Co., Ltd., etc.

Process 5-1 (Step 5-1)

By reacting the compounds represented by the Formula (XXVII) in an inert solvent with addition of a base and a sulfonylating agent, the compounds represented by the Formula (XXVIII) can be obtained.

As for the inert solvent, halogenated hydrocarbons such as dichloromethane or chloroform and the like, or ethers such as tetrahydrofuran and the like can be used alone, or a mixed solvent thereof can be also used. As for the base, a tertiary organic amine such as pyridine, triethylamine, diisopropylethylamine, or 1,8-diazabicyclo[5,4,0]-undecene and the like or an alkali metal compound such as potassium carbonate, sodium carbonate, cesium carbonate, or sodium hydrogen carbonate and the like can be mentioned. As for the sulfonylating agent, p-toluene sulfonyl chloride or methanesulfonyl chloride and the like can be mentioned.

With respect to the use amount of the sulfonylating agent, it can be 1 to 10 moles compared to the compounds represented by the Formula (XXVII), and preferably 1 to 2 moles. With respect to the use amount of the base, it can be 1 to 10 moles compared to the compounds represented by the Formula (XXVII), and preferably 1 to 2 moles. With respect to the reaction temperature, it can be −20° C. to heating under reflux, and preferably −10 to 50° C. With respect to the reaction time, it can be 0.1 to 24 hours. 1 to 10 hours is preferable, including a time required for dropwise addition of the reagents.

By treating the compounds represented by the Formula (XXVII) according to a method described in general chemistry literatures, for example, New Experimental Chemistry Series, $4^{th}$ ed. (Vol. 19, pages 438 to 446, published by Maruzen Company, Limited) or in view of the methods that are described in the references cited therein, the compounds represented by the Formula (XXVIII) can be obtained. As an appropriate example, a method in which the compounds represented by the Formula (XXVII) are reacted in an inert solvent with addition of a halogenating agent and a phosphine to obtain the compounds represented by the Formula (XXVIII) can be mentioned.

As for the inert solvent, halogenated hydrocarbons such as dichloromethane or chloroform and the like, ethers such as tetrahydrofuran and the like, or a hydrocarbon solvent such as benzene or toluene and the like can be used alone, or a mixed solvent thereof can be also used. As for the halogenating agent, carbon tetrachloride, N-chlorosuccinimide, N-bromosuccinimide, carbon tetrabromide, or N-iodosuccinimide and the like can be mentioned. As for the phosphine, triphenylphosphine or n-butylphosphine and the like can be mentioned. Triphenylphosphine is preferable.

With respect to the use amount of the halogenating agent, it is preferably 1 to 10 moles compared to the compounds represented by the Formula (XXVII). With respect to the use amount of the phosphine, it is preferably 1 to 10 moles compared to the compounds represented by the Formula (XXVII). With respect to the reaction temperature, it can be −10° C. to heating under reflux, and preferably −10 to 40° C. With respect to the reaction time, it can be 0.1 to 24 hours. 0.5 to 12 hours is preferable.

Further, as another method, by reacting the compounds represented by the Formula (XXVII)) with a halogenating agent in an inert solvent, if necessary, with addition of a base, the compounds represented by the Formula (XXVIII) can be obtained.

As for the inert solvent, halogenated solvents such as dichloromethane or chloroform and the like, ethers such as tetrahydrofuran and the like or a hydrocarbon solvent such as benzene or toluene and the like can be used alone, or a mixed solvent thereof can be also used.

As for the halogenating agent, thionyl chloride, thionyl bromide, phosphorus tribromide and the like can be mentioned. As for the base, a tertiary organic amine such as pyridine, 4-dimethylaminopyridine, triethylamine, diisopropylethylamine, or 1,8-diazabicyclo[5,4,0]-undecene and the like can be mentioned.

With respect to the use amount of the halogenating agent, it is preferably 1 to 10 moles compared to the compounds represented by the Formula (XXVII). With respect to the use amount of the base, it can be 0 to 10 moles compared to the compounds represented by the Formula (XXVII), and preferably 1 to 10 moles. With respect to the reaction temperature, it can be −10° C. to heating under reflux, and preferably −10 to 40° C. With respect to the reaction time, it can be 0.1 to 24 hours. 0.5 to 12 hours is preferable.

Process 5-2 (Step 5-2)

By reacting the compounds represented by the Formula (XIII) with the compounds represented by the Formula (XXVIII) in an inert solvent with addition of a base, the compounds represented by the Formula (XXIX) can be obtained.

As for the inert solvent, tetrahydrofuran, N,N-dimethyl formamide, N,N-dimethylacetamide, dimethyl sulfoxide, or acetonitrile and the like can be used alone, or a mixed solvent thereof can be also used. As for the base, an alkali metal compound such as potassium carbonate, sodium carbonate, cesium carbonate, sodium hydrogen carbonate, potassium hydroxide, sodium hydroxide, sodium methoxide, 28% sodium methoxide-methanol solution, or potassium t-butoxide and the like, or a tertiary organic amine such as pyridine, 4-dimethylaminopyridine, 1,8-diazabicyclo[5,4,0]-undecene, trimethylamine, or triethylamine and the like can be mentioned.

With respect to the use amount of the base, it can be 1 to 10 moles compared to the compounds represented by the Formula (XIII), and preferably 1 to 5 moles. With respect to the use amount of the compounds represented by the Formula (XXVIII), it can be 1 to 10 moles compared to the compounds represented by the Formula (XIII), and preferably 1 to 3 moles. With respect to the reaction temperature, it can be −20° C. to heating under reflux, and preferably 0 to 60° C. With respect to the reaction time, it can be 0.1 to 48 hours. 2 to 24 hours is preferable, including a time required for dropwise addition of the reagents.

When the reaction progresses slowly, a catalyst such as potassium iodide or sodium iodide and the like can be added in an amount of 0.1 to 1.5 moles compared to the compounds represented by the Formula (XXVIII), if necessary.

Process 5-3 (Step 5-3)

When removal of a protecting group included in the compounds represented by the Formula (XXIX) is required, selective deprotection of $R^{16}$ over $R^{10}$ and $R^{15}$ can be carried out according to the method described in Protective Groups in Organic Synthesis, published by John Wiley and Sons (2007 edition), for example. In addition, there is other embodiment in which selective deprotection of $R^{15}$ over $R^{10}$ and $R^{16}$ can be carried out. For example, when both $R^{15}$ and $R^{16}$ are a benzyl group in the Formula (XXIX), a reaction condition at which one benzyl group of $R^{15}$ or $R^{16}$ is selectively deprotected can be mentioned. As for such condition, a method in which the reaction is carried out in an inert solvent in the presence of atmospheric or increased hydrogen gas pressure while the reaction is controlled by adding a catalyst and hydrochloric acid to obtain the compounds represented by the Formula (XIX) can be mentioned.

As for the inert solvent, an alcohol solvent such as methanol or ethanol can be mentioned. Ethanol is preferable. As for the catalyst, palladium on carbon powder is preferable.

With respect to the use amount of the catalyst, it can be 1 to 40% by weight compared to the compounds represented by the Formula (XXIX), and preferably 5 to 40% by weight. With respect to the use amount of hydrochloric acid, it can be 0.05 to 3 moles compared to the compounds represented by the Formula (XXIX), and preferably 0.1 to 1 moles. With respect to the reaction temperature, it can be 0 to 60° C., and preferably 0 to 40° C. With respect to the reaction time, it can be 0.1 to 24 hours. 0.1 to 12 hours is preferable.

The compounds represented by the Formula (XXIX) are also obtainable by the method described in Scheme 6.

Scheme 6

[Chemical Formula 25]

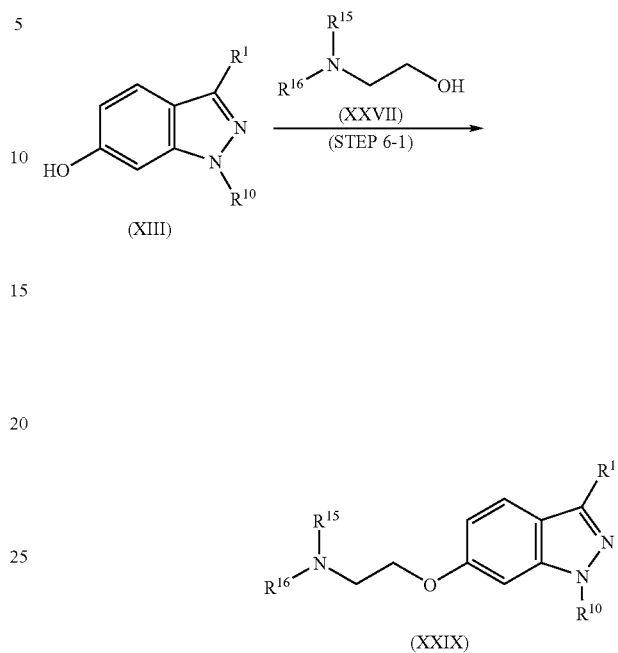

In each formula described in Scheme 6, $R^1$, $R^{10}$, $R^{15}$ and $R^{16}$ are as defined in the above.

Process 6-1 (Step 6-1)

By reacting the compounds represented by the Formula (XIII) with the compounds represented by the Formula (XXVII) in an inert solvent with addition of a phosphine and an azo compound, the compounds represented by the Formula (XXIX) can be obtained.

As for the inert solvent, ethers such as diethyl ether, tetrahydrofuran, or dimethoxyethane and the like, halogenated solvents such as chloromethylene and the like, or benzenes such as benzene, toluene or xylene and the like can be mentioned. Toluene or tetrahydrofuran is preferable. As for the phosphine, triphenylphosphine or tributylphosphine can be mentioned, and triphenylphosphine is preferable. As for the azo compound, diethyl azodicarboxylate, diisopropyl azodicarboxylate, N,N,N',N'-tetramethylazodicarboxamide, or 1,1'-(azodicarbonyl)dipiperidine, N,N,N',N'-tetraisopropylcarboxamide and the like can be mentioned. N,N,N',N'-tetramethylazodicarboxamide is preferable.

With respect to the use amount of the phosphine, it can be 1 to 10 moles compared to the compounds represented by the Formula (XIII), and preferably 1 to 5 moles. With respect to the use amount of the azo compound, it can be 1 to 10 moles compared to the compounds represented by the Formula (XIII), and preferably 1 to 5 moles. With respect to the use amount of the compounds represented by the Formula (XXVII), it can be 1 to 10 moles compared to the compounds represented by the Formula (XIII), and preferably 1 to 5 moles. With respect to the reaction temperature, it can be −20° C. to heating under reflux, and preferably 0 to 30° C. With respect to the reaction time, it can be 1 to 48 hours. 3 to 24 hours is preferable.

Scheme 7

[Chemical Formula 26]

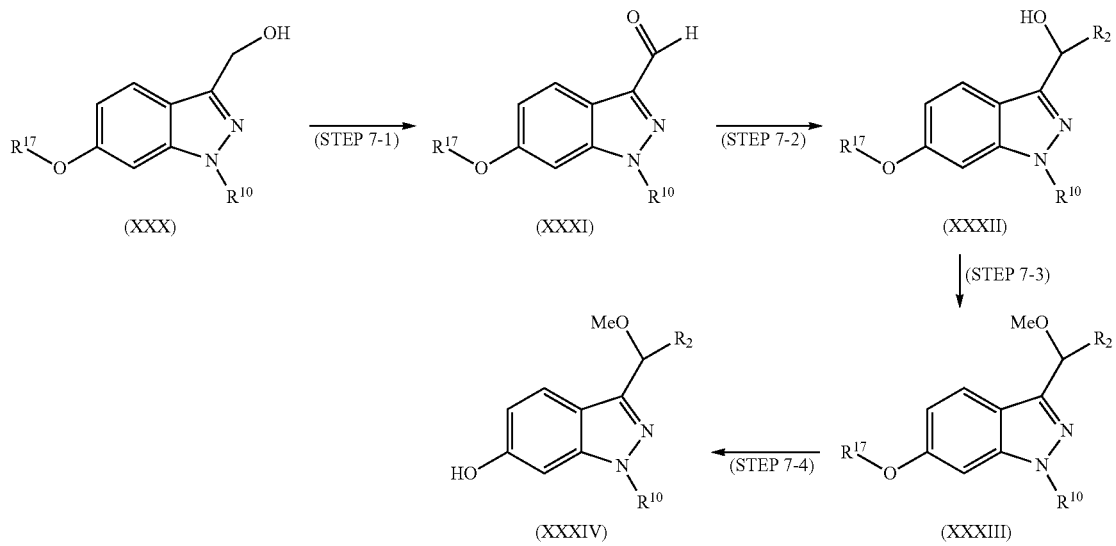

In each formula described in Scheme 7, $R^2$ and $R^{10}$ have the same meaning as defined in the above. $R^{17}$ represents a hydrogen atom or a protecting group of a hydroxyl group, and a benzyl group or a tert-butyldiphenylsilyl group is preferable. Further, the compounds represented by the Formula (XXX) are obtainable according to the method described in Scheme 9.

Process 7-1 (Step 7-1)

By treating the compounds represented by the Formula (XXX) according to a method described in general chemistry literatures, for example, New Experimental Chemistry Series, $4^{th}$ ed. (Vol. 21, pages 1 to 23, published by Maruzen Company, Limited) or in view of the methods that are described in the references cited therein, the compounds represented by the Formula (XXXI) can be obtained. As an appropriate example, a method in which the compounds represented by the Formula (XXX) are reacted in an inert solvent with addition of an oxidizing agent to obtain the compounds represented by the Formula (XXXI) can be mentioned.

As for the inert solvent, ethers such as diethyl ether, tetrahydrofuran, 1,4-dioxane, or dimethoxyethane and the like, benzenes such as benzene, toluene, or xylene and the like, or halogenated solvents such as dichloromethane, chloroform, or 1,2-dichloroethane and the like can be used alone, or a mixed solvent thereof can be also used. A mixed solvent of dichloromethane and tetrahydrofuran is preferable.

As for the oxidizing agent, 1,1,1-triacetoxy-1,1-dihydro-1,2-benziodoxol-3(1H)-one, 2-iodoxybenzoic acid, pyridinium chlorochromate, activated manganese dioxide, dimethyl sulfoxide-dicyclohexylcarbodiimide, dimethyl sulfoxide-acetic anhydride, dimethyl sulfoxide-trifluoroacetic anhydride, dimethyl sulfoxide-thionyl chloride, dimethyl sulfoxide-oxalyl chloride, dimethylsulfide-N-chlorosuccinimide, dimethyl sulfoxide-chlorine gas, oxoammonium salt, or tetrapropylammonium perruthenate can be mentioned. Activated manganese dioxide is preferable.

With respect to the required amount of the oxidizing agent, it can be 1 to 10 moles compared to the compounds represented by the Formula (XXX). With respect to the reaction temperature, it can be −20° C. to heating under reflux, and preferably −20 to 40° C. With respect to the reaction time, it can be 0.1 to 48 hours. 0.1 to 12 hours is preferable.

Further, by having both the oxidizing agent mentioned above and a reoxidizing agent such as 4-methylmorpholine-N-oxide and the like, it is possible to lower the amount of the oxidizing agent to a catalytic amount.

Process 7-2 (Step 7-2)

By treating the compounds represented by the Formula (XXXI) according to a method described in general chemistry literatures, for example, New Experimental Chemistry Series, $4^{th}$ ed. (Vol. 25, pages 60 to 72, published by Maruzen Company, Limited) or in view of the methods that are described in the references cited therein, the compounds represented by the Formula (XXXII) can be obtained. As an appropriate example, a method in which the compounds represented by the Formula (XXXI) are reacted in an inert solvent with addition of a Grignard reagent for introducing $R^2$ to obtain the compounds represented by the Formula (XXXII) can be mentioned.

As for the inert solvent, ethers such as diethyl ether, tetrahydrofuran, dimethoxyethane and the like, benzenes such as benzene, toluene, xylene and the like can be used alone, or a mixed solvent thereof can be also used. As for the Grignard reagent for introducing $R^2$, it is preferable that a commercially available Grignard reagent is used or it can be prepared according to a common method.

With respect to the use amount of the Grignard reagent for introducing $R^2$, it is preferably 1 to 5 moles compared to the compounds represented by the Formula (XXXI). With respect to the reaction temperature, it can be −20° C. to heating under reflux, and preferably −20 to 40° C. With respect to the reaction time, it can be 0.1 to 48 hours. 0.1 to 12 hours is preferable.

If no specific reaction for forming an asymmetric carbon-carbon bond is performed, the compounds of the Formula (XXXII) that are resulted from the present reaction are obtained as a racemic mixture.

Regarding a method of obtaining an optically active compound, a method for forming an asymmetric carbon-carbon bond can be mentioned. Reaction for forming an asymmetric carbon-carbon bond can be carried out according to a method described in general chemistry literatures, for example, New Experimental Chemistry Series, $4^{th}$ ed. (Vol. 26, pages 68 to 158, published by Maruzen Company, Limited) or in view of the methods that are described in the references cited therein.

Process 7-3 (Step 7-3)

By treating the compounds represented by the Formula (XXXII) according to a method described in general chemistry literatures, for example, New Experimental Chemistry Process 7-4 (Step 7-4)

When removal of a protecting group included in the compounds represented by the Formula (XXXIII) is required, it can be carried out according to the method described in Protective Groups in Organic Synthesis, published by John Wiley and Sons (2007 edition), for example, to give the compounds represented by the Formula (XXXIV). As an appropriate example, the method described in Reference example 26 can be mentioned.

Scheme 8

[Chemical Formula 27]

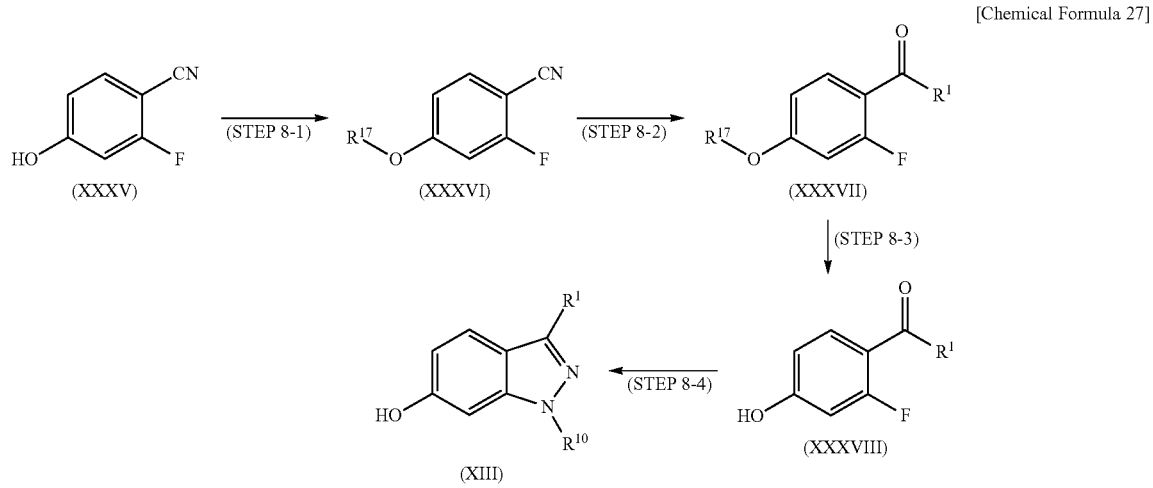

Series, $4^{th}$ ed. (Vol. 20, pages 187 to 200, published by Maruzen Company, Limited) or in view of the methods that are described in the references cited therein, the compounds represented by the Formula (XXXIII) can be obtained. As an appropriate example, a method in which the compounds represented by the Formula (XXXII) are reacted in an inert solvent with addition of a base and a methylating agent to obtain the compounds represented by the Formula (XXXIII) can be mentioned.

As for the inert solvent, ethers such as diethyl ether, tetrahydrofuran, 1,4-dioxane, or dimethoxyethane and the like, or aprotic polar solvents such as N,N-dimethyl formamide and the like can be used alone, or a mixed solvent thereof can be also used. N,N-dimethyl formamide is preferable. As for the base, an alkali metal compound such as potassium carbonate, sodium carbonate, cesium carbonate, sodium hydrogen carbonate, potassium hydroxide, cesium hydroxide, sodium hydroxide, barium hydroxide, sodium methoxide, sodium hydride, potassium hydride, or potassium t-butoxide and the like or a tertiary organic amine such as pyridine, 4-dimethylaminopyridine, 1,8-diazabicyclo[5,4,0]-undecene, trimethylamine, or triethylamine and the like can be mentioned. Sodium hydride is preferable. As for the methylating agent, dimethyl sulfate or methyl iodide and the like can be mentioned. Methyl iodide is preferable.

With respect to the use amount of the base, it is preferably 1 to 5 moles compared to the compounds represented by the Formula (XXXII). With respect to the use amount of the methylating agent, it is preferably 1 to 5 moles compared to the compounds represented by the Formula (XXXII). With respect to the reaction temperature, it can be −20° C. to heating under reflux, and preferably −20 to 40° C. With respect to the reaction time, it can be 0.1 to 48 hours. 0.1 to 12 hours is preferable.

In each formula of Scheme 8, $R^1$ is the same group as defined in the above except that —CH($R^2$)OMe is excluded. $R^{17}$ is a protecting group of a hydroxyl group, and a methoxymethyl group, a benzyl group, or a tert-butyldimethylsilyl group is preferable.

Process 8-1 (Step 8-1)

Protection of the hydroxyl group in Compound (XXXV), which is obtainable from Wako Pure Chemical Industries, Ltd., can be carried out according to the method described in Protective Groups in Organic Synthesis, published by John Wiley and Sons (2007 edition), for example. As an appropriate example, a method in which Compound (XXXV) is reacted in an inert solvent with addition of a base and a protecting reagent to obtain the compounds represented by the Formula (XXXVI) can be mentioned.

As for the inert solvent, halogenated solvents such as dichloromethane, chloroform, or 1,2-dichloroethane and the like, or aprotic polar solvents such as N,N-dimethyl formamide and the like can be used alone, or a mixed solvent thereof can be also used. As for the base, a tertiary organic amine such as triethylamine, diisopropylethylamine, or 1,8-diazabicyclo [5,4,0]-undecene and the like, or an alkali metal compound such as potassium carbonate, sodium carbonate, cesium carbonate, or sodium hydrogen carbonate and the like can be mentioned. Triethylamine, diisopropylethylamine, potassium carbonate, or imidazole is preferable. As for the protecting reagent, tert-butyldimethylchlorosilane, methoxymethyl chloride, benzyl chloride, or benzyl bromide and the like can be mentioned.

With respect to the use amount of the base, it can be 1 to 5 moles compared to Compound (XXXVI). With respect to the use amount of the protecting reagent, it can be 1 to 5 moles compared to Compound (XXXVI). With respect to the reaction temperature, it can be −20° C. to heating under reflux, and preferably 0 to 40° C. With respect to the reaction time, it can be 0.1 to 48 hours. 0.1 to 12 hours is preferable.

Process 8-2 (Step 8-2)

By treating the compounds represented by the Formula (XXXVI) according to a method described in general chemistry literatures, for example, New Experimental Chemistry Series, 4th ed. (Vol. 25, pages 59 to 82, published by Maruzen Company, Limited) or in view of the methods that are described in the references cited therein, the compounds represented by the Formula (XXXVII) can be obtained. As an appropriate example, a method in which the compounds represented by the Formula (XXXVI) are reacted in an inert solvent with addition of a Grignard reagent for introducing $R^1$ group to form an imine compound, which is then hydrolyzed with addition of an acidic aqueous solution to obtain compounds represented by the Formula (XXXVII), can be mentioned.

As for the inert solvent, ethers such as diethyl ether, tetrahydrofuran, or dimethoxyethane and the like, benzenes such as or benzene, toluene or xylene and the like can be used alone, or a mixed solvent thereof can be also used. Diethyl ether or tetrahydrofuran is preferable. As for the Grignard reagent of $R^1$, a commercially available Grignard reagent, or a Grignard reagent that is prepared according to a method described in the literature mentioned above, or in view of the methods that are described in the references cited therein, or a Grignard reagent that is prepared according to a method other than those can be mentioned. For example, cyclobutylmagnesium bromide can be prepared by adding magnesium, a small amount of iodine and bromocyclobutane in dehydrated diethyl ether solvent. As for the catalyst, a lithium salt such as lithium chloride and the like, a copper salt or a copper complex such as copper cyanide, copper chloride, copper bromide, copper bromide dimethyl sulfide complex, copper iodide and the like can be mentioned. Copper bromide is preferable.

With respect to the use amount of the Grignard reagent, it is preferably 1 to 5 moles compared to the compounds represented by the Formula (XXXVI). With respect to the ratio of the catalyst, it may satisfy the condition of the compounds represented by the Formula (XXXVI)/the catalyst amount=S/C=1 to 10000 moles. S/C=10 to 1000 moles is preferable. With respect to the reaction temperature, it can be −20° C. to heating under reflux, and preferably 0° C. to heating under reflux. With respect to the reaction time, it can be 0.1 to 48 hours. 0.1 to 12 hours is preferable.

Process 8-3 (Step 8-3)

When removal of a protecting group included in the compounds represented by the Formula (XXXVII) is required, it can be carried out according to the method described in Protective Groups in Organic Synthesis, published by John Wiley and Sons (2007 edition), for example, to give the compounds represented by the Formula (XXXVIII). By appropriately selecting $R^{17}$, Process 12-2 and Process 12-3 can be consecutively carried out.

Process 8-4 (Step 8-4)

By carrying out a reaction with addition of hydrazines in an inert solvent, and if necessary with addition of a base, to the compounds represented by the Formula (XXXVIII), Compound (XIII) can be obtained.

As for the inert solvent, alcohols such as methanol, ethanol, 1-butanol or 2-butanol and the like, ethers such as tetrahydrofuran, or dimethoxyethane and the like, benzenes such as benzene, toluene, or xylene and the like can be used alone, or a mixed solvent thereof can be also used. Xylene is preferable. As for the hydrazines, benzylhydrazine, benzylhydrazine-monohydrochloride, benzylhydrazine-dihydrochloride, hydrazine-monohydrate, or hydrazine-hydrate can be mentioned. Benzylhydrazine-monohydrochloride is preferable. As for the base, an alkali metal compound such as sodium acetate, potassium carbonate, sodium carbonate, cesium carbonate, or sodium hydrogen carbonate and the like can be mentioned. Sodium acetate is preferable.

With respect to the use amount of the hydrazines, it can be 1 to 5 moles compared to the compounds represented by the Formula (XXXVIII), and preferably 1 to 3 moles. With respect to the use amount of the base, it can be 0 to 10 moles compared to the compounds represented by the Formula (XXXVIII), and preferably 1 to 5 moles. With respect to the reaction temperature, it can be 0° C. to heating under reflux, and preferably 50° C. to heating under reflux. With respect to the reaction time, it can be 0.1 to 48 hours. 3 to 24 hours is preferable.

When the reaction progresses slowly, it is possible to seal the reaction vessel so that pressure in the reaction system is increased. In this case, with respect to the reaction temperature, it can be higher than the reflux temperature of a solvent, for example, heating under reflux to 250° C. Heating under reflux to 200° C. is preferable.

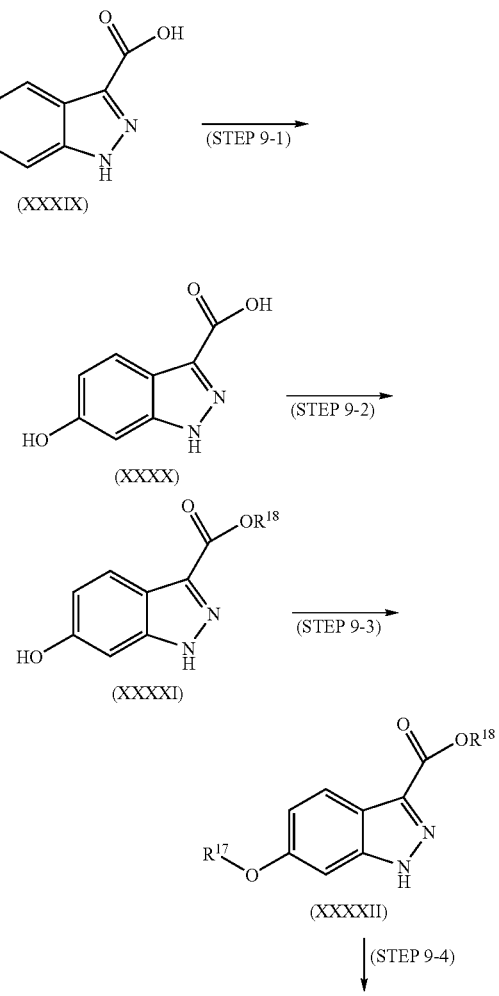

Scheme 9

[Chemical Formula 28]

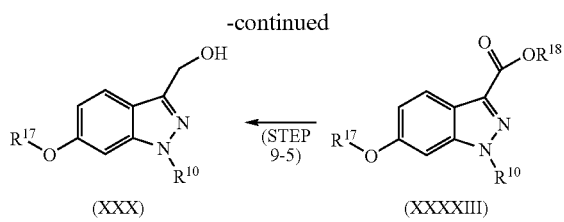

(XXX) ← (STEP 9-5) ← (XXXXIII)

In each formula of Scheme 9, $R^{10}$ is the same group as defined. $R^{17}$ is as defined in the above. With respect to $R^{18}$ as a protecting group of a carbonyl group, a methyl group, an ethyl group, an n-propyl group, or n-butyl group and the like can be mentioned. A methyl group or an ethyl group is preferable.

Process 9-1 (Step 9-1)

By subjecting Compound (XXXIX) that is obtainable from ChemPacific Corporation, etc. to a known method, for example a method described in Protective Groups in Organic Synthesis, published by John Wiley and Sons (2007 edition), etc., Compound (XXXX) can be obtained. As an appropriate example, the method described in Reference example 16 can be mentioned.

Process 9-2 (Step 9-2)

By subjecting Compound (XXXX) to a known method, for example a method described in Protective Groups in Organic Synthesis, published by John Wiley and Sons (2007 edition), etc., the compounds represented by the Formula (XXXXI) can be obtained. As an appropriate example, a method in which the reaction is carried out by adding an acid catalyst or thionyl chloride to Compound (XXXX) in an alcohol solvent to give the compounds represented by the Formula (XXXXI) can be mentioned.

As for the alcohol solvent, depending on type of $R^{18}$ to be introduced, it can be selected from methanol, ethanol, n-propanol, or n-butanol and the like. As for the acid catalyst, hydrochloric acid, sulfuric acid, p-toluene sulfonic acid, or trifluoroacetic acid and the like can be mentioned.

With respect to the use amount of the acid catalyst, it can be 0.01 to 10 moles compared to Compound (XXXX). With respect to the use amount of thionyl chloride, it can be 1 to 10 moles compared to Compound (XXXX), and preferably 1 to 5 moles. With respect to the reaction temperature, it can be 0° C. to heating under reflux, and preferably 40° C. to heating under reflux. With respect to the reaction time, it can be 0.1 to 48 hours. 1 to 24 hours is preferable.

Process 9-3 (Step 9-3)

When protection of the hydroxyl group included in the compounds represented by the Formula (XXXXI) is required, by selecting the protecting group of the hydroxyl group as described above, hydroxyl group protection can be carried out according to a known method, for example the method described in Protective Groups in Organic Synthesis, published by John Wiley and Sons (2007 edition), etc. to obtain the compounds represented by the Formula (XXXXII). As an appropriate example, a method in which the compounds represented by the Formula (XXXXI) are reacted with a silylating agent in an inert solvent with addition of a base to give the compounds represented by the Formula (XXXXII) can be mentioned.

As for the inert solvent, N,N-dimethyl formamide and the like can be mentioned. As for the base, imidazole and the like can be mentioned. As for the silylating agent, triethylchlorosilane or tert-butyldimethylchlorosilane and the like can be mentioned.

With respect to the use amount of the silylating agent, it can be 1 to 10 moles compared to the compounds represented by the Formula (XXXXI), and preferably 1 to 5 moles. With respect to the use amount of the base, it can be 1 to 10 moles compared to the compounds represented by the Formula (XXXXI), and preferably 1 to 5 moles. With respect to the reaction temperature, it can be −20° C. to heating under reflux, and preferably 0 to 40° C. With respect to the reaction time, it can be 0.1 to 48 hours, and preferably 0.1 to 12 hours.

Process 9-4 (Step 9-4)

When a protecting group is desired for the indazole group included in the compounds represented by the Formula (XXXXII), by selecting the protecting group of the indazole group as described above, indazole group protection can be carried out according to a known method, for example the method described in Protective Groups in Organic Synthesis, published by John Wiley and Sons (2007 edition), etc. to obtain the compounds represented by the Formula (XXXXIII). As an appropriate example, a method in which the compounds represented by the Formula (XXXXII) are added with a protecting agent in an inert solvent, if necessary with a base or an acid catalyst, to give the compounds represented by the Formula (XXXXIII) can be mentioned.

As for the inert solvent, ethers such as diethyl ether, tetrahydrofuran, or dimethoxyethane and the like, halogenated solvents such as dichloromethane, or 1,2-dichloroethane and the like, benzenes such as benzene, toluene or xylene and the like, or acetonitrile and the like can be used alone, or a mixed solvent thereof can be also used. As for the protecting agent, dihydropyrane, chloromethylmethyl ether, or 2-(chloromethoxy)ethoxytrimethylsilane and the like can be mentioned. As for the base, an alkali metal compound such as potassium carbonate, sodium carbonate, cesium carbonate, sodium hydrogen carbonate, potassium hydroxide, sodium hydroxide, sodium methoxide, or potassium t-butoxide and the like or a tertiary organic amine such as pyridine, 4-dimethylaminopyridine, 1,8-diazabicyclo[5,4,0]-undecene, trimethylamine, or triethylamine and the like can be mentioned.

As for the acid catalyst, hydrochloric acid, trifluoroacetic acid or p-toluene sulfonic acid and the like can be mentioned.

With respect to the use amount of the protecting agent, it can be 1 to 10 moles compared to the compounds represented by the Formula (XXXXII), and preferably 1 to 5 moles. With respect to the use amount of the base, it can be 0 to 10 moles compared to the compounds represented by the Formula (XXXXII), and preferably 0 to 5 moles. With respect to the use amount of the catalyst, it can be 0.001 to 1 moles compared to the compounds represented by the Formula (XXXXII), and preferably 0.01 to 0.5 moles. With respect to the reaction temperature, it can be −20° C. to heating under reflux, and preferably 0 to 100° C. With respect to the reaction time, it can be 0.1 to 48 hours. 1 to 24 hours is preferable.

Process 9-5 (Step 9-5)

By treating the compounds represented by the Formula (XXXXIII) according to a method described in general chemistry literatures, for example, New Experimental Chemistry Series, $4^{th}$ ed. (Vol. 26, pages 159 to 266, published by Maruzen Company, Limited) or in view of the methods that are described in the references cited therein, the compounds represented by the Formula (XXX) can be obtained. As an appropriate example, a method in which the compounds represented by the Formula (XXXXIII) are added with a reducing agent in an inert solvent for the reaction to obtain compounds represented by the Formula (XXX) can be mentioned.

As for the inert solvent, ethers such as diethyl ether, tetrahydrofuran, or dimethoxyethane and the like, benzenes such as benzene, toluene or xylene and the like, halogenated solvents such as dichloromethane, chloroform or 1,2-dichloroethane and the like can be used alone, or a mixed solvent thereof can be also used. As for the reducing agent, lithium aluminum hydride, diisobutyl aluminum hydride, lithium borohydride, or sodium bis(2-methoxyethoxy)aluminum hydride and the like can be mentioned.

With respect to the use amount of the reducing agent, it can be 1 to 10 moles compared to the compounds represented by the Formula (XXXXIII), and preferably 1 to 5 moles. With respect to the reaction temperature, it can be −20° C. to heating under reflux, and preferably 0 to 50° C. With respect to the reaction time, it can be 0.1 to 48 hours, and preferably 0.1 to 12 hours.

Herein below, from Scheme 10 to Scheme 15, one embodiment of the method of producing the compounds of the present invention will be explained in greater detail.

As for the inert solvent, ethyl acetate, 1,4-dioxane and MTBE can be mentioned. As for the acid, hydrochloric acid-1,4-dioxane solution or hydrochloric acid-ethyl acetate solution can be mentioned. With respect to the reaction temperature, it can be −20 to 60° C., and preferably 0 to 40° C. With respect to the reaction time, it can be 0.1 to 24 hours, and preferably 1 to 20 hours.

Process 10-2 (STEP 10-2)

By reacting the compounds represented by the Formula (XXXXV) with the compounds represented by the Formula (XXXXVI) in an inert solvent with addition of a base, the compounds represented by the Formula (XXXXIV) can be obtained.

As for the inert solvent, a ketone organic solvent such as methylisobutyl ketone and the like, a hydrocarbon solvent such as toluene and the like, a halogenated solvent such as Scheme 10

[Chemical Formula 29]

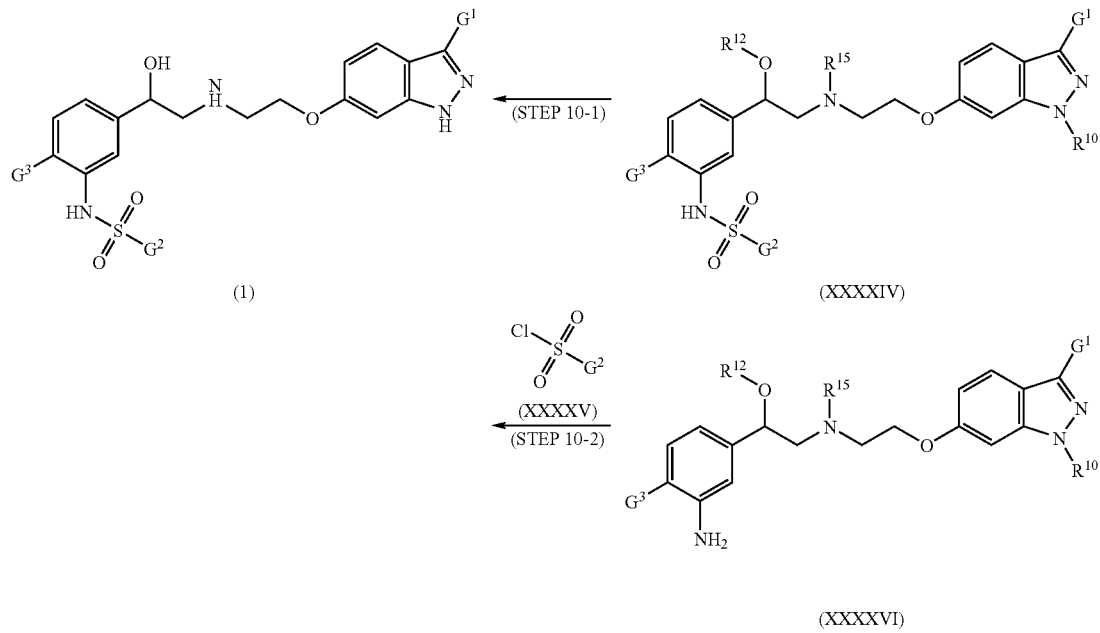

In each formula of Scheme 10, $G^1$, $G^2$, $G^3$, $R^{10}$, $R^{12}$ and $R^{15}$ are as defined in the above.

Process 10-1 (STEP 10-1)

By carrying out a deprotection reaction of the compounds represented by the Formula (XXXXIV) based on a well known method, for example, according to the method described in Protective Groups in Organic Synthesis, published by John Wiley and Sons (2007 edition), the compounds represented by the Formula (A-1) can be produced. As an appropriate example, deprotection is carried out under the acidic condition described above, or preferably deprotection reaction based on the hydrogenolysis described above is used alone or in combination with it. That is, a deprotection reaction which is suitable for each type of protecting groups that are present in the compounds of the Formula (XXXXIV) can be selected.

For example, according to deprotection under the acidic condition, a reaction is carried out in an inert solvent with addition of an acid to give the compounds represented by the Formula (A-1).

dichloromethane, chloroform, or 1,2-dichloroethane and the like, or acetonitrile are exemplified. Dichloromethane is preferable. As for the base, a tertiary organic amine such as 1,8-diazabicyclo[5,4,0]-undecene, trimethylamine, N,N-diisopropylethylamine, or triethylamine and the like, an organic base such as or pyridine, 4-dimethylaminopyridine and the like, or an inorganic base such as a potassium carbonate, or sodium hydrogen carbonate and the like can be mentioned. Pyridine or 1,8-diazabicyclo[5,4,0]-undecene is preferable.

With respect to the use amount of the base, it can be 1 to 10 moles compared to the compounds represented by the Formula (XXXXV), and preferably 1 to 5 moles. With respect to the use amount of the compounds represented by the Formula (XXXXV), it is generally 1 to 10 moles compared to the compounds represented by the Formula (XXXXVI), and preferably 1 to 5 moles.

With respect to the reaction temperature, it can be −10 to 60° C., and preferably −10 to 30° C. With respect to the reaction time, it can be 0.1 to 48 hours, and preferably 0.2 to 24 hours.

Compounds represented by the Formula (XXXXVI) can be also obtained, for example, according to the method shown in Scheme 11.

Scheme 11

[Chemical Formula 30]

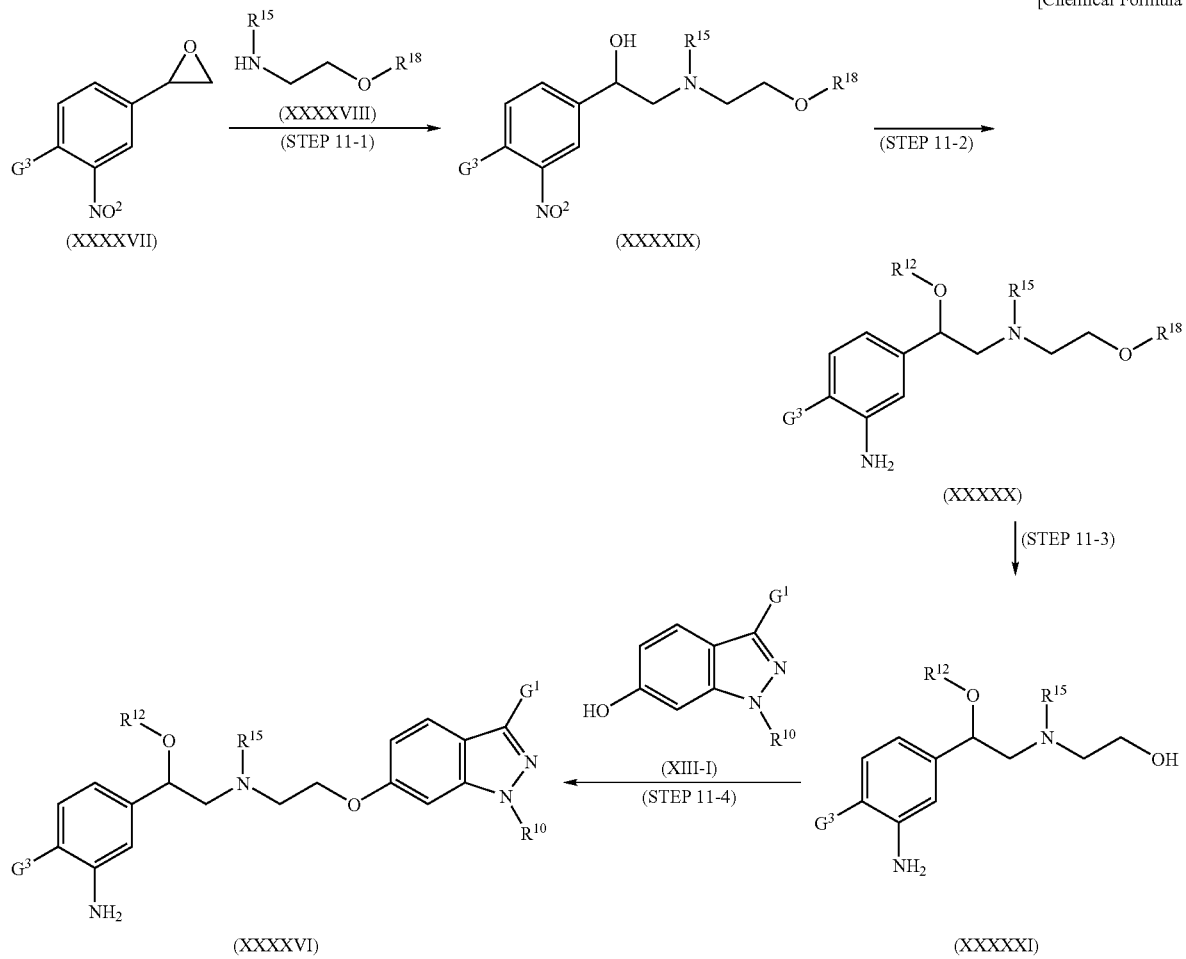

In each formula of Scheme 11, $G^1$, $G^3$, $R^{10}$, $R^{12}$ and $R^{18}$ have the same meaning as defined in the above, $R^{18}$ is a protecting group of a hydroxyl group, and a benzyl group is preferable.

Process 11-1 (Step 11-1)

By reacting the compounds represented by the Formula (XXXXVII) with the compounds represented by the Formula (XXXXVIII) in an inert solvent, the compounds represented by the Formula (XXXXIX) can be obtained.

As for the inert solvent, alcohols such as methanol, ethanol, 1-butanol, 2-butanol or 2-propanol and the like, or N,N-dimethyl formamide, N,N-dimethylacetamide, dimethyl sulfoxide, or acetonitrile and the like can be used alone, or a mixed solvent thereof can be also used. 2-Propanol is preferable.

With respect to the molar ratio between the compounds represented by the Formula (XXXXVII) and the compounds represented by the Formula (XXXXVIII)), it may satisfy the condition of the compounds represented by the Formula (XXXXVII)/the compounds represented by the Formula (XXXXVIII)=0.2 to 5 moles. 0.75 to 1.5 moles are preferable. With respect to the reaction temperature, it can be −10° C. to heating under reflux. 60° C. to heating under reflux is preferable. With respect to the reaction time, it can be 0.5 to 48 hours, and preferably 12 to 48 hours.

If necessary, a Lewis acid catalyst can be also added.

Process 11-2 (Step 11-2)

By carrying out a protection reaction of the hydroxyl group of the compounds represented by the Formula (XXXXIX) based on a well known method, for example, according to the method described in Protective Groups in Organic Synthesis, published by John Wiley and Sons (2007 edition), the compounds represented by the Formula (XXXXX) can be produced.

As an appropriate example, a method in which the compounds represented by the Formula (XXXXIX) are reacted in an inert solvent with a silylating agent with addition of a base to give the compounds represented by the Formula (XXXXX) can be mentioned.

As for the inert solvent, N,N-dimethyl formamide and the like can be mentioned. As for the base, imidazole and the like can be mentioned. As for the silylating agent, triethylchlorosilane or tert-butyldimethylchlorosilane and the like can be mentioned. With respect to the reaction temperature, it can be −20 to 60° C. 0 to 30° C. is preferable. With respect to the reaction time, it can be 0.5 to 48 hours, and preferably 1 to 24 hours.

Process 11-3 (Step 11-3)

By adding a catalyst to the compounds represented by the Formula (XXXXX) in an inert solvent and carrying out the reaction in the presence of hydrogen gas, the compounds represented by the Formula (XXXXXI) can be obtained.

As for the inert solvent, alcohols such as methanol, ethanol, 1-butanol, 2-butanol or 2-propanol and the like, ethers such as tetrahydrofuran, diethyl ether and the like can be used alone, or a mixed solvent thereof can be also used. Ethanol is preferable. As for the catalyst, palladium on carbon powder, platinum oxide ($PtO_2$), or activated nickel and the like can be mentioned and palladium on carbon powder is preferable. With respect to the reaction temperature, it can be 0° C. to heating under reflux. 0 to 60° C. is preferable. With respect to the reaction time, it can be 0.5 to 48 hours, and preferably 1 to 24 hours.

Further, as it is shown in Reference example 59, modification into an appropriate protecting group can be also made.

Process 11-4 (Step 11-4)

By reacting the compounds represented by the Formula (XXXXXI) with the compounds represented by the Formula (XIII-I) in an inert solvent with addition of phosphine and an azo compound, the compounds represented by the Formula (XXXXXI) can be obtained.

As for the inert solvent, ethers such as diethyl ether, tetrahydrofuran, or dimethoxyethane and the like, halogenated solvents such as methylene chloride and the like, or benzenes such as benzene, toluene, or xylene and the like can be mentioned. Toluene or tetrahydrofuran is preferable. As for the phosphine, triphenylphosphine or tributylphosphine can be mentioned, and triphenylphosphine is preferable. As for the azo compound, diethyl azodicarboxylate, diisopropyl azodicarboxylate, N,N,N',N'-tetramethylazodicarboxamide, or 1,1'-(azodicarbonyl)dipiperidine, N,N,N',N'-tetraisopropylcarboxamide and the like can be mentioned, and diisopropyl azodicarboxylate or N,N,N',N'-tetramethylazodicarboxamide is preferable.

With respect to the use amount of the phosphine, it can be 1 to 10 moles compared to the compounds represented by the Formula (XIII-I), and preferably it is 1 to 5 moles. With respect to the use amount of the azo compound, it can be 1 to 10 moles compared to the compounds represented by the Formula (XIII-I), and preferably it is 1 to 5 moles. With respect to the molar ratio between the compounds represented by the Formula (XXXXXI) and the compounds represented by the Formula (XIII-I), it may satisfy the condition of the compounds represented by the Formula (XXXXXI)/the compounds represented by the Formula (XIII-I)=0.2 to 5 moles, and preferably 0.75 to 1.5 moles. With respect to the reaction temperature, it can be −20° C. to heating under reflux, and preferably 0 to 50° C. With respect to the reaction time, it can be 0.5 to 48 hours, and preferably 1 to 24 hours.

Compounds represented by the Formula (XXXXVII) can be also obtained by the method described in Scheme 12, for example.

Scheme 12

[Chemical Formula 31]

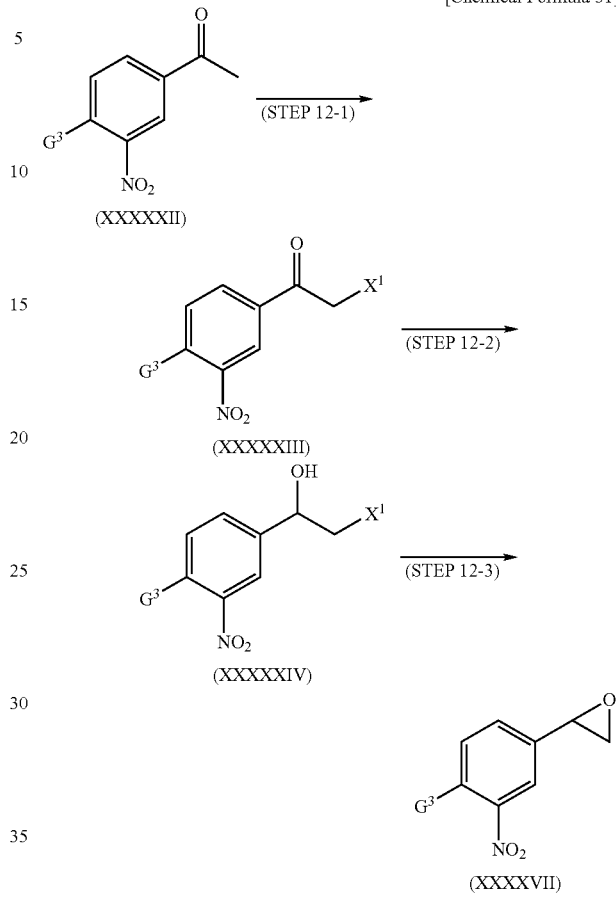

In each formula of Scheme 12, $G^3$ and $X^1$ are as defined in the above.

Process 12-1 (Step 12-1)

By reacting the compounds represented by the Formula (XXXXXII) with a halogenating agent in an inert solvent, if necessary, with further addition of methanol, the compounds represented by the Formula (XXXXXIII) can be obtained.

As for the inert solvent, halogenated hydrocarbons such as dichloromethane, 1,2-dichloroethane, or chloroform and the like can be mentioned. Dichloromethane is preferable. As for the halogenating agent, chlorine gas, bromine gas or sulfuryl chloride and the like can be mentioned, and sulfuryl chloride is preferable.

With respect to the use amount of the halogenating agent, it is preferably 1 to 3 moles compared to the compounds represented by the Formula (XXXXXII). With respect to the use amount of methanol, it can be 0 to 5 moles, and preferably 0.1 to 3 moles compared to the compounds represented by the Formula (XXXXXII). With respect to the reaction temperature, it is preferably −10 to 50° C. With respect to the reaction time, it is preferably 1 to 10 hours including a time required for dropwise addition of the halogenating agent and methanol.

Process 12-2 (Step 12-2)

By reacting the compounds represented by the Formula (XXXXXIII) with a reducing agent in an organic solvent, the compounds represented by the Formula (XXXXXIV) can be obtained.

As for the organic solvent, an alcohol solvent such as methanol or ethanol and the like or an ether solvent such as tetrahydrofuran and the like are exemplified. As for the reducing agent, sodium borohydride and the like is exemplified.

Unless asymmetric reduction is carried out separately, the compounds represented by the Formula (XXXXXIV) are obtained as a racemic mixture from this reduction reaction.

Regarding a method of obtaining an optically active compound, an asymmetric reduction can be mentioned. Asymmetric reduction can be carried out according to a method described in general chemistry literatures, for example, New Experimental Chemistry Series, $5^{th}$ ed. (Vol. 19, pages 65 to 171, published by Maruzen Company, Limited) or in view of the methods that are described in the references cited therein.

As an appropriate example, a method in which the compounds represented by the Formula (XXXXXIII) are reacted in an inert solvent with addition of an optically active ligand and a reducing agent to obtain the compounds represented by the Formula (XXXXXIV) can be mentioned.

As for the inert solvent, a halogen solvent such as dichloromethane and the like, a hydrocarbon solvent such as toluene and the like, an ether solvent such as tetrahydrofuran and the like can be used alone, or a mixed solvent thereof can be also used. A mixed solvent of toluene and tetrahydrofuran is preferable. As for the optically active ligand, (R)-2-methyl-CBS-oxazaborolidine, (R)-2-n-butyl-CBS-oxazaborolidine and the like can be mentioned. In this regard, (R)-2-methyl-CBS-oxazaborolidine-toluene solution, which is obtainable from Aldrich, etc. is preferable. As for the reducing agent, borane-tetrahydrofuran complex, borane-dimethyl sulfide complex, catecholborane and the like can be mentioned. Borane-dimethyl sulfide complex is preferable.

With respect to the use amount of the optically active ligand, it is preferably 0.05 to 1 moles compared to the compounds represented by the Formula (XXXXXIII). With respect to the use amount of the reducing agent, it is preferably 1 to 10 moles compared to the compounds represented by the Formula (XXXXXIII). With respect to the reaction temperature, it can be −78 to 50° C. and preferably −10 to 30° C. With respect to the reaction time, it can be 0.1 to 12 hours. 1 to 12 hours is preferable.

Process 12-3 (Step 12-3)

By reacting the compounds represented by the Formula (XXXXXIV) in an inert solvent with addition of a base, the compounds represented by the Formula (XXXXVII) can be obtained.

As for the inert solvent, water, an alcohol solvent such as methanol, 2-propanol, or ethanol and the like, or N,N-dimethyl formamide, tetrahydrofuran, 1,4-dioxane, acetone, 2-butanone, dimethyl sulfoxide, or acetonitrile and the like can be used alone, or a mixed solvent thereof can be also used. 2-Propanol is preferable. As for the base, an alkali metal compound such as potassium carbonate, sodium carbonate, cesium carbonate, sodium hydrogen carbonate, potassium hydroxide, sodium hydroxide, sodium methoxide, 28% sodium methoxide-methanol solution, or potassium t-butoxide and the like or a tertiary organic amine such as pyridine, 4-dimethylaminopyridine, 1,8-diazabicyclo[5,4,0]-undecene, trimethylamine, or triethylamine and the like can be mentioned. Sodium hydroxide is preferable.

With respect to the use amount of the base, it is preferably 1 to 10 moles compared to the compounds represented by the Formula (XXXXXIV). With respect to the reaction temperature, it is −40° C. to heating under reflux, and preferably −10 to 50° C. With respect to the reaction time, it is 0.1 to 48 hours, and preferably 0.1 to 12 hours. Compounds represented by the Formula (XXXXVI) can be also obtained by the method described in Scheme 13, for example.

Scheme 13

[Chemical Formula 32]

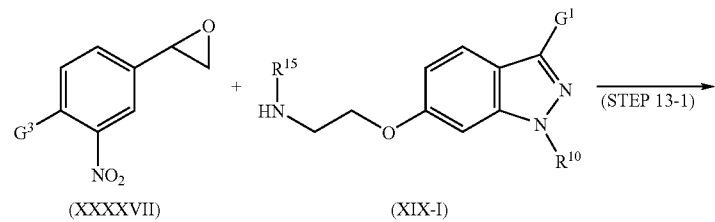

(XXXXVII) + (XIX-I) (STEP 13-1) →

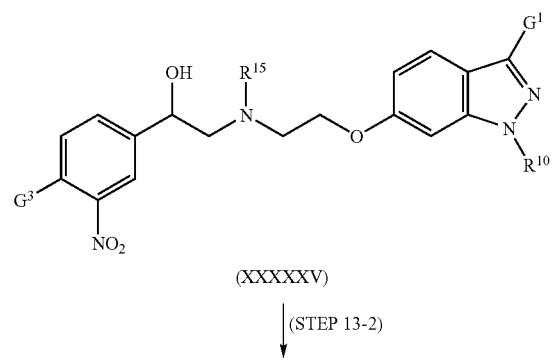

(XXXXV)

(STEP 13-2)

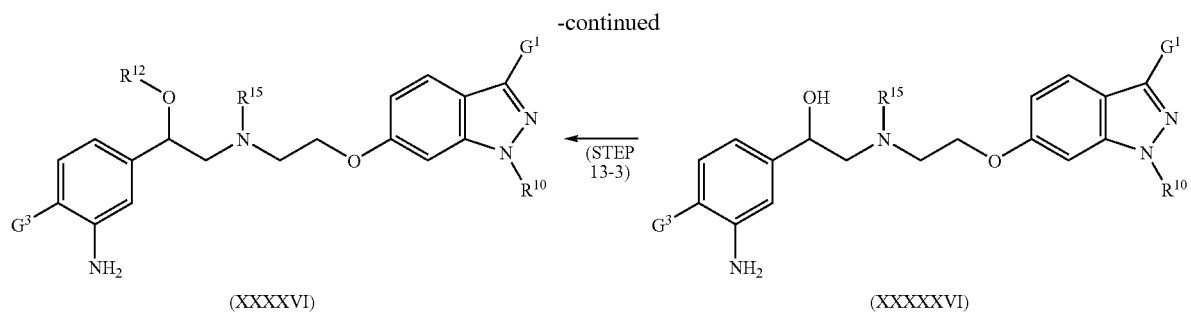

(XXXXVI) ←(STEP 13-3)— (XXXXXVI)

In each formula of Scheme 13, $G^1$, $G^3$, $R^{10}$, $R^{15}$ and $R^{12}$ have the same meaning as defined in the above.

Process 13-1 (Step 13-1)

By reacting the compounds represented by the Formula (XXXXVII) with the compounds represented by the Formula (XIX-I) in an inert solvent, the compounds represented by the Formula (XXXXXV) can be obtained.

As for the inert solvent; an alcohol solvent such as methanol, ethanol, 1-butanol, 2-butanol or 2-propanol and the like, or N,N-dimethyl formamide, N,N-dimethylacetamide, dimethyl sulfoxide, or acetonitrile and the like can be used alone, or a mixed solvent thereof can be also used. 2-Propanol is preferable.

With respect to the molar ratio between the compounds represented by the Formula (XXXXVII) and the compounds represented by the Formula (XIX-I), it may satisfy the condition of the compounds represented by the Formula (XXXX-VII)/the compounds represented by the Formula (XIX-I)=0.2 to 5 moles, and preferably 0.75 to 1.5 moles. With respect to the reaction temperature, it can be −10° C. to heating under reflux, and preferably 60° C. to heating under reflux. With respect to the reaction time, it can be 0.5 to 48 hours, and preferably 12 to 48 hours.

Process 13-2 (Step 13-2)

By reacting the compounds represented by the Formula (XXXXXV) with hydrogen gas in an inert solvent with addition of a catalyst, the compounds represented by the Formula (XXXXXVI) can be obtained.

As for the inert solvent, an alcohol solvent such as methanol, ethanol, 1-butanol, 2-butanol or 2-propanol and the like, or ethers such as tetrahydrofuran, diethyl ether and the like can be used alone, or a mixed solvent thereof can be also used. A mixed solution of ethanol or tetrahydrofuran-methanol is preferable. As for the catalyst, palladium on carbon powder, platinum oxide ($PtO_2$), CM-101 catalyst obtainable from N.E. Chemcat Corp., etc. or activated nickel and the like can be mentioned. Palladium on carbon powder or CM-101 catalyst is preferable. With respect to the reaction temperature, it is 0° C. to heating under reflux, and preferably 0 to 60° C. With respect to the reaction time, it can be 0.5 hours to 3 days, and preferably 1 hour to 3 days.

In addition, as it is shown in Reference example 68 and Reference example 73, modification into an appropriate protecting group can be made.

Process 13-3 (Step 13-3)

By carrying out a protection reaction of the hydroxyl group included in the compounds represented by the Formula (XXXXXVI) based on a well known method, for example, according to the method described in Protective Groups in Organic Synthesis, published by John Wiley and Sons (2007 edition), etc., the compounds represented by the Formula (XXXXVI) can be produced.

As an appropriate example, a method in which the compounds represented by the Formula (XXXXXVI) are reacted with the silylating agent in an inert solvent with addition of a base to obtain the compounds represented by the Formula (XXXXVI) can be mentioned.

As for the inert solvent, N,N-dimethyl formamide and the like can be mentioned. As for the base, imidazole and the like can be mentioned. As for the silylating agent, triethylchlorosilane or tert-butyldimethylchlorosilane and the like can be mentioned.

With respect to the reaction temperature, it can be −20 to 60° C., and 0 to 30° C. is preferable. With respect to the reaction time, it can be 0.5 to 48 hours, and preferably 1 to 24 hours.

Compounds represented by the Formula (XIII-I) can be also obtained by the method described in Scheme 14, for example.

Scheme 14

[Chemical Formula 33]

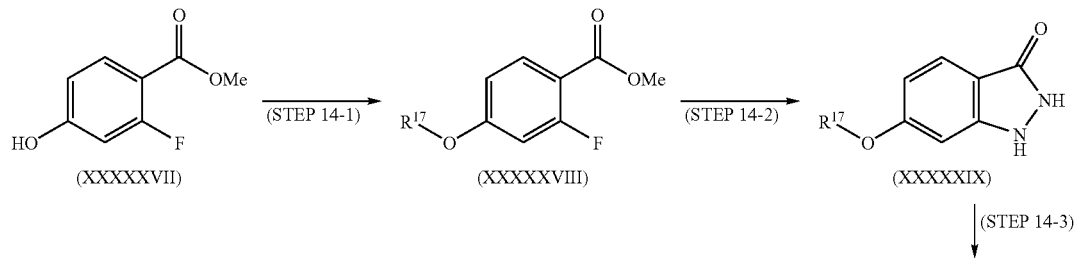

(XXXXVII) —(STEP 14-1)→ (XXXXVIII) —(STEP 14-2)→ (XXXXIX)

|(STEP 14-3)

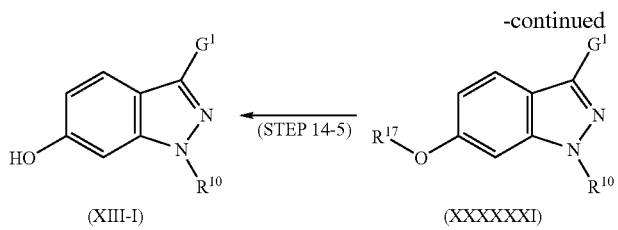
(XIII-I)

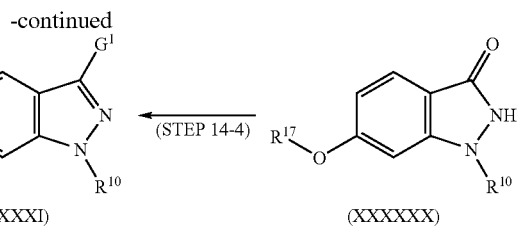
(XXXXXXI) (XXXXXX)

In each formula of Scheme 14, $G^1$ is a —$OCHF_2$ group or a —$OCF_3$ group and $R^{10}$ and $R^{17}$ are as defined in the above.

Process 14-1 (Step 14-1)

When protection of the hydroxyl group included in Compound (XXXXXVII), that is available from Changzhou KeweiFine Chemical Co., Ltd., is required, it can be carried out based on a well known method, for example, according to the method described in Protective Groups in Organic Synthesis, published by John Wiley and Sons (2007 edition), and the compounds represented by the Formula (XXXXXVIII) can be produced.

As an appropriate example, by reacting Compound (XXXXXVII) with a benzylating agent and a base in an inert solvent, the compounds represented by the Formula (XXXXXVIII) can be obtained.

As for the inert solvent, ketones such as acetone, methylethyl ketone and the like, ethers such as tetrahydrofuran, diethyl ether and the like, inert solvents such as N,N-dimethyl formamide and the like can be used alone, or a mixed solvent thereof can be also used. Acetone is preferable. As for the benzylating agent, benzyl chloride, benzyl bromide and the like can be mentioned. Benzyl bromide is preferable. As for the base, an inorganic base such as potassium carbonate, sodium carbonate, cesium carbonate, sodium hydrogen carbonate, potassium hydroxide, sodium hydroxide, sodium methoxide, potassium t-butoxide and the like, or an organic amine such as pyridine, 4-dimethylaminopyridine, 1,8-diazabicyclo[5,4,0]-undecene, trimethylamine, triethylamine and the like can be mentioned. Potassium carbonate is preferable.

Use amount of the base is preferably 1 to 10 moles compared to Compound (XXXXXVII). Use amount of the benzylating agent is preferably 1 to 10 moles compared to Compound (XXXXXVII).

With respect to the reaction temperature, it can be −20° C. to heating under reflux, and preferably 0 to 70° C. With respect to the reaction time, it can be 0.1 to 48 hours, and preferably 1 to 24 hours.

Process 14-2 (Step 14-2)

By carrying out a reaction with addition of hydrazines, and if necessary with addition of a base, to the compounds represented by the Formula (XXXXXVIII) in an inert solvent, Compound (XXXXXIX) can be obtained.

As for the inert solvent, alcohols such as methanol, ethanol, 1-butanol or 2-butanol and the like, ethers such as tetrahydrofuran, or dimethoxyethane and the like, benzenes such as benzene, toluene, or xylene and the like can be used alone, or a mixed solvent thereof can be also used. 1-Butanol is preferable. As for the hydrazines, hydrazine-monohydrate, hydrazine-monohydrochloride, hydrazine-dihydrochloride, or hydrazine-hydrate can be mentioned. Hydrazine-monohydrate is preferable. As for the base, an inorganic base such as sodium acetate, potassium carbonate, sodium carbonate, cesium carbonate, sodium hydrogen carbonate and the like can be mentioned.

With respect to the use amount of the hydrazines, it can be 1 to 20 moles, and preferably 1 to 15 moles compared to the compounds represented by the Formula (XXXXXVIII). With respect to the reaction temperature, it can be 0° C. to heating under reflux. Further, by carrying out a reaction in a sealed reaction vessel under microwave radiation, the reaction temperature can be raised above the reflux temperature of the solvent. In this case, the temperature is preferably 100 to 200° C. With respect to the reaction time, it can be 0.1 to 48 hours. 0.1 to 12 hours is preferable.

Process 14-3 (Step 14-3)

When a protecting group is desired for the amine group included in the compounds represented by the Formula (XXXXXIX), a reaction can be carried out according to a well known method, for example, according to the method described in Protective Groups in Organic Synthesis, published by John Wiley and Sons (2007 edition), and the compounds represented by the Formula (XXXXXX) can be produced. As an appropriate example, by reacting the compounds represented by the Formula (XXXXXIX) in an inert solvent with $Boc_2O$, a base, and if necessary with addition of a catalyst, the compounds represented by the Formula (XXXXXX) can be produced.

As for the inert solvent, ethers such as diethyl ether, tetrahydrofuran, dimethoxyethane and the like, halogenated hydrocarbons such as dichloromethane, 1,2-dichloroethane and the like, benzenes such as benzene, toluene, xylene and the like, and an inert solvent such as acetonitrile and the like can be used alone, or a mixed solvent thereof can be also used. Dichloromethane is preferable. As for the base, an inorganic base such as potassium carbonate, sodium carbonate, cesium carbonate, sodium hydrogen carbonate, potassium hydroxide, sodium hydroxide, sodium methoxide, or potassium t-butoxide and the like or a tertiary organic amine such as pyridine, 4-dimethylaminopyridine, 1,8-diazabicyclo[5,4,0]-undecene, trimethylamine, or triethylamine and the like can be mentioned. Triethylamine is preferable. As for the catalyst, 4-N,N-dimethylaminopyridine and the like can be mentioned.

$Boc_2O$ is preferably 1 to 10 moles compared to the compounds represented by the Formula (XXXXXIX). The base is preferably 1 to 10 moles compared to the compounds represented by the Formula (XXXXXIX). The catalyst is 0.001 to 1 moles compared to the compounds represented by the Formula (XXXXXIX). With respect to the reaction temperature, it can be −20 to 100° C., and preferably 0 to 50° C. With respect to the reaction time, it can be 0.1 to 48 hours, and preferably 1 to 24 hours.

Process 14-4 (Step 14-4)

By carrying out a reaction of the compounds represented by the Formula (XXXXXX) based on a well known method, for example, according to the method described in OrganoFluorine Chemistry (Kenji Uneyama, published by Blackwell, pages 257-292 or page 310), or in view of the methods that are described in the references cited therein, the compounds represented by the Formula (XXXXXXI) can be obtained. As an appropriate example, a method in which the compounds represented by the Formula (XXXXXX) are reacted in an inert solvent with an agent for difluoromethylation and a base to obtain the compounds represented by the Formula (XXXXXXI) can be mentioned.

As for the inert solvent, water, or an aprotic polar solvent such as N,N-dimethyl formamide, N,N-dimethylacetamide, dimethyl sulfoxide, N-methylpyrrolidone, or acetonitrile and the like can be used alone, or a mixed solvent thereof can be also used. N,N-dimethyl formamide is preferable.

As for the agent for difluoromethylation, chlorodifluoromethane, sodium chlorodifluoroacetic acid, chlorodifluoroacetic acid-tert-butyl ester, 2-chloro-2,2-difluoroacetophenone, 2,2-difluoro-2-(fluorosulfonyl)acetic acid, methyl chlorodifluoroacetic acid and the like can be mentioned. Sodium chlorodifluoroacetic acid is preferable.

As for the inert solvent, alcohols such as methanol, ethanol, 1-butanol, 2-butanol, or 2-propanol and the like, ethers such as tetrahydrofuran, diethyl ether and the like can be used alone, or a mixed solvent thereof can be also used. Tetrahydrofuran is preferable. As for the catalyst, palladium on carbon powder can be mentioned. With respect to the reaction temperature, it can be 0° C. to heating under reflux, and preferably 0 to 60° C. With respect to the reaction time, it can be 0.5 to 48 hours, and preferably 1 to 24 hours.

Compounds represented by the Formula (XIII-I) can be also obtained by the method described in Scheme 15, for example.

Scheme 15

[Chemical Formula 34]

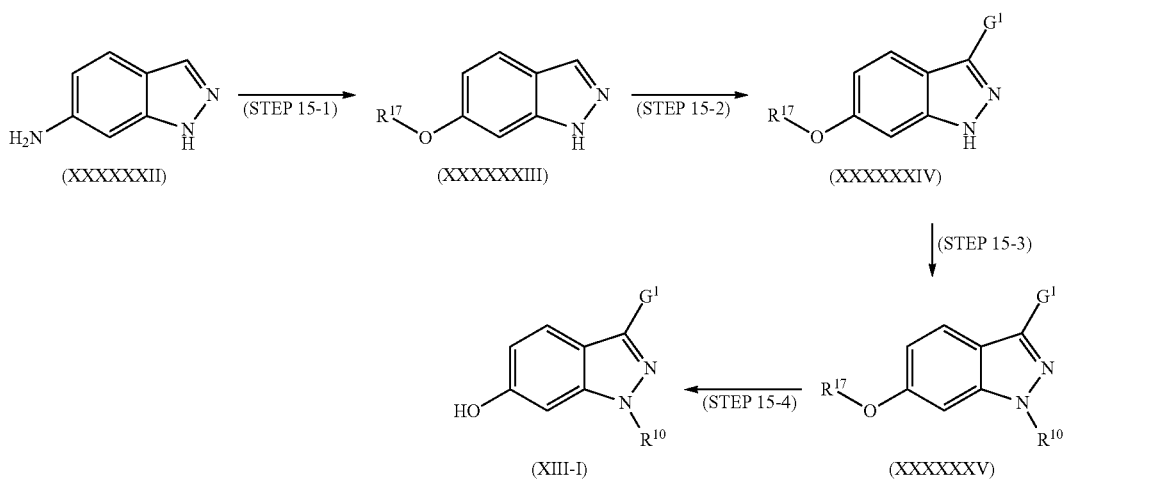

As for the base, an inorganic base and an alkali metal compound such as a potassium carbonate, sodium carbonate, cesium carbonate, sodium hydrogen carbonate, potassium hydroxide, sodium hydroxide, sodium methoxide, potassium t-butoxide and the like can be mentioned. Potassium carbonate is preferable.

With respect to the agent for difluoromethylation, it can be used in an amount of 1 to 20 moles, and preferably 1 to 10 moles compared to the compounds represented by the Formula (XXXXXX). With respect to the base, it can be used in an amount of 1 to 20 moles, and preferably 1 to 10 moles compared to the compounds represented by the Formula (XXXXXX). With respect to the reaction temperature, it can be 25° C. to heating under reflux, and preferably 25 to 100° C. With respect to the reaction time, it can be 0.1 to 48 hours, and preferably 1 to 24 hours.

Process 14-5 (Step 14-5)

When removal of a protecting group included in the compounds represented by the Formula (XXXXXXI) is required, it can be carried out according to the method described in Protective Groups in Organic Synthesis, published by John Wiley and Sons (2007 edition), for example, and as a result, the compounds represented by Formula (XIII-I) can be obtained.

As an appropriate example, by adding a catalyst to the compounds represented by the Formula (XXXXXXI) in an inert solvent and carrying out the reaction in the presence of hydrogen gas, the compounds represented by the Formula (XIII-I) can be obtained.

In each formula of Scheme 15, $G^1$ is a halogen atom and $R^{10}$ and $R^{17}$ are as defined in the above.

Process 15-1 (Step 15-1)

By carrying out a reaction of Compound (XXXXXXII), which is obtainable from Tokyo Chemical Industry Co., Ltd., based on a well known method, for example, according to the method described in New Experimental Chemistry Series, $4^{th}$ ed. (Vol. 20, pages 112 to 114, published by Maruzen Company, Limited) or in view of the methods that are described in the references cited therein, the compounds represented by the Formula (XXXXXXIII) can be obtained. As an appropriate example, a method in which Compound (XXXXXXII) is reacted in an inert solvent with an agent for introducing a diazonium salt or with a nitrosoating agent with addition of acid to form a diazonium salt of Compound of (XXXXXXII), which is then reacted with acetic acid and the like to obtain the compounds represented by the Formula (XXXXXXIII), can be mentioned.

As for the inert solvent, water, etc. is preferable. As for the agent for introducing a diazonium salt or a nitrosoating agent, sodium nitrite, tert-butyl nitrite or isoamyl nitrite and the like can be mentioned. Sodium nitrite is preferable. As for the acid, hydrochloric acid, sulfuric acid, or tetrafluoroboric acid and the like can be mentioned. Tetrafluoroboric acid is preferable.

With respect to the use amount of the agent for introducing a diazonium salt or a nitrosoating agent, 1 to 10 moles compared to Compound (XXXXXXII) is preferable. With respect to the use amount of acid, it is preferably 1 to large excess mole compared to Compound (XXXXXXII). With respect to the reaction temperature, it is preferably −20 to 100° C. With respect to the reaction time, it can be 0.1 to 48 hours, and preferably 1 to 24 hours.

Further, when $R^{17}$ is a hydrogen atom, protection of a hydroxyl group can be carried out. Protection reaction can be carried out according to the method described in Protective Groups in Organic Synthesis, published by John Wiley and Sons (2007 edition), for example.

Process 15-2 (Step 15-2)

By reacting the compounds represented by the Formula (XXXXXXIII) with a halogenating agent in an inert solvent, if necessary, with addition of a base, the compounds represented by the Formula (XXXXXXIV) can be obtained.

As for the inert solvent, ethers such as diethyl ether, tetrahydrofuran, or dimethoxyethane and the like, halogenated hydrocarbons such as dichloromethane, chloroform, or 1,2-dichloroethane and the like, benzenes such as benzene, toluene, or xylene and the like or, acetonitrile and the like can be used alone, or a mixed solvent thereof can be also used. Tetrahydrofuran or acetonitrile is preferable. As for the halogenating agent, chlorine gas, bromine, iodine, N-bromosuccinimide, N-chlorosuccinimide, or N-iodosuccinimide and the like can be mentioned. N-chlorosuccinimide is preferable. As for the base, an alkali metal compound such as potassium carbonate, sodium carbonate, cesium carbonate, sodium hydrogen carbonate, potassium hydroxide, sodium hydroxide, sodium methoxide, or potassium t-butoxide and the like, or a tertiary organic amine such as pyridine, 4-dimethylaminopyridine, 1,8-diazabicyclo[5,4,0]-undecene, trimethylamine, or triethylamine and the like can be mentioned. Potassium t-butoxide is preferable.

With respect to the use amount of the halogenating agent, it is preferably 1 to 10 moles compared to the compounds represented by the Formula (XXXXXXIII). With respect to the use amount of the base, it is 0 to 10 moles and preferably 0 to 5 moles compared to the compounds represented by the Formula (XXXXXXIII). With respect to the reaction temperature, it can be −20° C. to heating under reflux, and 0° C. to heating under reflux. With respect to the reaction time, it can be 0.1 to 24 hours. 0.1 to 12 hours is preferable.

Process 15-3 (Step 15-3)

When a protecting group is desired for the indazole group included in the compounds represented by the Formula (XXXXXXIV) is required, by selecting the protecting group of the indazole group as described above, indazole group protection can be carried out according to a known method, for example the method described in Protective Groups in Organic Synthesis, published by John Wiley and Sons (2007 edition), etc. to obtain the compounds represented by the Formula (XXXXXV). As an appropriate example, a method in which the compounds represented by the Formula (XXXXXXIV) are added with a protecting agent in an inert solvent, if necessary with a base or a catalyst, to give the compounds represented by the Formula (XXXXXXV) can be mentioned.

As for the inert solvent, ethers such as diethyl ether, tetrahydrofuran, or dimethoxyethane and the like, halogenated hydrocarbons such as dichloromethane or 1,2-dichloroethane and the like, benzenes such as benzene, toluene or xylene and the like or acetonitrile and the like can be used alone, or a mixed solvent thereof can be also used. As for the protecting agent, dihydropyran or di-tert-butyl carbonate and the like can be mentioned. As for the base, an alkali metal compound such as potassium carbonate, sodium carbonate, cesium carbonate, sodium hydrogen carbonate, potassium hydroxide, sodium hydroxide, sodium methoxide, or potassium t-butoxide and the like, or a tertiary organic amine such as pyridine, 4-dimethylaminopyridine, 1,8-diazabicyclo[5,4,0]-undecene, trimethylamine, or triethylamine and the like can be mentioned. Regarding the catalyst, an acid catalyst or a base catalyst can be used depending on a type of protection reaction. As for the acid catalyst, hydrochloric acid or p-toluene sulfonic acid and the like can be mentioned. As for the base catalyst, 4-dimethylaminopyridine and the like can be mentioned.

With respect to the use amount of the protecting agent, it can be 1 to 10 moles, and preferably 1 to 5 moles compared to the compounds represented by the Formula (XXXXXXIV). With respect to the use amount of the base, it can be 0 to 10 moles, and preferably 0 to 5 moles compared to the compounds represented by the Formula (XXXXXXIV). With respect to the use amount of the catalyst, it can be 0.001 to 1 moles, and preferably 0.01 to 0.5 moles compared to the compounds represented by the Formula (XXXXXXIV). With respect to the reaction temperature, it can be −20° C. to heating under reflux, and preferably 0 to 100° C. With respect to the reaction time, it can be 0.1 to 48 hours, and preferably 1 to 24 hours.

Process 15-4 (Step 15-4)

When removal of a protecting group included in the compounds represented by the Formula (XXXXXXV) is required, it can be carried out according to the method described in Protective Groups in Organic Synthesis, published by John Wiley and Sons (2007 edition), for example, to obtain the compounds represented by the Formula (XIII-I). As an appropriate example, a method in which the silyl group included in the compounds represented by the Formula (XXXXXXI) is removed in an inert solvent as described above to give the compounds represented by the Formula (XIII-I) can be mentioned.

With respect to the reaction temperature, it can be 0° C. to heating under reflux, and preferably 0 to 60° C. With respect to the reaction time, it can be 0.5 to 48 hours, and preferably 1 to 24 hours.

The compounds of the present invention, each reacting compound and the intermediate that are obtained by the methods described above can be separated and purified according to a general method including extraction, distillation, chromatography, crystallization and the like.

With respect to a method of producing the compounds of the present invention comprising an asymmetric carbon, in addition to the production method based on asymmetric reduction described before, a method which uses a commercially available reacting material in which a portion corresponding to the asymmetric carbon is already optically active (or, which can be produced according to a known method or in view of a known method) can be mentioned. In addition, there is a method by which the compounds of the present invention or a precursor thereof are resolved into an optically active isomer according to a generally known method. Such method includes a high pressure liquid chromatography (HPLC) method using an optically active column, a traditional optical fractional crystallization in which a salt is formed with an optically active reagent, followed by resolution via fractional crystallization, etc., and then degradation to give a free form, or a method in which a diastereomer is first formed by condensation with an optically active reagent, followed by isolation, purification and further degradation. When a precursor is separated to give an optically active form, the preparation method as described in the above can be then carried out to produce the optically active compounds of the present invention.

The compound of the present invention is not recognized of toxicity and is useful as a medicine. Further, as having β3 adrenergic receptor agonist activity, they can be used as a medicine for prevention and treatment of disorders that are related to β3 adrenergic receptor, for example. Disorders that are related to β3 adrenergic receptor indicate every disorder that can be improved by agonistic activity of the receptor, and the examples thereof include overactive bladder, urinary inconsistence, interstitial cystitis, diabetes, obesity, hyperlipidemia, fatty liver, digestive system disorders (preferably, abnormal movement or ulcer in digestive system), depression, biliary stone, a disorder derived from hyperactivity of biliary tract, or a disorder derived from decreased tear secretion, etc. In particular, the medicine of the present invention is preferably used for treatment and/or prevention of overactive bladder or urinary incontinence. More preferably, the medicine of the present invention is used for treatment of overactive bladder. In addition, there is also other embodiment in which the medicine of the present invention is more preferably used for treatment of urinary incontinence.

Overactive bladder is defined by ICS (The International Continence Society) as a "disorder which has urinary urgency as a main syndrome, generally accompanied with urinary frequency and nocturia, either with or without urge incontinence." In addition, urinary incontinence is generally defined by ICS as an "involuntary leakage of urine that is objectively demonstratable and causes a social or hygienic problem."

Further, the compounds of the present invention are useful as a selective β3/α1 adrenergic receptor agonist. In particular, it is preferable that, even when the compounds of the present invention are administered to a patient who is in need of activated β3 adrenergic receptor, they do not substantially activate α1 adrenergic receptor in the patient.

Herein, as a preferred mode of the compounds which can "selectively activate β3/α1 adrenergic receptor", a compound having Intrinsic Activity [I.A. (%)] ratio of 0.8 or less can be mentioned wherein Intrinsic Activity [I.A. (%)] ratio indicates a value that is obtained by dividing I.A. (%) of the compound in α1 adrenergic receptor by I.A. (%) of the compound in β3 adrenergic receptor as described in Test example 4 below. Preferably, a compound having intrinsic activity ratio of 0.7 or less, more preferably 0.5 or less, and still more preferably 0.3 or less can be mentioned. In addition, a compound having intrinsic activity ratio of 0.15 or less is also more preferred.

In addition, as another preferred mode of the compounds which can "selectively activate β3/α1 adrenergic receptor", a compound having the I.A. ratio of 0.8 or less and EC50 ratio of 5 or more can be mentioned wherein EC50 ratio indicates a value that is obtained by dividing EC50 of the compound in α1 adrenergic receptor by EC50 of the compound in β3 adrenergic receptor. As another preferred mode, a compound having the I.A. ratio of 0.5 or less and EC50 ratio of 5 or more can be mentioned. As another preferred mode, a compound having the I.A. ratio of 0.3 or less and EC50 ratio of 5 or more can be mentioned. As another preferred mode, a compound having the I.A. ratio of 0.15 or less and EC50 ratio of 5 or more can be mentioned.

In addition, as another preferred mode of the compounds which can "selectively activate β3/α1 adrenergic receptor", a compound having the I.A. ratio of 0.8 or less and EC50 ratio of 10 or more can be mentioned. As another preferred mode, a compound having the I.A. ratio of 0.5 or less and EC50 ratio of 10 or more can be mentioned. As another preferred mode, a compound having the I.A. ratio of 0.3 or less and EC50 ratio of 10 or more can be mentioned. As another preferred mode, a compound having the I.A. ratio of 0.15 or less and EC50 ratio of 10 or more can be mentioned.

In addition, as another preferred mode of the compounds which can "selectively activate β3/α1 adrenergic receptor", a compound having the I.A. ratio of 0.8 or less and EC50 ratio of 15 or more can be mentioned. As another preferred mode, a compound having the I.A. ratio of 0.5 or less and EC50 ratio of 15 or more can be mentioned. As another preferred mode, a compound having the I.A. ratio of 0.3 or less and EC50 ratio of 15 or more can be mentioned. As another preferred mode, a compound having the I.A. ratio of 0.15 or less and EC50 ratio of 15 or more can be mentioned.

Further, the expression "do not substantially activate α1 adrenergic receptor" indicates that, according to Test example 4 below, the compounds have the I.A. of 55% or less, preferably 45% or less, more preferably 35% or less, still more preferably 25% or less, particularly preferably 15% or less, and more particularly preferably 5% or less for the α1 adrenergic receptor.

Further explained, the compounds of the present invention have excellent safety (i.e., favorable toxicity or safety pharmacology) and pharmacokinetics of a drug, etc., and usefulness as an active ingredient for a medicine is confirmed.

Examples of safety test include the followings, but are not limited thereto. Cell toxicity test (test using HL60 cell or liver cell, etc.), Genetic Toxicity Test (Ames test, mouse lymphoma TK test, chromosome aberration test, micronucleus test, etc.), skin sensitization test (Buehler method, GPMT method, APT method, LLNA test, etc.), skin photosensitization test (Adjuvant and Strip method, etc.), eye irritancy test (a single instillation test, a continuous instillation for a short period of time, a repeated application test, etc.), safety pharmacology test regarding cardiovascular system (electrocardiogram, heart rate, and blood pressure measurement based on telemetry method, APD method, hERG inhibition evaluation test), safety pharmacology test regarding central nervous system (FOB method, modified Irwin method, etc.), safety pharmacology test regarding respiratory system (measurement using an instrument for measuring respiratory function (plethysmography method), measurement using an instrument for determining blood gas analysis, etc.), general toxicity test, sexual reproduction toxicity test, etc.

In addition, regarding a test for pharmacokinetics of a drug, the followings are included, but not limited thereto. Inhibition or induction test regarding cytochrome P450 enzyme, cell permeation test (i.e., a test using CaCO-2 cells or MDCK cells, etc.), drug-transporter ATPase assay, oral absorption test, blood concentration time profile test, metabolism test (stability test, metabolic molecular species test, reactivity test, etc.), solubility test (i.e., solubility test based on turbidity, etc.) and the like.

Usefulness of the compounds of the present invention as an active ingredient for a medicine can be determined based on a cell toxicity test, for example. Regarding a cell toxicity test, a method using various cultured cells like human pre-leukemia HL-60 cells, primarily-isolated cultured liver cells, neutrophil fraction prepared from human peripheral blood, etc. can be mentioned. Test can be carried out according to the method described below, but it is not limited thereto. Cells are prepared in suspension comprising $10^6$ to $10^7$ cells/ml. 0.01 mL to 1 mL suspension is aliquoted to a micro tube or a micro plate, etc. Then, a solution comprising the test compound dissolved therein is added thereto in an amount of 1/100 to 1 times the cell suspension, followed by culturing under the condition of 37° C., 5% $CO_2$ for 30 minutes to several days.

Once the cell culture is completed, cell viability ratio is determined using MTT method or WST-1 method (Ishiyama, M., et al., In Vitro Toxicology, 8, p. 187, 1995), etc. By measuring cell toxicity expressed by the compounds of the present invention, their usefulness as an active ingredient of a medicine can be confirmed.

Usefulness of the compounds of the present invention as an active ingredient for a medicine can be determined based on a Genetic Toxicity Test, for example. Examples of Genetic Toxicity Test include Ames test, mouse lymphoma TK test, chromosome aberration test, micronucleus test, etc. The Ames test is a method for determining reversion mutation by culturing designated cells such as *Salmonella* or *E. Coli* on a culture dish comprising a test compound (see, II-1. Genetic Toxicity Test under "Guidelines for Genetic Toxicity Test", Pharmaceuticals Examination, Vol. 1604, 1999). Further, the mouse lymphoma TK test is a test for determining a mutational property of a gene in which thymidine kinase gene of mouse lymphoma cell L5178Y is used as a target (see, II-3. Mouse Lymphoma TK Test under "Guidelines for Genetic Toxicity Test", Pharmaceuticals Examination, Vol. 1604, 1999; Clive, D. et al., Mutat. Res., 31, pp. 17-29, 1975; Cole, J., et al., Mutat. Res., 111, pp. 371-386, 1983, etc.). Further, the chromosome aberration test is a method in which mammalian cells are cultured in the presence of a test compound and the cells are fixed, and the chromosome is stained and observed to determine any activity which may cause chromosomal aberration (see, 11-2. Chromosome Aberration Test Using Cultured Mammalian Cells under "Guidelines for Genetic Toxicity Test", Pharmaceuticals Examination, Vol. 1604, 1999). Further, the micronucleus test is a method of determining an ability to form a micronucleus which is caused by chromosomal aberration, and it includes a method in which rodents are used (i.e., in vivo test, II-4. Micronucleus Test Using Rodents, under "Guidelines for Genetic Toxicity Test", Pharmaceuticals Examination, Vol. 1604, 1999; Hayashi, M. et al., Mutat. Res., 312, pp. 293-304, 1994; Hayashi, M. et al., Environ. Mol. Mutagen., 35, pp. 234-252, 2000) or cultured cells are used (i.e., in vitro test, Fenech, M. et al., Mutat. Res., 147, pp. 29-36, 1985; Miller, B., et al., Mutat. Res., 392, pp. 45-59, 1997), etc. By running one, two or more tests based on these methods, gene toxicity of the compounds of the present invention can be clearly identified so that their usefulness as an active ingredient of a medicine can be confirmed.

Usefulness of the compounds of the present invention as an active ingredient for a medicine can be determined based on a skin sensitization test, for example. Examples of skin sensitization test include Buehler method (Buehler, E. V. Arch. Dermatol., 91, pp. 171-177, 1965), GPMT method (i.e., Maximization method, Magnusson, B. et al., J. Invest. Dermatol., 52, pp. 268-276, 1969), or APT method (i.e., Adjuvant and Patch method, Sato, Y. et al., Contact Dermatitis, 7, pp. 225-237, 1981), wherein a guinea pig is used for a skin sensitization test. Further, as a skin sensitization method wherein a mouse is used, there is LLNA method (Local Lymph Node Assay method, OECD Guideline for the testing of chemicals 429, skin sensitization 2002; Takeyoshi, M. et al., Toxicol. Lett., 119(3), pp. 203-8, 2001; Takeyoshi, M. et al., J. Appl. Toxicol., 25(2), pp. 129-34, 2005) and the like. By running one, two or more tests based on these methods, skin sensitization property of the compounds of the present invention can be clearly identified so that their usefulness as an active ingredient of a medicine can be confirmed.

Usefulness of the compounds of the present invention as an active ingredient for a medicine can be determined based on a skin photosensitization test, for example. Examples of skin photosensitization test include a test using a guinea pig (see, Guidelines for Non-clinical test of pharmaceuticals—Explanation, 2002, YAKUJI NIPPO LIMITED 2002, 1-9: Skin Photosensitization Test, etc.). Further, specific methods include Adjuvant and Strip method (Ichikawa, H. et al., J. Invest. Dermatol., 76, pp. 498-501, 1981), Harber method (Harber, L. C., Arch. Dermatol., 96, pp. 646-653, 1967), Horio method (Horio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and man", Tokyo Univ. Press, Tokyo, pp. 529-557, 1974), Vinson method (Vinson, L. J., J. Soc. Cosm. Chem., 17, pp. 123-130, 1966) and the like. By running one, two or more tests based on these methods, skin photosensitization property of the compounds of the present invention can be clearly identified so that their usefulness as an active ingredient of a medicine can be confirmed.

Usefulness of the compounds of the present invention as an active ingredient for a medicine can be determined based on an ocular irritation test, for example. Examples of ocular irritation test include a single application test (eye drop is applied only one time), a continuous application for a short period of time (eye drop is applied multiple times at regular intervals for a short period of time), a repeated application test (eye drop is applied intermittently for several days to several tens of days), etc. using a rabbit eye, a monkey eye, etc. In addition, there is a method by which eye irritation at certain time point after eye drop application is measured by Draize score, etc. (Fukui, N. et al., Gendai no Rinsho, 4(7), pp. 277-289, 1970). By running one, two or more tests based on these methods, compounds' characteristics regarding eye irritation can be clearly identified so that their usefulness as an active ingredient of a medicine can be confirmed.

Usefulness of the compounds of the present invention as an active ingredient for a medicine can be determined by carrying out a safety pharmacology test regarding cardiovascular system. Examples of safety pharmacology test regarding cardiovascular system include a telemetry method (i.e., a method by which compound's effect on an electrocardiogram, heart rate, blood pressure, blood flow, and the like is determined under non-anesthetized condition (Shigeru Kanno, Hirokazu Tsubone, Yoshitaka Nakata eds., Electrocardiography, Echocardiography, Blood Pressure, and Pathology test of an Animal for Basic and Clinical Medicine, 2003, published by Maruzen)), APD method (i.e., a method for measuring action potential duration of a myocardial cell (Muraki, K. et al., AM. J. Physiol., 269, H524-532, 1995; Ducic, I. et al., J. Cardiovasc. Pharmacol., 30(1), pp. 42-54, 1997)), measurement of hERG inhibition (patch clamp method (Chachin, M. et al., Nippon Yakurigaku Zasshi, 119, pp. 345-351, 2002), Binding assay method (Gilbert, J. D. et al., J. Pharm. Tox. Methods, 50, pp. 187-199, 2004), $Rb^+$ efflux assay method (Cheng, C. S. et al., Drug Develop. Indust. Pharm., 28, pp. 177-191, 2002), Membrane potential assay method (Dorn, A. et al., J. Biomol. Screen., 10, pp. 339-347, 2005) etc.), etc. By running one, two or more tests based on these methods, effect of the compounds of the present invention on a cardiovascular system can be clearly identified so that their usefulness as an active ingredient of a medicine can be confirmed.

Usefulness of the compounds of the present invention as an active ingredient for a medicine can be determined by carrying out a safety pharmacology test regarding a central nervous system. Examples of safety pharmacology test regarding a central nervous system include FOB method (i.e., a method for evaluating overall function, Mattson, J. L. et al., J. American College of Technology 15 (3), pp. 239-254, 1996), modified Irwin method (i.e., a method for evaluating general symptoms and behavioral characteristics (Irwin, S. Comprehensive Observational Assessment (Berl.) 13, pp. 222-257, 1968)), etc. By running one, two or more tests based on these methods, effect of the compounds of the present invention on a central nervous system can be clearly identified so that their usefulness as an active ingredient of a medicine can be confirmed.

Usefulness of the compounds of the present invention as an active ingredient for a medicine can be determined by carrying out a safety pharmacology test regarding a respiratory system, for example. Examples of safety pharmacology test regarding a respiratory system include a measurement using an instrument for measuring respiratory function (i.e., a method which measures breathing number, amount of air per single breathing, amount of breathing air per minute or hour, (Drorbaugh, J. E. et al., Pediatrics, 16, pp. 81-87, 1955; Epstein, M. A. et al., Respir. Physiol., 32, pp. 105-120, 1978), or a measurement using a blood gas analyzer (i.e., a method which measures blood gas, hemoglobin oxygen saturation, etc., Matsuo, S. Medicina, 40, pp. 188, 2003), etc. By running one, two or more tests based on these methods, effect of the compounds of the present invention on a respiratory system can be clearly identified so that their usefulness as an active ingredient of a medicine can be confirmed.

Usefulness of the compounds of the present invention as an active ingredient for a medicine can be determined by carrying out a general toxicity test. Specifically, according to a general toxicity test, a test compound which is either dissolved or suspended in an appropriate solvent is orally administered or intravenously administered of a single time or multiple times (for several days) to rodents such as rat, mouse, and the like or non-rodents such as monkey, dog and the like as a subject animal, and then animal's general state or any change in clinical chemistry or tissue in terms of pathology, etc. is determined. By identifying general toxicity of a compound based on this method, usefulness of the compounds of the present invention as an active ingredient for a medicine can be confirmed.

Usefulness of the compounds of the present invention as an active ingredient for a medicine can be determined by carrying out a sexual reproduction toxicity test. The test is to determine any side effect caused by a test compound on sexual reproduction process by using rodents such as rat, mouse, and the like or non-rodents such as monkey, dog and the like (Guidelines for Non-clinical test of pharmaceuticals—Explanation, 2002, YAKUJI NIPPO LIMITED 2002, 1-6: Sexual Reproduction Toxicity Test, etc.). With respect to a sexual reproduction toxicity test, a test relating to development of an early embryo from fertilization to implantation, a test relating to development before and after birth and an activity of a mother, a test relating to development of an embryo and a fetus (see, [3] Sexual Reproduction Toxicity Test under "Guidelines for Toxicity Test for Pharmaceuticals", Pharmaceuticals Examination, Vol. 1834, 2000), etc. can be mentioned. By identifying sexual reproduction toxicity of the compounds of the present invention based on this method, usefulness of a compound as an active ingredient for a medicine can be confirmed.

Usefulness of the compounds of the present invention as an active ingredient for a medicine can be determined by carrying out an inhibition or induction test of cytochrome P450 enzyme (Gomez-Lechon, M. J. et al., Curr. Drug Metab. 5(5), pp. 443-462, 2004). Examples of the test include a method of determining in vitro an inhibitory effect of a compound on an enzyme activity by using cytochrome P450 enzyme of each molecular species that is either purified from a cell or prepared using a genetic recombinant, or a microsome as a human P450 expression system (Miller, V. P. et al., Arm. N.Y. Acad. Sci., 919, pp. 26-32, 2000), a method of determining expression of cytochrome P450 enzyme for each molecular species or variation in enzyme activity by using a human liver microsome or cell homogenate (Hengstler, J. G. et al., Drug Metab. Rev., 32, pp. 81-118, 2000), a method of examining compound's activity of inducing the enzyme by extracting the RNA from human liver cells that have been exposed to the compound and comparing the amount of mRNA expression with that of a control (Kato, M. et al., Drug Metab. Pharmacokinet, 20 (4), pp. 236-243, 2005), etc. By running one, two or more tests based on these methods, effect of the compounds of the present invention on induction or inhibition of cytochrome P450 enzyme can be clearly identified so that their usefulness as an active ingredient of a medicine can be confirmed.

Usefulness of the compounds of the present invention as an active ingredient for a medicine can be determined by carrying out a cell permeation test, for example. Examples of the test include a method of determining compound's ability of penetrating cell membrane under in vitro cell culture system by using CaCO-2, for example (Delie, F. et al., Crit. Rev. Ther. Drug Carrier Syst., 14, pp. 221-286, 1997; Yamashita, S. et al., Eur. J. Pham. Sci., 10, pp. 195-204, 2000; Ingels, F. M. et al., J. Pham. Sci., 92, pp. 1545-1558, 2003), or a method of determining compound's ability of penetrating cell membrane under in vitro cell culture system by using MDCK cell (Irvine, J. D. et al., J. Pham. Sci., 88, pp. 28-33, 1999), etc. By running one, two or more tests based on these methods, the compounds' ability of penetrating cell membrane can be clearly identified so that their usefulness as an active ingredient of a medicine can be confirmed.

Usefulness of the compounds of the present invention as an active ingredient for a medicine can be determined by carrying out a drug transporter ATPase assay using ATP-Binding Cassette (ABC) transporter, for example. Examples of the ATPase assay include a method of determining whether or not the test compound is a substrate for P-gp by using P-glycoprotein (P-gp) baculovirus expression system (Germann, U. A., Methods Enzymol., 292, pp. 427-41, 1998), etc. Further, determination can be also carried out based on a transport assay using oocytes obtained from *Xenopus laevis*, as a solute carrier (SLC) transporter. With respect to transport assay, oocytes which express OATP2 can be used to confirm whether or not the test compound is a substrate for OATP2 (Tamai I. et al., Pharm Res. 2001 September; 18 (9): 1262-1269). By identifying the compounds' activity on ABC transporter or SLC transporter based on this method, usefulness of the compounds of the present invention as an active ingredient for a medicine can be confirmed.

Usefulness of the compounds of the present invention as an active ingredient for a medicine can be determined by carrying out oral absorptivity test, for example. Examples of the assay include a method of determining blood transfer property of the test compound after oral administration using LC-MS/MS method by preparing a certain amount of the test compound dissolved or suspended in a solvent, orally administering it to a rodent, a monkey or a dog, and measuring blood concentration of the compound over time (Harada Kenichi et al., eds. "Newest aspects in mass spectrometry for biological sciences", 2002, Kodansha Scientific, etc.). By identifying compound's oral absorptivity based on this method, usefulness of the compounds of the present invention as an active ingredient for a medicine can be confirmed.

Usefulness of the compounds of the present invention as an active ingredient for a medicine can be determined by carrying out a blood concentration time profile test, for example. Examples of the test include a method of determining blood concentration profile of the test compound using LC-MS/MS method by administering the compound to a rodent, a monkey or a dog and measuring blood concentration of the test compound over time (Harada Kenichi et al., eds. "Newest aspects in mass spectrometry for biological sciences", 2002, Kodansha Scientific, etc.). By identifying compound's blood concentration time profile based on this method, usefulness of the compounds of the present invention as an active ingredient for a medicine can be confirmed.

Usefulness of the compounds of the present invention as an active ingredient for a medicine can be determined by carrying out a metabolism test, for example. Examples of the test include a method of determining stability in blood (i.e., a method by which in vivo metabolism clearance of a compound is calculated by measuring its metabolism rate in a liver microsome of a human or other animal; Shou, W. Z. et. al., J. Mass Spectrom., 40(10), pp. 1347-1356, 2005; Li, C. et al., Drug Metab. Dispos., 34(6), 901-905, 2006), a metabolite molecular species test, a reactive metabolite testing method, etc. By running one, two or more tests based on these methods, the compounds' metabolic profile can be clearly identified so that their usefulness as an active ingredient of a medicine can be confirmed.

Usefulness of the compounds of the present invention as an active ingredient for a medicine can be determined by carrying out a dissolution test, for example. Examples of the dissolution test include a method of determining solubility based on turbidity (Lipinski, C. A. et al., Adv. Drug Deliv. Rev., 23, pp. 3-26, 1997; Bevan, C. D. et al., Anal. Chem., 72, pp. 1781-1787, 2000), etc. By identifying compound's dissolution property based on this method, usefulness of the compounds of the present invention as an active ingredient for a medicine can be confirmed.

Usefulness of the compounds of the present invention as an active ingredient for a medicine can be determined by examining problems associated with an upper gastrointestinal tract or a kidney, etc., for example. With respect to a pharmacological test for an upper gastrointestinal tract, compound's effect on gastric mucosal membrane using a fasted rat model having damaged gastric mucosal membrane can be mentioned. With respect to a pharmacological test for kidney function, a method of measuring renal blood flow and glomerular filtration rate [Physiology, $18^{th}$ ed. Bunkoto, 1986, Chapter 17] can be mentioned. By running one, two or more tests based on these methods, the compounds' effect on an upper gastrointestinal tract or a kidney function can be clearly identified so that their usefulness as an active ingredient of a medicine can be confirmed.

When the medicine of the present invention is administered to a human, it can be orally administered in form of a tablet, powder, a granule, a capsule, a sugar-coated tablet, a liquid or syrup, etc. Further, it can be also administered via parenteral route in form of an injection solution, a drop solution, a suppository, a trans-dermal or absorbing agent, etc. Still further, inhalation in spray form such as aerosol, dry powder, etc. can be also mentioned as preferable administration form.

Administration period of the medicine of the present invention is not specifically limited. However, when it is administered under the purpose of treatment, a period during which clinical signs of a disorder is found can be taken as a time period for the administration, in principle. In general, the administration is continued from several weeks to one year. However, depending on symptoms, it can be further administered, or can be continuously administered even after recovery from clinical symptoms. In addition, even when no clinical signs are observed, it can be administered for a preventative purpose based on clinician's judgment. Dosage of the medicine of the present invention is not specifically limited. For example, it can be generally in an effective amount of 0.01 to 2000 mg per day for an adult, a single or divided in several portions. Administration frequency can be from once a month to everyday. Preferably, it is once a week to three times a week, or five times a week, or can be administered every day. Single time dosage, administration period, and administration frequency, etc. may be either increased or decreased according to age, body weight, overall health of a subject, or disorder to be treated and severeness of the disorder, etc.

It is needless to say that the medicine of the present invention can be administered with other preventative and/or therapeutic agent that are used against various symptoms or disorders, aside from the preventative and/or therapeutic purpose of the medicine of the present invention.

EXAMPLES

Herein below, the present invention will be explained in greater detail in view of the Examples, Reference examples and Test examples. However, scope of the present invention is not limited to them.

Regarding the Examples described below, various analyses were carried out according to the following description.

(1) For thin layer chromatography (TLC), Precoated Silica Gel 60 F254 (i.e., TLC plate manufactured by Merck Co., Germany, product number 5715-1M) was used. After development using chloroform:methanol (1:0-1:1), or ethyl acetate:hexane (1:0-0:1), UV ray (254 nm or 365 nm) illumination was carried out, followed by chromogenic reaction using iodine solution, aqueous solution of potassium permanganate, phosphorus molybdenum acid (ethanol solution), ninhydrin, or dinitrophenyl hydrazine hydrochloride solution for identification.

(2) Column chromatography was carried out according to the following method.

With respect to those described as "COLUMN-A", multi-flap YFLC (manufactured by Yamazen Corp.) was used and Hi-Flash™ Column-Silicagel (manufactured by the same company) series was used as a column.

With respect to those described as "COLUMN-B", multi-flap YFLC (manufactured by Yamazen Corp.) was used and Purif Pack-Si (manufactured by Moritex Corp.) series was used as a column.

With respect to those described as "COLUMN-C", 2ch parallel purification device "Purif-α2 (50F)" (manufactured by Moritex Corp.) was used and PurifPack-Si (manufactured by the same company) series was used as a column.

With respect to those described as "COLUMN-D", 2ch parallel purification device "Purif-α2 (50F)" (manufactured by Moritex Corp.) was used and Hi-Flash™ Column-Silicagel (manufactured by Yamazen Corp.) series was used as a column.

With respect to those described as "COLUMN-E", silica gel 60N (globular, neutral and 40 to 100 μm, manufactured by Kanto Chemical Co., Inc.) was used.

With respect to those described as "COLUMN-F", BOND ELUT series (MEGABE-Si; manufactured by Varian) was used.

With respect to those described as "COLUMN-G", Quad1 fractionation system (manufactured by Biotage) was used and one or several cartridge columns selected from KP-Sil- 12M, 40S or 40M (manufactured by the same company) were used as a column depending on sample amount.

With respect to those described as "COLUMN-H", silica gel (manufactured by Merck Company) was used.

With respect to those described as "COLUMN-I", BOND-ESIL-SCX 40UM (manufactured by Varian) was used.

(3) For HPLC purification, LCMS fractionation system (manufactured by Waters Company) was used. With respect to those described as "HPLC-A", Develosil C-30-UG-5 (manufactured by Nomura Chemical Co., Ltd.) was used. With respect to those described as "HPLC-B", ODS column was used. As an elution solution, water-acetonitrile solvent comprising 0.1% acetic acid was used. For the HPLC purification, a target compound was obtained by having molecular weight as trigger and the solvent was removed via freeze drying, unless specifically described otherwise.

(4) For nuclear magnetic resonance (NMR) spectrum measurement, AL-300 (FT-NMR, manufactured by JEOL Co.), Gemini-300 (FT-NMR, manufactured by Varian) or LA-400 (FT-NMR, manufactured by JEOL Co.) was used. The chemical shift value was measured by using tetramethylsilane (TMS) as an internal standard and expressed in $\delta$ (ppm). In addition, a coupling constant was expressed in J (Hz). Further, symbols which describe splitting pattern are as follows—s; singlet, d; doublet, t; triplet, q; quartet, qu; quintet, dd; doublet doublet, td; triplet doublet, m; multiplet, brs; broad singlet, brd; broad doublet, brdd; broad doublet doublet, brddd; broad doublet doublet doublet.

(5) For "LCMS", liquid chromatography mass analysis spectrum (LC-MS) was used to obtain mass spectrum. For the analysis, expression "LCMS condition; A" indicates that measurement was carried out under the condition (LCMS-A) described below, expression "LCMS condition; B" indicates that measurement was carried out under the condition (LCMS-B) described below, expression "LCMS condition; C" indicates that measurement was carried out under the condition (LCMS-C) described below, and expression "LCMS condition; D" indicates that measurement was carried out under the condition (LCMS-D) described below, (LCMS-A) As a mass spectrometer, Platform-LC type mass spectrometer (manufactured by Micromass, England) was used and the measurement was made based on an electrospray method (ESI). The liquid chromatography instrument used was the apparatus manufactured by GILSON. As a separation column, Develosil C30-UG-5 (50×4.6 mm, manufactured by NOMURA CHEMICAL CO., LTD) was used. General condition for elution was as follows; with flow rate of 2 ml/minute, solution A as a solvent=water [comprising 0.1% (v/v) acetic acid] and solution B=acetonitrile [comprising 0.1% (v/v) acetic acid] were used, and from minute 0 to minute 4, 5 to 98% (v/v) linear gradient of solution B was applied, followed by elution with 98% of solution B until minute 6 for the measurement.

(LCMS-B) As a mass spectrometer, Platform-LC type mass spectrometer (manufactured by Micromass, England) was used and the measurement was made based on an electrospray method (ESI). The liquid chromatography instrument used was the apparatus manufactured by GILSON. As a separation column, Develosil C30-UG-5 (50×4.6 mm, manufactured by NOMURA CHEMICAL CO., LTD) was used. General condition for elution was as follows; with flow rate of 2 ml/minute, solution A as a solvent=water [comprising 0.1% (v/v) acetic acid] and solution B=acetonitrile [comprising 0.1% (v/v) acetic acid] were used, and from minute 0 to minute 5, 5 to 100% (v/v) linear gradient of solution B was applied, followed by elution with 100% of solution B until minute 9 and elution with 5% of solution B from minute 9.01 to minute 10 for the measurement.

(LCMS-C) As a mass spectrometer, Quadrupole type mass spectrometer, i.e., UPLC/SQD system (manufactured by Waters Company) was used and the measurement was made based on an electrospray method (ESI). The liquid chromatography instrument used was Acquity Ultra Performance LC system manufactured by Waters Company. As a separation column, ACQUITY UPLC BEH C18 (2.1×50 mm 1.7 µm, manufactured by Waters Company) was used. General condition for elution was as follows; with flow rate of 0.6 ml/minute, solution A=water [comprising 0.1% (v/v) acetic acid] and solution B=acetonitrile [comprising 0.1% (v/v) acetic acid] were used, and from minute 0 to minute 2.0, 5 to 90% (v/v) linear gradient of solution B was applied, followed by 90 to 98% (v/v) linear gradient of solution B minute 2.0 to minute 2.5 and elution with 5% of solution B from minute 2.6 to minute 2.8 for the measurement.

(LCMS-D) As a mass spectrometer, Quadrupole type mass spectrometer, i.e., UPLC/SQD system (manufactured by Waters Company) was used and the measurement was made based on an electrospray method (ESI). The liquid chromatography instrument used was Acquity Ultra Performance LC system manufactured by Waters Company. As a separation column, ACQUITY UPLC BEH C18 (2.1×50 mm 1.7 µm, manufactured by Waters Company) was used. General condition for elution was as follows; with flow rate of 0.6 ml/minute, solution A=water [comprising. 0.1% (v/v) acetic acid] and solution B=acetonitrile [comprising 0.1% (v/v) acetic acid] were used, and from minute 0 to minute 2.0, 50 to 90% (v/v) linear gradient of solution B was applied, followed by 90 to 98% (v/v) linear gradient of solution B minute 2.0 to minute 2.5 and elution with 50% of solution B from minute 2.6 to minute 2.8 for the measurement.

(LCMS-E) As a mass spectrometer, Quadrupole type mass spectrometer, i.e., UPLC/SQD system (manufactured by Waters Company) was used and the measurement was made based on an electrospray method (ESI). The liquid chromatography instrument used was Acquity Ultra Performance LC system manufactured by Waters Company. As a separation column, ACQUITY UPLC BEH C18 (2.1×50 mm 1.7 µm, manufactured by Waters Company) was used. General condition for elution was as follows; with flow rate of 0.6 ml/minute, solution A=water [comprising 0.1% (v/v) acetic acid] and solution B=acetonitrile [comprising 0.1% (v/v) acetic acid] were used, and from minute 0 to minute 2.0, 70 to 90% (v/v) linear gradient of solution B was applied, followed by 90 to 98% (v/v) linear gradient of solution B minute 2.0 to minute 2.5 and elution with 50% of solution B from minute 2.6 to minute 2.8 for the measurement.

(6) Regarding ion chromatography, IonPac AS14 (manufactured by Nippon Dionex) was used as a column, 1.0 mmol/L aqueous solution of sodium hydrogen carbonate comprising 3.5 mmol/L sodium carbonate was used as an eluent at flow rate of 1.2 mL/minute, column temperature was 30° C., and an electroconductivity detector was used as a detector for anion measurement. As a standard solution, anion mixed standard solution anion mixed standard solution IV (manufactured by Kanto Chemical Co., Inc.) was used. Further, for cation measurement, IonPac CS14 (manufactured by Nippon Dionex) was used as a column, 10 mmol/L aqueous solution of methanesulfonic acid was used as an eluent at flow rate 1.0 mL/minute, column temperature was 30° C., and an electroconductivity detector was used as a detector for cation measurement. As a standard solution, cation mixed standard solution anion mixed standard solution II (manufactured by Kanto Chemical Co., Inc.) was used.

For the examples described herein below, following abbreviations and terms are used.

THF; tetrahydrofuran
Boc₂O; di-tert-butyl bicarbonate
DMF; N,N-dimethyl formamide
TBDMSCl; tert-butyldimethylsilyl chloride
TBDPSCl; tert-butyldiphenylsilyl chloride
DMAP; 4-dimethylaminopyridine
TBAF; tetra-n-butylammonium fluoride
TMAD; N,N,N',N'-tetramethylazodicarboxamide
MTBE; methyl-tert-butyl ether
DBU; 1,8-diazabicyclo[5,4,0]-7-undecene
DIAD; diisopropyl azodicarboxylate
Et₂O; diethyl ether
(R)—CBS; (R)-5,5-diphenyl-2-methyl-3,4-propano-1,3,2-oxazaborolidine, Further, in the chemical formula which represents a chemical structure, following abbreviations and terms are used.

Bn; benzyl group
Boc; tert-butoxycarbonyl group
TBDMSO; tert-butyldimethylsilyloxy group
TBDPSO; tert-butyldiphenylsilyloxy group
THP; tetrahydro-2H-pyranyl group
Cbz; benzyloxycarbonyl group Regarding the intermediates of which preparation method and references are not described in the Examples or the Reference examples, descriptions are given below together with the references which describe the preparation method.

(R)—N-Benzyl-N-(3-(2-(benzyl (2-hydroxyethyl) amino)-1-(triethylsilyloxy)ethyl)phenyl)methanesulfonamide; Reference example 1 of International Publication No. WO03/035620

[Chemical Formula 35]

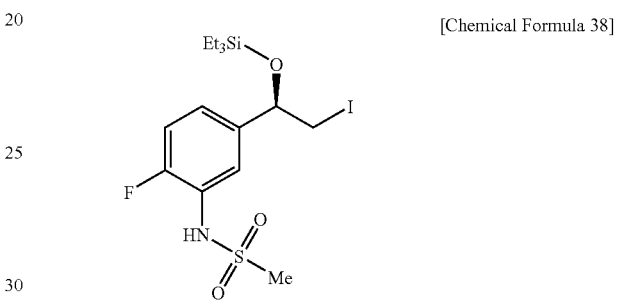

(R)-2-(3-Nitrophenyl)oxirane; Example 6 of International Publication No. WO01/17962 (incorporated herein as a reference)

[Chemical Formula 36]

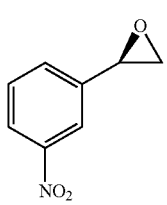

(R)-2-(4-Chloro-3-nitrophenyl)oxirane; Example 19 of International Publication No. WO01/17962

[Chemical Formula 37]

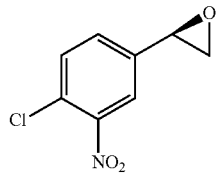

(R)—N-(2-Fluoro-5-(2-iodo-1-(triethylsilyloxy)ethyl) phenyl)methanesulfonamide; Intermediate 101 of International Publication No. WO97/25311 (incorporated herein as a reference)

[Chemical Formula 38]

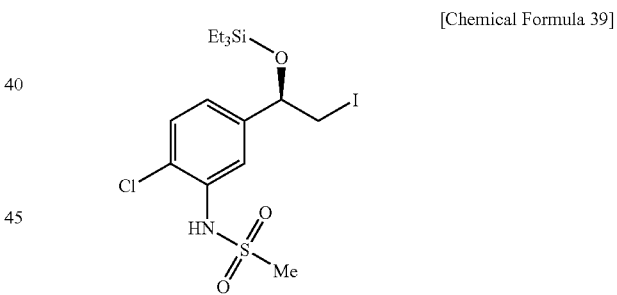

(R)—N-(2-Chloro-5-(2-iodo-1-(triethylsilyloxy)ethyl) phenyl)methanesulfonamide; Intermediate 107 of International Publication No. WO97/25311

[Chemical Formula 39]

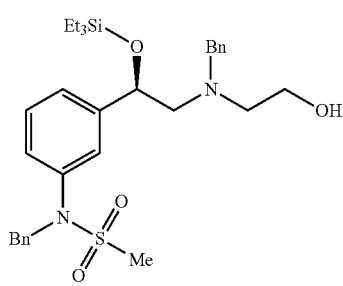

Reference Example 1

4-(Tert-butyldimethylsilyloxy)-2-fluorobenzonitrile

[Chemical Formula 40]

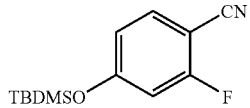

2-Fluoro-4-hydroxybenzonitrile (30.1 g; manufactured by Wako Pure Chemical Industries, Ltd.) and imidazole (18.3 g; manufactured by Tokyo Chemical Industry Co., Ltd.) were dissolved in dehydrated DMF (436 mL; manufactured by Kanto Chemical Co., Inc.). After cooling to 0° C., TBDMSCl (48.3 g; manufactured by Tokyo Chemical Industry, Co., Ltd.) was added and the mixture was stirred for 1 hour while warming to room temperature. Solvent contained in the reaction solution was evaporated under reduced pressure. After adding water, extraction was carried out twice with ethyl acetate. The organic layer was washed twice with water and brine and dried over anhydrous sodium sulfate. After the solvent was evaporated under reduced pressure, purification was carried out with column chromatography ("COLUMN-A"; n-hexane:ethyl acetate=100:0→94:6) to obtain the title compound (40.3 g).

$^1$H-NMR (300 MHz, CDCl$_3$); δ (ppm) 0.25 (3H, s), 0.25 (3H, s), 0.98 (9H, s), 6.62-6.70 (2H, m), 7.44-7.50 (1H, m)

Reference Example 2

Cyclopropyl(2-fluoro-4-hydroxyphenyl)methanone

[Chemical Formula 41]

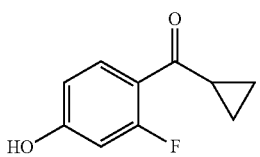

Under argon atmosphere, 4-(tert-butyldimethylsilyloxy)-2-fluorobenzonitrile (10.00 g), which can be prepared according to the method described in Reference example 1, etc., was dissolved in dehydrated THF (30 mL; manufactured by Kanto Chemical Co., Inc.). After cooling to 0° C., 1 mol/L-cyclopropylmagnesium bromide-THF solution (80 mL; manufactured by Tokyo Chemical Industry, Co., Ltd.) was added dropwise thereto. Upon the completion of the dropwise addition, the reaction solution was stirred for 10 minutes at 0° C., and stirred for 1.5 hours at reflux. The reaction solution was cooled to 0° C., added with water (50 mL) and 5 mol/L hydrochloric acid (50 mL), and stirred at reflux overnight. After cooling to the room temperature, the reaction solution was extracted three times with ethyl acetate. The organic layer was washed with water and brine and dried over anhydrous sodium sulfate. After the solvent was evaporated under reduced pressure, the residue was dissolved in dehydrated THF (100 mL; manufactured by Kanto Chemical Co., Inc.), added with 1 mol/L-TBAF-THF solution (31.5 mL; manufactured by Tokyo Chemical Industry, Co., Ltd.), and stirred for 20 minutes at room temperature. To the reaction solution, water and brine were added and extraction was carried out three times with ethyl acetate. The organic layer was washed with water and brine, dried over anhydrous sodium sulfate, and the solvent was evaporated under reduced pressure. N-hexane was added to the residue and the insoluble matters were suspended by ultrasonication. The insoluble matters were filtered to obtain the target compound as a crude product (6.5156 g).

$^1$H-NMR (300 MHz, DMSO-d$_6$); δ (ppm) 0.97-1.04 (4H, m), 2.56-2.65 (1H, m), 6.61-6.72 (2H, m), 7.64-7.72 (1H, m)

LCMS: 179.1 [M–H]; retention time: 3.20 minutes: LCMS condition: B

Reference Example 3

1-Benzyl-3-cyclopropylindazol-6-ol

[Chemical Formula 42]

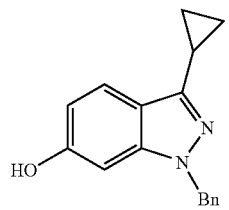

Cyclopropyl(2-fluoro-4-hydroxyphenyl)methanone (6.51 g) which can be prepared according to the method described in Reference example 2, etc., sodium acetate (14.3163 g; manufactured by Wako Pure Chemical Industries, Ltd.), and benzylhydrazine-dihydrochloride (10.72 g; manufactured by Sigma-Aldrich Co.) were suspended in xylene (180 mL). By using a dean-stark apparatus, the mixture was stirred overnight at reflux. After cooling to room temperature, the mixture was added with water and extracted twice with ethyl acetate. The organic layer was washed twice with water and brine and dried over anhydrous sodium sulfate. After the solvent was evaporated under reduced pressure, insoluble matters were dissolved by adding n-hexane to the residue and the title compound was obtained as a crude product (10.97 g).

$^1$H-NMR (300 MHz, DMSO-d$_6$); δ (ppm) 0.87-0.99 (4H, m), 2.14-2.26 (1H, m), 5.38 (2H, s), 6.61 (1H, dd, J=2.0, 8.8), 6.69 (1H, d, J=1.8), 7.11-7.31 (5H, m), 7.53 (1H, d, J=8.8), 9.57 (1H, brs)

LCMS: 265.3 [M+H]; retention time: 4.02 minutes: LCMS condition: A

Reference Example 4

3-Cyclopropylindazol-6-ol

[Chemical Formula 43]

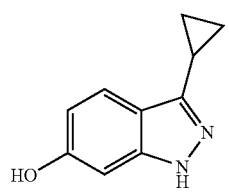

1-Benzyl-3-cyclopropylindazol-6-ol (6.68 g) which can be prepared according to the method described in Reference example 3, etc. and 10% palladium on carbon-PE-type-50% wet with water (2.68 g; manufactured by N. E. Chemcat Corp.) were suspended in ethanol (246 mL; manufactured by Wako Pure Chemical Industries, Ltd.), added with conc. hydrochloric acid (2.05 mL; manufactured by Kanto Chemical Co., Inc.), and then the reaction system was replaced with hydrogen to obtain hydrogen atmosphere and stirred for 3 hours at 60° C. After cooling to room temperature, the system was replaced with nitrogen and then filtered. The filtrate was concentrated under reduced pressure to obtain hydrochloride of the title compound as a crude product (5.82 g).

LCMS: 175.1 [M+H]; retention time: 2.85 minutes: LCMS condition: A

Reference Example 5

6-(Tert-butyldiphenylsilyloxy)-3-cyclopropylindazole

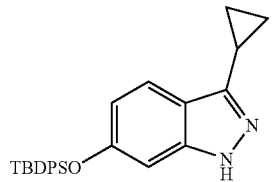

[Chemical Formula 44]

3-Cyclopropylindazol-6-ol hydrochloride (5.18 g) which can be prepared according to the method described in Reference example 4, etc. and imidazole (4.21 g; manufactured by Tokyo Chemical Industry, Co., Ltd.) were dissolved in dehydrated DMF (122 mL; manufactured by Kanto Chemical Co., Inc.). Then, TBDPSCl (15.67 mL; manufactured by Tokyo Chemical Industry, Co., Ltd.) was added and the mixture was stirred overnight at 20° C. To the reaction solution, imidazole (1.8 g; manufactured by Tokyo Chemical Industry, Co., Ltd.) and TBDPSCl (6.27 mL; manufactured by Tokyo Chemical Industry, Co., Ltd.) were added and the mixture was stirred for 2 hours at 20° C. To the reaction solution, water was added and extraction was carried out twice with ethyl acetate. The organic layer was washed twice with water and once with brine and dried over anhydrous sodium sulfate. After the solvent was evaporated under reduced pressure, the residue was purified by column chromatography ("COLUMN-A"; n-hexane:ethyl acetate=95:5→74:26) to obtain the title compound (4.71 g).

$^1$H-NMR (300 MHz, CDCl$_3$); δ (ppm) 0.95-1.00 (4H, m), 1.11 (9H, s), 2.04-2.14 (1H, m), 6.59 (1H, d, J=2.2), 6.73 (1H, dd, J=2.2, 8.8), 7.33-7.49 (7H, m), 7.72-7.75 (4H, m)

LCMS: 413.2 [M+H]; retention time: 6.23 minutes: LCMS condition: B

Reference Example 6

Tert-butyl6-(tert-butyldiphenylsilyloxy)-3-cyclopropylindazole-1-carboxylate

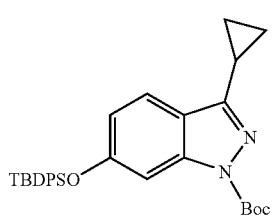

[Chemical Formula 45]

6-(Tert-butyldiphenylsilyloxy)-3-cyclopropylindazole (4.70 g) which can be prepared according to the method described in Reference example 5, etc. was dissolved in dehydrated THF (113 mL; manufactured by Kanto Chemical Co., Inc.), and added with triethylamine (1.905 mL; manufactured by Kokusan Chemical Co., Ltd.), DMAP (0.721 g; manufactured by Wako Pure Chemical Industries, Ltd.) and Boc$_2$O (3.14 mL), followed by stirring overnight at room temperature. The reaction solution was concentrated under reduced pressure, and the residue was purified by column chromatography ("COLUMN-A"; n-hexane:ethyl acetate=100:0→490:10) to obtain the title compound (8.02 g).

$^1$H-NMR (300 MHz, CDCl$_3$); δ (ppm) 0.97-1.28 (13H, m), 1.41 (9H, s), 2.07-2.15 (1H, m), 6.78 (1H, dd, J=2.2, 8.4), 7.33-7.45 (8H, m), 7.66-7.74 (4H, m)

LCMS: 513.1 [M+H]; retention time: 7.59 minutes: LCMS condition: B

Reference Example 7

Tert-butyl6-hydroxy-3-cyclopropylindazole-1-carboxylate

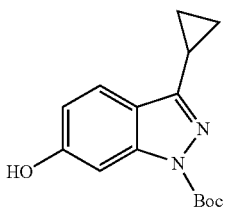

[Chemical Formula 46]

Tert-butyl6-(tert-butyldiphenylsilyloxy)-3-cyclopropylindazole-1-carboxylate (5.08 g) which can be prepared according to the method described in Reference example 6, etc. was dissolved in THF (53 mL; manufactured by Kanto Chemical Co., Inc.), and added with 1 mol/L-TBAF-THF solution (19.82 mL), followed by stirring at room temperature for 0.5 hours. To the reaction solution, water and brine were added and extraction was carried out three times with ethyl acetate. The organic layer was washed water and brine and dried over anhydrous sodium sulfate. After the solvent was evaporated under reduced pressure, the residue was purified by column chromatography ("COLUMN-B"; n-hexane:ethyl acetate=95:5→74:26) to obtain the title compound (2.54 g).

$^1$H-NMR (300 MHz, CDCl$_3$); δ (ppm) 0.96-1.23 (4H, m), 1.64 (9H, s), 2.12-2.22 (1H, m), 6.26 (1H, brs), 6.87 (1H, dd, J=2.2, 8.8), 7.50-7.61 (2H, m)

LCMS: 275.1 [M+H]; retention time: 4.08 minutes: LCMS condition: B

Reference Example 8

(R)-Tert-butyl6-(2-(tert-butoxycarbonyl(2-(3-(N-(tert-butoxycarbonyl)methylsulfonamide)phenyl)-2-triethylsilyloxy)ethyl)amino)ethoxy)-3-cyclopropylindazole-1-carboxylate

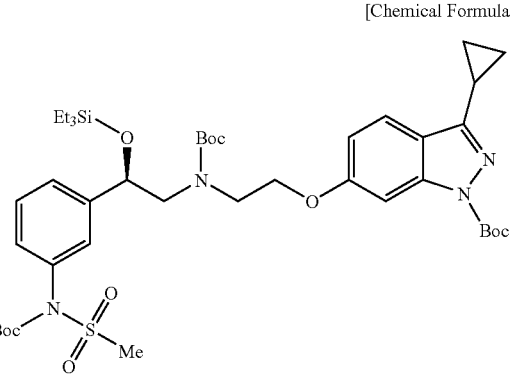

[Chemical Formula 47]

Tert-Butyl 6-hydroxy-3-cyclopropylindazole-1-carboxylate (1.415 g) which can be prepared according to the method described in Reference example 7, etc. was dissolved in toluene (50 mL; manufactured by Kanto Chemical Co., Inc.), added with (R)-(3-(2-(N-tert-butoxycarbonyl-N-(2-hydroxyethyl)amino)-1-triethylsilyloxy)ethyl)phenyl)-N-tert-butoxycarbonylmethanesulfonamide-toluene solution which can be prepared according to the method described in Reference example 29, etc. [10 mL; solution prepared by dissolving (R)-(3-(2-(N-tert-butoxycarbonyl-N-(2-hydroxyethyl)amino)-1-triethylsilyloxy)ethyl)phenyl]-N-tert-butoxycarbonylmethanesulfonamide (22.4 g) in dehydrated toluene (38 mL)], triphenylphosphine (2.9100 g; manufactured by Tokyo Chemical Industry, Co., Ltd.) and TMAD (1.915 g; manufactured by Masuda Chemical Industries Co., Ltd.), and then stirred overnight at room temperature. The reaction solution was purified by column chromatography ("COLUMN-A"; n-hexane:ethyl acetate=95:5→74:26) to obtain the title compound (3.7793 g).

$^1$H-NMR (300 MHz, CDCl$_3$); δ (ppm) 0.54 (6H, q, J=7.7), 0.89 (9H, t, J=7.7), 1.03-1.19 (4H, m), 1.44-1.65 (18H, m), 1.68 (9H, s), 2.13-2.17 (1H, m), 3.18-3.63 (7H, m), 4.02-4.16 (2H, m), 4.94-5.14 (1H, m), 6.84 (1H, dd, J=1.8, 8.4), 7.13-7.53 (6H, m)

LCMS: 845.3 [M+H]; retention time: 8.18 minutes: LCMS condition: B

Example 1

(R)—N-(3-(1-Hydroxy-2-(2-(3-cyclopropylindazol-6-yloxy)ethylamino)ethyl)phenyl)methanesulfonamide

[Chemical Formula 48]

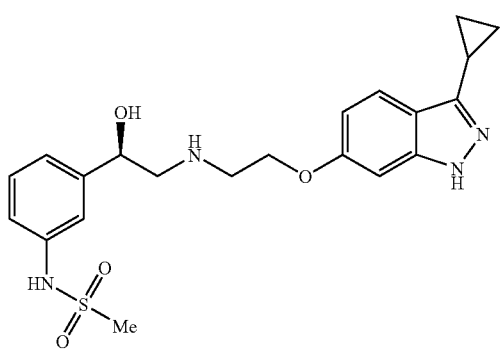

(R)-Tert-butyl 6-(2-(tert-butoxycarbonyl(2-(3-(N-(tert-butoxycarbonyl)methylsulfonamide)phenyl)-2-(triethylsilyloxy)ethyl)amino)ethoxy)-3-cyclopropylindazole-1-carboxylate (3.77 g) which can be prepared according to the method described in Reference example 8, etc. was dissolved in 1,4-dioxane (9 mL; manufactured by Kanto Chemical Co., Inc.), added with 4 mol/L-hydrogen chloride-1,4-dioxane solution (20 mL; manufactured by Kokusan Chemical Co., Ltd.), and then stirred overnight at room temperature. The reaction solution was subjected to ultrasonication treatment, and added with 4 mol/L-hydrogen chloride-1,4-dioxane solution (14 mL; manufactured by Kokusan Chemical Co., Ltd.), followed by stirring at room temperature for 2 hours. Solid obtained after filtration of the precipitates was dissolved in water (20 mL), subjected to freeze-drying, and dissolved by adding water (85 mL). To the residue obtained after returning the solvent three times under reduced pressure, water (80 mL) was added for dissolution. After freeze-drying, the title compound was obtained as a hydrochloride (2.033 g).

$^1$H-NMR (300 MHz, DMSO-d$_6$); δ (ppm) 0.92-0.99 (4H, m), 2.19-2.28 (1H, m), 3.00 (3H, s), 3.08-3.46 (4H, m), 4.30-4.40 (2H, m), 5.01 (1H, d, J=8.3), 6.77 (1H, dd, J=2.0, 8.8) 6.89 (1H, d, J=1.8), 7.11-7.17 (2H, m), 7.30-7.37 (2H, m), 7.67 (1H, d, J=9.0), 9.02 (1H, brs), 9.33 (1H, brs), 9.86 (1H, s)

LCMS: 431.1 [M+H]; retention time: 2.32 minutes: LCMS condition: B

Reference Example 9

Cyclobutyl(2-fluoro-4-hydroxyphenyl)methanone

[Chemical Formula 49]

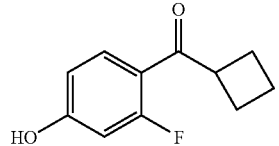

Under nitrogen atmosphere, 4-(tert-butyldimethylsilyloxy)-2-fluorobenzonitrile (9.49 g), which can be prepared according to the method described in Reference example 1, etc., was dissolved in dehydrated THF (30 mL; manufactured by Kanto Chemical Co., Inc.), and then 0.78 mol/L-cyclobutylmagnesium bromide-diethyl ether solution [60 mL; magnesium (9.18 g) was suspended in diethyl ether (20 mL; manufactured by Kanto Chemical Co., Inc.), added with a small amount of iodine, and then stirred at room temperature for 15 minutes. To the reaction solution, dehydrated diethyl ether (10 mL; manufactured by Kanto Chemical Co., Inc.) was added and bromocyclobutane (6.974 mL) dissolved in dehydrated diethyl ether (50 mL; manufactured by Kanto Chemical Co., Inc.) was added dropwise thereto. Upon the completion of the dropwise addition, the mixture was stirred at room temperature for 1 hour to obtain a solution. Part of the solution was titrated by using 0.1 mol/L hydrochloric acid to obtain the concentration of 0.78 mol/L.] was added dropwise thereto. Upon the completion of the dropwise addition, the reaction solution was stirred at room temperature for 15 minutes, added with copper bromide (95.4 mg) and stirred for 0.5 hours at reflux. After cooling to 0° C., water (30 mL) and 5 mol/L hydrochloric acid (30 mL) were added to the reaction solution. After stirring for 1 hour at reflux, the reaction solution was cooled to the room temperature, and then extracted three times with ethyl acetate. The organic layer was washed with water and brine and dried over anhydrous sodium sulfate. After the solvent was evaporated under reduced pressure, the residue was dissolved in dehydrated THF (76 mL; manufactured by Kanto Chemical Co., Inc.), added with 1 mol/L-TBAF-THF solution (38 mL; manufactured by Tokyo Chemical Industry, Co., Ltd.), and stirred for 5 minutes at room temperature. To the reaction solution, water and brine were added and extraction was carried out twice with ethyl acetate. The organic layer was washed with water and brine, dried over anhydrous sodium sulfate, and the solvent was evaporated under reduced pressure. The residue was dissolved with diethyl ether, extracted with an aqueous solution of 2 mol/L-sodium hydroxide. The aqueous layer was washed six times with diethyl ether. To the aqueous layer, 2 mol/L hydrochloric acid was added, and extraction was carried out twice with ethyl acetate. The organic layer was washed with water and brine, dried over anhydrous sodium sulfate, and the solvent was evaporated under reduced pressure, the title compound (6.967 g) was obtained.

$^1$H-NMR (300 MHz, DMSO-$d_6$); δ (ppm) 1.71-1.80 (1H, m), 1.92-2.04 (1H, m), 2.15-2.23 (4H, m), 3.79-3.85 (1H, m), 6.61 (1H, dd, J=2.0, 13.5), 6.72 (1H, dd, J=2.0, 8.42), 7.70-7.76 (1H, m), 10.80 (1H, brs)

LCMS: 195.1 [M+H]; retention time; 3.68 minutes: LCMS condition: B.

Reference Example 10

1-Benzyl-3-cyclobutylindazol-6-ol

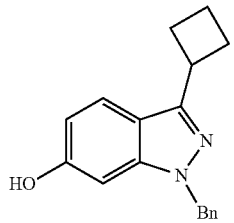

[Chemical Formula 50]

Cyclobutyl(2-fluoro-4-hydroxyphenyl)methanone (6.967 g) which can be prepared according to the method described in Reference example 9, etc., sodium acetate (14.16 g; manufactured by Kanto Chemical Co., Inc.), and benzylhydrazine-dihydrochloride (10.55 g; manufactured by Sigma-Aldrich Co.) were suspended in xylene (85 mL; manufactured by Wako Pure Chemical Industries, Ltd.). By using a dean-stark apparatus, the mixture was stirred overnight at reflux. After cooling to room temperature, solid obtained after filtering the precipitate was dissolved in water and ethyl acetate. The aqueous layer was extracted twice with ethyl acetate. The organic layer was combined, washed twice with water and brine and dried over anhydrous sodium sulfate. After the solvent was evaporated under reduced pressure, the title compound was obtained (8.003 g).

$^1$H-NMR (300 MHz, DMSO-$d_6$); δ (ppm) 1.89-2.10 (2H, m), 2.32-2.41 (4H, m), 3.78-3.84 (1H, m), 5.44 (2H, s), 6.62 (1H, dd, J=1.8, 8.4), 6.72 (1H, d, J=1.8), 7.14-7.32 (5H, m), 7.51 (1H, d, J=8.4), 10.33 (1H, brs)

LCMS: 279.2 [M+H]; retention time; 4.25 minutes: LCMS condition: B

Reference Example 11

3-Cyclobutylindazol-6-ol

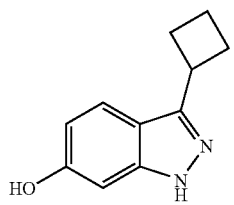

[Chemical Formula 51]

1-Benzyl-3-cyclobutylindazol-6-ol (8 g), which can be prepared according to the method described in Reference example 10, etc. and 10% palladium on carbon-PE-type-50% wet with water (3.22 g; manufactured by N. E. Chemcat Corp.) were suspended in ethanol (287.4 mL), added with conc. hydrochloric acid (2.40 mL), and then the reaction system was replaced with hydrogen to obtain hydrogen atmosphere and stirred for 1.5 hours at 60° C. After cooling to room temperature, the system was replaced with nitrogen and then filtered. The filtrate was concentrated under reduced pressure to obtain hydrochloride of the title compound as a crude product (6.5 g).

$^1$H-NMR (300 MHz, DMSO-$d_6$); 1.87-2.20 (2H, m), 2.25-2.42 (4H, m), 3.43-3.92 (1H, m), 6.65 (1H, dd, J=2.0, 8.8), 6.73 (1H, d, J=2.0), 7.56 (1H, d, J=8.8)

LCMS: 189.1 [M+H]; retention time: 3.06 minutes: LCMS condition: A

Reference Example 12

6-(Tert-butyldiphenylsilyloxy)-3-cyclobutylindazole

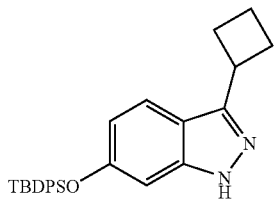

[Chemical Formula 52]

3-Cyclobutylindazol-6-ol hydrochloride (6.45 g) which can be prepared according to the method described in Reference example 11, etc. and imidazole (5.039 g) were dissolved in DMF (100 mL; manufactured by Kanto Chemical Co., Inc.). Then, TBDPSCl (18.44 mL) was added and the mixture was stirred overnight at room temperature. To the reaction solution, water was added and extraction was carried out twice with ethyl acetate. The organic layer was washed twice with water and once with brine and dried over anhydrous sodium sulfate. After the solvent was evaporated under reduced pressure, the residue was purified by column chromatography ("COLUMN-A"; n-hexane:ethyl acetate=95:5→74:26) to obtain the title compound (9.93 g).

$^1$H-NMR (300 MHz, CDCl$_3$); δ (ppm) 1.11 (9H, s), 1.94-2.16 (2H, m), 2.39-2.49 (4H, m), 3.80-3.86 (1H, m), 6.61 (1H, d, J=1.8), 6.72 (1H, dd, J=1.8, 8.4) 7.33-7.47 (7H, m), 7.72-7.75 (4H, m)

LCMS: 427.1 [M+H]; retention time: 6.63 minutes: LCMS condition: B

Reference Example 13

Tert-butyl6-(tert-butyldiphenylsilyloxy)-3-cyclobutylindazole-1-carboxylate

[Chemical Formula 53]

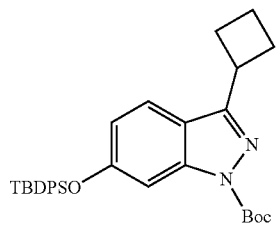

6-(Tert-butyldiphenylsilyloxy)-3-cyclobutylindazole (9.93 g) which can be prepared according to the method described in Reference example 12, etc. was dissolved in dehydrated THF (200 mL; manufactured by Kanto Chemical Co., Inc.), and added with triethylamine (3.90 mL), DMAP (1.51 g) and Boc$_2$O (3.14 mL), followed by stirring for 4 hours at room temperature. The reaction solution was concentrated under reduced pressure, and the residue was added with ethyl acetate, and then washed twice with 1 mol/L hydrochloric acid. The organic layer was dried over anhydrous sodium sulfate, and the solvent was evaporated under reduced pressure to obtain the title compound as a crude product (12.92 g).

$^1$H-NMR (300 MHz, CDCl$_3$); δ (ppm) 1.11 (9H, s), 1.42 (9H, s), 1.98-2.13 (2H, m), 2.38-2.57 (4H, m), 3.79-3.85 (1H, m), 6.77 (1H, dd, J=2.0, 8.6), 7.32-7.44 (8H, m), 7.70-7.74 (4H, m)

LCMS: 527.4 [M+H]; retention time: 7.99 minutes: LCMS condition: B

Reference Example 14

Tert-butyl6-hydroxy-3-cyclobutylindazole-1-carboxylate

[Chemical Formula 54]

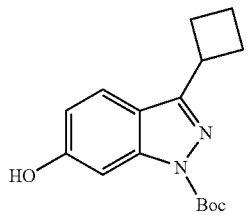

Tert-butyl6-(tert-butyldiphenylsilyloxy)-3-cyclobutylindazole-1-carboxylate (12.26 g) which can be prepared according to the method described in Reference example 13, etc. was dissolved in THF (83 mL; manufactured by Kanto Chemical Co., Inc.). Then, 1 mol/L-TBAF-THF solution (46 mL) was added and the mixture was stirred for 1 hour at room temperature. To the reaction solution, water and brine were added and extraction was carried out three times with ethyl acetate. The organic layer was washed with water and brine and dried over anhydrous sodium sulfate. After the solvent was evaporated under reduced pressure, the residue was purified by column chromatography ("COLUMN-B"; n-hexane: ethyl acetate=95:5→74:26) to obtain the title compound (6.4457 g).

$^1$H-NMR (300 MHz, CDCl$_3$); δ (ppm) 1.63 (9H, s), 1.94-2.17 (2H, m), 2.37-2.59 (4H, m), 3.87-3.89 (1H, m), 6.86 (1H, dd, J=1.8, 8.4), 7.53-7.55 (2H, m)

LCMS: 289.1 [M+H]; retention time: 4.42 minutes: LCMS condition: B

Reference Example 15

(R)-Tert-butyl6-(2-(tert-butoxycarbonyl(2-(3-(N-(tert-butoxycarbonyl)methylsulfonamide)phenyl)-2-(triethylsilyloxy)ethyl)amino)ethoxy)-3-cyclobutyl-indazole-1-carboxylate

[Chemical Formula 55]

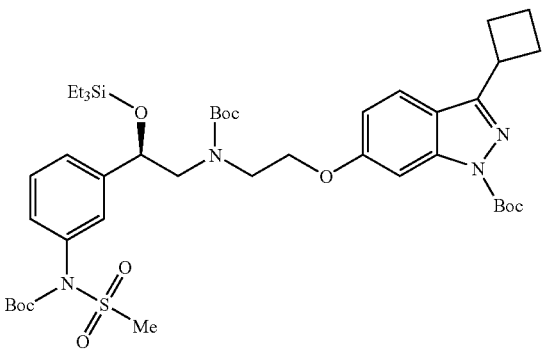

Tert-butyl6-hydroxy-3-cyclobutylindazole-1-carboxylate (1.426 g) which can be prepared according to the method described in Reference example 14, etc. was dissolved in toluene (25 mL; manufactured by Kanto Chemical Co., Inc.), added with (R)-(3-(2-(N-tert-butoxycarbonyl-N-(2-hydroxyethyl)amino)-1-triethylsilyloxy)ethyl)phenyl)-N-tert-butoxycarbonylmethanesulfonamide-toluene solution which can be prepared according to the method described in Reference example 29, etc. [10 mL; prepared by dissolving (R)-(3-(2-(N-tert-butoxycarbonyl-N-(2-hydroxyethyl)amino)-1-triethylsilyloxy)ethyl)phenyl]-N-tert-butoxycarbonyl methanesulfonamide (22.4 g) in dehydrated toluene (38 mL)], triphenylphosphine (2.914 g; manufactured by Tokyo Chemical Industry, Co., Ltd.) and TMAD (1.911 g; manufactured by Masuda Chemical Industries Co., Ltd.), and then stirred overnight at room temperature. The reaction solution was purified by column chromatography ("COLUMN-A"; n-hexane:ethyl acetate=88:12→67:33) to obtain the title compound (3.8476 g).

$^1$H-NMR (300 MHz, CDCl$_3$); δ (ppm) 0.54 (6H, q, J=7.7), 0.89 (9H, t, J=8.1), 1.44-1.70 (27H, m), 1.91-2.23 (2H, m), 2.39-2.59 (4H, m), 3.22-3.63 (7H, m), 3.84-3.87 (1H, m), 4.02-4.12 (2H, m), 4.94-5.14 (1H, m), 6.84 (1H, dd, J=1.8, 8.8), 7.13-7.54 (6H, m)

LCMS: 859.3 [M+H]; retention time: 8.50 minutes: LCMS condition: B

Example 2

(R)—N-(3-(1-Hydroxy-2-(2-(3-cyclobutylindazol-6-yloxy)ethylamino)ethyl)phenyl)methanesulfonamide

[Chemical Formula 56]

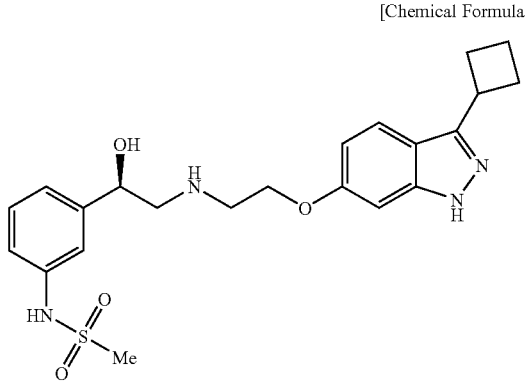

(R)-Tert-butyl6-(2-(tert-butoxycarbonyl(2-(3-(N-(tert-butoxycarbonyl)methylsulfonamide)phenyl)-2-(triethylsilyloxy)ethyl)amino)ethoxy)-3-cyclobutylindazole-1-carboxylate (3.84 g) which can be prepared according to the method described in Reference example 15, etc. was added with 4 mol/L-hydrogen chloride-ethyl acetate solution (75 mL; manufactured by Kokusan Chemical Co., Ltd.), and then stirred for 2 hours at room temperature. The reaction solution was subjected to ultrasonication treatment, and added with 4 mol/L-hydrogen chloride-ethyl acetate solution (5 mL; manufactured by Kokusan Chemical Co., Ltd.), followed by stirring at room temperature overnight. The precipitate was filtered to obtain the title compound as a hydrochloride (2.1659 g).

$^1$H-NMR (300 MHz, DMSO-d$_6$); δ (ppm) 1.89-2.14 (2H, m), 2.33-2.41 (4H, m), 3.00 (3H, s), 3.05-3.08 (1H, m), 3.22-3.25 (1H, m), 3.46-3.47 (2H, m), 3.82-3.88 (1H, m), 4.35-4.49 (2H, m), 5.01 (1H, d, J=8.1), 6.77 (1H, dd, J=2.0, 8.8), 6.92 (1H, d, J=2.0), 7.11-7.17 (2H, m), 7.30-7.37 (2H, m), 7.64 (1H, d, J=8.8), 9.01 (1H, brs), 9.31 (1H, brs), 9.85 (1H, s)

LCMS: 445.1 [M+H]; retention time: 2.43 minutes: LCMS condition: B

Reference Example 16

6-Hydroxyindazole-3-carboxylic acid

[Chemical Formula 57]

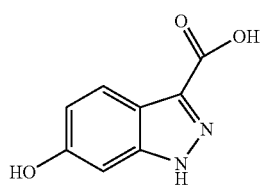

6-Methoxyindazole-3-carboxylic acid (1.015 g; manufactured by Chem Pacific) was dissolved in hydrobromic acid (52 mL; manufactured by Kanto Chemical Co., Inc.), and stirred overnight at reflux. After cooling to room temperature, disappearance of the reacting material and generation of the target compound was confirmed based on LCMS. The solvent was evaporated under reduced pressure to obtain the target compound as a crude product (1.504 g).

LCMS: 179.1 [M+H]; retention time: 1.94 minutes: LCMS condition: A

Reference Example 17

Ethyl 6-hydroxyindazole-3-carboxylate

[Chemical Formula 58]

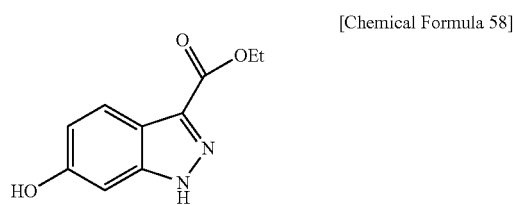

Crude product of 6-hydroxyindazole-3-carboxylic acid (1.504 g) which can be prepared according to the method described in Reference example 16, etc. was dissolved in ethanol, cooled to 0° C., and then thionyl chloride (7.6 mL; manufactured by Wako Pure Chemical Industries, Ltd.) was added dropwise thereto. The reaction solution was stirred overnight at 60° C. After cooling to room temperature, disappearance of the reacting material and generation of the target compound was confirmed based on LCMS. The solvent was evaporated under reduced pressure. To the residue, ethanol (50 mL) was added, and to the residue which had been obtained by evaporation of the solvent under reduced pressure, THF (50 mL) was added and the solvent was removed again by evaporation under reduced pressure to obtain the target compound as a crude product (1.457 g).

LCMS: 207.1 [M+H]; retention time: 2.80 minutes: LCMS condition: A

Reference Example 18

Ethyl6-tert-butyldiphenylsilyloxyindazole-3-carboxylate

[Chemical Formula 59]

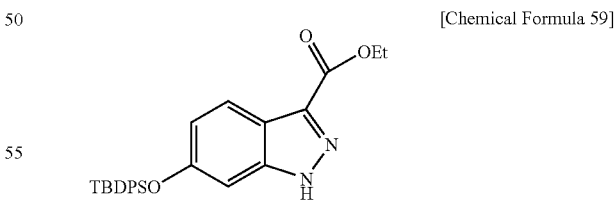

Ethyl6-hydroxyindazole-3-carboxylate (1.457 g) which can be prepared according to the method described in Reference example 17, etc. was dissolved in dehydrated DMF (15.6 mL; manufactured by Kanto Chemical Co., Inc.), added with imidazole (1.425 g; manufactured by Tokyo Chemical Industry, Co., Ltd.) and TBDPSCl (4.06 mL), followed by stirring overnight at room temperature. The reaction solution was poured to a saturated aqueous solution of sodium hydrogen carbonate and extracted twice with ethyl acetate. The organic layer was washed with brine and insoluble matters were filtered using Celite. The organic layer was washed twice with water and dried over anhydrous magnesium sulfate. After the solvent was evaporated under reduced pressure, the residue was purified by column chromatography ("COLUMN-A"; n-hexane:ethyl acetate=81:19→60:40) to obtain the title compound (1.467 g).

¹H-NMR (300 MHz, CDCl₃); δ (ppm) 1.14 (9H, s), 1.42 (3H, t, J=6.9), 1.47-2.18 (5H, m), 3.46-3.54 (1H, m), 3.84-3.87 (1H, m), 4.44 (2H, q, J=7.1), 5.47 (1H, dd, J=2.7, 9.9), 6.86 (1H, d, J=2.0), 7.33-7.46 (6H, m), 7.71-7.76 (4H, m), 7.90 (1H, d, J=8.6)

LCMS: 445.1 [M+H]; retention time: 6.09 minutes: LCMS condition: B

Reference Example 19

Ethyl6-(tert-butyldiphenylsilyloxy)-1-(tetrahydro-2H-pyran-2-yl)-indazole-3-carboxylate

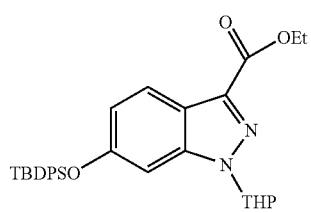

[Chemical Formula 60]

Ethyl6-tert-butyldiphenylsilyloxyindazole-3-carboxylate (1.461 g) which can be prepared according to the method described in Reference example 18, etc. was dissolved in toluene (16.5 mL; manufactured by Wako Pure Chemical Industries, Ltd.), added with 3,4-dihydro-2H-pyran (0.6 mL; manufactured by Tokyo Chemical Industry, Co., Ltd.) and toluene sulfonic acid-monohydrate (0.1293 g), followed by stirring overnight at 60° C. under nitrogen atmosphere. The reaction solution was poured to a saturated aqueous solution of sodium hydrogen carbonate and extracted once with ethyl acetate. The organic layer was washed twice with water and once with brine and dried over anhydrous magnesium sulfate. After the solvent was evaporated under reduced pressure, the residue was purified by column chromatography "COLUMN-A"; n-hexane:ethyl acetate=96:4→75:25) to obtain the title compound (1.334 g).

¹H-NMR (300 MHz, CDCl₃); δ (ppm) 1.14 (9H, s), 1.42 (3H, t, J=6.9), 1.47-2.18 (5H, m), 3.46-3.54 (1H, m), 3.84-3.87 (1H, m), 4.44 (2H, q, J=7.1), 5.47 (1H, dd, J=2.7, 9.9), 6.86 (1H, d, J=2.0), 7.33-7.46 (6H, m), 7.71-7.76 (4H, m), 7.90 (1H, d, J=8.6)

LCMS: 529.2 [M+H]; retention time: 6.83 minutes: LCMS condition: B

Reference Example 20

Ethyl6-hydroxy-1-(tetrahydro-2H-pyran-2-yl)-indazole-3-carboxylate

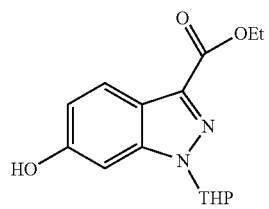

[Chemical Formula 61]

Ethyl6-(tert-butyldiphenylsilyloxy)-1-(tetrahydro-2H-pyran-2-yl)-indazole-3-carboxylate (1.299 g) which can be prepared according to the method described in Reference example 19, etc. was dissolved in dehydrated THF (12.3 mL; manufactured by Kanto Chemical Co., Inc.), added with 1 mol/L-TBAF-THF solution (3.69 mL; manufactured by Sigma-Aldrich Co.), followed by stirring for 2 hours at room temperature under nitrogen atmosphere. The reaction solution was added with ethyl acetate, washed three times with brine, and dried over anhydrous magnesium sulfate. After the solvent was evaporated under reduced pressure, the residue was purified by column chromatography "COLUMN-A"; n-hexane:ethyl acetate=100:0→81:19) to obtain the title compound (0.660 g).

¹H-NMR (300 MHz, CDCl₃); δ (ppm) 1.45 (3H, t, J=7.1), 1.60-1.76 (3H, m), 2.03-2.08 (2H, m), 2.42-2.53 (1H, m), 3.67-3.75 (1H, m), 4.01-4.05 (1H, m), 4.48 (2H, q, J=7.1), 5.40 (1H, brs), 5.71 (1H, dd, J=2.7, 9.7), 6.88 (1H, dd, J=2.0, 8.8), 7.07 (1H, d, J=2.0), 8.03 (1H, d, J=8.8)

LCMS: 291.2 [M+H]; retention time: 3.69 minutes: LCMS condition: A

Reference Example 21

Ethyl6-benzyloxy-1-(tetrahydro-2H-pyran-2-yl)-indazole-3-carboxylate

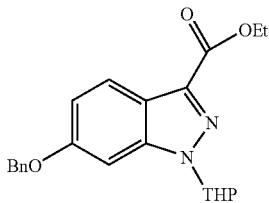

[Chemical Formula 62]

Ethyl6-hydroxy-1-(tetrahydro-2H-pyran-2-yl)-indazole-3-carboxylate (148 mg) which can be prepared according to the method described in Reference example 20, etc. was dissolved in dehydrated DMF (5.2 mL; manufactured by Kanto Chemical Co., Inc.), added with potassium carbonate (227 mg; manufactured by Sigma-Aldrich Co.) and benzyl bromide (73.6 µL; manufactured by Wako Pure Chemical Industries, Ltd.), followed by stirring for overnight at 60° C. After cooling to room temperature, the reaction solution was added to water, and then extraction was carried out twice with ethyl acetate. The organic layer was washed twice with water and once with ethyl acetate, and dried over anhydrous sodium sulfate. After the solvent was evaporated under reduced pressure, the residue was purified by column chromatography "COLUMN-A"; n-hexane:ethyl acetate=95:5→74:26) to obtain the title compound (187 mg).

$^1$H-NMR (300 MHz, CDCl$_3$); δ (ppm) 1.46 (3H, t, J=7.2), 1.67-1.78 (3H, m), 2.04-2.12 (2H, m), 2.42-2.49 (1H, m), 3.69-3.75 (1H, m), 4.01-4.05 (1H, m), 4.49 (2H, q, J=7.2), 5.16 (2H, s), 5.75 (1H, dd, J=2.6, 9.2), 7.04 (1H, dd, J=2.2, 8.8), 7.11 (1H, d, J=1.7), 7.32-7.49 (5H, m), 8.06 (1H, d, J=8.9)

Reference Example 22

(6-(Benzyloxy)-1-(tetrahydro-2H-pyran-2-yl)-indazol-3-yl)methanol

[Chemical Formula 63]

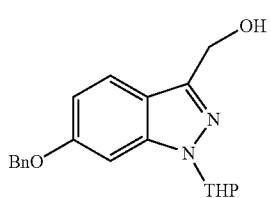

Ethyl6-benzyloxy-1-(tetrahydro-2H-pyran-2-yl)-indazole-3-carboxylate (182 mg) which can be prepared according to the method described in Reference example 21, etc. was dissolved in dehydrated THF (4.78 mL; manufactured by Kanto Chemical Co., Inc.). After the replacement with nitrogen, LiAlH$_4$ (54 mg) was added at 0° C., and the mixture was stirred for 1 hour while warming to room temperature. After cooling to 0° C., THF/water=1/1(5 mL), rochelle salt (manufactured by Kanto Chemical Co., Inc.), and saturated aqueous solution of sodium hydrogen carbonate were added, and extraction was carried out twice with ethyl acetate. The organic layer was washed twice with water and once with brine and dried over anhydrous sodium sulfate. After the solvent was evaporated under reduced pressure, hexane was added to the residue and the solvent was evaporated under reduced pressure to give the title compound (155 mg).

$^1$H-NMR (300 MHz, CDCl$_3$); δ (ppm) 1.54-1.79 (3H, m), 1.98-2.14 (2H, m), 2.05 (1H, t, J=5.9), 2.46-2.59 (1H, m), 3.72-3.77 (1H, m), 4.02-4.06 (1H, m), 4.98 (2H, d, J=5.9), 5.15 (2H, s), 5.58 (1H, dd, J=2.8, 9.5), 6.91 (1H, dd, J=2.2, 8.8), 6.98 (1H, d, J=2.0), 7.32-7.49 (5H, m), 7.65 (1H, d, J=8.6)

LCMS: 339.0 [M+H]; retention time: 4.02 minutes: LCMS condition: A

Reference Example 23

(6-(Benzyloxy)-1-(tetrahydro-2H-pyran-2-yl)-indazole-3-carbaldehyde

[Chemical Formula 64]

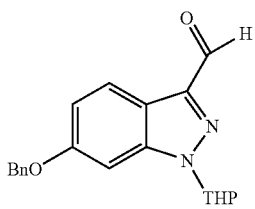

6-(Benzyloxy)-1-(tetrahydro-2H-pyran-2-yl)-indazol-3-yl) methanol (1.70 g) which can be prepared according to the method described in Reference example 22, etc. was dissolved in dichloromethane (25 mL; manufactured by Kanto Chemical Co., Inc.) and THF (25 mL; manufactured by Kanto Chemical Co., Inc.). Activated manganese dioxide (7.48 g; manufactured by Sigma-Aldrich Co.) was added thereto and the mixture was stirred overnight at room temperature. The reaction solution was filtered through a thin pad of anhydrous magnesium sulfate, and the filtrate was again filtered by using membrane-filter (0.2 µm, Advantec). After the solvent was evaporated under reduced pressure, the residue was purified by column chromatography ("COLUMN-B"; n-hexane:ethyl acetate=100:0→82:18) to obtain the title compound (1.20 g).

$^1$H-NMR (300 MHz, CDCl$_3$); δ (ppm) 1.66-1.87 (3H, m), 2.04-2.22 (2H, m), 2.49-2.61 (1H, m), 3.71-3.79 (1H, m), 3.96-4.01 (1H, m), 5.16 (2H, s), 5.74 (1H, dd, J=3.1, 8.8), 7.06-7.10 (2H, m), 7.32-7.49 (5H, m), 8.15 (1H, d, J=9.4), 10.19 (1H, s)

LCMS: 337.3 [M+H]; retention time: 5.14 minutes: LCMS condition: A

Reference Example 24

1-(6-(Benzyloxy)-1-(tetrahydro-2H-pyran-2-yl)-indazol-3-yl)ethanol

[Chemical Formula 65]

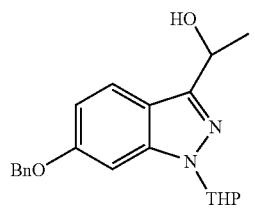

(6-(Benzyloxy)-1-(tetrahydro-2H-pyran-2-yl)-indazole-3-carbaldehyde (16.7 mg) which can be prepared according to the method described in Reference example 23, etc. was dissolved in dehydrated THF (0.5 mL; manufactured by Kanto Chemical Co., Inc.). After cooling to 0° C. with the replacement with nitrogen, 0.96 mol/L-methylmagnesium bromide-THF solution (57 µL; manufactured by Kanto Chemical Co., Inc.) and the mixture was stirred overnight while warming to room temperature. To the reaction solution, dehydrated THF (1 mL; manufactured by Kanto Chemical Co., Inc.) and 0.96 mol/L-methylmagnesium bromide-THF solution (1 mL; manufactured by Kanto Chemical Co., Inc.) were added and the mixture was stirred at room temperature for 4.5 hours. To the reaction solution, 2 mol/L hydrochloric acid was added and extraction was carried out twice with ethyl acetate. The organic layer was washed twice with water and once with brine and dried over anhydrous sodium sulfate. After the solvent was evaporated under reduced pressure, the residue was purified by column chromatography ("COLUMN-F"; n-hexane:ethyl acetate 2:1) to obtain the title compound (11.4 mg).

$^1$H-NMR (300 MHz, CDCl$_3$); δ (ppm) 1.64-1.78 (6H, m), 1.98-2.03 (2H, m), 2.55-2.58 (1H, m), 3.68-3.76 (1H, m), 4.02-4.06 (1H, m), 5.14 (2H, s), 5.24-5.28 (1H, m), 5.55-5.59 (1H, m), 6.89 (1H, dd, J=2.0, 8.5), 6.98 (1H, s), 7.31-7.49 (5H, m), 7.68 (1H, dd, J=3.5, 8.8)

LCMS: 353.2 [M+H]; retention time: 1.68 minutes: LCMS condition: C

Reference Example 25

6-(Benzyloxy)-3-(1-methoxyethyl)-1-(tetrahydro-2H-pyran-2-yl)-indazole

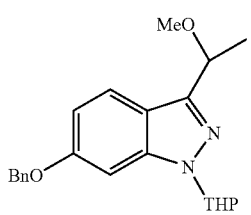

[Chemical Formula 66]

1-(6-(Benzyloxy)-1-(tetrahydro-2H-pyran-2-yl)-indazol-3-yl)ethanol (10 mg) which can be prepared according to the method described in Reference example 24, etc. was dissolved in dehydrated DMF (0.12 mL; manufactured by Kanto Chemical Co., Inc.), added with sodium hydride-comprising 400 oil (2.0 mg; manufactured by Kanto Chemical Co., Inc.), followed by stirring at room temperature for 5 minutes. To the reaction solution, methyl iodide (4.87 µL; manufactured by Tokyo Chemical Industry, Co., Ltd.) was added and the mixture was stirred overnight at room temperature. Water was added to the reaction solution, which was then extracted twice with ethyl acetate. The organic layer was washed twice with water and once with brine and dried over anhydrous sodium sulfate. After the solvent was evaporated under reduced pressure, the residue was purified by column chromatography ("COLUMN-F"; n-hexane:ethyl acetate=5:1) to obtain the title compound (10.2 mg).

$^1$H-NMR (300 MHz, CDCl$_3$); δ (ppm) 1.61-1.75 (6H, m), 1.99-2.04 (2H, m), 2.47 (1H, brs), 3.26 (3H, d, J=5.9), 3.70-3.76 (1H, m), 4.04-4.08 (1H, m), 4.72-4.76 (1H, m), 5.14 (2H, s), 5.56 (1H, d, J=7.7), 6.88 (1H, dd, J=2.0, 8.6), 6.99 (1H, s), 7.31-7.49 (5H, m), 7.77 (1H, d, J=8.6)

LCMS: 367.2 [M+H]; retention time: 1.97 minutes: LCMS condition: C

Reference Example 26

3-(1-Methoxyethyl)-1-(tetrahydro-2H-pyran-2-yl)-indazol-6-ol

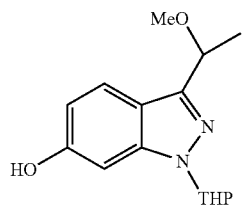

[Chemical Formula 67]

5% Palladium on carbon-STD-type-50% wet with water (79.5 mg; manufactured by N. E. Chemcat Corp.) and 6-(benzyloxy)-3-(1-methoxyethyl)-1-(tetrahydro-2H-pyran-2-yl)-indazole (195 mg) which can be prepared according to the method described in Reference example 25, etc. were dissolved in THF (5.6 mL; manufactured by Kanto Chemical Co., Inc.). After replacing the reaction system with hydrogen, it was stirred overnight at room temperature under hydrogen atmosphere. After replacing the reaction solution with nitrogen, the mixture was filtered and the filtrate was concentrated under reduced pressure to obtain the title compound (167 mg).

$^1$H-NMR (300 MHz, CDCl$_3$); δ (ppm) 1.59-1.78 (6H, m), 1.99-2.12 (2H, m), 2.48-2.51 (1H, m), 3.26 (3H, d, J=4.4), 3.68-3.76 (1H, m), 4.05-4.16 (1H, m), 4.72-4.78 (1H, m), 5.27 (1H, brs), 5.51-5.56 (1H, m), 6.70 (1H, dd, J=2.0, 8.6), 6.92 (1H, s), 7.74 (1H, d, J=8.6)

LCMS: 277.1 [M+H]; retention time: 1.24 minutes: LCMS condition: C

Reference Example 27

(R)-6-(2-(Tert-butoxycarbonyl(2-(3-(N-(tert-butoxycarbonyl)methylsulfonamide)phenyl)-2-hydroxyethyl)amino)ethoxy)-1-(tetrahydro-2H-pyran-2-yl)-3-(1-methoxyethyl)-indazole

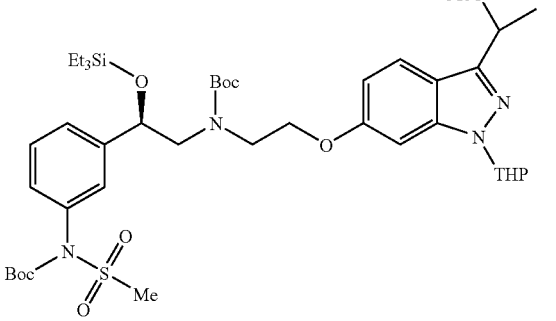

[Chemical Formula 68]

3-(1-Methoxyethyl)-1-(tetrahydro-2H-pyran-2-yl)-indazol-6-ol (30 mg) which can be prepared according to the method described in Reference example 26, etc. and (R)-(3-(2-(N-tert-butoxycarbonyl-N-(2-hydroxyethyl)amino)-1-triethylsilyloxy)ethyl)phenyl)-N-tert-butoxycarbonylmethanesulfonamide-toluene solution which can be prepared according to the method described in Reference example 29, etc. [0.34 mL; solution obtained by dissolving (R)-(3-(2-(N-tert-butoxycarbonyl-N-(2-hydroxyethyl)amino)-1-triethylsilyloxy)ethyl)phenyl]-N-tert-butoxycarbonylmethanesulfonamide (3.889 g) in toluene (6.60 mL)] were dissolved in toluene (1 mL; manufactured by Kanto Chemical Co., Inc.), added with triphenylphosphine (91.4 mg; manufactured by Tokyo Chemical Industry, Co., Ltd.) and TMAD (66.7 mg; manufactured by Masuda Chemical Industries Co., Ltd.), followed by stirring overnight at room temperature. To the reaction solution, triphenylphosphine (94.5 mg; manufactured by Tokyo Chemical Industry, Co., Ltd.) and TMAD (63.3 mg; manufactured by Masuda Chemical Industries Co., Ltd.) were added and stirred overnight at room temperature. This reaction solution was referred to as "M-1". Further, 3-(1-methoxyethyl)-1-(tetrahydro-2H-pyran-2-yl)-indazol-6-ol (30 mg) which can be prepared according to the method described in Reference example 26, etc. and (R)-(3-(2-(N-tert-butoxycarbonyl-N-(2-hydroxyethyl)amino)-1-triethylsilyloxy)ethyl)phenyl)-N-tert-butoxycarbonylmethanesulfonamide-toluene solution which can be prepared according to the method described in Reference example 29, etc. [0.34 mL; solution obtained by dissolving (R)-(3-(2-(N-tert-butoxycarbonyl-N-(2-hydroxyethyl)amino)-1-triethylsilyloxy)ethyl)phenyl]tert-butoxycarbonylmethanesulfonamide (4.78 g) in dehydrated toluene (8.12 mL)] were dissolved in toluene (1 mL; manufactured by Kanto Chemical Co., Inc.), added with triphenylphosphine (91.4 mg; manufactured by Tokyo Chemical Industry, Co., Ltd.) and TMAD (66.7 mg; manufactured by Masuda Chemical Industries Co., Ltd.) followed by stirring overnight at room temperature. To the reaction solution, triphenylphosphine (94.5 mg; manufactured by Tokyo Chemical Industry, Co., Ltd.) and TMAD (63.3 mg; manufactured by Masuda Chemical Industries Co., Ltd.) were added and stirred overnight at room temperature. This reaction solution was referred to as "M-2". These "M-1" and "M-2" were purified by column chromatography ("COLUMN-B"; n-hexane:ethyl acetate=85:15→64:34) to obtain the title compound (106.3 mg).

$^1$H-NMR (300 MHz, CDCl$_3$); δ (ppm) 0.51-0.59 (6H, m), 0.87-0.92 (9H, m), 1.44-1.75 (24H, m), 2.01-2.13 (2H, m), 3.49-2.53 (1H, m), 3.24-3.29 (3H, m), 3.41-3.75 (6H, m), 4.06 (3H, m), 4.71-4.75 (3H, m), 4.94-5, 14 (1H, m), 5.54-5.57 (1H, m), 6.73-6.87 (2H, m), 7.14-7.41 (4H, m), 7.69-7.74 (1H, m)

LCMS: 847.4 [M+H]; retention time: 2.47 minutes: LCMS condition: D

Example 3

N-(3-((R)-1-Hydroxy-2-(2-(3-(1-methoxyethyl)-indazol-6-yloxy)ethylamino)ethyl)phenyl)methanesulfonamide

[Chemical Formula 69]

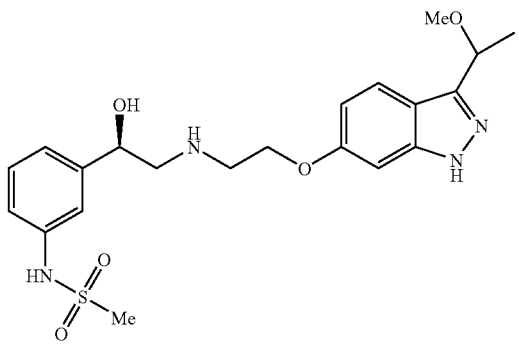

(R)-6-(2-(Tert-butoxycarbonyl(2-(3-(N-(tert-butoxycarbonyl)methylsulfonamide)phenyl)-2-hydroxyethyl)amino) ethoxy)-1-(tetrahydro-2H-pyran-2-yl)-3-(1-methoxyethyl)-indazole (101 mg) which can be prepared according to the method described in Reference example 27, etc. was dissolved in MTBE (0.45 mL; manufactured by Wako Pure Chemical Industries, Ltd.), added with 4 mol/L-hydrogen chloride-1,4-dioxane solution (2 mL; manufactured by Kokusan Chemical Co., Ltd.), followed by shaking (600 min$^{-1}$) overnight at room temperature. To the reaction solution, methanol (0.5 mL) was added, followed by shaking (600 min$^{-1}$) overnight at room temperature. Nitrogen gas was blown into the reaction solution to evaporate the solvent, and methanol (1 mL) was added. Nitrogen gas was blown again into the solution to evaporate the solvent. To the residue, diethyl ether was added and the process of evaporating the solvent by blowing with nitrogen gas was repeated three times to obtain the title compounds as a hydrochloride (55.2 mg).

$^1$H-NMR (300 MHz, DMSO-d$_6$); δ (ppm) 1.51 (3H, d, J=6.6), 2.98 (3H, s), 3.07-3.25 (5H, m), 3.45-3.46 (2H. m), 4.34-4.36 (2H, m), 4.67 (1H, q, J=6.6), 4.99 (1H, d, J=8.1), 6.78 (1H, dd, J=1.8, 8.8) 6.94 (1H, d, J=2.0), 7.10-7.16 (2H, m), 7.29-7.36 (2H, m), 7.70 (1H, d, J=8.8) 9.00 (1H, brs), 9.29 (1H. brs), 9.84 (1H, brs)

LCMS: 449.1 [M+H]; retention time: 0.84 minutes: LCMS condition: C

Reference Example 28

(R)—N-(3-(2-(2-Hydroxyethylamino)-1-(triethylsilyloxy)ethyl)phenyl)methanesulfonamide

[Chemical Formula 70]

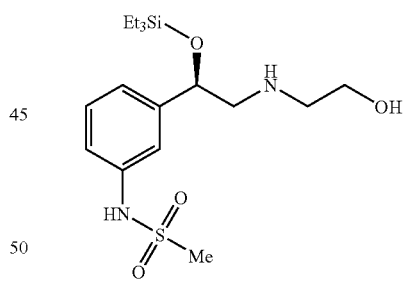

(R)—N-Benzyl-N-(3-(2-(benzyl(2-hydroxyethyl)amino)-1-(triethylsilyloxy)ethyl)phenyl)methanesulfonamide (500 mg; intermediate described in Reference example 1 of International Publication No. WO03/035620) was dissolved in THF (1.76 mL; manufactured by Wako Pure Chemical Industries, Ltd.) and methanol (1.76 mL; manufactured by Wako Pure Chemical Industries, Ltd.) under nitrogen atmosphere, and added with 20% palladium hydroxide on carbon-49.94% wet with Water (102.7 mg; manufactured by N. E. Chemcat Corp.). The reaction system was replaced with hydrogen, and stirred at 50° C. for 15 hours under hydrogen atmosphere. After cooling the reaction solution to room temperature and replacement with nitrogen, filtration was carried out. The filtrate was concentrated under reduced pressure to obtain the title compound (364 mg).

$^1$H-NMR (300 MHz, CDCl$_3$); δ (ppm) 0.50-0.58 (6H, m), 0.81-0.91 (9H, m), 1.81-1.87 (2H, m), 2.99 (3H, s), 3.53-3.61 (2H, m), 3.72-3.76 (2H, m), 4.77-4.81 (1H, m), 7.11-7.33 (4H, m)

LCMS: 389.2 [M+H]; retention time: 2.65 minutes: LCMS condition: A

Reference Example 29

(R)-(3-(2-(N-Tert-butoxycarbonyl-N-(2-hydroxyethyl)amino)-1-triethylsilyloxy)ethyl)phenyl)-N-tert-butoxycarbonyl methanesulfonamide

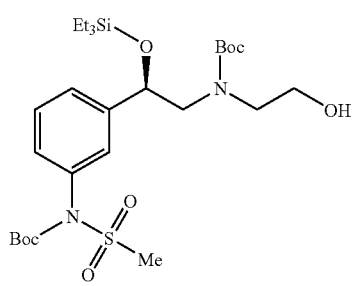

[Chemical Formula 71]

(R)—N-(3-(2-(2-Hydroxyethylamino)-1-(triethylsilyloxy))ethyl)phenyl)methanesulfonamide (337 mg) which can be prepared according to the method described in Reference example 28, etc. was dissolved in dehydrated THF (4.3 mL; manufactured by Kanto Chemical Co., Inc.), and added with triethylamine (0.12 mL; manufactured by Wako Pure Chemical Industries, Ltd.), (Boc)$_2$O (0.437 mL; manufactured by Wako Pure Chemical Industries, Ltd.), and 4-N,N-dimethylaminopyridine (21 mg; manufactured by Wako Pure Chemical Industries, Ltd.), followed by stirring for 16 hours at room temperature under nitrogen atmosphere. The reaction solution was added with ethyl acetate and washed twice with water and once with brine, followed by drying over anhydrous sodium sulfate. The solvent was evaporated under reduced pressure, and the residue was purified by column chromatography ("COLUMN-A"; n-hexane:ethyl acetate=71:29→50:50) to obtain a crude product, which was again purified by column chromatography ("COLUMN-A"; n-hexane:ethyl acetate=71:29→50:50) to obtain the title compound (254 mg).

$^1$H-NMR (300 MHz, CDCl$_3$); δ (ppm) 0.49-0.57 (6H, m), 0.85-0.90 (9H, m), 1.44 (9H, s), 1.44-1.53 (9H, m), 3.03-4.83 (9H, m), 5.00-5.29 (1H, m), 7.10-7.42 (4H, m)

LCMS: 589.2 [M+H]; retention time: 5.98 minutes: LCMS condition: A

Reference Example 30

Methyl 4-(benzyloxy)-2-fluorobenzoate

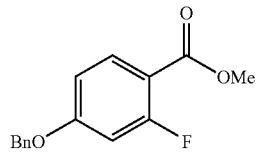

[Chemical Formula 72]

Methyl 2-fluoro-4-hydroxybenzoate (1.4685 g, manufactured by Changzhou Fine Chemical Corp.) and potassium carbonate (3.6917 g; manufactured by Sigma-Aldrich Co.) were suspended in dehydrated DMF (21 mL; manufactured by Kanto Chemical Co., Inc.), added with benzyl bromide (1.22 mL; manufactured by Wako Pure Chemical Industries, Ltd.), and stirred at 50° C. overnight. After cooling to the room temperature, it was added to water and extraction was carried out twice with ethyl acetate. The organic layer was washed twice with water and once with brine and dried over anhydrous sodium sulfate. After the solvent was evaporated under reduced pressure, the residue was purified by column chromatography ("COLUMN-B"; n-hexane:ethyl acetate=97:3→77:23) to obtain the title compound (2.2207 g).

$^1$H-NMR (300 MHz, CDCl$_3$); δ (ppm) 3.89 (3H, s), 5.09 (2H, s), 6.70 (1H, dd, J=2.3, 12.6), 6.78 (1H, dd, J=2.3, 8.8), 7.31-7.41 (5H, m), 7.89 (1H, t, J=8.6)

Reference Example 31

6-(Benzyloxy)-1,2-dihydroindazol-3-one

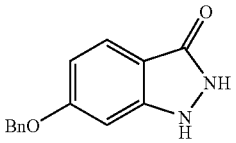

[Chemical Formula 73]

Methyl 4-(benzyloxy)-2-fluorobenzoate (52.4 mg) which can be prepared according to the method described in Reference example 30, etc. was dissolved in n-butanol (1 mL; manufactured by Kanto Chemical Co., Inc.), added with hydrazine monohydrate (96 μL; manufactured by Sigma-Aldrich Co.), and stirred in a sealed tube under microwave for 1 hour at 160° C. Precipitates from the reaction solution were filtered and washed with n-butanol to obtain the title compound (39.6 mg).

$^1$H-NMR (300 MHz, DMSO-d$_6$); δ (ppm) 5.13 (2H, s), 6.66 (1H, dd, J=2.0, 8.6), 6.74 (1H, d, J=2.0), 7.30-7.48 (6H, m)

LCMS: 241 [M+H]; retention time; 3.18 minutes: LCMS condition: A

Reference Example 32

Tert-butyl 6-(benzyloxy)-3-oxo-2,3-dihydroindazole-1-carboxylate

[Chemical Formula 74]

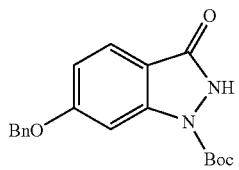

6-(Benzyloxy)-1,2-dihydroindazol-3-one (1.9209 g) which can be prepared according to the method described in Reference example 31, etc. was suspended in $CH_2Cl_2$ (80 mL; manufactured by Wako Pure Chemical Industries, Ltd.), added with triethylamine (2.78 mL; manufactured by Kokusan Chemical Co., Ltd.), $Boc_2O$ (4.6 mL; manufactured by Wako Pure Chemical Industries, Ltd.) and DMAP (0.4947 g; manufactured by Wako Pure Chemical Industries, Ltd.), and stirred overnight at room temperature after the replacement with nitrogen. The reaction solution was washed twice with 1 mol/L-hydrochloric acid and once with water, and the organic layer was dried over magnesium sulfate. The solvent was removed under reduced pressure. The residue was dissolved in methanol (64 mL; manufactured by Wako Pure Chemical Industries, Ltd.) and added with 7 mol/L-ammonia-methanol solution (16 mL; manufactured by Sigma-Aldrich Co.), followed by stirring at room temperature for 4 hours. The reaction solution was concentrated under reduced pressure, ethanol was added to the residue and then resulting precipitate was filtered to obtain the title compound (1.5822 g).
$^1$H-NMR (300 MHz, $CDCl_3$); δ (ppm) 1.70 (9H, s), 5.15 (2H, s), 6.96 (1H, dd, J=2.0, 8.6), 7.32-7.60 (6H, m), 7.68 (1H, d, J=8.6)
LCMS: 341 [M+H]; retention time: 4.57 minutes: LCMS condition: A Reference Example 33

Tert-butyl 6-(benzyloxy)-3-(difluoromethoxy)-indazole-1-carboxylate

[Chemical Formula 75]

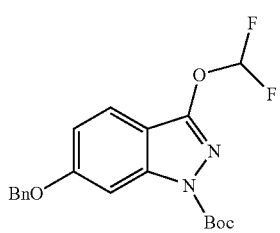

Tert-butyl 6-(benzyloxy)-3-oxo-2,3-dihydroindazole-1-carboxylate (342 mg) which can be prepared according to the method described in Reference example 32, etc. and potassium carbonate (2.0887 g; manufactured by Sigma-Aldrich Co.) were suspended in dehydrated DMF (10 mL; manufactured by Kanto Chemical Co., Inc.), added with sodium chlorodifluoroacetic acid (853 mg; manufactured by Tokyo Chemical Industry, Co., Ltd.), and stirred at 80° C. for 12 hours. The reaction solution was added to water and extraction was carried out twice with ethyl acetate. The organic layer was washed twice with water and once with brine and dried over sodium sulfate. After the solvent was evaporated under reduced pressure, the residue was purified by column chromatography ("COLUMN-A"; n-hexane:ethyl acetate=100:0→87:13) to obtain the title compound (264.7 mg).
$^1$H-NMR ($CDCl_3$); δ (ppm) 1.68 (9H, s), 5.15 (2H, s), 7.02 (1H, dd, J=2.2, 8.8), 7.32-7.60 (5H, m), 7.36 (1H, t, J=72.0), 7.56 (1H, d, J=8.8), 7.63 (1H, brs)
LCMS: 391 [M+H]; retention time: 5.97 minutes: LCMS condition: A Reference Example 34

Tert-butyl 3-(difluoromethoxy)-6-hydroxyindazole-1-carboxylate

[Chemical Formula 76]

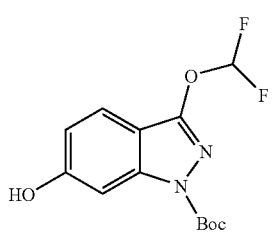

Tert-butyl 6-(benzyloxy)-3-(difluoromethoxy)-indazole-1-carboxylate (262.5 mg) which can be prepared according to the method described in Reference example 33, etc. and 5% palladium on carbon-STD-type-50% wet with water (109.9 mg; manufactured by N. E. Chemcat Corp.) were suspended in dehydrated THF (3.4 mL; manufactured by Kanto Chemical Co., Inc.). After replacing the reaction system with hydrogen, it was stirred overnight at room temperature. After replacing the reaction solution with nitrogen, the mixture was filtered and the filtrate was concentrated under reduced pressure to obtain the title compound (197.2 mg).
$^1$H-NMR ($CDCl_3$); δ (ppm) 1.68 (9H, s), 6.08 (1H, brs), 6.89 (1H, dd, J=2.2, 8.6), 7.34 (1H, t, J=72.0), 7.48 (1H, brs), 7.54 (1H, d, J=8.6)
LCMS: 301 [M+H]; retention time: 4.04 minutes: LCMS condition: A Reference Example 35

Indazol-6-ol

[Chemical Formula 77]

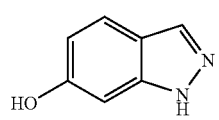

Indazol-6-amine (24.33 g; manufactured by Tokyo Chemical Industry, Co., Ltd.) was dissolved in water (100 mL) and 48% by weight of tetrafluoroboric acid solution (242 mL;

manufactured by Sigma-Aldrich Co.). After cooling to 0° C., an aqueous solution of sodium nitrite [20 mL (sodium nitrite (13.87 g; manufactured by Kanto Chemical Co., Inc.) was dissolved in water (20 mL) to give the solution] was added dropwise thereto for 10 minutes, followed by stirring at 0° C. for 30 minutes. The precipitate from the reaction solution was filtered and washed with chloroform. Thus-obtained precipitate was dissolved in acetic acid (250 mL) and stirred for 10 minutes at 50° C., 10 minutes at 110° C., and 10 minutes at 130° C. The reaction solution was cooled and added with a saturated aqueous solution of sodium carbonate, followed by extraction with ethyl acetate. The organic layer was washed with brine, dried over anhydrous magnesium sulfate, and then dried. Thereafter, the solvent was evaporated under reduced pressure. Thus-obtained residue was dissolved in ethanol (240 mL), added with an aqueous solution of 2 mol/L-sodium hydroxide (365 mL), followed by stirring at room temperature for 1 hour. The reaction solution was concentrated under reduced pressure, and 2 mol/L-hydrochloric acid (200 mL), water and a saturated aqueous solution of ammonium chloride were added to the residue to obtain pH 7 approximately, and the extraction was carried out with ethyl acetate. The organic layer was washed with brine, dried over anhydrous magnesium sulfate, and the solvent was evaporated under reduced pressure. To the residue, chloroform was added, and then the insoluble matters were filtered, washed with chloroform to obtain the target compound as a crude product (13.5401 g).

$^1$H-NMR (DMSO-$d_6$); δ (ppm) 6.64 (1H, dd, J=1.8, 8.8), 6.78 (1H, dd, J=0.7, 1.8), 7.52 (1H, d, J=8.8), 7.86 (1H, d, J=0.7), 9.54 (1H, s), 12.56 (1H, s)

LCMS: 134 [M+H]; retention time; 0.72 minutes: LCMS condition: C

Reference Example 36

6-Tert-butyldiphenylsilyloxyindazole

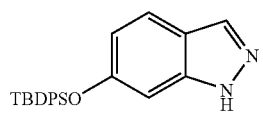

[Chemical Formula 78]

Indazol-6-ol (4.029 g) which can be prepared according to the method described in Reference example 35, etc. was dissolved dehydrated DMF (60 mL; manufactured by Kanto Chemical Co., Inc.), and added with imidazole (4.49 g; manufactured by Tokyo Chemical Industry, Co., Ltd.) and TBDP-SCl (17.1 mL; manufactured by Tokyo Chemical Industry, Co., Ltd.). The mixture was stirred overnight at room temperature. The reaction solution was added to water and extraction was carried out three times with ethyl acetate. The organic layer was washed three times with water and dried over anhydrous magnesium sulfate. After the solvent was evaporated under reduced pressure, the residue was purified by column chromatography ("COLUMN-A"; n-hexane:ethyl acetate=92:8→71:29) to obtain the title compound (9.214 g).

$^1$H-NMR (CDCl$_3$); δ (ppm) 1.11 (9H, s), 6.66-6.67 (1H, m), 6.78 (1H, dd, J=2.0, 8.8), 7.33-7.45 (6H, m), 7.48 (1H, dd, J=0.5, 8.8), 7.71-7.74 (4H, m), 7.88 (1H, s)

LCMS: 373 [M+H]; retention time: 5.88 minutes: LCMS condition: A

Reference Example 37

6-(Tert-butyldiphenylsilyloxy)-3-chloroindazole

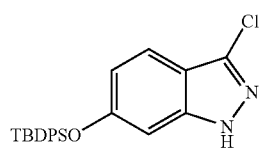

[Chemical Formula 79]

Under nitrogen atmosphere, 6-tert-butyldiphenylsilyloxyindazole (29.246 g) which can be prepared according to the method described in Reference example 36, etc. was dissolved in dehydrated THF (200 mL). After cooling to 0° C., potassium tert-butoxide (18.2190 g; manufactured by Kanto Chemical Co., Inc.) and N-chlorosuccinimide (17.0497 g; manufactured by Kanto Chemical Co., Inc.) were added and then stirred for four hours while increasing the temperature from 0° C. to room temperature. The reaction solution was added to a saturated aqueous solution of ammonium chloride and extraction was carried out twice with ethyl acetate. The organic layer was washed once with brine and dried over magnesium sulfate. After the solvent was evaporated under reduced pressure, the resulting residue was purified by column chromatography ("COLUMN-A"; n-hexane:ethyl acetate=88:12→67:33) to obtain the title compound (18.592 g).

$^1$H-NMR (CDCl$_3$); δ (ppm) 1.11 (9H, s), 6.60 (1H, d, J=2.1), 6.83 (1H, dd, J=2.1, 8.7), 7.33-7.46 (6H, m), 7.69-7.74 (5H, m), 9.53 (1H, brs)

LCMS: 407 [M+H]; retention time: 2.44 minutes: LCMS condition: C

Reference Example 38

Tert-butyl 6-(tert-butyldiphenylsilyloxy)-3-chloroindazole-1-carboxylate

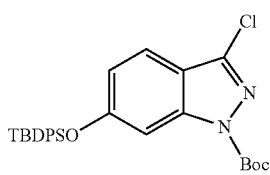

[Chemical Formula 80]

6-(Tert-butyldiphenylsilyloxy)-3-chloroindazole (18.458 g) which can be prepared according to the method described in Reference example 37, etc. was dissolved in dehydrated THF (200 mL), added with triethylamine (7.67 mL; manufactured by Wako Pure Chemical Industries, Ltd.), Boc$_2$O (manufactured by Wako Pure Chemical Industries, Ltd.) and 4-N,N-dimethylaminopyridine (550 mg; manufactured by Wako Pure Chemical Industries, Ltd.), and stirred overnight at room temperature. The reaction solution was added with ethyl acetate and the organic layer was washed twice with 1 mol/L-hydrochloric acid and once with brine, and then dried over magnesium sulfate. The solvent was removed under reduced pressure. The resulting residue was purified by column chromatography ("COLUMN-A"; n-hexane:ethyl acetate=97:3→80:20) to obtain the title compound (17.513 g).

$^1$H-NMR (CDCl$_3$); δ (ppm) 1.11 (9H, s), 1.71 (9H, s), 6.82 (1H, d, J=8.7), 7.34-7.43 (6H, m), 7.69-7.72 (6H, m)

Reference Example 39

Tert-butyl 3-chloro-6-hydroxyindazole-1-carboxylate

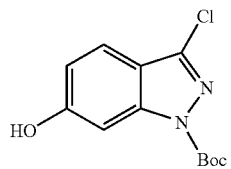

[Chemical Formula 81]

Tert-butyl 6-(tert-butyldiphenylsilyloxy)-3-chloroindazole-1-carboxylate (17.415 g) which can be prepared according to the method described in Reference example 38, etc. was dissolved in dehydrated THF (150 mL), added with 1 mol/L-TBAF-THF solution (42 mL; manufactured by Tokyo Chemical Industry, Co., Ltd.), and stirred overnight at room temperature. The reaction solution was added with ethyl acetate and the organic layer was washed once with brine, once with water, and once with brine and dried over anhydrous sodium sulfate. After the solvent was evaporated under reduced pressure, the resulting residue was added with n-hexane (150 mL) and the suspension was subjected to ultrasonication treatment. The precipitate was filtered to obtain the title compound (6.3815 g).

$^1$H-NMR (CDCl$_3$); δ (ppm) 1.68 (9H, s), 6.03 (1H, s), 6.95 (1H, dd, J=2.1, 8.7), 7.53 (1H, d, J=8.7), 7.60 (1H, d, J=2.1)

LCMS: 269 [M+H]; retention time: 1.60 minutes: LCMS condition: C

Reference Example 40

Benzyl 2-bromoethylcarbamate

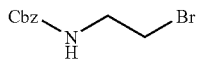

[Chemical Formula 82]

To a 1,4-dioxane (50 mL) solution comprising benzylchloroformate (17.5729 g; manufactured by Wako Pure Chemical Industries, Ltd.), an aqueous solution of 2-bromoethane amine hydrogen bromide salt-1,4-dioxane [104 mL; solution which was prepared by dissolving 2-bromoethane amine hydrogen bromide salt (21.3617 g; manufactured by Tokyo Chemical Industry, Co., Ltd.) in water (54 mL) and 1,4-dioxane (54 mL)] and an aqueous solution of 2 mol/L-sodium hydroxide (104 mL; manufactured by Kanto Chemical Co., Inc.) were added dropwise simultaneously, and stirred at 0° C. for 2 hours. The reaction solution was added with water and extraction was carried out twice with ethyl acetate. The organic layer was washed twice with saturated sodium hydride, dried over magnesium sulfate, and then concentrated under reduced pressure. The resulting residue was purified by column chromatography ("COLUMN-A"; n-hexane:ethyl acetate=94:6→73:27) to obtain the title compound (19.2014 g).

$^1$H-NMR (300 MHz, CDCl$_3$); δ (ppm) 3.47 (2H, t, J=5.8), 3.60 (2H, t, J=5.8), 5.11 (2H, s), 7.27-7.40 (5H, m)

LCMS: 258 [M+H]; retention time: 1.42 minutes: LCMS condition: C

Reference Example 41

Benzyl 2-(1-benzyl-3-cyclopropylindazol-6-yloxy)ethylcarbamate

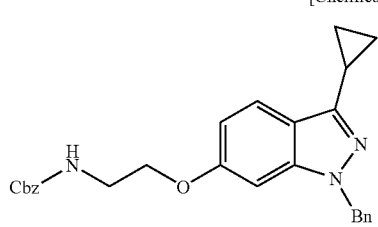

[Chemical Formula 83]

Benzyl 2-bromoethylcarbamate (1.0563 g) which can be prepared according to the method described in Reference example 40, etc. was dissolved in dehydrated DMF (5 mL), added with 1-benzyl-3-cyclopropylindazol-6-ol (533.4 mg) which can be prepared according to the method described in Reference example 3, etc. and potassium carbonate (879.1 mg), and stirred overnight at 50° C. under nitrogen atmosphere. After cooling to room temperature, the reaction solution was added to water and extraction was carried out twice with ethyl acetate. The organic layer was washed twice with water and once with brine and dried over sodium sulfate. After the solvent was evaporated under reduced pressure, the resulting reside was purified by column chromatography ("COLUMN-B"; n-hexane:ethyl acetate=81:19→60:40) to obtain the title compound as a crude product (508.2 mg).

LCMS: 442 [M+H]; retention time: 5.04 minutes: LCMS condition: A

Reference Example 42

2-(3-Cyclopropylindazol-6-yloxy)ethane amine

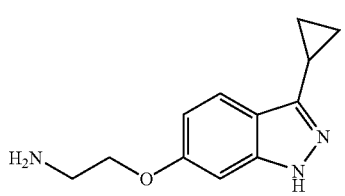

[Chemical Formula 84]

Benzyl 2-(1-benzyl-3-cyclopropylindazol-6-yloxy)ethylcarbamate (507 mg) which can be prepared according to the method described in Reference example 41, etc. and 10% palladium on carbon-PE-type-50% wet with water (205.4 mg; manufactured by N. E. Chemcat Corp.) were suspended in ethanol (12 mL), added with conc. hydrochloric acid (0.19 mL; manufactured by Wako Pure Chemical Industries, Ltd.), and then the reaction system was replaced with hydrogen to obtain hydrogen atmosphere and stirred for 1 hour at 60° C. After cooling to room temperature, the system was replaced with nitrogen and then filtered. To the filtrate, MP-Carbonate

[1.7176 g (2.73 mmol/g); manufactured by Argonaut] was added and the mixture was stirred at room temperature for 1 hour. The reaction solution was filtered, and the filtrate was concentrated under reduced pressure to obtain the title compound as a crude product (227.9 mg).

LCMS: 218 [M+H]; retention time: 0.46 minutes, 1.68 minutes (detected as a double-peak); LCMS condition: A Reference Example 43

(R)—N-(2-Fluoro-5-(oxiran-2-yl)phenyl)methanesulfonamide

[Chemical Formula 85]

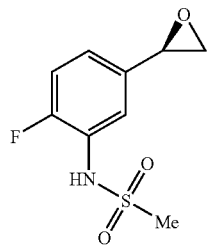

(R)—N-(2-Fluoro-5-(2-iodo-1-(triethylsilyloxy)ethyl)phenyl)methanesulfonamide (2.4190 g) was dissolved in dehydrated THF (40 mL), and added with 1 mol/L-TBAF-THF solution (10 mL; manufactured by Sigma-Aldrich Co.), followed by replacement with nitrogen and stirring at room temperature for 1 hour. The reaction solution was added to brine, and extraction was carried out once with ethyl acetate. The organic layer was washed once with water and dried over magnesium sulfate. After the solvent was evaporated under reduced pressure, the resulting residue was purified by column chromatography ("COLUMN-B"; n-hexane:ethyl acetate=71:29→50:50) to obtain the title compound (0.5995 g).

$^1$H-NMR (300 MHz, CDCl$_3$) 2.75 (1H, dd, J=2.5, 5.3), 3.04 (1H, s), 3.14 (1H, dd, J=4.0, 5.3), 3.85 (1H, dd, J=2.5, 4.0), 6.58 (1H, brs), 7.04-7.19 (2H, m), 7.50 (1H, dd, J=2.0, 7.5)

LCMS: 232 [M+H]; retention time: 0.96 minutes: LCMS condition: C

Reference Example 44

(R)—N-(2-Chloro-5-(oxiran-2-yl)phenyl)methanesulfonamide

[Chemical Formula 86]

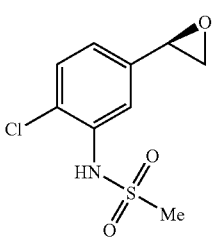

(R)—N-(2-Chloro-5-(2-iodo-1-(triethylsilyloxy)ethyl)phenyl)methanesulfonamide (2.2308 g) was dissolved in dehydrated THF (40 mL), and added with 1 mol/L-TBAF-THF solution (10 mL; manufactured by Sigma-Aldrich Co.), followed by replacement with nitrogen and stirring at room temperature for 1 hour. The reaction solution was added to brine, and extraction was carried out once with ethyl acetate. The organic layer was washed once with water and dried over magnesium sulfate. After the solvent was evaporated under reduced pressure, the resulting residue was purified by column chromatography ("COLUMN-B"; n-hexane:ethyl acetate=71:29→50:50) to obtain the title compound (0.564 g).

$^1$H-NMR (300 MHz, CDCl$_3$); δ (ppm) 3.03 (3H, s), 3.38 (1H, dd, J=8.0, 10.4), 3.50 (1H, dd, J=3.8, 10.4), 4.80 (1H, dt, J=3.8, 10.4), 6.81 (1H, brs), 7.20 (1H, dd, J=1.8, 8.4), 7.43 (1H, d, J=8.4), 7.65 (1H, d, J=1.8)

LCMS: 248 [M+H]; retention time: 1.09 minutes: LCMS condition: C

Example 4

(R)—N-(5-(2-(2-(3-Cyclopropylindazol-6-yloxy)ethylamino)-1-hydroxyethyl)-2-fluorophenyl)methanesulfonamide

[Chemical Formula 87]

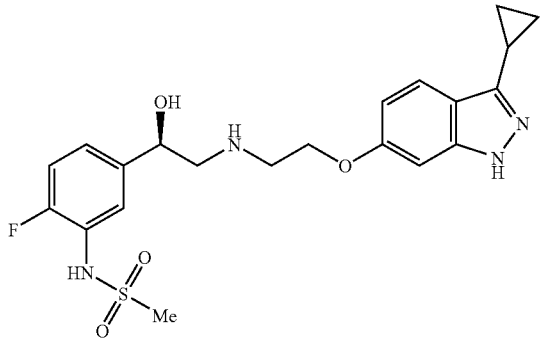

(R)—N-(2-Fluoro-5-(oxiran-2-yl)phenyl)methanesulfonamide (26.4 mg) which can be prepared according to the method described in Reference example 43, etc. was dissolved in 2-propanol (1.5 mL), added with 2-(3-cyclopropylindazol-6-yloxy)ethane amine (34.1 mg) which can be prepared according to the method described in Reference example 42, etc., followed by stirring overnight at reflux. After cooling to room temperature, the reaction solution was blown with nitrogen gas to evaporated the solvent. Thus-obtained residue was purified by HPLC, and the purified product was dissolved in water (1 mL) and 1 mol/L hydrochloric acid solution (150 μL; manufactured by Kanto Chemical Co., Inc.). After the freeze-drying, the title compound was obtained as a hydrochloride (19.2 mg).

LCMS: 449 [M+H]; retention time: 0.92 minutes: LCMS condition: C

Example 5

(R)—N-(2-Chloro-5-(2-(2-(3-cyclopropylindazol-6-yloxy)ethylamino)-1-hydroxyethyl)phenyl)methanesulfonamide

[Chemical Formula 88]

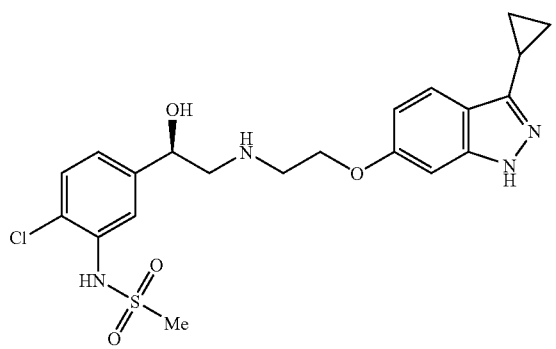

By using (R)—N-(2-chloro-5-(oxiran-2-yl)phenyl)methanesulfonamide (28.3 mg) which can be prepared according to the method described in Reference example 44, etc. instead of (R)—N-(2-fluoro-5-(oxiran-2-yl)phenyl)methanesulfonamide, the title compound was obtained as a hydrochloride (20.1 mg) in the same method as Example 4.

LCMS: 465 [M+H]; retention time: 0.95 minutes: LCMS condition: C

Reference Example 45

(R)-Tert-butyl 5-(2-(benzyl(2-hydroxyethyl)amino)-1-(triethylsilyloxy)ethyl)-2-fluorophenyl(methanesulfonyl)carbamate

[Chemical Formula 89]

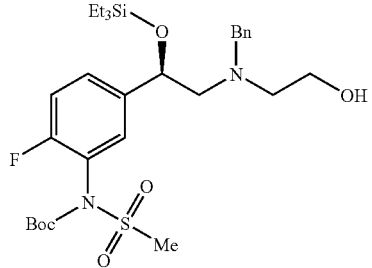

(R)—N-(2-Fluoro-5-(2-iodo-1-(triethylsilyloxy)ethyl)phenyl)methanesulfonamide (500 mg) and 2-(benzylamino)ethanol (1.6 g) were admixed with each other and stirred overnight at 100° C. After cooling to room temperature, the reaction solution was purified by column chromatography ("COLUMN-H"; n-hexane:ethyl acetate=2:1) to obtain (R)—N-(5-(2-(benzyl(2-hydroxyethyl)amino)-1-(triethylsilyloxy)ethyl)-2-fluorophenyl)methanesulfonamide (477.5 mg), which was then added with 4-N,N-dimethylaminopyridine (12 mg), triethylamine (163 μL), and THF (15 mL), and then Boc₂O-THF solution [10 mL; solution prepared by dissolving Boc₂O (230 mg) in THF (10 mL)] was added dropwise thereto. The mixture was stirred at room temperature for 3 hours. After concentrating the reaction solution under reduced pressure, the residue was purified by column chromatography ("COLUMN-H"; n-hexane:ethyl acetate=3:1) to obtain the title compound (500.3 mg).

¹H-NMR (300 MHz, CDCl₃); δ (ppm) 0.41-0.63 (6H, m), 0.82-0.99 (9H, m), 1.42-1.44 (9H, m), 2.59-2.83 (4H, m), 3.42-3.43 (3H, m), 3.45-3.86 (4H, m), 4.54-4.67 (1H, m), 7.04-7.12 (1H, m), 7.19-7.37 (7H, m)

LCMS: 597 [M+H]; retention time: 0.76 minutes: LCMS condition: D

Reference Example 46

(R)-Tert-butyl 2-fluoro-5-(2-(2-hydroxyethylamino)-1-(triethylsilyloxy)ethyl)phenyl(methylsulfonyl)carbamate

[Chemical Formula 90]

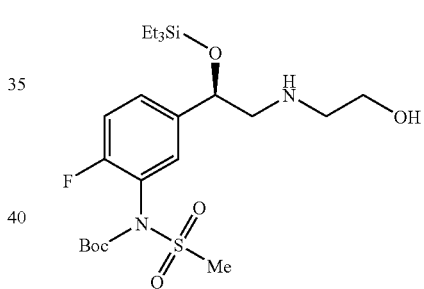

(R)-Tert-butyl 5-(2-(benzyl(2-hydroxyethyl)amino)-1-(triethylsilyloxy)ethyl)-2-fluorophenyl(methanesulfonyl)carbamate (1.1717 g) which can be prepared according to the method described in Reference example 45, etc. and 10% palladium on carbon-PE-type-50% wet with water (374 mg; manufactured by N. E. Chemcat Corp.) were suspended in ethanol (5 mL). Thereafter, the reaction system was replaced with hydrogen to obtain hydrogen atmosphere and stirred for 2.5 hours at 50° C. The reaction solution was replaced with nitrogen gas and filtered. The filtrate was concentrated under reduced pressure to obtain the title compound (0.8781 g).

¹H-NMR (300 MHz, CDCl₃); δ (ppm) 0.55 (6H, q, J=7.6), 0.88 (9H, t, J=7.6), 1.43 (9H, s), 2.68-2.83 (4H, m), 3.42 (3H, s), 3.57 (2H, t, J=5.1), 4.77 (1H, dt, J=2.5, 4.7), 7.11 (1H, t, J=9.1), 7.34-7.36 (2H, m)

LCMS: 507 [M+H]; retention time: 1.56 minutes: LCMS condition: C

Reference Example 47

(R)-(2-Fluoro-5-(2-(N-tert-butoxycarbonyl-N-(2-hydroxyethyl)amino)-1-triethylsilyloxy)ethyl)phenyl)-N-tert-butoxycarbonylmethanesulfonamide

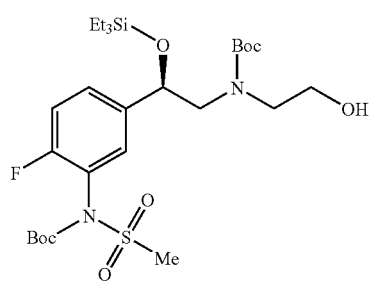

[Chemical Formula 91]

(R)-Tert-butyl 2-fluoro-5-(2-(2-hydroxyethylamino)-1-(triethylsilyloxy)ethyl)phenyl(methylsulfonyl)carbamate (0.861 mg) which can be prepared according to the method described in Reference example 46, etc. was dissolved in dehydrated THF (8 mL), added with Boc$_2$O (459 μL; manufactured by Wako Pure Chemical Industries, Ltd.) and stirred overnight at room temperature. The reaction solution was concentrated under reduced pressure. The resulting residue was purified by column chromatography ("COLUMN-B"; n-hexane:ethyl acetate=88:12→67:33) to obtain the title compound (755.3 mg).

$^1$H-NMR (300 MHz, CDCl$_3$); δ (ppm) 0.53 (6H, q, J=8.0), 0.87 (9H; t, J=8.0), 1.44 (9H, s), 1.48-1.58 (9H, m), 3.08-3.65 (6H, m), 3.42 (3H, s), 4.98-5.24 (1H, m), 7.12 (1H, t, J=9.1), 7.31-7.38 (2H, m)

Reference Example 48

(R)-Tert-butyl 6-(2-(tert-butoxycarbonyl(2-(3-(N-(tert-butoxycarbonyl)methylsulfonamide)-4-fluorophenyl)-2-(triethylsilyloxy)ethyl)amino)ethoxy)-3-cyclobutylindazole-1-carboxylate

[Chemical Formula 92]

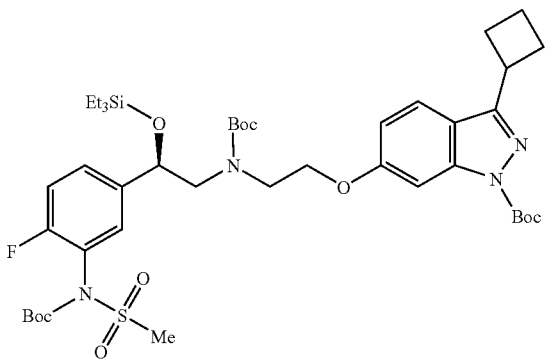

Tert-butyl 6-hydroxy-3-cyclobutylindazole-1-carboxylate (28.6 mg) which can be prepared according to the method described in Reference example 14, etc., (R)-(2-fluoro-5-(2-(N-tert-butoxycarbonyl-N-(2-hydroxyethyl)amino)-1-triethylslyloxy)ethyl)phenyl)-N-tert-butoxycarbonylmethanesulfonamide-toluene solution [0.5 mL; solution prepared by dissolving (R)-(2-fluoro-5-(2-(N-tert-butoxycarbonyl-N-(2-hydroxyethyl)amino)-1-triethylsilyloxy)ethyl)phenyl)-N-tert-butoxycarbonylmethanesulfonamide (755.3 mg) which can be prepared according to the method described in Reference example 47, etc. in dehydrated toluene (3.15 mL)] was dissolved in dehydrated toluene (0.5 mL), added with triphenylphosphine (60.5 mg; manufactured by Wako Pure Chemical Industries, Ltd.) and TMAD (38.7 mg; manufactured by Masuda Chemical Industries Co., Ltd.), followed by stirring at room temperature for 3 days. The reaction solution was purified by column chromatography ("COLUMN-B"; n-hexane:ethyl acetate=88: 12→67:33) to obtain the title compound (78.6 mg).

$^1$H-NMR (300 MHz, CDCl$_3$); δ (ppm) 0.49-0.57 (6H, m), 0.87 (9H, t, J=8.0), 1.43 (9H, s), 1.47-1.51 (9H, m), 1.70 (9H, s), 2.13-2.19 (2H, m), 2.42-2.59 (4H, m), 3.28-3.57 (4H, m), 3.42 (3H, s), 3.87 (1H, qu, J=8.4), 4.03-4.09 (2H, m), 4.91-5.09 (1H, m), 6.84 (1H, d, J=8.7), 7.11 (1H, dt, J=4.7, 9.1), 7.33-7.36 (2H, m), 7.51-7.53 (2H, m)

Example 6

(R)—N-(5-(2-(2-(3-Cyclobutylindazol-6-yloxy)ethylamino)-1-hydroxyethyl)-2-fluorophenyl)methanesulfonamide

[Chemical Formula 93]

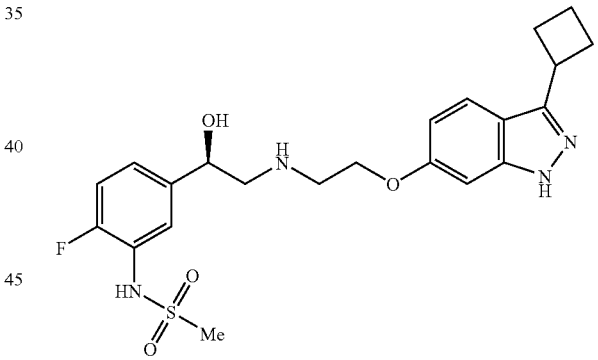

(R)-Tert-butyl 6-(2-(tert-butoxycarbonyl(2-(3-(N-(tert-butoxycarbonyl)methylsulfonamide)-4-fluorophenyl)-2-(triethylsilyloxy)ethyl)amino)ethoxy)-3-cyclobutylindazole-1-carboxylate (78.6 mg) which can be prepared according to the method described in Reference example 48, etc. was dissolved in ethyl acetate (200 μL), added with 4 mol/L-hydrogen chloride-ethyl acetate solution (1.5 mL; manufactured by Kokusan Chemical Co., Ltd.), and then the mixture was shaken (600 min$^{-1}$) overnight at room temperature. To the resulting solution, nitrogen gas was blown to evaporate the solvent, and then ethyl acetate (1.5 mL) was added. To the suspension, nitrogen gas was blown to evaporate the solvent, and then the target compound was obtained as a hydrochloride (55 mg).

$^1$H-NMR (300 MHz, DMSO-d$_6$); δ (ppm) 1.89-2.14 (2H, m), 2.34-2.39 (4H, m), 3.04 (3H, s), 3.05-3.10 (1H, m), 3.25-3.27 (1H, m), 3.45 (2H, brs), 3.86 (1H, qu, J=8.4), 4.35-4.37 (2H, m), 5.05 (1H, d, J=7.6), 6.78 (1H, dd, J=1.8, 8.7), 6.92

(1H, d, J=1.8), 7.25-7.35 (2H, m), 7.46 (1H, dd, J=1.8, 8.0), 7.65 (1H, d, J=8.7), 9.09 (1H, brs), 9.38 (1H, brs), 9.70 (1H, s)

LCMS: 463 [M+H]; retention time: 1.04 minutes: LCMS condition: C

Reference Example 49

(R)-Tert-butyl 6-(2-(tert-butoxycarbonyl(2-(3-(N-(tert-butoxycarbonyl)methylsulfonamide)-4-fluorophenyl)-2-(triethylsilyloxy)ethyl)amino)ethoxy)-3-(difluoromethoxy)-indazole-1-carboxylate

[Chemical Formula 94]

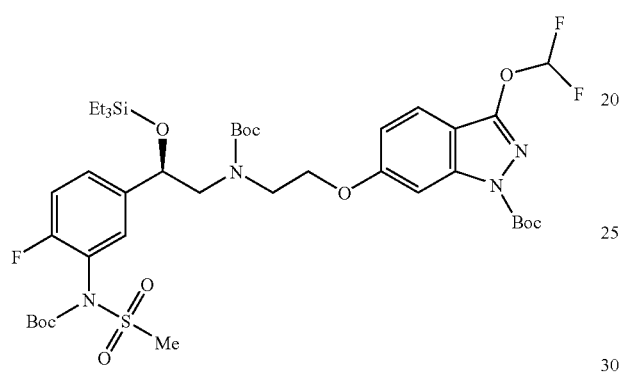

By using tert-butyl 3-(difluoromethoxy)-6-hydroxyindazole-1-carboxylate (30.6 mg) which can be prepared according to the method described in Reference example 34, etc. instead of tert-butyl 6-hydroxy-3-cyclobutylindazole-1-carboxylate, the title compound was obtained (80.4 mg) in the same method as Reference example 48.

LCMS: 889 [M+H]; retention time: 7.77 minutes: LCMS condition: B

Example 7

(R)—N-(5-(2-(2-(3-(Difluoromethoxy)-indazol-6-yloxy)ethylamino)-1-hydroxyethyl)-2-fluorophenyl)methanesulfonamide

[Chemical Formula 95]

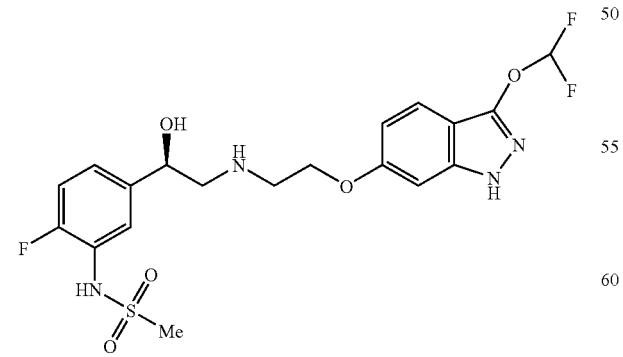

(R)-Tert-butyl 6-(2-(tert-butoxycarbonyl(2-(3-(N-(tert-butoxycarbonyl)methylsulfonamide)-4-fluorophenyl)-2-(triethylsilyloxy)ethyl)amino)ethoxy)-3-(difluoromethoxy)-indazole-1-carboxylate (80.4 mg) which can be prepared according to the method described in Reference example 49, etc. was dissolved in ethyl acetate (200 μL), added with 4 mol/L-hydrogen chloride-ethyl acetate solution (1.5 mL; manufactured by Kokusan Chemical Co., Ltd.), and then the mixture was shaken (600 min$^{-1}$) overnight at room temperature. To the reaction solution, nitrogen gas was blown to evaporate the solvent, and then ethyl acetate (1 mL) was added. By filtering the insoluble matters, the target compound was obtained as a hydrochloride (27.5 mg).

$^1$H-NMR (300 MHz, DMSO-d$_6$); δ (ppm) 3.04 (3H, s), 3.09-3.13 (1H, m), 3.26-3.30 (1H, m), 3.45-3.46 (2H, m), 4.38 (2H, t, J=5.1), 5.02 (1H, d, J=7.6), 6.84 (1H, dd, J=1.8, 9.1), 6.93 (1H, d, J=1.8), 7.24-7.35 (2H, m), 7.46 (1H, dd, J=1.4, 9.1), 7.47 (1H, t, J=73.3), 7.56 (1H, d, J=9.1), 9.02 (1H, brs), 9.24 (1H, brs), 9.69 (1H, s), 12.55 (1H, s)

LCMS: 475 [M+H]; retention time: 0.95 minutes: LCMS condition: C

Reference Example 50

(R)—N-(5-(2-(Benzyl(2-hydroxyethyl)amino)-1-(triethylsilyloxy)ethyl)-2-chlorophenyl)methanesulfonamide

[Chemical Formula 96]

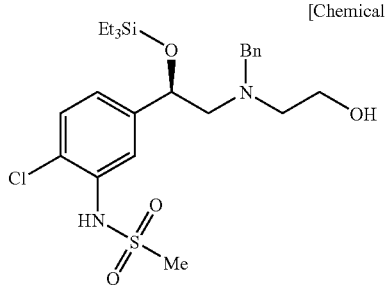

(R)—N-(2-Chloro-5-(2-iodo-1-(triethylsilyloxy)ethyl)phenyl)methanesulfonamide (3 g) and 2-(benzylamino)ethanol (6 mL; Tokyo Chemical Industry, Co., Ltd.) were admixed with each other and stirred overnight at 100° C. The reaction solution was cooled to room temperature, added with toluene and Et$_2$O, and then washed with water three times. The organic layer was dried over magnesium sulfate and the solvent was evaporated under reduced pressure. The residue was purified by column chromatography ("COLUMN-B"; n-hexane:ethyl acetate=84:16→64:36) to obtain the title compound (2.1894 g).

$^1$H-NMR (300 MHz, CDCl$_3$); δ (ppm) 0.44-0.53 (6H, m), 0.85 (9H, t, J=8.0), 2.53-2.84 (4H, m), 2.99 (3H, s), 3.37 (2H, t, J=5.4), 3.68 (2H, d, J=2.1), 4.55 (1H, t, J=6.5), 7.08 (1H, dd, J=1.8, 8.4), 7.19-7.34 (5H, m), 7.36 (1H, d, J=8.4), 7.58 (1H, d, J=1.8)

LCMS: 513 [M+H]; retention time: 1.54 minutes: LCMS condition: C

Reference Example 51

(R)-Tert-butyl 5-(2-(benzyl(2-hydroxyethyl)amino)-1-(triethylsilyloxy)ethyl)-2-chlorophenyl(methylsulfonyl)carbamate

[Chemical Formula 97]

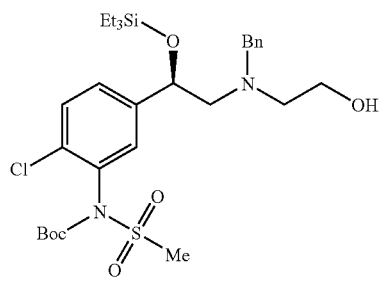

(R)—N-(5-(2-(Benzyl(2-hydroxyethyl)amino)-1-(triethylsilyloxy)ethyl)-2-chlorophenyl)methanesulfonamide (2.1515 g) which can be prepared according to the method described in Reference example 50, etc. was dissolved in dehydrated THF (20 mL) and added with triethylamine (0.884 mL; manufactured by Kokusan Chemical Co., Ltd.). The mixture was then cooled to 0° C. To the solution, Boc$_2$O (1.14 mL; manufactured by Wako Pure Chemical Industries, Ltd.) and 4-N,N-dimethylaminopyridine (51.4 mg; manufactured by Wako Pure Chemical Industries, Ltd.) were added and stirred overnight while warming to room temperature. The reaction solution was concentrated under reduced pressure and the residue was purified by column chromatography ("COLUMN-B"; n-hexane:ethyl acetate=88:12→67:33) to obtain the title compound (1.5265 g).

$^1$H-NMR (300 MHz, CDCl$_3$); δ (ppm) 0.42-0.53 (6H, m), 0.82-0.90 (9H, m), 1.41-1.43 (9H, m), 2.51-2.80 (4H, m), 3.42-3.50 (2H, m), 3.51-3.53 (3H, m), 4.51-4.59 (1H, m), 7.12-7.37 (8H, m)

LCMS: 613 [M+H]; retention time: 1.03 minutes: LCMS condition: D

Reference Example 52

(R)-Tert-butyl 6-(2-(benzyl(2-(3-(N-(tert-butoxycarbonyl)methylsulfonamide)-4-chlorophenyl)-2-(triethylsilyloxy)ethyl)amino)ethoxy)-3-cyclobutylindazole-1-carboxylate

[Chemical Formula 98]

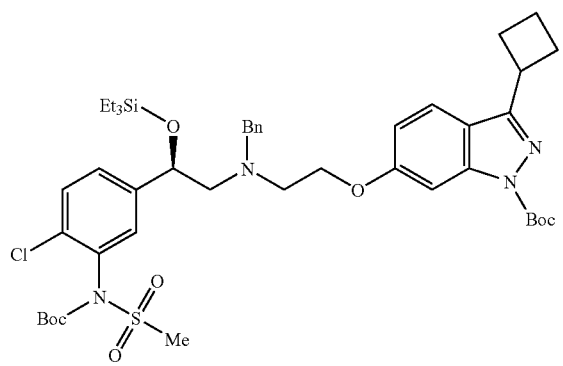

Tert-butyl 6-hydroxy-3-cyclobutylindazole-1-carboxylate (29.0 mg) which can be prepared according to the method described in Reference example 14, etc. and (R)-tert-butyl 5-(2-(benzyl(2-hydroxyethyl)amino)-1-(triethylsilyloxy)ethyl)-2-chlorophenyl(methylsulfonyl)carbamate-toluene solution [0.5 mL; solution prepared by dissolving (R)-tert-butyl 5-(2-(benzyl(2-hydroxyethyl)amino)-1-(triethylsilyloxy)ethyl)-2-chlorophenyl(methylsulfonyl)carbamate (1.5265 g) which can be prepared according to the method described in Reference example 51, etc. in dehydrated toluene (10 mL)] were dissolved in dehydrated toluene (0.5 mL), added with triphenylphosphine (58.6 mg; manufactured by Wako Pure Chemical Industries, Ltd.) and TMAD (36.9 mg; manufactured by Masuda Chemical Industries Co., Ltd.), and then stirred at room temperature for three days. The reaction solution was purified by column chromatography ("COLUMN-B"; n-hexane:ethyl acetate=92:8→72:28) to obtain the title compound (85.9 mg).

$^1$H-NMR (300 MHz, CDCl$_3$); δ (ppm) 0.46 (6H, q, J=8.0), 0.83 (9H, t, J=8.0), 1.37 (9H, s), 1.70 (9H, s), 2.02-2.17 (2H, m), 2.43-2.60 (4H, m), 2.79-2.90 (4H, m), 3.44-3.49 (3H, m), 3.75-3.96 (5H, m), 4.58 (1H, brs), 6.81 (1H, brs), 7.18-7.31 (8H, m), 7.31-7.47 (1H, m), 7.53 (1H, d, J=8.7)

Reference Example 53

(R)-Tert-butyl 6-(2-(tert-butoxycarbonyl(2-(3-(N-(tert-butoxycarbonyl)methylsulfonamide)-4-chlorophenyl)-2-(triethylsilyloxy)ethyl)amino)ethoxy)-3-cyclobutylindazole-1-carboxylate

[Chemical Formula 99]

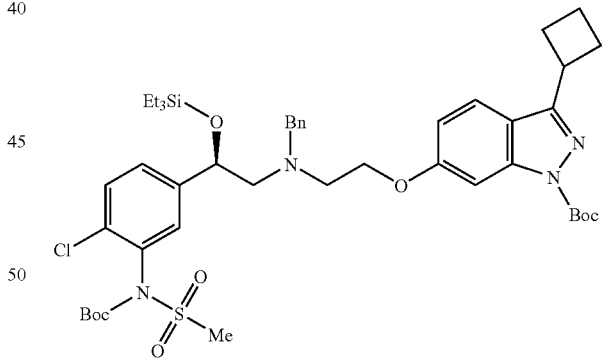

(R)-Tert-butyl 6-(2-(benzyl(2-(3-(N-(tert-butoxycarbonyl)methylsulfonamide)-4-chlorophenyl)-2-(triethylsilyloxy)ethyl)amino)ethoxy)-3-cyclobutylindazole-1-carboxylate (87.1 mg) which can be prepared according to the method described in Reference example 52, etc. and 10% palladium on carbon-PE-type-50% wet with water (21.8 mg; manufactured by N. E. Chemcat Corp.) were suspended in ethanol (0.5 mL) and added with 0.1 mol/L-hydrochloric acid-ethanol solution (1 mL; manufactured by Kanto Chemical Co., Inc.).

After replacing the reaction system with hydrogen, the mixture was stirred for 1 hour at room temperature under hydrogen atmosphere. The reaction system was replaced with nitrogen and filtered. To the filtrate, triethylamine (20 μL; manufactured by Kokusan Chemical Co., Ltd.) was added and then concentrated under reduced pressure. The residue was dissolved in CH$_2$Cl$_2$ (1.5 mL), added with Boc$_2$O (30 μL; manufactured by Wako Pure Chemical Industries, Ltd.), and then stirred overnight at room temperature. To the reaction solution, triethylamine (20 μL; manufactured by Kokusan Chemical Co., Ltd.) and Boc$_2$O (30 μL; manufactured by Wako Pure Chemical Industries, Ltd.) were added, and stirred overnight at room temperature. By blowing nitrogen gas to the reaction solution, the solvent was evaporated and the residue was purified by column chromatography ("COLUMN-B"; n-hexane:ethyl acetate=84:16→64:36) to obtain the title compound (72.6 mg).

LCMS: 893 [M+H]; retention time: 8.78 minutes: LCMS condition: B

Example 8

(R)—N-(2-Chloro-5-(2-(2-(3-cyclobutylindazol-6-yloxy)ethylamino)-1-hydroxyethyl)phenyl)methanesulfonamide

[Chemical Formula 100]

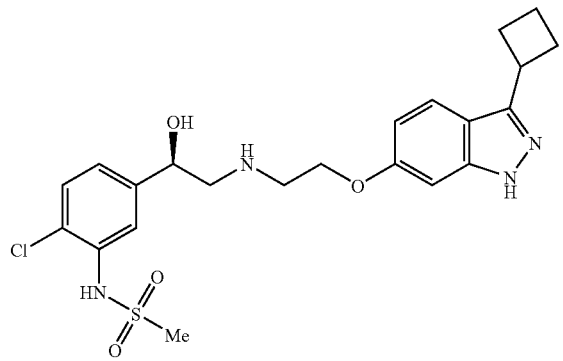

(R)-Tert-butyl 6-(2-(tert-butoxycarbonyl(2-(3-(N-(tert-butoxycarbonyl)methylsulfonamide)-4-chlorophenyl)-2-(triethylsilyloxy)ethyl)amino)ethoxy)-3-cyclobutylindazole-1-carboxylate (70.3 mg) which can be prepared according to the method described in Reference example 53, etc. was dissolved in MTBE (200 μL), added with 4 mol/L-hydrogen chloride-1,4-dioxane solution (1.5 mL; manufactured by Kokusan Chemical Co., Ltd.), and then the mixture was shaken (600 min$^{-1}$) overnight at room temperature. To the resulting solution, nitrogen gas was blown to evaporate the solvent, and then MTBE (1.5 mL) was added. By blowing nitrogen gas to the suspension, the solvent was evaporated to obtain the target compound as a hydrochloride (48.2 mg).

$^1$H-NMR (300 MHz, DMSO-d$_6$); δ (ppm) 1.90-2.14 (2H, m), 2.33-2.41 (4H, m), 3.46 (3H, s), 3.10-3.28 (2H, m), 3.46-3.48 (2H, m), 3.85 (1H, qu, J=8.4), 4.34-4.35 (2H, m), 5.05 (1H, d, J=7.6), 6.76 (1H, dd, 1.8, 8.7), 6.91 (1H, d, J=1.8, 2.1), 7.29 (1H, d, J=1.8, 8.4), 7.51 (1H, d, J=1.8), 7.55 (1H, d, J=8.4), 7.63 (1H, d, J=8.7), 9.04 (1H, brs), 9.26 (1H, brs), 9.54 (1H, s)

LCMS: 479 [M+H]; retention time: 1.04 minutes: LCMS condition: C

Reference Example 54

(R)-Tert-butyl 6-(2-(benzyl(2-(3-(N-(tert-butoxycarbonyl)methylsulfonamide)-4-chlorophenyl)-2-(triethylsilyloxy)ethyl)amino)ethoxy)-3-(difluoromethoxy)-indazole-1-carboxylate

[Chemical Formula 101]

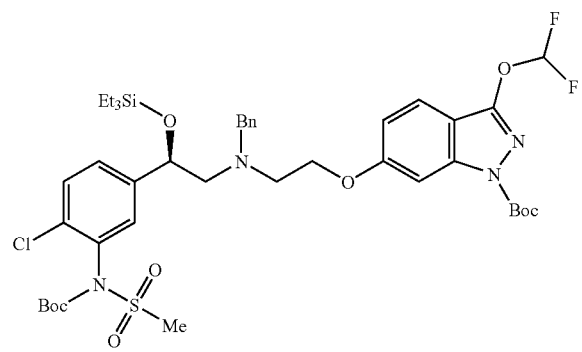

By using tert-butyl 3-(difluoromethoxy)-6-hydroxyindazole-1-carboxylate (30.3 mg) which can be prepared according to the method described in Reference example 34, etc. instead of tert-butyl 6-hydroxy-3-cyclobutylindazole-1-carboxylate, the title compound was obtained (82.8 mg) in the same method as Reference example 52.

$^1$H-NMR (300 MHz, CDCl$_3$); δ (ppm) 0.42-0.50 (6H, m), 0.83 (9H, t, J=8.0), 1.38 (9H, s), 1.68-1.69 (9H, m), 2.75-2.95 (4H, m), 3.47-3.50 (3H, m), 3.71-3.96 (4H, m), 4.59-4.60 (1H, m), 6.84-6.91 (1H, m), 7.22-7.31 (8H, m), 7.36 (1H, t, J=72.2), 7.43 (1H, d, J=1.8), 7.53 (1H, d, J=8.7)

Reference Example 55

(R)-Tert-butyl(2-(tert-butoxycarbonyl(2-(3-(N-(tert-butoxycarbonyl)methylsulfonamide)-4-chlorophenyl)-2-(triethylsilyloxy)ethyl)amino)ethoxy)-3-(difluoromethoxy)-indazole-1-carboxylate

[Chemical Formula 102]

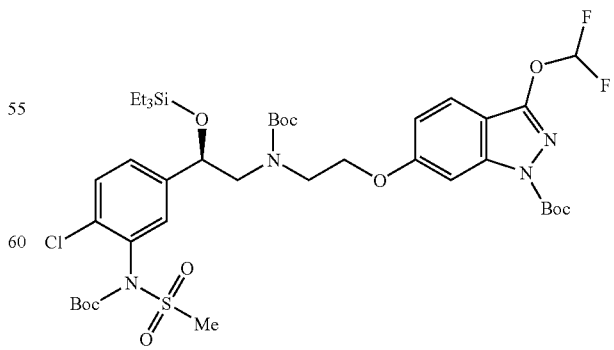

By using (R)-tert-butyl 6-(2-(benzyl(2-(3-(N-(tert-butoxycarbonyl)methylsulfonamide)-4-chlorophenyl)-2-(triethylsilyloxy)ethyl)amino)ethoxy)-3-(difluoromethoxy)-indazole-1-carboxylate (80.1 mg) which can be prepared according to the method described in Reference example 54, etc. instead of (R)-tert-butyl 6-(2-(benzyl(2-(3-(N-(tert-butoxycarbonyl)methylsulfonamide)-4-chlorophenyl)-2-(triethylsilyloxy)ethyl)amino)ethoxy)-3-cyclobutylindazole-1-carboxylate, the title compound was obtained (63.1 mg) in the same method as Reference example 53.

$^1$H-NMR (300 MHz, CDCl$_3$); δ (ppm) 0.49-0.58 (6H, m), 0.85-0.97 (9H, m), 1.42 (9H, s), 1.47-1.51 (9H, m), 1.67 (9H, s), 3.21-3.64 (4H, m), 3.51 (3H, s), 4.03-4.07 (2H, m), 4.92-5.11 (1H, m), 6.87-6.91 (1H, m), 7.29-7.59 (5H, m), 7.42 (1H, t, J=71.8)

Example 9

(R)—N-(2-Chloro-5-(2-(2-(3-(difluoromethoxy)-indazol-6-yloxy)ethylamino)-1-hydroxyethyl)phenyl)methanesulfonamide

[Chemical Formula 103]

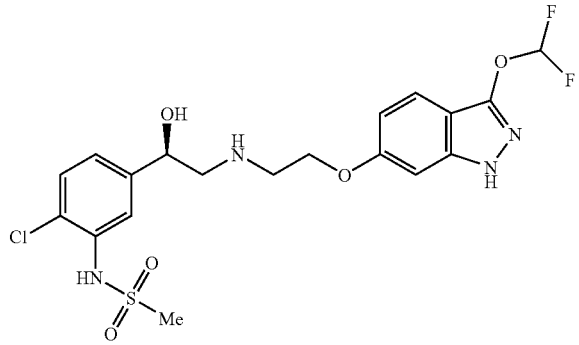

By using (R)-tert-butyl 6-(2-(tert-butoxycarbonyl(2-(3-(N-(tert-butoxycarbonyl)methylsulfonamide)-4-chlorophenyl)-2-(triethylslyloxy)ethyl)amino)ethoxy)-3-(difluoromethoxy)-indazole-1-carboxylate (60.4 mg) which can be prepared according to the method described in Reference example 55, etc. instead of (R)-tert-butyl 6-(2-(tert-butoxycarbonyl(2-(3-(N-(tert-butoxycarbonyl)methylsulfonamide)-4-chlorophenyl)-2-(triethylsilyloxy)ethyl)amino)ethoxy)-3-cyclobutylindazole-1-carboxylate, the title compound was obtained as a hydrochloride (41.0 mg) in the same method as Example 8.

$^1$H-NMR (300 MHz, DMSO-d$_6$); δ (ppm) 3.05 (3H, s), 3.07-3.33 (2H, m), 3.46-3.49 (2H, m), 4.35-4.37 (2H, m), 5.02 (1H, d, J=10.2), 6.36 (1H, d, J=4.0), 6.84 (1H, dd, J=1.8, 8.7), 6.92 (1H, d, J=1.8), 7.29 (1H, dd, J=1.8, 8.4, 8.7), 7.47 (1H, t, J=73.3), 7.51-7.58 (3H, m), 8.97 (1H, brs), 9.10 (1H, brs), 9.55 (1H, s), 12.52 (1H, s)

LCMS: 491 [M+H]; retention time: 1.03 minutes: LCMS condition: C

Reference Example 56

N-Benzyl-2-(benzyloxy)ethane amine

[Chemical Formula 104]

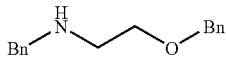

2-(Benzyloxy)ethane amine (12.3146 g; manufactured by Bionet) was dissolved in CH$_2$Cl$_2$ (150 mL), added with benzaldehyde (8.7219 g; manufactured by Kanto Chemical Co., Inc.) and anhydrous sodium sulfate (67.7879 g; manufactured by Wako Pure Chemical Industries, Ltd.), and then stirred overnight at room temperature. After filtering the reaction solution, the filtrate was concentrated under reduced pressure. The resulting residue was dissolved in methanol (150 mL), added with sodium borohydride (3.4129 g; manufactured by Kanto Chemical Co., Inc.), and then stirred at room temperature for 2 hours. The reaction solution was concentrated under reduced pressure, added with water and then extracted twice with ethyl acetate. The organic layer was washed twice with water and once with brine, and dried over anhydrous magnesium sulfate. The organic layer was concentrated under reduced pressure to obtain the title compound (20.188 g).

$^1$H-NMR (300 MHz, CDCl$_3$); δ (ppm) 2.84 (2H, t, J=5.1), 3.62 (2H, t, J=5.1), 3.80 (2H, s), 4.52 (2H, s), 7.20-7.37 (10H, m)

Reference Example 57

(R)-2-(Benzyl(2-(benzyloxy)ethyl)amino)-1-(3-nitrophenyl)ethanol

[Chemical Formula 105]

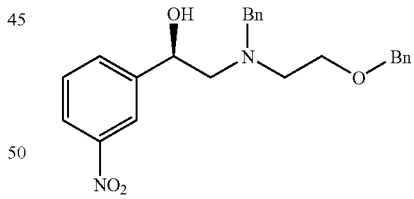

N-Benzyl-2-(benzyloxy)ethane amine (13.6532 g) which can be prepared according to the method described in Reference example 56, etc. was added with (R)-2-(3-nitrophenyl)oxirane (20.21 g) and 2-propanol (205 mL), followed by stirring for 36 hours at reflux. After cooling to room temperature, the reaction solution was concentrated under reduced pressure. Toluene (100 mL) was added to the residue and the mixture was concentrated under reduced pressure. The resulting residue was purified by column chromatography ("COLUMN-D"; n-hexane:ethyl acetate=85:15→80:20) to obtain the title compound (30.761 g).

$^1$H-NMR (300 MHz, CDCl$_3$); δ (ppm) 2.61 (1H, dd, J=3.2, 10.2), 2.75-3.01 (3H, m), 3.51-3.63 (2H, m), 3.78 (2H, dd, J=13.5, 68.9), 4.53 (2H, s), 4.70 (1H, dd, J=3.2, 10.2), 7.27-

7.39 (10H, m), 7.44 (1H, t, J=8.0), 7.59 (1H, d, J=8.0), 8.08 (1H, qd, J=1.1, 8.0), 8.16 (1H, d, J=1.1)

LCMS: 407 [M+H]; retention time: 1.31 minutes: LCMS condition: C

Reference Example 58

(R)—N-Benzyl-N-(2-(benzyloxy)ethyl)-2-(3-nitrophenyl)-2-(triethylsilyloxy)ethane amine

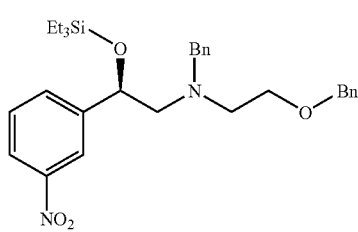

[Chemical Formula 106]

(R)-2-(Benzyl(2-(benzyloxy)ethyl)amino)-1-(3-nitrophenyl)ethanol (30.371 g) which can be prepared according to the method described in Reference example 57, etc. and imidazole (6.1318 g; manufactured by Tokyo Chemical Industry, Co., Ltd.) were dissolved in dehydrated DMF (150 mL), added with chlorotriethylsilane (15.1 mL; manufactured by Shin-Etsu Chemical Co., Ltd.), followed by stirring overnight at room temperature. The reaction solution was poured to water and extracted twice with ethyl acetate. The organic layer was washed twice with water and once with brine and dried over magnesium sulfate. After concentrating under reduced pressure, the residue was purified by column chromatography ("COLUMN-A"; n-hexane:ethyl acetate=100:0→87:13) to obtain the title compound (36.655 g).

$^1$H-NMR (300 MHz, CDCl$_3$); δ (ppm) 0.44-0.53 (6H, m), 0.85 (9H, t, J=8.0), 2.67-2.85 (4H, m), 3.40-3.45 (2H, m), 3.62 (2H, dd, J=13.5, 42.8), 4.42 (2H, s), 4.68 (1H, dd, J=7.3), 7.05-7.36 (10H, m), 7.56 (1H, d, J=7.6), 8.02-8.06 (1H, m), 8.11-8.12 (1H, m)

Reference Example 59

(R)-Tert-butyl 2-(3-aminophenyl)-2-(triethylsilyloxy)ethyl(2-hydroxyethyl)carbamate

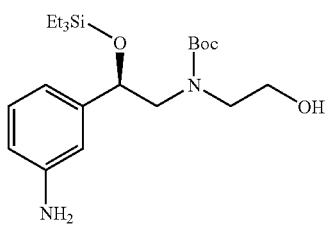

[Chemical Formula 107]

(R)—N-Benzyl-N-(2-(benzyloxy)ethyl)-2-(3-nitrophenyl)-2-(triethylsilyloxy)ethane amine (36.455 g) which can be prepared according to the method described in Reference example 58, etc. and 10% palladium on carbon-PE-type-50% wet with water (15.1241 g; manufactured by N. E. Chemcat Corp.) were suspended in ethanol (175 mL), and then the reaction system was replaced with hydrogen to obtain hydrogen atmosphere and stirred for 9 hours at 50° C. The reaction system was again replaced with hydrogen to obtain hydrogen atmosphere and stirred for 4 hours at 50° C. After cooling the reaction solution to room temperature, the system was replaced with nitrogen and then filtered. The filtrate was concentrated under reduced pressure, and the resulting residue (25.083 g) was dissolved in THF (175 mL), added with Boc$_2$O (14.6029 g; manufactured by Wako Pure Chemical Industries, Ltd.) and stirred for 1.5 hours at room temperature. The reaction solution was concentrated under reduced pressure. To the resulting residue, 20% palladium hydroxide on carbon-50% wet with water (15.0214 g; manufactured by N. E. Chemcat Corp.), THF (80 mL) and methanol (80 mL) were added to obtain suspension, and then the reaction system was replaced with hydrogen to obtain hydrogen atmosphere and stirred for 8 hours at 50° C. After cooling the reaction solution to room temperature, the system was replaced with nitrogen and then filtered. The filtrate was concentrated under reduced pressure and the resulting residue was purified by column chromatography ("COLUMN-A"; n-hexane:ethyl acetate=75:25→54:46) to obtain the title compound (16.918 g).

$^1$H-NMR (300 MHz, CDCl$_3$); δ (ppm) 0.43-0.57 (6H, m), 0.87 (9H, t, J=8.0), 1.48-1.50 (9H, m), 2.04-3.86 (6H, m), 4.08-5.19 (1H, m), 6.57-6.77 (3H, m), 7.09 (1H, t, J=7.6)

LCMS: 411 [M+H]; retention time: 2.03 minutes: LCMS condition: C

Reference Example 60

(R)-Tert-butyl 6-(2-((2-(3-aminophenyl)-2-(triethylsilyloxy)ethyl)(tert-butoxycarbonyl)amino)ethoxy)-3-cyclopropylindazole-1-carboxylate

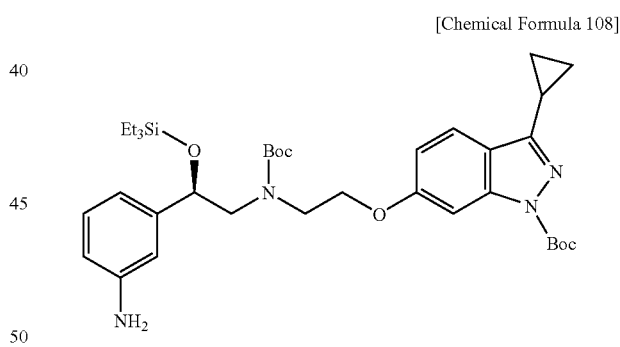

[Chemical Formula 108]

(R)-Tert-butyl 2-(3-aminophenyl)-2-(triethylsilyloxy)ethyl(2-hydroxyethyl)carbamate (1.6143 g) which can be prepared according to the method described in Reference example 59, etc. and tert-butyl 6-hydroxy-3-cyclopropylindazole-1-carboxylate (924 mg) which can be prepared according to the method described in Reference example 7, etc. and triphenylphosphine (1.1419 g; manufactured by Kanto Chemical Co., Inc.) were dissolved in dehydrated toluene (18 mL), added with DIAD (808 μL; manufactured by Sigma-Aldrich Co.), and stirred overnight at room temperature. The reaction solution was purified by column chromatography ("COLUMN-A"; n-hexane:ethyl acetate=82:18→61:39) to obtain a crude product (1.669 g), which was then dissolved in CH$_2$Cl$_2$ (20 mL). After adding MP-Carbonate [5.15 g (2.73 mol/g); manufactured by Argonaut] to the mixture, it was stirred overnight at room temperature. After filtering the reaction solution, the filtrate was concentrated under reduced pressure to obtain the title compound (1.0644 g).

¹H-NMR (300 MHz, CDCl₃); δ (ppm) 0.53 (6H, q, J=8.0), 0.88 (9H, t, J=8.0), 1.02-1.09 (2H, m), 1.15-1.20 (2H, m), 1.47 (9H, s), 1.68 (9H, s), 2.12-2.19 (1H, m), 3.37-3.77 (4H, m), 4.03-4.11 (2H, m), 4.79-4.99 (1H, m), 6.56-6.87 (4H, m), 7.08 (1H, t, J=7.6), 7.49-7.52 (2H, m)

LCMS: 667 [M+H]; retention time: 2.06 minutes: LCMS condition: E

Reference Example 61

(R)-Tert-butyl 6-(2-((2-(3-aminophenyl)-2-(triethylsilyloxy)ethyl)(tert-butoxycarbonyl)amino)ethoxy)-3-cyclobutylindazole-1-carboxylate

[Chemical Formula 109]

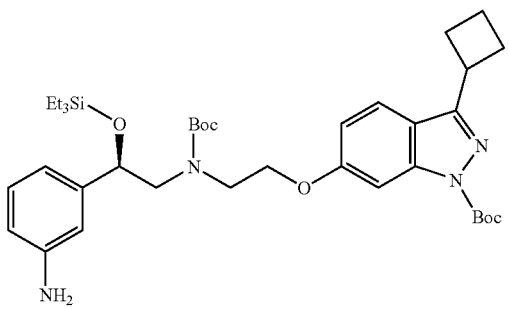

By using tert-butyl 6-hydroxy-3-cyclobutylindazole-1-carboxylate (434.5 mg) which can be prepared according to the method described in Reference example 14, etc. instead of tert-butyl 6-hydroxy-3-cyclopropylindazole-1-carboxylate, the title compound was obtained (619.1 mg) in the same method as Reference example 60.

¹H-NMR (300 MHz, CDCl₃); δ (ppm) 0.48-0.57 (6H, m), 0.87 (9H, t, J=8.0), 1.47 (9H, s), 1.69 (9H, s), 2.01-2.17 (2H, m), 2, 42-2.59 (4H, m), 3.20-3.72 (4H, m), 3.87 (1H, qu, J=8.7), 4.03-4.12 (2H, m), 4.79-4.96 (1H, m), 6.56-6.87 (4H, m), 7.08 (1H, t, J=7.6), 7.50-7.53 (2H, m)

LCMS: 681 [M+H]; retention time: 2.28 minutes: LCMS condition: E

Reference Example 62

(R)-Tert-butyl 6-(2-((2-(3-aminophenyl)-2-(triethylsilyloxy)ethyl)(tert-butoxycarbonyl)amino)ethoxy)-3-(difluoromethoxy)-indazole-1-carboxylate

[Chemical Formula 110]

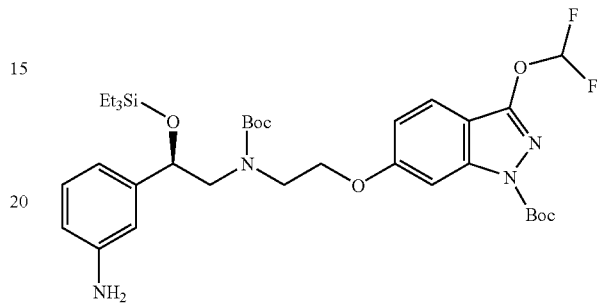

By using tert-butyl 3-(difluoromethoxy)-6-hydroxyindazole-1-carboxylate (1.4889 g) which can be prepared according to the method described in Reference example 34, etc. instead of tert-butyl 6-hydroxy-3-cyclopropylindazole-1-carboxylate, the title compound was obtained (2.0404 g) in the same method as Reference example 60.

¹H-NMR (300 MHz, CDCl₃); δ (ppm) 0.55 (6H, q, J=8.0), 0.88 (9H, t, J=8.0), 1.48-1.49 (9H, m), 1.67 (9H, s), 3.14-3.75 (4H, m), 4.01-4.11 (2H, M), 4.80-4.99 (1H, m), 6.57-6.92 (4H, m), 7.09 (1H, t, J=7.6), 7.35 (1H, t, J=72.2), 7.48-7.54 (2H, m)

LCMS: 693 [M+H]; retention time: 7.24 minutes: LCMS condition: B

Reference Example 63

(R)-Tert-butyl 6-(2-((2-(3-aminophenyl)-2-(triethylsilyloxy)ethyl)(tert-butoxycarbonyl)amino)ethoxy)-3-chloroindazole-1-carboxylate

[Chemical Formula 111]

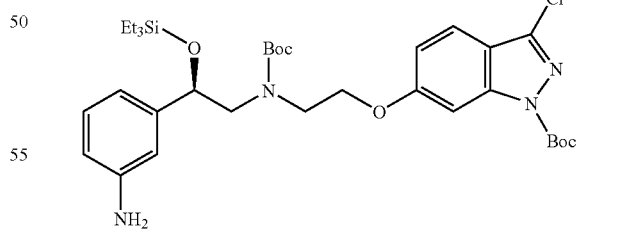

By using tert-butyl 3-chloro-6-hydroxyindazole-1-carboxylate (1.3084 g) which can be prepared according to the method described in Reference example 39, etc. instead of tert-butyl 6-hydroxy-3-cyclopropylindazole-1-carboxylate, the title compound was obtained (1.862 g) in the same method as Reference example 60.

¹H-NMR (300 MHz, CDCl₃); δ (ppm) 0.56 (6H, q, J=8.0), 0.88 (9H, t, J=8.0), 1.48 (9H, s), 1.69 (9H, s), 3.15-3.77 (4H, m), 4.06-4.13 (2H, m), 4.80-4.99 (1H, m), 6.58-6.79 (3H, m), 6.92-6.95 (1H, m), 7.09 (1H, t, J=7.6), 7.50 (1H, dd, J=2.9, 8.7), 7.57 (1H, s)

LCMS: 661 [M+H]; retention time: 2.22 minutes: LCMS condition: E

Example 10

(R)—N-(3-(2-(2-(3-Cyclopropylindazol-6-yloxy)ethylamino)-1-hydroxyethyl)phenyl)benzenesulfonamide

[Chemical Formula 112]

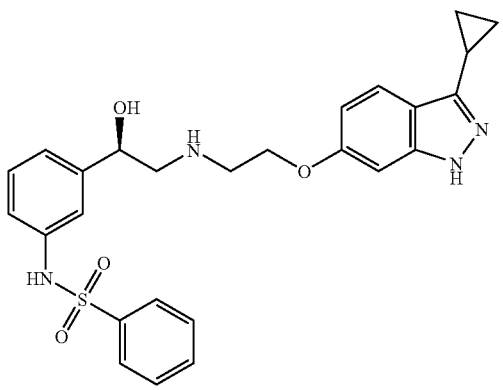

(R)-Tert-butyl 6-(2-((2-(3-aminophenyl)-2-(triethylsilyloxyethyl)(tert-butoxycarbonyl)amino)ethoxy)-3-cyclopropylindazole-1-carboxylate-CH$_2$Cl$_2$ solution [0.5 mL; solution prepared by dissolving (R)-tert-butyl 6-(2-((2-(3-aminophenyl)-2-(triethylsilyloxyethyl)(tert-butoxycarbonyl)amino)ethoxy)-3-cyclopropylindazole-1-carboxylate (133 mg) which can be prepared according to the method described in Reference example 60, etc. in dehydrated CH$_2$Cl$_2$ (1 mL)] was added with dehydrated pyridine (12 μL; manufactured by Kanto Chemical Co., Inc.) and benzenesulfonyl chloride-CH$_2$Cl$_2$ solution [0.5 mL; solution in which benzenesulfonyl chloride (130 mg; manufactured by Wako Pure Chemical Industries, Ltd.) is dissolved in dehydrated CH$_2$Cl$_2$ (3 mL)], and stirred overnight at room temperature. The reaction solution was purified by column chromatography ("COLUMN-G"; n-hexane:ethyl acetate=1:3). The purified product was dissolved in 1,4-dioxane (0.2 mL), added with 4 mol/L-hydrochloric acid-1,4 dioxane solution (1.6 mL), and shaken (600 min$^{-1}$) overnight at room temperature. To the reaction solution, nitrogen gas was blown to evaporate the solvent to obtain the title compounds as a hydrochloride (18.5 mg).

LCMS: 493 [M+H]; retention time: 0.97 minutes: LCMS condition: C

Example 11 to 24

By using reagent-1 instead of (R)-tert-butyl 6-(2-((2-(3-aminophenyl)-2-(triethylsilyloxyethyl)(tert-butoxycarbonyl)amino)ethoxy)-3-cyclopropylindazole-1-carboxylate and reagent-2 instead of benzenesulfonyl chloride, Compounds of Table 1 were obtained as a hydrochloride in the same method as Example 10.

In the Table 1, symbols have the meanings as follows.

"ex" indicates the example number, for instance, ex 11 means Example 11.

"ref" indicates the Reference example number, for instance, ref-61 means Reference example 61.

"LCMS" indicates liquid chromatography mass analysis data (m/z). Specifically, it consists of "method", "R.T." and "MS", which will be described below.

"MS" indicates mass spectrum data. "R.T." indicates retention time in LCMS, and has minutes as a unit. "method" indicates the LCMS condition which has been described in detail above. For instances, the expression "C" indicates the (LCMS-C) condition.

Regarding the chemicals used, RSO$_2$Cl-1 is a product of Wako Pure Chemical Industries, Ltd., RSO$_2$Cl-2 is a product of Tokyo Chemical Industry, Co., Ltd., RSO$_2$Cl-3 is a product of Sigma-Aldrich Co., RSO$_2$Cl-4 is a product of Sigma-Aldrich Co., and RSO$_2$Cl-5 is a product of Sigma-Aldrich Co.

TABLE 1

| ex | reagent-1 | reagent-2 | Compound | Compound Name | MS | R.T. | method |
|---|---|---|---|---|---|---|---|
| ex11 | ref-61 | RSO$_2$Cl-1 | | (R)-N-(3-(2-(2-(3-cyclobutylIndazol-6-yloxy)ethylamino)-1-hydroxyethyl)phenyl)-benzenesulfonamide | 507 [M + H] | 1.08 | C |

TABLE 1-continued

| ex | reagent-1 | reagent-2 | Compound | Compound Name | LCMS MS | R.T. | method |
|---|---|---|---|---|---|---|---|
| ex12 | ref-62 | 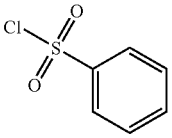 RSO$_2$Cl-1 | 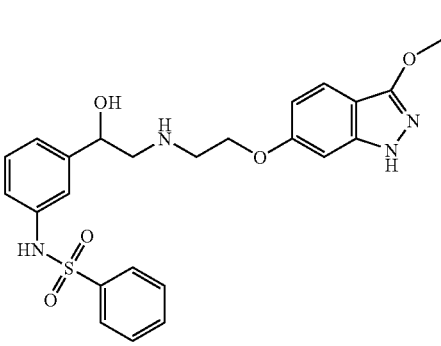 | (R)-N-(3-(2-(2-(3-(difluoromethoxy)-indazol-6-yloxy)ethylamino)-1-hydroxyethyl)phenyl)-benzenesulfonamide | 519 [M + H] | 1.19 | C |
| ex13 | ref-63 | 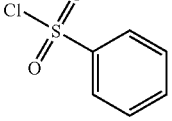 RSO$_2$Cl-1 | 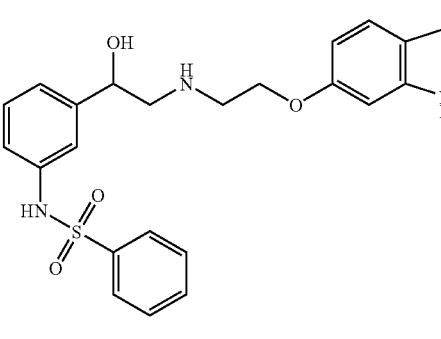 | (R)-N-(3-(2-(2-(3-chloroindazol-6-yloxy)ethylamino)-1-hydroxyethyl)phenyl)-benzenesulfonamide | 487 [M + H] | 0.98 | C |
| ex14 | ref-62 | 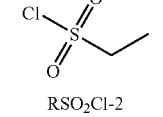 RSO$_2$Cl-2 | 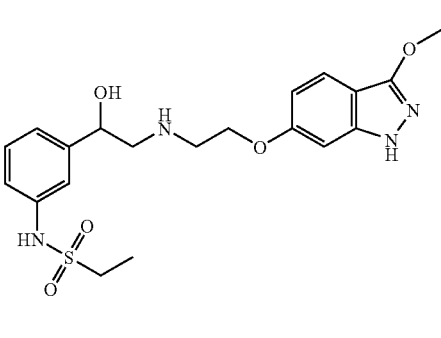 | (R)-N-(3-(2-(2-(3-(difluoromethoxy)indazol-6-yloxy)ethylamino)-1-hydroxyethyl)phenyl)-ethanesulfonamide | 471 [M + H] | 1.02 | C |
| ex15 | ref-63 | 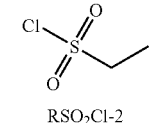 RSO$_2$Cl-2 | 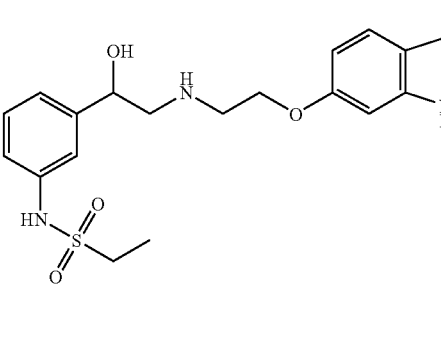 | (R)-N-(3-(2-(2-(3-chloroindazol-6-yloxy)ethylamino)-1-hydroxyethyl)phenyl)-ethanesulfonamide | 439 [M + H] | 0.93 | C |

TABLE 1-continued

| ex | reagent-1 | reagent-2 | Compound | Compound Name | LCMS MS | R.T. | method |
|---|---|---|---|---|---|---|---|
| ex16 | ref-60 | 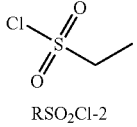 RSO₂Cl-2 | 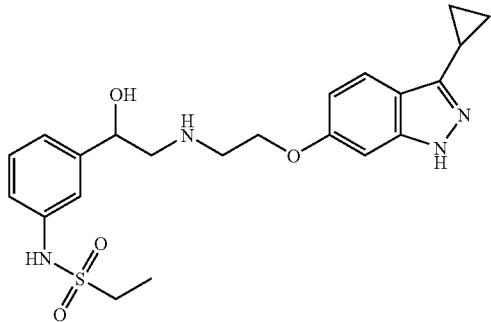 | (R)-N-(3-(2-(2-(3-cyclopropylindazol-6-yloxy)ethylamino)-1-hydroxyethyl)phenyl)-ethanesulfonamide | 445 [M + H] | 0.82 | C |
| ex17 | ref-61 | 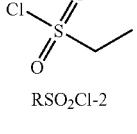 RSO₂Cl-2 | 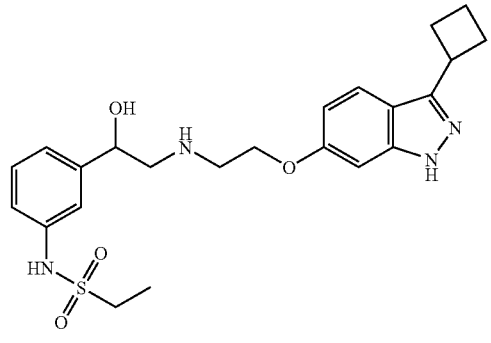 | (R)-N-(3-(2-(2-(3-cyclobutylindazol-6-yloxy)ethylamino)-1-hydroxyethyl)phenyl)-ethanesulfonamide | 459 [M + H] | 0.96 | C |
| ex18 | ref-63 | 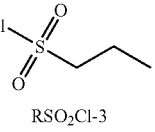 RSO₂Cl-3 | 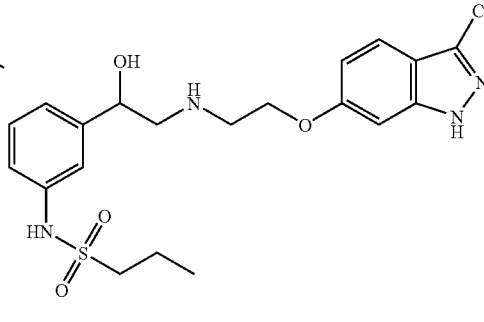 | (R)-N-(3-(2-(2-(3-chloroindazol-6-yloxy)ethylamino)-1-hydroxyethyl)phenyl)propane-1-sulfonamide | 453 [M + H] | 1.00 | C |
| ex19 | ref-62 | 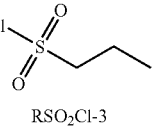 RSO₂Cl-3 | 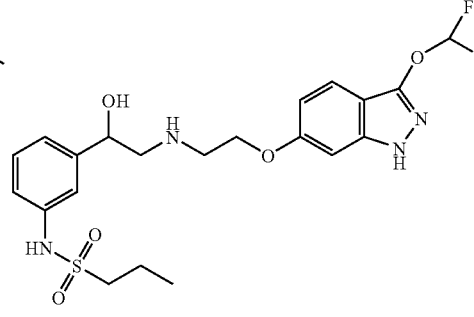 | (R)-N-(3-(2-(2-(3-(difluoromethoxy)-indazol-6-yloxy)ethylamino)-1-hydroxyethyl)phenyl)propane-1-sulfonamide | 485 [M + H] | 1.06 | C |

TABLE 1-continued

| ex | reagent-1 | reagent-2 | Compound | Compound Name | LCMS MS | R.T. | method |
|---|---|---|---|---|---|---|---|
| ex20 | ref-60 | 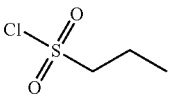 RSO₂Cl-3 | 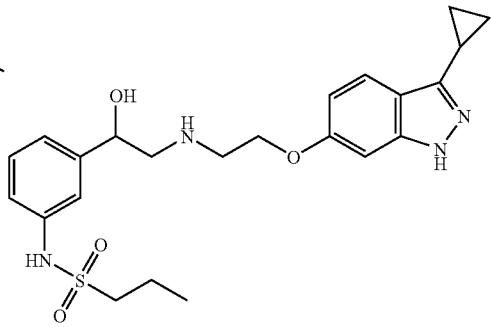 | (R)-N-(3-(2-(2-(3-cyclopropylindazol-6-yloxy)ethylamino)-1-hydroxyethyl)phenyl)propane-1-sulfonamide | 459 [M + H] | 1.02 | C |
| ex21 | ref-63 | 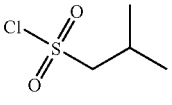 RSO₂Cl-4 | 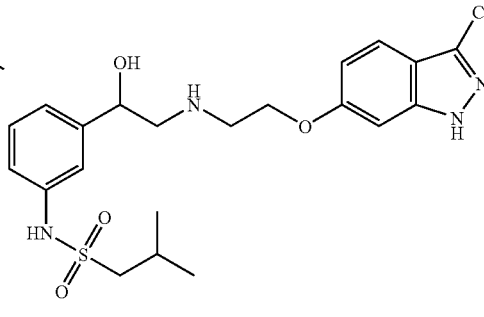 | (R)-N-(3-(2-(2-(3-chloroindazol-6-yloxy)ethylamino)-1-hydroxyethyl)phenyl)-2-methylpropane-1-sulfonamide | 467 [M + H] | 1.09 | C |
| ex22 | ref-62 | 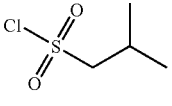 RSO₂Cl-4 | 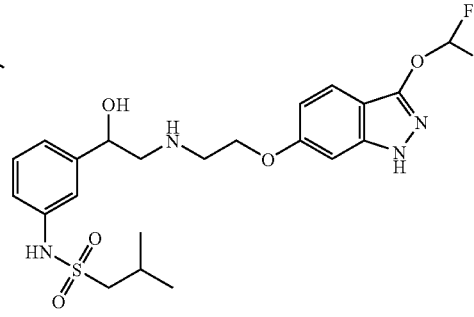 | (R)-N-(3-(2-(2-(3-(difluoromethoxy)indazol-6-yloxy)ethylamino)-1-hydroxyethyl)phenyl)-2-methylpropane-2-sulfonamide | 499 [M + H] | 1.14 | C |
| ex23 | ref-60 | 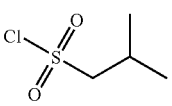 RSO₂Cl-4 | 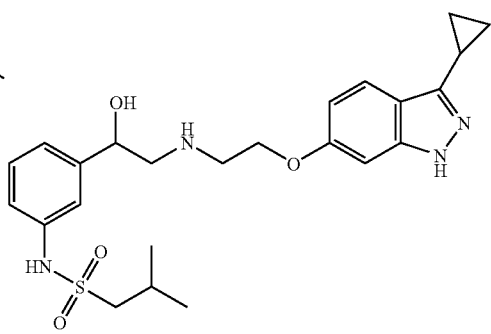 | (R)-N-(3-(2-(2-(3-cyclopropylindazol-6-yloxy)ethylamino)-1-hydroxyethyl)phenyl)-2-methylpropane-1-sulfonamide | 473 [M + H] | 1.09 | C |

TABLE 1-continued

| ex | reagent-1 | reagent-2 | Compound | Compound Name | LCMS MS | R.T. | method |
|---|---|---|---|---|---|---|---|
| ex24 | ref-62 | 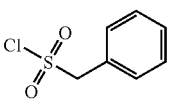 RSO₂Cl-5 | 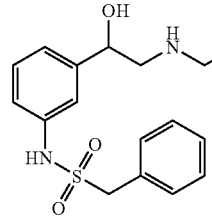 | (R)-N-(3-(2-(2-(3-(difluoromethoxy)-indazol-6-yloxy)ethylamino)-1-hydroxyethyl)phenyl)-1-phenyl-methanesulfonamide | 533 [M + H] | 1.15 | C |

Example 25

(R)—N-(3-(2-(2-(3-(Difluoromethoxy)-indazol-6-yloxy)ethylamino)-1-hydroxyethyl)phenyl)propane-2-sulfonamide

[Chemical Formula 113]

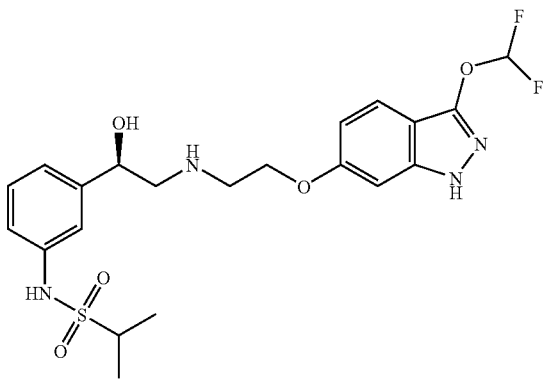

(R)-Tert-butyl 6-(2-((2-(3-aminophenyl)-2-(triethylsilyloxyethyl)(tert-butoxycarbonyl)amino)ethoxy)-3-(difluoromethoxy)-indazole-1-carboxylate (102.7 mg) which can be prepared according to the method described in Reference example 62, etc. was dissolved in dehydrated CH₂Cl₂, added with DBU (70 μL; manufactured by Tokyo Chemical Industry, Co., Ltd.) and propane-2-sulfonyl chloride (34 μL; manufactured by Tokyo Chemical Industry, Co., Ltd.), and shaken (600 min⁻¹) overnight at room temperature. To the reaction solution, DBU (90 μL) and propane-2-sulfonyl chloride (68 μL) were added and the mixture was shaken (600 min⁻¹) overnight at room temperature. The reaction solution was purified by column chromatography ("COLUMN-B"; n-hexane:ethyl acetate=80:20→59:41) to obtain a crude product, which was then dissolved in dehydrated CH₂Cl₂ (1 mL). After adding MP-Isocyanate (250 mg; manufactured by Argonaut, 1.46 mmol/g), the mixture was stirred overnight at room temperature. After filtering the reaction solution, the solvent was evaporated under reduced pressure and the residue was dissolved in MTBE (200 μL). To the MTBE solution, 4 mol/L-hydrochloric acid-1,4-dioxane solution (1.5 mL) was added and the mixture was shaken (600 min⁻¹) overnight at room temperature. To the reaction solution, nitrogen gas was blown to evaporate the solvent, and the resulting residue was added with MTBE to obtain suspension. Nitrogen gas was blown to the suspension to evaporate the solvent, and as a result, the title compound was obtained as a hydrochloride (27.7 mg).

LCMS: 485 [M+H]; retention time: 1.06 minutes: LCMS condition: C

Examples 26 and 27

By using reagent-1 instead of (R)-tert-butyl 6-(2-((2-(3-aminophenyl)-2-(triethylsilyloxyethyl)(tert-butoxycarbonyl)amino)ethoxy)-3-(difluoromethoxy)-indazole-1-carboxylate, Compounds of Table 2 were obtained as a hydrochloride in the same method as Example 25.

In the Table 2, symbols have the meanings as follows.

"ex" indicates the example number, for instance, ex 26 means Example 26.

"ref" indicates the Reference example number, for instance, ref-63 means Reference example 63.

"LCMS" indicates liquid chromatography mass analysis data (m/z). Specifically, it consists of "method", "R.T." and "MS", which will be described below.

"MS" indicates mass spectrum data. "R.T." indicates retention time in LCMS, and has minutes as a unit. "method" indicates the LCMS condition which has been described in detail above. For instances, the expression "C" indicates the (LCMS-C) condition.

Regarding RSO₂Cl-6, the product of Tokyo Chemical Industry was used.

TABLE 2

| ex | reagent-1 | reagent-2 | Compound | Compound Name | LCMS MS | R.T. | method |
|---|---|---|---|---|---|---|---|
| ex26 | ref-63 | RSO₂Cl-6 (Cl-S(=O)₂-iPr) | (structure with chloroindazole) | (R)-N-(3-(2-(2-(3-chloroindazol-6-yloxy)ethylamino)-1-hydroxyethyl)phenyl)propane-2-sulfonamide | 453 [M + H] | 1.03 | C |
| ex27 | ref-60 | RSO₂Cl-6 (Cl-S(=O)₂-iPr) | (structure with cyclopropylindazole) | (R)-N-(3-(2-(2-(3-cyclopropylindazol-6-yloxy)ethylamino)-1-hydroxyethyl)phenyl)propane-2-sulfonamide | 459 [M + H] | 1.00 | C |

Reference Example 64

2-Chloro-1-(4-fluoro-3-nitrophenyl)ethanone

[Chemical Formula 114]

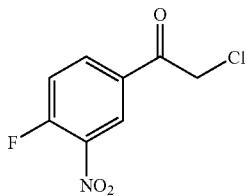

1-(4-Fluoro-3-nitrophenyl)ethanone (18.4249 g; manufactured by Sigma-Aldrich Co.) was dissolved in CH₂Cl₂ (400 mL), added with methanol (3.04 mL), followed by replacement with nitrogen gas and cooling to 0° C. To the resulting solution, $SO_2Cl_2$-$CH_2Cl_2$ solution [109.32 mL; solution obtained by dissolving $SO_2Cl_2$ (9.32 mL; manufactured by Wako Pure Chemical Industries, Ltd.) in $CH_2Cl_2$ (100 mL)] was added dropwise over 30 minutes, and the mixture was stirred overnight while warming to room temperature. The reaction solution was cooled to 0° C., added with methanol (1.52 mL), and then $SO_2Cl_2$-$CH_2Cl_2$ solution [64.66 mL; solution obtained by dissolving $SO_2Cl_2$ (4.66 mL; manufactured by Wako Pure Chemical Industries, Ltd.) in $CH_2Cl_2$ (60 mL)] was added dropwise thereto. While warming to room temperature, the mixture was stirred for 3 hours. The reaction solution was washed once with a saturated aqueous solution of sodium carbonate and once with brine. The organic layer was dried over anhydrous sodium sulfate, and the solvent was evaporated under reduced pressure. The solidified crystal, which had been obtained during purification of the resulting residue by column chromatography ("COLUMN-A"; n-hexane:ethyl acetate=88:12→67:33), was extracted with ethyl acetate, and then filtered. The filtrate was evaporated under reduced pressure, and as a result, the title compound was obtained (6.403 g).

$^1$H-NMR (300 MHz, CDCl₃); δ (ppm) 4.66 (2H, s), 7.46 (1H, dd, J=8.7, 9.8), 8.28 (1H, ddd, J=2.1, 4.0, 8.7), 8.67 (1H, dd, J=2.1, 7.3)

Reference Example 65

(R)-2-(4-Fluoro-3-nitrophenyl)oxirane

[Chemical Formula 115]

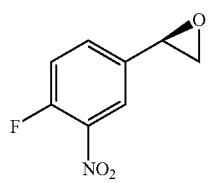

Under nitrogen atmosphere, 2-chloro-1-(4-fluoro-3-nitrophenyl)ethanone (5.4667 g) which can be prepared according to the method described in Reference example 64, etc. was dissolved in dehydrated THF (100 mL), added with 1 mol/L-(R)—CBS-toluene solution (7.5 mL; manufactured by Sigma-Aldrich Co.), followed by cooling to 0° C. To the resulting solution, $BH_{32}$·$SMe_2$ (10 mL; manufactured by Sigma-Aldrich Co.) was added dropwise over 10 minutes and the mixture was stirred at 0° C. for 2 hours. An aqueous solution of ammonium chloride was added to the reaction solution and extraction was carried out twice with ethyl acetate. The organic layer was washed once with brine, dried over magnesium sulfate, and then the solvent was evaporated under reduced pressure. The resulting residue was added with 2-propanol (100 mL) and an aqueous solution of 1 mol/L-sodium hydroxide (25 mL; manufactured by Kanto Chemical Co., Inc.), and the mixture was stirred at 0° C. for 10 minutes. The reaction solution was poured to water and extracted twice with ethyl acetate. The organic layer was washed once with brine, dried over anhydrous sodium sulfate, and then concentrated under reduced pressure. The resulting residue was purified by column chromatography ("COLUMN-8"; n-hexane:ethyl acetate=88:12→67:33) to obtain the title compound (4.2885 g, optical purity; 92% ee).

Optical resolution condition [column; As-H (manufactured by Daicel Chemical Industries, Ltd.), eluent; hexane:ethanol=90:10, flow rate; 0.5 mL/min, detection UV; 254 nM, temperature; 40° C.]

$^1$H-NMR (300 MHz, CDCl$_3$); δ (ppm) 2.76 (1H, dd, J=2.5, 5.4), 3.20 (1H, dd, J=4.0, 5.4), 3.92 (1H, dd, J=2.5, 4.0), 7.28 (1H, dd, J=8.4, 10.2), 7.54 (1H, ddd, J=2.1, 4.0, 8.4), 7.99 (1H, dd, J=2.1, 6.9)

Reference Example 66

Tert-butyl 3-chloro-6-(2-(dibenzylamino)ethoxy)indazole-1-carboxylate

[Chemical Formula 116]

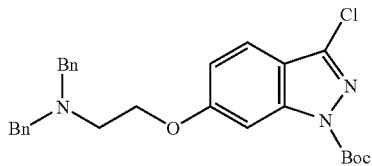

Tert-butyl 3-chloro-6-hydroxyindazole-1-carboxylate (4.3611 g) which can be prepared according to the method described in Reference example 39, etc. and 2-(dibenzylamino)ethanol (4.1529 g; manufactured by Tokyo Chemical Industry Co., Ltd.) were dissolved in dehydrated THF (100 mL), added with triphenylphosphine (7.9370 g; manufactured by Kanto Chemical Co., Inc.) and TMAD (5.2270 g; manufactured by Masuda Chemical Industries Co., Ltd.), and then stirred overnight at room temperature. The reaction solution was filtered and the filtrate was concentrated under reduced pressure. The resulting residue was dissolved in toluene, and the solvent was evaporated under reduced pressure. The resulting residue was purified by column chromatography ("COLUMN-D"; n-hexane:ethyl acetate=90:10→75:25) to obtain the title compound (7.1028 g).

LCMS: 492 [M+H]; retention time: 2.29 minutes: LCMS condition: C

Reference Example 67

Tert-butyl 6-(2-benzylamino)ethoxy) 3-chloroindazole-1-carboxylate

[Chemical Formula 117]

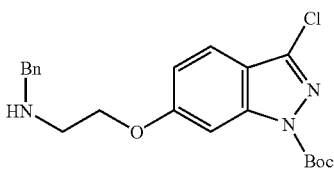

Tert-butyl 3-chloro-6-(2-(dibenzylamino)ethoxy)indazole-1-carboxylate (7.010 g) which can be prepared according to the method described in Reference example 66, etc. and 5% palladium on carbon-STD-type-50% wet with water (1.8534 g; manufactured by N. E. Chemcat Corp.) were suspended in methanol (20 mL), and added with 5 mol/L-hydrochloric acid (2.9 mL; manufactured by Kanto Chemical Co., Inc.). After replacing the reaction system with hydrogen to obtain hydrogen atmosphere, the mixture was stirred for 10 minutes at room temperature. Then, the reaction system was replaced with nitrogen and added with ethanol (20 mL) and water (10 mL). After replacing the reaction system with hydrogen to obtain hydrogen atmosphere, the mixture was stirred for 1 hour at room temperature. Then, the reaction system was replaced with nitrogen and then filtered. The filtrate was concentrated under reduced pressure to obtain the title compound as a crude product (3.6082 g).

$^1$H-NMR (300 MHz, CDCl$_3$); δ (ppm). 1.70 (9H, s), 3.08 (2H, t, J=5.1), 3.89 (2H, s), 4.17-4.21 (2H, m), 6.98 (1H, dd, J=1.8, 8.7), 7.27-7.37 (5H, m), 7.53 (1H, d, J=8.7), 7.63 (1H, d, J=1.8)

LCMS; 402 [M+H]; retention time: 1.29 minutes: LCMS condition: C

Reference Example 68

(R)-Tert-butyl 6-(2-(benzyl(2-(4-fluoro-3-nitrophenyl)-2-hydroxyethyl)amino)ethoxy)-3-chloroindazole-1-carboxylate

[Chemical Formula 118]

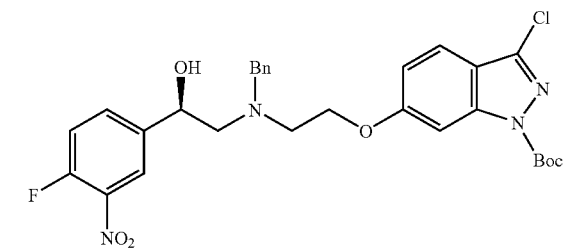

Tert-butyl 6-(2-benzylamino)ethoxy) 3-chloroindazole-1-carboxylate (1.6144 g) which can be prepared according to the method described in Reference example 67, etc. was added with (R)-2-(4-fluoro-3-nitrophenyl)oxirane (732 mg)

which can be prepared according to the method described in Reference example 65, etc. and 2-propanol (8 mL), and the mixture was stirred overnight at reflux. After cooling to room temperature, the reaction solution was concentrated under reduced pressure. The resulting residue was purified by column chromatography ("COLUMN-C"; n-hexane:ethyl acetate=75:25→70:30) to obtain the title compound (0.7936 g).

$^1$H-NMR (300 MHz, CDCl$_3$); δ (ppm) 1.70 (9H, s), 2.65 (1H, dd, J=10.2, 12.8), 2.92 (1H, dd, J=3.2, 12.8), 3.03-3.23 (2H, m), 3.86 (2H, dd, J=13.5, 68.9), 4.08-4.18 (2H, m), 4.71 (1H, dd, J=3.2, 10.2), 7.00 (1H, dd, J=1.8, 8.7), 7.21 (1H, dd, J=1.8, 8.7), 7.27-7.33 (5H, m), 7.54-7.63 (3H, m), 8.00 (1H, dd, J=2.1, 6.9)

LCMS: 585 [M+H]; retention time: 2.05 minutes: LCMS condition: C

Reference Example 69

(R)-Tert-butyl 6-(2-((2-(3-amino-4-fluorophenyl)-2-hydroxyethyl)(tert-butoxycarbonyl)amino)ethoxy)-3-chloroindazole-1-carboxylate

[Chemical Formula 119]

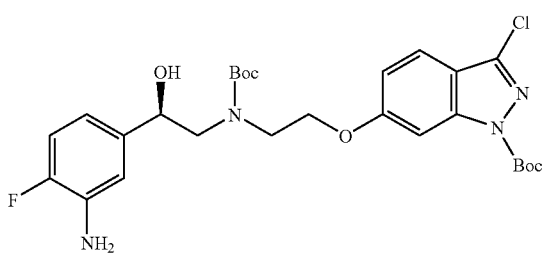

(R)-Tert-butyl 6-(2-(benzyl(2-(4-fluoro-3-nitrophenyl)-2-hydroxyethyl)amino)ethoxy)-3-chloroindazole-1-carboxylate (785.3 mg) which can be prepared according to the method described in Reference example 68, etc. and 10% palladium on carbon-PE-type-50% wet with water (175.8 mg; manufactured by N. E. Chemcat Corp.) were suspended in 0.1 mol/L-hydrochloric acid-ethanol solution (27 mL; manufactured by Kanto Chemical Co., Inc.). After replacing the reaction system with hydrogen to obtain hydrogen atmosphere, the mixture was stirred for 1 hour at room temperature. Then, the reaction system was replaced with nitrogen and filtered. To the filtrate, triethylamine (752 µL; manufactured by Kanto Chemical Co. Inc.) was added and the mixture was concentrated under reduced pressure. The resulting residue was dissolved in CH$_2$Cl$_2$ (10 mL) and methanol (10 mL), added with Boc$_2$O (294 µL; manufactured by Wako Pure Chemical Industries, Ltd.), and then stirred overnight at room temperature. The reaction solution was concentrated under reduced pressure, and the resulting residue was purified by column chromatography ("COLUMN-B"; n-hexane ethyl acetate=71:29→50:50) to obtain the title compound (604.4 mg).

$^1$H-NMR (300 MHz, CDCl$_3$); δ (ppm) 1.49 (9H, s) 1.70 (9H, s), 3.36-3.74 (4H, m), 4.11-4.32 (2H, m), 4.90 (1H, brs), 6.68-6.97 (4H, m), 7.53 (1H, d, J=8.7), 7.62 (1H, brs)

LCMS: 565 [M+H]; retention time: 2.05 minutes: LCMS condition: C

Reference Example 70

(R)-Tert-butyl 6-(2-((2-(3-amino-4-fluorophenyl)-2-(triethylsilyloxy)ethyl)(tert-butoxycarbonyl)amino)ethoxy)-3-chloroindazole-1-carboxylate

[Chemical Formula 120]

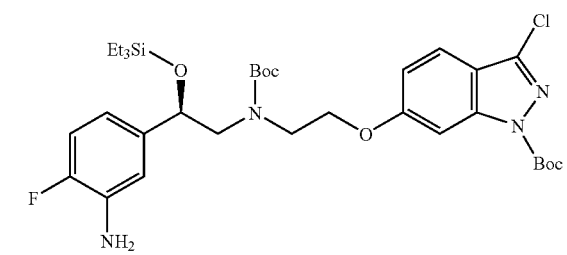

(R)-Tert-butyl 6-(2-((2-(3-amino-4-fluorophenyl)-2-hydroxyethyl)(tert-butoxycarbonyl)amino)ethoxy)-3-chloroindazole-1-carboxylate (601.2 mg) which can be prepared according to the method described in Reference example 69, etc. and imidazole (290.3 mg; Tokyo Chemical Industry Co., Ltd) were dissolved in dehydrated DMF (5 mL), added with chlorotriethylsilane (705 µL; manufactured by Shin-Etsu Chemical Co., Ltd.), and then the mixture was stirred for three hours at room temperature. The reaction solution was added to saturated solution of sodium hydrogen carbonate solution and extracted twice with ethyl acetate. The organic layer was washed twice with water and once with brine, dried over anhydrous sodium sulfate, and then the solvent was evaporated under reduced pressure. The resulting residue was purified by column chromatography ("COLUMN-B"; n-hexane: ethyl acetate=84:16→64:36) to obtain the title compound (480 mg).

$^1$H-NMR (300 MHz, CDCl$_3$); δ (ppm) 0.52 (6H, q, J=8.0), 0.88 (9H, q, J=8.0), 1.47 (9H, s), 1.69 (9H, s), 3.12-3.76 (4H), 4.06-4.12 (2H, m), 4.77-4.97 (1H, m), 6.57-6.96 (4H, m), 7.51 (1H, dd, J=2.1, 8.4), 7.58 (1H, s)

LCMS: 679 [M+H]; retention time: 2.29 minutes: LCMS condition: E

Reference Example 71

(R)-Tert-butyl 6-(2-(benzyl(2-(4-chloro-3-nitrophenyl)-2-hydroxyethyl)amino)ethoxy)-3-chloroindazole-1-carboxylate

[Chemical Formula 121]

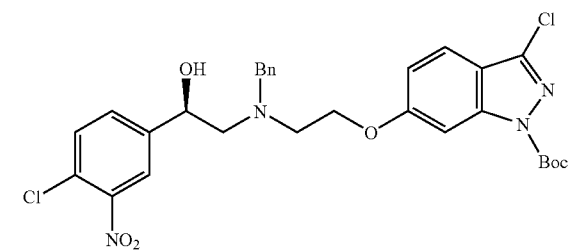

Tert-butyl 6-(2-benzylamino)ethoxy) 3-chloroindazole-1-carboxylate (1.91 g) which can be prepared according to the method described in Reference example 67, etc. was added with (R)-2-(4-chloro-3-nitrophenyl)oxirane (971.8 mg) and 2-propanol (8 mL), and then the mixture was stirred overnight at reflux. The reaction solution was cooled to room temperature and concentrated under reduced pressure. The resulting residue was purified by column chromatography ("COLUMN-C"; n-hexane:ethylacetate=90:10→75:25) to obtain the title compound (0.9411 g).

$^1$H-NMR (300 MHz, CDCl$_3$); δ (ppm) 1.70 (9H, s), 2.64 (1H, dd, J=10.2, 13.1), 2.92 (1H, dd, J=3.6, 13.1), 3.01-3.23 (2H, m), 3.85 (2H, dd, J=13.5, 67.8), 4.06-4.19 (2H, m), 4.70 (1H, dd, J=3.6, 10.2), 6.98 (1H, dd, J=2.1, 8.7), 7.27-7.35 (5H, m), 7.42-7.49 (2H, m), 7.56 (1H, d, J=8.7), 7.62 (1H, d, J=2.1), 7.83 (1H, d, J=1.4)

LCMS: 601 [M+H]; retention time: 5.88 minutes: LCMS condition: C

Reference Example 72

(R)-Tert-butyl 6-(2-((2-(3-amino-4-chlorophenyl)-2-hydroxyethyl)(benzyl)amino)ethoxy)-3-chloroindazole-1-carboxylate

[Chemical Formula 122]

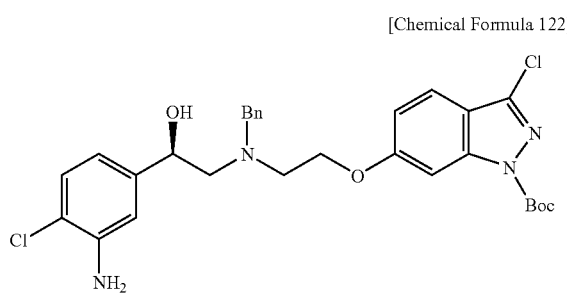

(R)-Tert-butyl 6-(2-(benzyl(2-(4-chloro-3-nitrophenyl)-2-hydroxyethyl)amino)ethoxy)-3-chloroindazole-1-carboxylate (931.5 mg) which can be prepared according to the method described in Reference example 71, etc. and CM-101 catalyst (2.0962 g; manufactured by N. E. Chemcat Corp.) were suspended in methanol (10 mL) and THF (10 mL). After replacing the reaction system with hydrogen to obtain hydrogen atmosphere, the mixture was stirred overnight at room temperature. Then, the reaction system was replaced with nitrogen and filtered. The filtrate was concentrated under reduced pressure, and the resulting residue was added with CH$_2$Cl$_2$. The organic layer was dried over anhydrous sodium sulfate. After the solvent was evaporated under reduced pressure, the title compound was obtained as a crude product (707 mg).

LCMS: 571 [M+H]; retention time: 2.02 minutes: LCMS condition: C

Reference Example 73

(R)-Tert-butyl 6-(2-((2-(3-amino-4-chlorophenyl)-2-hydroxyethyl)(tert-butoxycarbonyl)amino)ethoxy)-3-chloroindazole-carboxylate

[Chemical Formula 123]

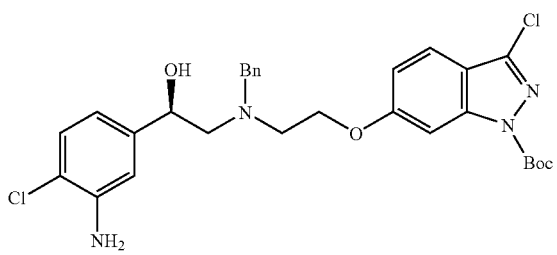

(R)-Tert-butyl 6-(2-((2-(3-amino-4-chlorophenyl)-2-hydroxyethyl)(benzyl))amino)ethoxy)-3-chloroindazole-1-carboxylate (707 mg) which can be prepared according to the method described in Reference example 72, etc. and 10% palladium on carbon-PE-type-50% wet with water (157.3 mg; manufactured by N. E. Chemcat Corp.) were suspended in 0.1 mol/L-hydrochloric acid-ethanol solution (24.6 mL; manufactured by Kanto Chemical Co., Inc.). After replacing the reaction system with hydrogen to obtain hydrogen atmosphere, the mixture was stirred for 20 minutes at room temperature. Then, the reaction system was replaced with nitrogen and filtered. To the filtrate, triethylamine (684 µL; manufactured by Kanto Chemical Co., Inc.) was added and the mixture was concentrated under reduced pressure. The resulting residue was dissolved in CH$_2$Cl$_2$ (10 mL), added with Boc$_2$O (266 µL; manufactured by Wako Pure Chemical Industries, Ltd.), and then stirred at room temperature for three days. The reaction solution was concentrated under reduced pressure, and the resulting residue was purified by column chromatography ("COLUMN-B"; n-hexane:ethyl acetate=75:25→54:46) to obtain the title compound (406.9 mg).

$^1$H-NMR (300 MHz, CDCl$_3$); δ (ppm) 1-48 (9H, s), 1.70 (9H, s) 3.33-3.76 (4H, m), 4.06-4.24 (2H, m), 4.90 (1H, brs), 6.68-6.97 (3H, m), 7.20 (1H, d, J=8.0), 7.53 (1H, d, J=8.7), 8.04 (1H, brs)

LCMS: 581 [M+H]; retention time: 2.14 minutes: LCMS condition: C

Reference Example 74

(R)-Tert-butyl 6-(2-((2-(3-amino-4-chlorophenyl)-2-(triethylsilyloxy)ethyl)(tert-butoxycarbonyl)amino)ethoxy)-3-chloroindazole-1-carboxylate

[Chemical Formula 124]

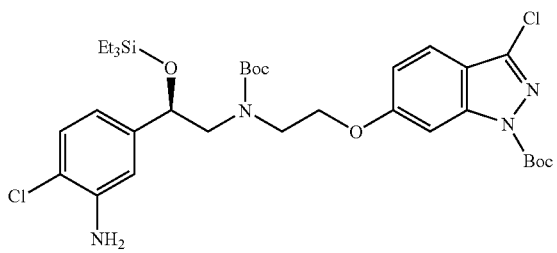

(R)-Tert-butyl 6-(2-((2-(3-amino-4-chlorophenyl)-2-hydroxyethyl)(tert-butoxycarbonyl)amino)ethoxy)-3-chloroindazole-carboxylate (404.3 mg) which can be prepared according to the method described in Reference example 73, etc. was dissolved in dehydrated DMF (5 mL), added with imidazole (197.8 mg; Tokyo Chemical Industry Co., Ltd) and chlorotriethylsilane (470 μL; manufactured by Shin-Etsu Chemical Co., Ltd.), and then the mixture was stirred for six hours at room temperature. The reaction solution was added to saturated sodium hydrogen carbonate, and then extracted once with ethyl acetate. The organic layer was washed once with water and once with brine, dried over anhydrous sodium sulfate, and then the solvent was evaporated under reduced pressure. The resulting residue was purified by column chromatography ("COLUMN-B"; n-hexane:ethyl acetate=92:8→71:29) to obtain the title compound (278.7 mg).

$^1$H-NMR (300 MHz, CDCl$_3$); δ (ppm) 0.53 (6H, q, J=7.6), 0.88 (9H, t, J=7.6), 1.46-1.47 (9H, m), 1.69 (9H, s), 3.11-3.77 (4H, m), 4.03-4.12 (2H, m), 4.77-4.98 (1H, m), 6.59-6.95 (3H, m), 7.17 (1H, d, J=8.0), 7.51 (1H, dd, J=1.8, 8.7), 7.58 (1H, s)

LCMS: 694 [M+H]; retention time: 2.56 minutes: LCMS condition: E

Example 28

(R)—N-(5-(2-(2-(3-Chloroindazol-6-yloxy)ethylamino)-1-hydroxyethyl)-2-fluorophenyl)benzenesulfonamide

[Chemical Formula 125]

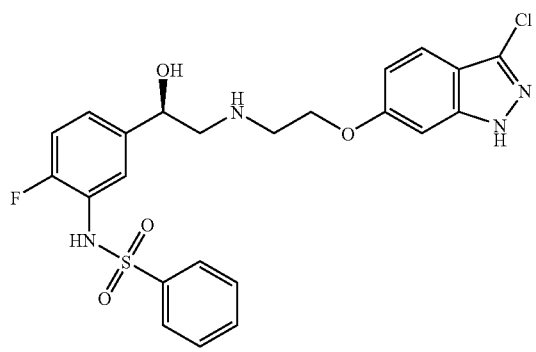

(R)-Tert-butyl 6-(2-((2-(3-amino-4-fluorophenyl)-2-(triethylsilyloxy)ethyl)(tert-butoxycarbonyl)amino)ethoxy)-3-chloroindazole-1-carboxylate-CH$_2$Cl$_2$ solution [0.5 mL; solution obtained by dissolving (R)-tert-butyl 6-(2-((2-(3-amino-4-fluorophenyl)-2-(triethylsilyloxy)ethyl)(tert-butoxycarbonyl)amino)ethoxy)-3-chloroindazole-1-carboxylate (480 mg) which can be prepared according to the method described in Reference example 70, etc. in dehydrated CH$_2$Cl$_2$ (3.52 mL)] was added with dehydrated pyridine (42 μL), benzenesulfonyl chloride-CH$_2$Cl$_2$ solution [0.5 mL; solution obtained by dissolving benzenesulfonyl chloride (466.3 mg; manufactured by Wako Pure Chemical Industries, Ltd.) in dehydrated CH$_2$Cl$_2$ (4 mL)] and dehydrated CH$_2$Cl$_2$, and the mixture was shaken (600 min$^{-1}$) overnight at room temperature. To the reaction solution, PS-Trisamine [300 mg (3.6 mmol/g); manufactured by Argonaut] was added and the mixture was shaken (600 min$^{-1}$) for 5 hours at room temperature. The reaction solution was filtered and the solvent was evaporated by blowing nitrogen gas to the filtrate. The resulting residue was purified by column chromatography ("COLUMN-I"; methanol). The resulting purified product was dissolved in 1,4-dioxane (0.2 mL), added with 4 mol/L-hydrochloric acid-1,4 dioxane solution (1.5 mL), and then shaken (600 min$^{-1}$) overnight at room temperature. To the reaction solution, nitrogen gas was blown to evaporate the solvent, and the resulting residue was added with MTBE to obtain suspension. Nitrogen gas was blown to the suspension to evaporate the solvent, and as a result, the title compound was obtained as a hydrochloride (40.7 mg).

LCMS: 505 [M+H]; retention time: 1.05 minutes: LCMS condition: C

Example 29

(R)—N-(2-Chloro-5-(2-(2-(3-chloroindazol-6-yloxy)ethylamino)-1-hydroxyethyl)phenyl)benzenesulfonamide

[Chemical Formula 126]

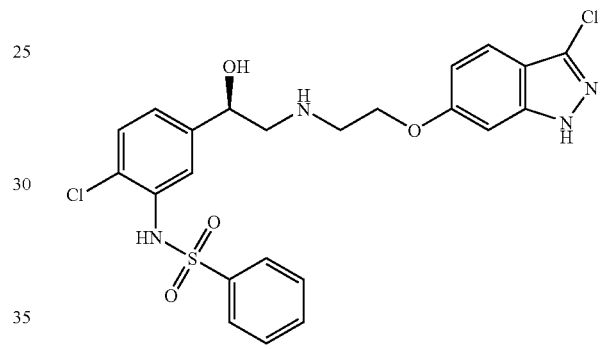

By using (R)-tert-butyl 6-(2-((2-(3-amino-4-chlorophenyl)-2-(triethylsilyloxy)ethyl)(tert-butoxycarbonyl)amino)ethoxy)-3-chloroindazole-1-carboxylate which can be prepared according to the method described in Reference example 74, etc. instead (R)-tert-butyl 6-(2-((2-(3-amino-4-fluorophenyl)-2-(triethylsilyloxy)ethyl)(tert-butoxycarbonyl)amino)ethoxy)-3-chloroindazole-1-carboxylate, the title compound was obtained as a hydrochloride (11.8 mg) in the same method as Example 28.

LCMS: 521 [M+H]; retention time: 1.16 minutes: LCMS condition: C

Test Example-1-A

Measurement of Human β3 Adrenergic Receptor Agonist Activity

Human β3 adrenergic receptor agonist activity is determined using CHO (Chinese hamster ovary) cells transfected with pcDNA3 (Invitrogen) to which human β3 gene has been inserted. Human β3 cDNA fragment is first obtained from human adipose tissue cDNA (Clonetech) by PCR using the primers of β3 gene (Krief. et al., J. Clin. Invest., vol, 91, pp. 344-349 (1993)). This human β3 cDNA fragment is used as a probe to obtain the full length human β3 gene from a human genomic library (Clonetech). The above cells are cultured in a Ham's F-12 medium containing 10% fetal bovine serum and 400 μg/mL geneticin (Invitrogen). After seeding these cells into a 24-well plate (1×10$^5$ cells/well) and culturing them for about 20 hours, they are allowed to stand in a serum-free Ham's F-12 medium for 2 hours. The test compound is first dissolved in DMSO, serially is diluted with Ham's F-12 comprising 20 mmol/L HEPES, 1 mmol/L isobutylmethylxanthine, and 1 mmol/L ascorbic acid, and then is added to the cells. After the cells are cultured for 30 minutes, the medium is removed, followed by addition of 0.1 mL of 1 N NaOH. The cells are allowed to stand for 20 minutes, and then are added with 0.1 mL of 1 N acetic acid and are stirred. The resulting cell lysate is centrifuged, followed by quantitating cAMP using cAMP EIA kit (Cayman). Maximum response to isoproterenol as a positive control is taken as 100%, and the maximum response ratio of each test compound is obtained as Intrinsic Activity [I.A. (%)]. Further, the concentration of a drug solution which gives 50% of the maximum response (EC50) is also obtained.

Test Example 1-B

Measurement of Human β3 Adrenergic Receptor Agonist Activity

Human β3 adrenergic receptor agonist activity is determined using CHO (Chinese hamster ovary) cells transfected with pcDNA3 (Invitrogen) to which human β3 gene has been inserted. Human β3 cDNA fragment is first obtained from human adipose tissue cDNA (Clonetech) by PCR using the primers for β3 gene (Krief. et al., J. Clin. Invest., vol, 91, pp. 344-349 (1993)). This human β3 cDNA fragment is used as a probe to obtain the full length human β3 gene from a human genomic library (Clonetech). The above cells are cultured in a Ham's F-12 medium containing 10% fetal bovine serum and 400 µg/mL geneticin (Invitrogen). After seeding these cells into a 96-well plate ($2 \times 10^4$ cells/well) and culturing them for about 20 hours, they are allowed to stand in a serum-free Ham's F-12 medium (80 µL) for 15 minutes. The test compound is first dissolved in DMSO, serially diluted with Ham's F-12 comprising 100 mmol/L HEPES and 1 mmol/L isobutylmethylxanthine, and then 20 µL of the solution is added to the cells. After the cells are cultured for 30 minutes, the medium is removed, followed by addition of assay/lysis buffer (0.1 ml) included in cAMP-Screen Kit (manufactured by Applied Biosystems). The cells are incubated for 30 minutes at 37° C. The resulting cell lysate is determined to cAMP quantitation by using cAMP-Screen kit described above. Maximum response to isoproterenol as a positive control is taken as 100%, and the maximum response ratio of each test compound is obtained as Intrinsic Activity [I.A. (%)]. Further, the concentration of a drug solution which gives 50% of the maximum response (EC50) is also obtained.

Test Example 2-A

Measurement of Human β1 Adrenergic Receptor Agonist Activity

Human β1 adrenergic receptor agonist activity is determined in the same method as Test example 1-A by using CHO (Chinese hamster ovary) cells transfected with pcDNA3 (Invitrogen) to which human β1 gene has been inserted. Maximum response to isoproterenol as a positive control is taken as 100%, and the maximum response ratio of each test compound is obtained as Intrinsic Activity [I.A. (%)]. Further, the concentration of a drug solution which gives 50% of maximum response (EC50) is also obtained.

Test Example 2-B

Measurement of human β1 Adrenergic Receptor Agonist Activity

Human β1 adrenergic receptor agonist activity is determined in the same method as Test example 1-B by using CHO (Chinese hamster ovary) cells transfected with pcDNA3 (Invitrogen) to which human β1 gene has been inserted. Maximum response to isoproterenol as a positive control is taken as 100%, and the maximum response ratio of each test compound is obtained as Intrinsic Activity [I.A. (%)]. Further, the concentration of a drug solution which gives 50% of maximum response (EC50) is also obtained.

Test Example 3-A

Measurement of Human β2 Adrenergic Receptor Agonist Activity

Human β2 adrenergic receptor agonist activity is determined in the same method as Test example 1-A by using CHO (Chinese hamster ovary) cells transfected with pcDNA3 (Invitrogen) to which human β2 gene has been inserted. Maximum response to isoproterenol as a positive control is taken as 100%, and the maximum response ratio of each test compound is obtained as Intrinsic Activity [I.A. (%)]. Further, the concentration of a drug solution which gives 50% of maximum response (EC50) is also obtained.

Test Example 3-B

Measurement of Human β2 Adrenergic Receptor Agonist Activity

Human β2 adrenergic receptor agonist activity is determined in the same method as Test example 1-B by using CHO (Chinese hamster ovary) cells transfected with pcDNA3 (Invitrogen) to which human β2 gene has been inserted. Maximum response to isoproterenol as a positive control is taken as 100%, and the maximum response ratio of each test compound is obtained as Intrinsic Activity [I.A. (%)]. Further, the concentration of a drug solution which gives 50% of maximum response (EC50) is also obtained.

Test Example 4

Measurement of Human α1A Adrenergic Receptor Agonist Activity

Human α1A adrenergic receptor agonist activity is determined by using HEK293 cells transfected with pcDNA3.1(−) (Invitrogen) to which human α1A gene has been inserted. These cells are cultured in a DMEM medium containing 10% fetal bovine serum, 400 µg/mL geneticin (Gibco BRL), 100 U/ml penicillin and 100 µg/ml streptomycin. Then, the cells are prepared to $5 \times 10^6$ cells/ml by using an assay buffer (20 mmol/L HEPES-KOH (pH 7.4), 115 mmol/L NaCl, 5.4 mmol/L KCl, 0.8 mmol/L $MgCl_2$, 1.8 mmol/L $CaCl_2$, 13.8 mmol/L D-glucose, 0.1% bovine serum albumin) comprising 0.2% Pluronic F-127 (Invitrogen) and 20 µmol/L Fura-2AM (manufactured by Wako Pure Chemical Industries, Ltd.). After carrying out the loading for 30 minutes in a $CO_2$ incubator, excess Fura-2AM is removed by washing the cells twice with the assay buffer. The cells obtained after the centrifuge is prepared to 5×10$^6$ cells/ml by using the assay buffer, and aliquoted into a 96-well UV plate (manufactured by Corning Inc.) to give a cell plate (80 μl/well). The sample plate to which the test compound that has been diluted by ten times from 10$^{-5}$ to 10$^{-12}$ M with the assay buffer is added and the cell plate are placed in FDSS4000 (manufactured by Hamamatsu Photonics K.K.), and 180 seconds after the preincubation, fluorescence intensity measurement is started with the interval of two seconds (excitation wavelength; 340 nm and 380 nm, measurement wavelength; 500 nm). After the measurement for about 30 seconds, 20 μl of the test sample from the sample plate is added to the cell plate and the measurement is continued for another 270 seconds. Ca flux caused by the test compound is obtained from the peak height difference between the maximum value of fluorescence intensity ratio at 340 nm and 380 nm after the addition of the test compound and the fluorescence intensity ratio before the addition of the test compound. Maximum response to norepinephrine as a positive control is taken as 100%, and the maximum response ratio of each test compound is obtained as Intrinsic Activity [I.A. (%)]. Further, the concentration of a drug solution which gives 50% of maximum response (EC50) is also obtained.

Test Example 5

Measurement of Human α1B Adrenergic Receptor Agonist Activity

Human α1B adrenergic receptor agonist activity is determined using HEK293 cells which are transiently co-transfected with pcDNA3.1 (Invitrogen) to which human α1B gene has been inserted and pSRE-Luc. plasmid (Stratagene) as an expression vector for luciferase gene. After seeding into a 96-well plate (40,000 cells/well), these cells are cultured overnight in a DMEM medium containing 2% fetal bovine serum under the condition of 37° C. and 5% CO$_2$. The test compound is dissolved in DMSO, is diluted in the medium and then is added to the cells for reaction for several hours. The medium is removed by aspiration, and then Pica Gene LT2.0 (30 μl/well; manufactured by TOYO INK MFG. CO., LTD.) is added to the cells. After thirty minutes, luminescence value is measured. Maximum response to phenylephrine as a positive control is taken as 100%, and the maximum response ratio of each test compound is obtained as Intrinsic Activity [I.A. (%)]. Further, the concentration of a drug solution which gives 50% of maximum response (EC50) is also obtained.

Test Example 6

Measurement of Human α1D Adrenergic Receptor Agonist Activity

Human α1D adrenergic receptor agonist activity is determined using HEK293 cells which are transiently co-transfected with pcDNA3.1 (Invitrogen) to which human α1D gene has been inserted and pSRE-Luc. plasmid (Stratagene) as an expression vector for luciferase gene. After seeding into a 96-well plate (40,000 cells/well), these cells are cultured overnight in a DMEM medium containing 20 fetal bovine serum under the condition of 37° C. and 5% CO$_2$. The test compound is dissolved in DMSO, is diluted in the medium and then is added to the cells for reaction for several hours. The medium is removed by aspiration, and then Pica Gene LT2.0 (30 μl/well; manufactured by TOYO INK MFG. CO., LTD.) is added to the cells. After thirty minutes, luminescence value is measured. Maximum response to phenylephrine as a positive control is taken as 100%, and the maximum response ratio of each test compound is obtained as Intrinsic Activity [I.A. (%)]. Further, the concentration of a drug solution which gives 50% of maximum response (EC50) is also obtained.

Results of Test example 1-A, Test example 2-A, Test example 3-A and Test example 4 were shown in Table 3.

Symbols described in the Table 3 are defined as follows.

β3 receptor indicates the human β3 adrenergic receptor agonist activity, β1 receptor indicates the human β1 adrenergic receptor agonist activity, β2 receptor indicates the human β2 adrenergic receptor agonist activity, and α1A receptor indicates the human α1A adrenergic receptor agonist activity.

EC50 and IA have the same meanings as those described in Test example 1-A, Test example 2-A, Test example 3-A, or Test example 4.

Further, "N" described in the Table 3 indicates the number of the test. Specifically, it is as follows—A; n=3, triplicate, B; n=2, triplicate, C; n=1, duplicate, D; n=4, triplicate, E; n=3, duplicate, F; n=2, duplicate, G; n=1, triplicate.

"Compound" indicates the test compound. "ex" indicates the Example, for instance, ex1 indicates the Example 1. "Z" indicates the Comparative example, for example, Z1 indicates the Comparative example 1. The comparative examples are related to the compounds that are disclosed in the pamphlet of the International Publication No. WO03/035620. The Comparative example 1, Comparative example 2, and Comparative example 3 correspond to the Example 86, Example 88, and Example 90 of this international publication, respectively.

Further, from the results of the Test example 5, it was found that Z1 had no α1B agonist activity. Still further, from the results of the Test example 6, it was found that Z1 had no α1D agonist activity, either.

TABLE 3

| compound | β3 receptor | | | β1 receptor | | | β2 receptor | | | α1A receptor | | |
|---|---|---|---|---|---|---|---|---|---|---|---|---|
| | N | EC50 [nM] | I.A. [%] | N | EC50 [nM] | I.A. [%] | N | EC50 [nM] | I.A. [%] | N | EC50 [nM] | I.A. [%] |
| Z1 | B | 26 | 64 | B | a) | 7.2 | B | 150 | 23 | C | 252 | 60 |
| Z2 | B | 4.7 | 52 | B | 140 | 22 | B | 18 | 15 | F | 39 | 59 |
| Z3 | B | 14 | 72 | B | 220 | 26 | B | 53 | 20 | F | 402 | 83 |
| isoproterenol | A | 54 | 100 | A | 1.3 | 100 | A | 5.8 | 100 | | c) | |
| Norepinephrine | | c) | | | c) | | | c) | | A | 6.5 | 100 | a); much weaker activities
b); Not active
c); Not tested

Results of Test example 1-B, Test example 2-B, Test example 3-B and Test example 4 were shown in Table 4.

Symbols described in the Table 4 are defined as follows.

β3 receptor indicates the human β3 adrenergic receptor agonist activity, β1 receptor indicates the human β1 adrenergic receptor agonist activity, β2 receptor indicates the human β2 adrenergic receptor agonist activity, and α1A receptor indicates the human α1A adrenergic receptor agonist activity.

EC50 and IA, have the same meanings as those described in Test example 1-B, Test example 2-B, Test example 3-B, or Test example 4.

Further, "N" described in the Table 4 indicates the number of the test. Specifically, it is as follows—A; n=3, triplicate, B; n=2, triplicate, C; n=1, duplicate; D; n=4, triplicate, E; n=3, duplicate, F; n=2, duplicate, G; n=1, triplicate.

"Compound" indicates the test compound. "ex" indicates the Example, for instance, ex1 indicates the Example 1. "Z" indicates the Comparative example, for example, Z1 indicates the Comparative example 1. The comparative examples are related to the compounds that are disclosed in the pamphlet of the International Publication No. WO03/035620. The Comparative example 1, Comparative example 2, and Comparative example 3 correspond to the Example 86, Example 88, and Example 90 of this international publication, respectively.

Further, from the results of the Test example 5, it was found that Z1 had no α1B agonist activity. Still further, from the results of the Test example 6, it was found that Z1 had no α1D agonist activity, either.

mixed gas of 95% $O_2$ and 5% $CO_2$. A resting tension of 1 g is applied to the strips, which is then equilibrated for more than 30 minutes. After the resting tension of the strips is equilibrated, KCl with final concentration of 40 mmol/L is added repeatedly and almost stable contraction caused by KCl is confirmed. After contracting the strips by KCl with final concentration of 40 mmol/L and subsequently obtaining stably generated tension, the test compound is cumulatively added with the ratio of ten times (with the interval of 20 minutes), and then a relaxation response is observed. The final concentration is $10^{-9}$, $10^{-8}$, $10^{-7}$, $10^{-8}$, $10^{-5}$ and $10^{-4}$ mol/L. Upon the completion of the relaxation response to the test compound at the highest concentration, papaverine with final concentration of $10^{-4}$ mol/L is added and the maximum relaxation response is obtained for each strip. This relaxation response is taken as 100%, and the relaxation ratio (%) is obtained for the test compound at the concentrations of $10^{-5}$ and $10^{-4}$ mol/L.

Results of Test example 7 were shown in Table 5. Further, "n" described in the Table 5 indicates the number of the test. "Relaxant activity (%)" corresponds to the relaxation ratio (%). Terms such as "compound" and "ex" are as described the above.

TABLE 4

| | β3 receptor | | | β1 receptor | | | β2 receptor | | | α1A receptor | | |
|---|---|---|---|---|---|---|---|---|---|---|---|---|
| compound | N | EC50 [nM] | I.A. [%] | N | EC50 [nM] | I.A. [%] | N | EC50 [nM] | I.A. [%] | N | EC50 [nM] | I.A. [%] |
| Z1 | B | 40 | 67 | B | a) | 2.4 | | c) | | C | 252 | 60 |
| Z2 | | c) | | | c) | | | c) | | F | 39 | 59 |
| Z3 | | c) | | | c) | | | c) | | F | 402 | 83 |
| ex1 | A | 15 | 77 | B | a) | 10 | B | a) | 6.3 | E | 1669 | 20 |
| ex2 | G | 56 | 68 | B | a) | 9.9 | B | a) | 3.8 | C | a) | 10 |
| ex3 | B | 45 | 60 | B | a) | 4.0 | B | a) | 5.0 | C | a) | 15 |
| ex4 | B | 24 | 52 | B | a) | 9.0 | B | a) | 8.0 | C | b) | 0 |
| ex5 | B | 19 | 59 | B | a) | 23 | B | a) | 9.0 | C | b) | 0 |
| ex6 | B | 54 | 41 | | c) | | | c) | | F | b) | 0 |
| ex7 | B | 584 | 51 | | c) | | | c) | | F | a) | 5.0 |
| ex8 | B | 29 | 70 | G | a) | 34 | G | a) | 10 | F | b) | 0 |
| ex9 | B | 56 | 51 | G | a) | 30 | G | a) | 1.0 | F | a) | 5.0 |
| isoproterenol | n = 16 triplicate | 114 | 100 | n = 8 triplicate | 1.8 | 100 | n = 8 triplicate | 16 | 100 | | c) | |
| Norepinephrine | | c) | | | c) | | | c) | | A | 6.5 | 100 | a); much weaker activities
b); Not active
c); Not tested

Test Example 7

Test for Relaxant Activity on Urinary Bladder Smooth Muscle Isolated from Common Marmoset In view of the descriptions in British Journal of Pharmacology, 1997, Vol. 122, pages 1720-1724, the test is carried out. Accordingly, the relaxant activity of a test compound on urinary bladder smooth muscle from a common marmoset can be confirmed. Specifically, a common marmoset (CLEA Japan, Inc.) is bled to exsanguinated death, and then the urinary bladder is taken out of the marmoset via laparotomy. Smooth muscle strips are prepared from the isolated urinary bladder, and then are suspended in an organ bath which is filled with Krebs-Henseleit solution (10 mL) infused with a

TABLE 5

| | | relaxant activity (%) | |
|---|---|---|---|
| compound | n | $10^{-5}$ M | $10^{-4}$ M |
| ex1 | 3 | 38.6 | 55.7 |
| ex2 | 2 | 50.8 | 65.6 |
| isoproterenol | 5 | 60.9 | 66.2 |

Test Example 8

Test for Measuring an Activity of Relaxing Human Urinary Bladder Smooth Muscle In view of the descriptions in The Journal of Urology, 2003, Vol. 170, pages 649-653, the test is carried out. Accordingly, the test compound's activity of relaxing human urinary bladder smooth muscle can be confirmed. Specifically, the smooth muscle strips obtained from the excised human urinary bladder are hung in an organ bath which was filled with Krebs-Henseleit solution infused with a mixed gas of 95% $O_2$ and 5% $CO_2$. A resting tension of 1 g is applied to the strips, which is then equilibrated for more than 30 minutes. After the resting tension of the strips is equilibrated, carbachol with final concentration of 0.1 μmol/L is added repeatedly and almost stable contraction caused by carbachol is confirmed. After contracting the strips by carbachol with final concentration of 0.1 μmol/L. and subsequently obtaining stably generated tension, the test compound is cumulatively added with the ratio of ten times (with the interval of 10 minutes), and then a relaxation response is observed. The final concentration is $10^{-9}$, $10^{-8}$, $10^{-7}$, $10^{-8}$, $10^{-5}$ and $10^{-4}$ mol/L. Upon the completion of the relaxation response to the test compound at the highest concentration, papaverine with final concentration of $10^{-4}$ mol/L is added and the maximum relaxation response is obtained for each strips. This relaxation response is taken as 100%, and the relaxation ratio is obtained.

Test Example 9

Effect on Blood Pressure Heart Rate of a Rat Under Pentobarbital Anesthesia

After measuring blood pressure and heart rate of a rat under pentobarbital anesthesia, an effect of intravenous bolus administration of a test compound on blood pressure and heart rate can be determined. To a male SD rat (Japan SLC Inc.), sodium pentobarbital (Tokyo Chemical Industry Co., Ltd.) is intraperitoneally administered for induction of anesthesia (50 mg/kg). As maintenance anesthetics, sodium pentobarbital is subcutaneously administered (25 mg/kg). Left femoral vein is exposed and stripped, and then a polyethylene tube SP10 (connected to a three-way stopcock via ¼ vein needle) which has been filled with physiological saline is inserted and left in the vein.

Left medial femoral region is cut to expose and strip the femoral artery, and then a polyethylene tube (SP31, connected to a three-way stopcock via 22 G injection needle by TERUMO Corporation) which has been filled with heparin physiological saline is inserted and connected to a pressure transducer. Blood pressure is measured from the pressure transducer by using a modified pressure amplifier (AP-641 G, Nihon Kohden Corporation). Heart rate is measured by using the Heart rate Counter (AT-601 g, Nihon Kohden Corporation) while having the pulse wave of the blood pressure as a trigger. The blood pressure, mean blood pressure and heart rate are transmitted to the data recorder for recordation. In addition, the mean blood pressure is recorded using a modified pressure amplifier (AP-641 G) according to the equation of {diastolic blood pressure+(systolic blood pressure−diastolic blood pressure)/3}.

Blood pressure and heart rate measurement is started, and after confirming that each value remains almost constant, the test compound (3 mg/kg) is administered to the left femoral vein for 30 seconds. Specifically, the test compound with 3 mg/mL concentration is bolus administered at the administration dose of 1 mL/kg. Relative value (%) at each time point compared to the mean blood pressure and the heart rate before the administration is obtained for each individual. Then, mean value±standard deviation is obtained for the relative value (%) at which the change is the greatest for each parameter.

Results of Test example 9 were shown in Table 6. Further, "n" described in the Table 6 indicates the number of the animals. Terms such as "compound", "ex", and "Z" are as described in the above. Further, "MBP" indicates mean blood pressure.

TABLE 6

| compound | n | increase in MBP (%) |
| --- | --- | --- |
| Z1 | 3 | 12.8 ± 4.4 |
| Z2 | 3 | 12.6 ± 4.1 |
| ex1 | 3 | 2.7 ± 0.5 |
| ex2 | 6 | 4.0 ± 2.6 |
| ex3 | 3 | 2.3 ± 0.9 |

Test Example 10

Saturation Solubility in Pure Water

Test compound is prepared to saturation state in pure water. The resulting solution is shaken at room temperature for 1 hour. To a filter tube, the entire solution obtained after the shaking is transferred and is subjected to centrifugal filtration at room temperature. The filtrate is analyzed by HPLC, and by using a calibration curve, saturation solubility of the test compound is obtained from the peak area value.

Standard solution is prepared by precisely weighing each test compound and fully dissolving it in pure water. Calibration curve is established by having the concentration of the standard solution as a horizontal axis and the HPLC area value at the corresponding concentration as a vertical axis.

As a separation column, YMC-Pack C18 (4.6 mm×150 mm, manufactured by YMC) is used. Detection is made at UV-254 nm and the temperature inside the column is 40° C. Condition for elution is as follows; with flow rate of 1 ml/minute, solution A as a solvent=water [comprising 0.1% (v/v) acetic acid] and solution B=acetonitrile are used, and from minute 0 to minute 20, 5 to 98% (v/v) linear gradient of solution B is applied, followed by elution with 98% of solution B until minute 25 and elution with 5% of solution B from minute 25.01 to minute 35.

As a result, it was found to be 55 mg/mL for the compound of the Example 1, and 53 mg/mL for the compound of the Example 2.

Test Example 11

Solubility Test in Hydrochloric Acid Buffer Solution Having pH 1.2

500 μg of the test compound is precisely weighed, and then added with hydrochloric acid buffer solution having pH 1.2 until the concentration of 1000 μg/mL is obtained. The filtrate is shaken at 37° C. for 1 hour. To a filter tube, the entire solution obtained after the shaking is transferred and is subjected to centrifugal filtration at room temperature. The filtrate is analyzed by HPLC, and by using a calibration curve, saturation solubility of the test compound is obtained from the peak area value.

Standard solution is prepared by precisely weighing 500 μg of the test compound and dissolving it DMSO to obtain the concentration of 1 mg/mL.

As a separation column, YMC-Pack C18 (4.6 mm×150 mm, manufactured by YMC) is used. Detection is made at UV-254 nm and the temperature inside the column is 40° C. Condition for elution is as follows; with flow rate of 1 ml/minute, solution A as a solvent=water [comprising 0.1% (v/v) acetic acid] and solution B=acetonitrile are used, and from minute 0 to minute 20, 5 to 98% (v/v) linear gradient of solution B is applied, followed by elution with 98% of solution B until minute 25 and elution with 5% of solution B from minute 25.01 to minute 35.

As a result, it was found to be 982 μg/mL for the compound of the Example 1, and more than 1000 μg/mL (i.e., 1041 μg/mL) for the compound of the Example 2.

Test Example 12

Solubility Test in Physiological Saline

Except that the hydrochloric acid buffer solution having pH 1.2 is replaced with physiological saline, the test is carried out in the same method as Test example 11 to obtain the solubility of the test compound.

As a result, it was found to be 999 μg/mL for the compound of the Example 1, and 999 μg/mL for the compound of the Example 2.

Test Example 13

Stability Test in Pure Water

Test compound is prepared to saturation state in pure water. The resulting solution is shaken at room temperature for 1 hour. To a filter tube, the entire solution obtained after the shaking is transferred and is subjected to centrifugal filtration at room temperature. The filtrate is analyzed by HPLC right after the filtration, 24 hours, and 48 hours after the filtration. Then, by using a calibration curve, stability of the test compound is obtained from the peak area value.

Standard solution is prepared by precisely weighing each test compound and fully dissolving it in pure water. Calibration curve is established by having the concentration of the standard solution as a horizontal axis and the HPLC area value at the corresponding concentration as a vertical axis.

As a separation column, YMC-Pack C18 (4.6 mm×150 mm, manufactured by YMC) is used. Detection is made at UV-254 nm and the temperature inside the column is 40° C. Condition for elution is as follows; with flow rate of 1 ml/minute, solution A as a solvent=water [comprising 0.1% (v/v) acetic acid] and solution B=acetonitrile are used, and from minute 0 to minute 20, 5 to 98% (v/v) linear gradient of solution B is applied, followed by elution with 98% of solution B until minute 25 and elution with 5% of solution B from minute 25.01 to minute 35.

As a result, HPLC area percentage of the compound of the Example 1 was 95.7% right after the filtration, 95.6% at 24 hours after the filtration, and 95.6% at 48 hours after the filtration, and therefore found to be stable. In addition, HPLC area percentage of the compound of the Example 2 was 95.2% right after the filtration, 95.2% at 24 hours after the filtration, and 95.0% at 48 hours after the filtration, and therefore also found to be stable.

Test Example 14

Solubility Test in Phosphate Buffer Solution Having pH 6.8

Except that pure water is replaced with phosphate buffer solution having pH 6.8, the test is carried out in the same method as Test example 13 to obtain the stability of the test compound.

As a result, HPLC area percentage of the compound of the Example 1 was 95.7% right after the filtration, 95.5% at 24 hours after the filtration, and 95.5% at 48 hours after the filtration, and therefore found to be stable. In addition, HPLC area percentage of the compound of the Example 2 was 95.1% right after the filtration, 93.3% at 24 hours after the filtration, and 94.5% at 48 hours after the filtration, and therefore also found to be stable.

INDUSTRIAL APPLICABILITY

The compounds represented by the Formula (A-1) or the Formula (1) of the present invention, a possible stereoisomer or a racemate thereof, or a pharmaceutically acceptable salt thereof, or a hydrate and/or solvate thereof, and a crystal thereof have a β3 adrenergic receptor agonist activity, and therefore are useful as an agent for the prevention and treatment of diabetes, obesity, hyperlipidemia, depression, biliary stone, a disorder derived from hyperactivity of biliary tract, a disorder derived from hyperactivity of digestive tract, interstitial cystitis, overactive bladder or urinary incontinence, etc. or as an agent for the prevention and treatment of a disorder derived from decreased tear secretion, and thus they can be used in the corresponding pharmaceutical field.

The invention claimed is:

1. A compound having the following Formula (A-1)

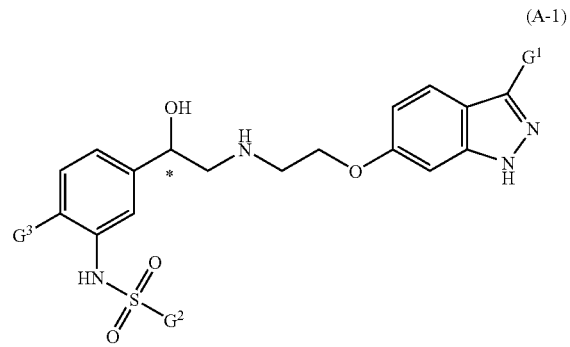

in the Formula (A-1), $G^1$ represents —CH($G^4$)OMe, —OCHF$_2$, —OCF$_3$, a halogen atom, or a group that is represented by the following Formula (A-2) or (A-3),

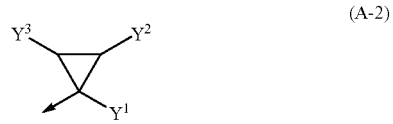

(A-3)

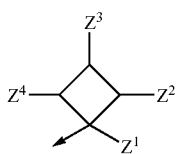

G² represents a methyl group, an ethyl group, an n-propyl group, an isopropyl group, an isobutyl group, a sec-butyl group, a benzyl group, or a phenyl group, G³ represents a hydrogen atom or a halogen atom, G⁴ represents a methyl group, an ethyl group, an n-propyl group, or an isopropyl group, $Y^1$, $Y^2$, $Y^3$, $Z^1$, $Z^2$, $Z^3$, and $Z^4$ can be the same or different and each independently represents a hydrogen atom or a methyl group; with the proviso that, compounds in which G² represents a methyl group and G³ represents a hydrogen atom or a halogen atom when G¹ represents a halogen atom and a compound in which G² represents a methyl group and G³ represents a hydrogen atom when G¹ represents —OCHF₂ are excluded; asterisk (*) represents an asymmetric carbon, or salt thereof.

2. A compound having the following Formula (1)

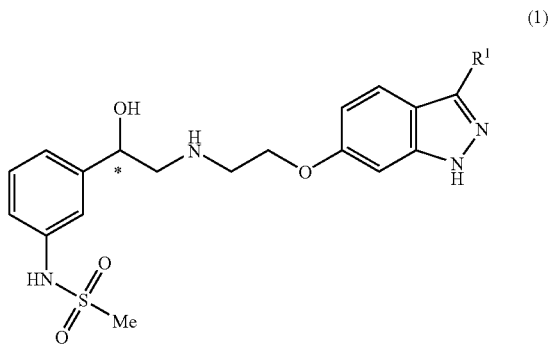

(1)

in the Formula (1), R¹ represents —CH(R²)OMe or a group that is represented by the following Formula (2-1) or (2-2), (2-1)

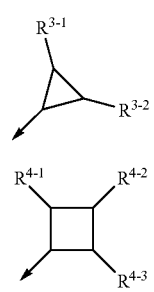

(2-2)

R² represents a methyl group, an ethyl group, an n-propyl group, or an isopropyl group, $R^{3-1}$, $R^{3-2}$, $R^{4-1}$, $R^{4-2}$, and $R^{4-3}$ can be the same or different and each independently represents a hydrogen atom or a methyl group; asterisk (*) represents an asymmetric carbon, or salt thereof.

3. The compound according to claim 1 or salt thereof in which G¹ represents —OCHF₂, a halogen atom, a cyclopropyl group, a cyclobutyl group, G² represents a methyl group, an ethyl group, an n-propyl group, an isopropyl group, an isobutyl group, a sec-butyl group, a benzyl group, or a phenyl group, and G³ represents a hydrogen atom, a fluorine atom, or a chlorine atom; with the proviso that, compounds in which G² represents a methyl group and G³ represents a hydrogen atom when G¹ represents a halogen atom and a compound in which G² represents a methyl group and G³ represents a hydrogen atom when G¹ represents —OCHF₂ are excluded.

4. The compound according to claim 1 or salt thereof in which G¹ represents —CH(Me)OMe, a cyclopropyl group, or a cyclobutyl group.

5. The compound according to claim 2 or salt thereof in which R¹ represents —CH(Me)OMe, a cyclopropyl group, or a cyclobutyl group.

6. The compound according to claim 1 or salt thereof in which stereo configuration of the asymmetric carbon that is marked with asterisk (*) is (R) configuration.

7. The compound according to claim 2 or salt thereof in which stereo configuration of the asymmetric carbon that is marked with asterisk (*) is (R) configuration.

8. The compound according to claim 3 or salt thereof in which stereo configuration of the asymmetric carbon that is marked with asterisk (*) is (R) configuration.

9. A compound that is selected from a group consisting of
(R)—N-(3-(2-(2-(3-(1-methoxyethyl)indazol-6-yloxy)ethylamino)-1-hydroxyethyl)phenyl)methanesulfonamide;
(R)—N-(3-(2-(2-(3-cyclopropylindazol-6-yloxy)ethylamino)-1-hydroxyethyl)phenyl)methanesulfonamide;
(R)—N-(3-(2-(2-(3-cyclobutylindazol-6-yloxy)ethylamino)-1-hydroxyethyl)phenyl)methanesulfonamide;
(R)—N-(5-(2-(2-(3-cyclopropylindazol-6-yloxy)ethylamino)-1-hydroxyethyl)-2-fluorophenyl)methanesulfonamide;
(R)—N-(2-chloro-5-(2-(2-(3-cyclopropylindazol-6-yloxy)ethylamino)-1-hydroxyethyl)phenyl)methanesulfonamide;
(R)—N-(2-chloro-5-(2-(2-(3-cyclobutylindazol-6-yloxy)ethylamino)-1-hydroxyethyl)phenyl)methanesulfonamide; and
(R)—N-(2-chloro-5-(2-(2-(3-(difluoromethoxy)-indazol-6-yloxy)ethylamino)-1-hydroxyethyl)phenyl)methanesulfonamide;
or salt thereof.

10. A compound that is selected from a group consisting of
(R)—N-(3-(2-(2-(3-(1-methoxyethyl)indazol-6-yloxy)ethylamino)-1-hydroxyethyl)phenyl)methanesulfonamide;
(R)—N-(3-(2-(2-(3-cyclopropylindazol-6-yloxy)ethylamino)-1-hydroxyethyl)phenyl)methanesulfonamide; and
(R)—N-(3-(2-(2-(3-cyclobutylindazol-6-yloxy)ethylamino)-1-hydroxyethyl)phenyl)methanesulfonamide;
or salt thereof.

11. A β3 adrenergic receptor agonist, comprising:
the compound described in claim 1 or salt thereof as an active ingredient.

12. A medicine, comprising:
the compound described in 1 or salt thereof as an active ingredient.

13. The medicine according to claim 12, which is a therapeutic agent for overactive bladder and urinary incontinence.

14. A method of activating β3 adrenergic receptor in a living body of a patient, wherein the compound described in claim 1 or salt thereof is administered to a patient who is in need of treatment of overactive bladder and urinary incontinence.

15. A method of treatment of overactive bladder and urinary incontinence, wherein a therapeutically effective amount of the compound described in claim 1 or salt thereof is administered to a patient.

16. A method of treatment of urinary incontinence, wherein a therapeutically effective amount of the compound described in claim 1 or salt thereof is administered to a patient.

\* \* \* \* \*